US008426403B2

(12) United States Patent
Zhu et al.

(10) Patent No.: US 8,426,403 B2
(45) Date of Patent: Apr. 23, 2013

(54) GAMMA SECRETASE MODULATORS

(76) Inventors: Zhaoning Zhu, Plainsboro, NJ (US);
William J. Greenlee, Teaneck, NJ (US);
Xianhai Huang, Warren, NJ (US);
Brian A. McKittrick, New Vernon, NJ (US); John W. Clader, Cranford, NJ (US); Mark D. McBriar, Clinton, NJ (US); Anandan Palani, Bridgewater, NJ (US)

( * ) Notice: Subject to any disclaimer, the term of this patent is extended or adjusted under 35 U.S.C. 154(b) by 498 days.

(21) Appl. No.: 12/601,322

(22) PCT Filed: May 28, 2008

(86) PCT No.: PCT/US2008/006734
§ 371 (c)(1),
(2), (4) Date: May 28, 2010

(87) PCT Pub. No.: WO2008/153793
PCT Pub. Date: Dec. 18, 2008

(65) Prior Publication Data
US 2010/0256128 A1  Oct. 7, 2010

Related U.S. Application Data

(60) Provisional application No. 60/941,405, filed on Jun. 1, 2007, provisional application No. 60/984,484, filed on Nov. 1, 2007.

(51) Int. Cl.
*A61K 31/5365* (2006.01)
*A61K 31/5395* (2006.01)
*C07D 498/04* (2006.01)
*A61P 25/28* (2006.01)

(52) U.S. Cl.
USPC .......... 514/229.2; 514/230.5; 544/63; 544/66

(58) Field of Classification Search .............. 544/63, 544/66; 514/229.2, 230.5
See application file for complete search history.

(56) References Cited

U.S. PATENT DOCUMENTS

| 4,003,890 | A | 1/1977 | Riovnyak |
| 4,065,617 | A | 12/1977 | Krapcho et al. |
| 6,096,745 | A * | 8/2000 | Poindexter et al. ...... 514/252.05 |
| 6,887,872 | B2 * | 5/2005 | Literati Nagy et al. .... 514/239.5 |
| 2005/0042284 | A1 | 2/2005 | Hobden et al. |
| 2006/0004013 | A1 | 1/2006 | Kimura et al. |
| 2007/0117798 | A1 | 5/2007 | Kimura et al. |

FOREIGN PATENT DOCUMENTS

| CH | 594667 | 5/1974 |
| JP | 50-160271 | 12/1975 |
| JP | 52-36692 | 8/1976 |
| WO | 2004/071431 | 8/2004 |
| WO | 2004/110350 | 12/2004 |
| WO | 2005/110422 | 11/2005 |
| WO | 2006/001877 | 1/2006 |
| WO | 2006045554 | 5/2006 |
| WO | 2008/137139 A1 | 11/2008 |
| WO | 2008/153792 A2 | 12/2008 |
| WO | 2010/056849 A1 | 5/2010 |

OTHER PUBLICATIONS

CAplus Accession No. 1998598707, (1997).
CA Registry No. 30386040, (1984).
CA Registry No. 57770873, (1984).
CA Registry No. 57770884, (1984).
CA Registry No. 57770908, (1984).
CA Registry No. 215674252, (1998).
CA Registry No. 215674062, (1984).
CA Registry No. 215674309, (1998).
CA Registry No. 215674263, (1998).
CA Registry No. 215674274, (1998).
CA Registry No. 215674296, (1998).
Ca Registry No. 215674285, (1998).
Al-Omar, et al., "Synthesis and In Vitro Antioxidant Activity of some New Fused Pyridine Analogs," Arch. Pharm. Chem. Life Sci., vol. 338, 2005, pp. 175-180.
Bilgin, et al., "Synthesis and Antidepressant Activity of Some New 8-Thiocarbamoyl-7,8-diazabicyclo[4,3,0]non-6-ene Derivatives," Arzneim-Forsch./Drug Research, vol. 42 (II), 1992, pp. 1271-1273.
Daboun, et al., "Reactions With Thiohydantoins: New Routes for Synthesis of Imidazoquinazolines and Imidazo-1,2,4-Triazoles," Heterocycles, vol. 19, No. 8, 1992, pp. 1375-1379.
Harb, et al., Synthesis of Some Heterocycles of Potential Biological Activity, Arch. Pharm. Res., vol. 13, No. 2, 1990, pp. 187-191.
Karthikeyan, et al., "Microwave assisted synthesis of 1-methyl-5-arul-3-[(E)-arylethenyl]-4,5-dihydro-1H-pyrazoles and 2-methyl-3-aryl-7-[(E)-aryl-methylidene]-3,3a,4,5,6,7-hexahydro-2H-indazoles," Indian Journal of Chemistry, vol. 43B, Jul. 2004, pp. 1565-1568.
Kassab, et al., "The Synthesis of a New Fused Thiazolo[4,3-c]-1,2,4-triazole System and its Derivatives," Aeitschrift fuer Naturforschung, Teil B: Anorganische Chemie, Organische Chemie, 1976, vol. 31B, No. 6, pp. 853-856.
Nasr., Novel 3,3a,4,5,6,7-Hexahydroindazole and Arylthiazolylpyrazoline derivatives as Anti-inflammatory Agents, Arch. Pharm. Pharm. Med. Chem, vol. 336, 2003, pp. 551-559.
Reddy, et al., Synthesis of some substituted imidazolino-[3,4-a]-2,3-dihydroimidazoles/benzimidazoles as possible nonsteroidal, non-acidic antiinflammatory agents, Indian Journal of Heterocyclic Chemistry, vol. 12, No. 4, 2003, pp. 347-350.

* cited by examiner

*Primary Examiner* — Niloofar Rahmani
(74) *Attorney, Agent, or Firm* — Susan L. Hess; Henry Jeanette; Gerard M. Devlin

(57) ABSTRACT

In its many embodiments, the present invention provides a novel class of heterocyclic compounds of the formula: as modulators of gamma secretase, methods of preparing such compounds, pharmaceutical compositions containing one or more such compounds, methods of preparing pharmaceutical formulations comprising one or more such compounds, and methods of treatment, prevention, inhibition, or amelioration of one or more diseases associated with the central nervous system using such compounds or pharmaceutical compositions.

9 Claims, No Drawings

GAMMA SECRETASE MODULATORS

REFERENCE TO RELATED APPLICATION

This application claims the benefit of U.S. Provisional Application No. 60/941,405 filed Jun. 1, 2007, and of U.S. Provisional Application No. 60/984,484 filed Nov. 1, 2007.

FIELD OF THE INVENTION

The present invention relates to certain heterocyclic compounds useful as gamma secretase modulators (including inhibitors, antagonists and the like), pharmaceutical compositions containing the compounds, and methods of treatment using the compounds and compositions to treat various diseases including central nervous system disorders such as, for example, neurodegenerative diseases such as Alzheimer's disease and other diseases relating to the deposition of amyloid protein. They are especially useful for reducing Amyloid beta (hereinafter referred to as Aβ) production which is effective in the treatment of diseases caused by Aβ such as, for example, Alzheimers and Down Syndrome.

BACKGROUND OF THE INVENTION

Alzheimer's disease is a disease characterized by degeneration and loss of neurons and also by the formation of senile plaques and neurofibrillary change. Presently, treatment of Alzheimer's disease is limited to symptomatic therapies with a symptom-improving agent represented by an acetylcholinesterase inhibitor, and the basic remedy which prevents progress of the disease has not been developed. A method of controlling the cause of onset of pathologic conditions needs to be developed for creation of the basic remedy of Alzheimer's disease.

Aβ protein, which is a metabolite of amyloid precursor protein (hereinafter referred to as APP), is considered to be greatly involved in degeneration and loss of neurons as well as onset of demential conditions (for example, see Klein W L, et al *Proceeding National Academy of Science USA*, Sep. 2, 2003, 100(18), p. 10417-22, suggest a molecular basis for reversible memory loss.

Nitsch R M, and 16 others, *Antibodies against β-amyloid slow cognitive decline in Alzheimer's disease*, Neuron, May 22, 2003, 38(4), p. 547-554) suggest that the main components of Aβ protein are Aβ40 consisting of 40 amino acids and Aβ42 having two additional amino acids at the C-terminal. The Aβ40 and Aβ42 tend to aggregate (for example, see Jarrell J T et al, *The carboxy terminus of the β amyloid protein is critical for the seeding of amyloid formation: implications for the pathogenesis of Alzheimer's disease*, Biochemistry, May 11, 1993, 32(18), p. 4693-4697) and constitute main components of senile plaques (for example, (Glenner G G, et al, *Alzheimer's disease: initial report of the purification and characterization of a novel cerebrovascular amyloid protein*, Biochemical and Biophysical Research Communications, May 16, 1984, 120(3), p. 885-90. See also Masters C L, et al, *Amyloid plaque core protein in Alzheimer disease and Down syndrome*, Proceeding National Academy of Science USA, June 1985, 82(12), p. 4245-4249.).

Furthermore, it is known that mutations of APP and presenelin genes, which is observed in familial Alzheimer's disease, increase production of Aβ40 and Aβ42 (for example, see Gouras G K, et al, *Intraneuronal Aβ142 accumulation in human brain*, American Journal of Pathology, January 2000, 156(1), p. 15-20. Also, see Scheuner D, et al, Nature Medicine, August 1996, 2(8), p. 864-870; and Forman M S, et al, *Differential effects of the Swedish mutant amyloid precursor protein on β-amyloid accumulation and secretion in neurons and nonneuronal cells*, Journal of Biological Chemistry, Dec. 19, 1997, 272(51), p. 32247-32253.). Therefore, compounds which reduce production of Aβ40 and Aβ42 are expected as an agent for controlling progress of Alzheimer's disease or for preventing the disease.

These Aβs are produced when APP is cleaved by beta secretase and subsequently clipped by gamma secretase. In consideration of this, creation of inhibitors of γ secretase and β secretase has been attempted for the purpose of reducing production of Aβs. Many of these secretase inhibitors already known are peptides or peptidomimetics such as L-685,458. L-685,458, an aspartyl protease transition stale mimic, is a potent inhibitor of amyloid β-protein precursor γ-secretase activity, Biochemistry, Aug. 1, 2000, 39(30), p. 8698-8704).

Also of interest in connection with the present invention are: US 2007/0117798 (Eisai, published May 24, 2007); US2007/0117839 (Eisai, published May 24, 2007); US2006/0004013 (Eisai, published Jan. 5, 2006); WO 2005/110422 (Boehringer Ingelheim, published Nov. 24, 2005); WO 2006/045554 (Cellzone AG, published May 4, 2006); WO 2004/110350 (Neurogenetics, published Dec. 23, 2004); WO 2004/071431 (Myriad Genetics, published Aug. 26, 2004); US2005/0042284 (Myriad Genetics, published Feb. 23, 2005) and WO 2006/001877 (Myriad Genetics, published Jan. 5, 2006).

There is a need for new compounds, formulations, treatments and therapies to treat diseases and disorders associated with Aβ. It is, therefore, an object of this invention to provide compounds useful in the treatment or prevention or amelioration of such diseases and disorders.

SUMMARY OF THE INVENTION

In its many embodiments, the present invention provides a novel class of heterocyclic compounds as gamma secretase modulators (including inhibitors, antagonists and the like), methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the Aβ using such compounds or pharmaceutical compositions.

The compounds of this invention (Formula I) can be useful as gamma secretase modulators and can be useful in the treatment and prevention of diseases such as, for example, Alzheimers disease, mild cognitive impairment (MCI), Downs Syndrome, Glaucoma (Guo et. al., Proc. Natl. Acad. Sci. USA 104, 13444-13449 (2007)), Cerebral amyloid angiopathy, stroke or dementia (Frangione et al., Amyloid: J. Protein folding Disord. 8, suppl. 1, 36-42 (2001), Microgliosis and brain inflammation (M P Lamber, Proc. Natl. Acad. Sci. USA 95, 6448-53 (1998)), Olfactory function loss (Getchell, et.al. Neurobiology of Aging, 663-673, 24, 2003).

This invention provides compounds of formula I:

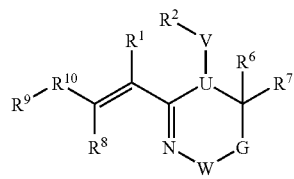

Formula I wherein $R^1, R^2, R^6, R^7, R^8, R^9, R^{10}$, G, U and W are as defined below.

In one embodiment, the present application discloses a compound, or pharmaceutically acceptable salts, solvates, esters or prodrugs of said compound, said compound having the general structure shown in Formula IA:

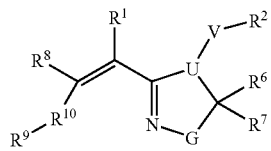

Formula IA wherein $R^1$, $R^2$, $R^6$, $R^7$, $R^8$, $R^9$, $R^{10}$, G, U and V are as defined below.

The compounds of Formula I can be useful as gamma secretase modulators and can be useful in the treatment and prevention of diseases such as, for example, central nervous system disorders such as Alzheimers disease and Downs Syndrome.

This invention also provides compounds of formula I.

This invention also provides pharmaceutically acceptable salts of the compounds of formula I.

This invention also provides pharmaceutically acceptable esters of the compounds of formula I.

This invention also provides pharmaceutically solvates of the compounds of formula I.

This invention also provides compounds of formula I in pure and isolated form.

This invention also provides compounds of formula I in pure form.

This invention also provides compounds of formula I in isolated form.

This invention also provides compounds 1 to 24, B10-B21, C5-C10, D9-D26, G4-G9, H3-H11, I5, I6, I6A, I7, I8, I8A, J4-J9, K1-K6, L4-L8, M5-M15, N6-N23, O4__1, and P8__1.

This invention also provides compounds 1 to 20 (i.e., the compounds in Table 1).

This invention also provides compounds 1 to 20, and 23.

This invention also provides compounds 21, 22, and 24.

This invention also provides pharmaceutical compositions comprising an effective amount of one or more (e.g., one) compounds of formula I, or a pharmaceutically acceptable salt, ester or solvate thereof, and a pharmaceutically acceptable carrier.

This invention also provides pharmaceutical compositions comprising an effective amount of one or more (e.g., one) compounds of formula I, or a pharmaceutically acceptable salt, ester or solvate thereof, and an effective amount of one or more (e.g., one) other pharmaceutically active ingredients (e.g., drugs), and a pharmaceutically acceptable carrier.

This invention also provides a method for modulating (including inhibiting, antagonizing and the like) gamma-secretase, comprising administering an effective (i.e., therapeutically effective) amount of one or more compounds of formula I to a patient in need of treatment.

This invention also provides a method for modulating (including inhibiting, antagonizing and the like) gamma-secretase, comprising administering an effective (i.e., therapeutically effective) amount of a compound of formula I to a patient in need of treatment.

This invention also provides a method of treating one or more neurodegenerative diseases, comprising administering an effective (i.e., therapeutically effective) amount of one or more compounds of formula I to a patient in need of treatment.

This invention also provides a method of treating one or more neurodegenerative diseases, comprising administering an effective (i.e., therapeutically effective) amount of a compound of formula I to a patient in need of treatment.

This invention also provides a method of inhibiting the deposition of amyloid protein (e.g., amyloid beta protein) in, on or around neurological tissue (e.g., the brain), comprising administering an effective (i.e., therapeutically effective) amount of one or more compounds of formula I to a patient in need of treatment.

This invention also provides a method of inhibiting the deposition of amyloid protein (e.g., amyloid beta protein) in, on or around neurological tissue (e.g., the brain), comprising administering an effective (i.e., therapeutically effective) amount of a compound of formula I to a patient in need of treatment.

This invention also provides a method of treating Alzheimer's disease, comprising administering an effective (i.e., therapeutically effective) amount of one or more compounds of formula I to a patient in need of treatment.

This invention also provides a method of treating Alzheimer's disease, comprising administering an effective (i.e., therapeutically effective) amount of a compound of formula I to a patient in need of treatment.

This invention also provides a method of treating Alzheimer's disease, comprising administering an effective (i.e., therapeutically effective) amount of one or more compounds of formula I, in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1 H-inden-1-one hydrochloride, i.e., donepezil hydrochloride, available as the Aricept® brand of donepezil hydrochloride), to a patient in need of treatment.

This invention also provides a method of treating Alzheimer's disease, comprising administering an effective (i.e., therapeutically effective) amount of one or more compounds of formula I, in combination with an effective (i.e., therapeutically effective) amount of one or more compounds selected from the group consisting of Aβ antibody inhibitors, gamma secretase inhibitors and beta secretase inhibitors.

This invention also provides combinations comprising an effective (i.e., therapeutically effective) amount of one or more compounds of formula I, in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1 H-inden-1-one hydrochloride, i.e., donepezil hydrochloride, available as the Aricept® brand of donepezil hydrochloride), Aβantibody inhibitors, gamma secretase inhibitors and beta secretase inhibitors.

This invention also provides a method of treating Alzheimer's disease, comprising administering an effective (i.e., therapeutically effective) amount of a compound of formula I, in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides a method of treating Downs syndrome, comprising administering an effective (i.e., therapeutically effective) amount of one or more compounds of formula I to a patient in need of treatment.

This invention also provides a method of treating Downs syndrome, comprising administering an effective (i.e., therapeutically effective) amount of a compound of formula I to a patient in need of treatment.

This invention also provides a method of treating Downs syndrome, comprising administering an effective (i.e., therapeutically effective) amount of one or more compounds of formula I, in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides a method of treating Downs syndrome, comprising administering an effective (i.e., therapeutically effective) amount of a compound of formula I, in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of an effective amount of one or more (e.g. one) compounds of formula I and the administration of an effective amount of one or more (e.g., one) other pharmaceutical active ingredients (e.g., drugs).

This invention also provides a method of treating mild cognitive impairment, comprising administering an effective amount of one or more (e.g., one) compounds of formula I to a patient in need of treatment.

This invention also provides a method of treating glaucoma, comprising administering an effective amount of one or more (e.g., one) compounds of formula I to a patient in need of treatment.

This invention also provides a method of treating cerebral amyloid angiopathy, comprising administering an effective amount of one or more (e.g., one) compounds of formula I to a patient in need of treatment.

This invention also provides a method of treating stroke, comprising administering an effective amount of one or more (e.g., one) compounds of formula I to a patient in need of treatment.

This invention also provides a method of treating dementia, comprising administering an effective amount of one or more (e.g., one) compounds of formula I to a patient in need of treatment.

This invention also provides a method of treating microgliosis, comprising administering an effective amount of one or more (e.g., one) compounds of formula I to a patient in need of treatment.

This invention also provides a method of treating brain inflammation, comprising administering an effective amount of one or more (e.g., one) compounds of formula I to a patient in need of treatment.

This invention also provides a method of treating olfactory function loss, comprising administering an effective amount of one or more (e.g., one) compounds of formula I to a patient in need of treatment.

This invention also provides pharmaceutical compositions comprising a combination of an effective amount of one or more (e.g., one) compounds of formula I, in combination with an effective amount of one or more compounds selected from the group consisting of cholinesterase inhibitors, Aβ antibody inhibitors, gamma secretase inhibitors and beta secretase inhibitors. The pharmaceutical compositions also comprise a pharmaceutically acceptable carrier.

This invention also provides a kit comprising, in separate containers, in a single package, pharmaceutical compositions for use in combination, wherein one container comprises an effective amount of a compound of formula I in a pharmaceutically acceptable carrier, and another container (i.e., a second container) comprises an effective amount of another pharmaceutically active ingredient, the combined quantities of the compound of formula I and the other pharmaceutically active ingredient being effective to: (a) treat Alzheimer's disease, or (b) inhibit the deposition of amyloid protein in, on or around neurological tissue (e.g., the brain), or (c) treat neurodegenerative diseases, or (d) modulate the activity of gamma-secretase.

This invention also provides a kit comprising, in separate containers, in a single package, pharmaceutical compositions for use in combination, wherein one container comprises an effective amount of a compound of formula I in a pharmaceutically acceptable carrier, and another container (i.e., a second container) comprises an effective amount of another pharmaceutically active ingredient (as described below), the combined quantities of the compound of formula I and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

This invention also provides any one of the methods disclosed above and below wherein the compound is selected from the group consisting of the compounds 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

This invention also provides any one of the methods disclosed above and below wherein the compound of formula I is selected from the group consisting of the compounds 1 to 20, and 23.

This invention also provides any one of the methods disclosed above and below wherein the compound of formula I is selected from the group consisting of the compounds 21, 22 and 24.

This invention also provides any one of the methods disclosed above and below wherein the compound of formula I is selected from the group consisting of the compounds 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

This invention also provides any one of the pharmaceutical compositions disclosed above and below wherein the compound is selected from the group consisting of the compounds 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

This invention also provides any one of the pharmaceutical compositions disclosed above and below wherein the compound is any one of the compounds 1 to 20, and 23.

This invention also provides any one of the pharmaceutical compositions disclosed above and below wherein the compound is any one of the compounds 21, 22 and 24.

This invention also provides any one of the pharmaceutical compositions disclosed above and below wherein the compound is any one of the compounds 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

Other embodiments of this invention are directed to any one of the embodiments above or below that are directed to formula I, or the use of formula I (e.g. the embodiments directed to methods of treatment, pharmaceutical compositions and kits), wherein the compound is a compound of formula IA instead of formula I. Those skilled in the art will appreciate that the compounds of formula I and formula IA are isomers of each other.

This invention also provides any one of the above mentioned methods of treatment wherein the compound of formula I is selected from the group consisting of the compounds in Table 1.

DETAILED DESCRIPTION

In one embodiment, the present invention discloses compounds which are represented by structural Formula I, or a pharmaceutically acceptable salt, solvate, ester or prodrug thereof, wherein the various moieties are described below.

In one embodiment, the present application discloses a compound, or pharmaceutically acceptable salts, solvates, esters or prodrugs of said compound, said compound having the general structure shown in Formula I:

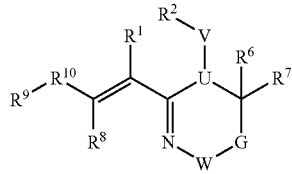

Formula I wherein:
either (i) $R^1$ and $R^2$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; or (ii) $R^2$ and $R^6$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; or (iii) $R^1$ and $R^2$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; and $R^2$ and $R^6$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; or (iv) $R^6$ and either $R^3$ or $R^4$ of the $-C(R^3)(R^4)-$ G moiety, are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; or (v) $R^6$ and $R^{13}$ of the $-N(R^{13})-$ G moiety, are joined together to form a 5-8 membered heterocyclyl or 5-8 membered heterocyclenyl moiety, with said heterocyclyl moiety being unsubstituted or optionally independently being substituted with 1-5 substituents which can be the same or different, each substituent being independently selected from the group consisting of the moieties shown below; and U is

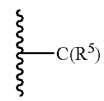

or N;

W is selected from the group consisting of a bond, $-O-$, $-C(O)-$, $-S-$, $-S(O)-$, $-S(O_2)-$, and $-C(R^{11})(R^{12})-$;

G is selected from the group consisting of $-C(R^3)(R^4)-$, $-C(O)-$ and $-N(R^{13})-$, with the proviso that when W is $-O-$ or $-S-$, G is not $-N(R^{13})-$ or $-C(O)-$;

V is selected from the group consisting of a bond, $-O-$, $-C(O)-$, and $-N(R^{14})-$;

$R^1$ (when $R^1$ is not joined to $R^2$), $R^2$ (when $R^2$ is not joined to $R^1$ or $R^6$), $R^5$, $R^6$ (when $R^6$ is not joined to $R^2$), and $R^7$ can be the same or different, each being independently selected from the group consisting of H, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below;

or, alternatively, $R^1$ (when $R^1$ is not joined to $R^2$) and $R^8$ are taken together to form a bond (i.e., there is a triple bond between the carbon atom to which $R^1$ was bonded to and the carbon to which $R^8$ was bonded to, i.e., the compound of formula I is a compound of formula II:

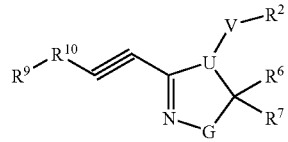

formula II and $R^2$, $R^5$, $R^6$, and $R^7$ are as defined above, and $R^3$, $R^4$, $R^{11}$ and $R^{12}$ are as defined below);

$R^3$ is selected from the group consisting of H, halo (and in one example, F), $-OR^{15}$ (and in one example $R^{15}$ is H), $-CN$, $-SR^{15}$, $-NR^{15}R^{16}$, $-N(R^{15})C(O)R^{16}$, $-N(R^{15})S(O)R^{16}$, $-N(R^{15})S(O)_2R^{16}$, $-N(R^{15})S(O)_2N(R^{16})(R^{17})$, $-N(R^{15})S(O)N(R^{16})(R^{17})$, $-N(R^{15})C(O)N(R^{16})(R^{17})$, $-N(R^{15})C(O)OR^{16}$, $-C(O)R^{15}$, $-C(O)OR^{15}$, $-C(=NOR^{15})R^{16}$, $-C(O)N(R^{15})(R^{16})$, $-S(O)N(R^{15})(R^{16})$, $S(O)_2N(R^{15})(R^{16})$, $-S(O)R^{15}$, $-S(O)_2R^{15}$, $-P(O)(OR^{15})(OR^{16})$, $=NOR^{15}$, $-N_3$, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below; or $R^3$ and $R^6$ taken together form a bond (i.e., $R^3$ and $R^6$ form a bond between G and the carbon to which $R^6$ is bound), provided that when $R^3$ and $R^6$ form a bond: (1) W is not a bond, (2) $R^2$ and $R^6$ are not joined together to form a cycloalkyl, cycloalkenyl, heterocyclyl or heterocyclenyl moiety (as described in (ii) and (iii) above) (3) $R^6$ and either $R^3$ or $R^4$ of the $-C(R^3)(R^4)-$ G moiety are not joined together to form a cycloalkyl, cycloalkenyl, heterocyclyl or heterocyclenyl moiety (as described in (iv) above), and (4) $R^6$ and $R^{13}$ of the $-N(R^{13})-$ G moiety are not joined together to form a heterocyclyl or heterocyclenyl moiety (as described in (v) above);

$R^4$, $R^{11}$ and $R^{12}$ can be the same or different, each being independently selected from the group consisting of H, halo (and in one example, F), $-OR^{15}$ (and in one example $R^{15}$ is H), $-CN$, $-SR^{15}$, $-NR^{15}R^{16}$, $-N(R^{15})C(O)R^{16}$, $-N(R^{15})S(O)R^{16}$, $-N(R^{15})S(O)_2R^{16}$, $-N(R^{15})S(O)_2N(R^{16})(R^{17})$, $-N(R^{15})S(O)N(R^{16})(R^{17})$, $-N(R^{15})C(O)N(R^{16})(R^{17})$, $-N(R^{15})C(O)OR^{16}$, $-C(O)R^{15}$, $-C(O)OR^{15}$, $-C(=NOR^{15})R^{16}$, $-C(O)N(R^{15})(R^{16})$, $-S(O)N(R^{15})(R^{16})$, $-S(O)_2N(R^{15})(R^{16})$, $-S(O)R^{15}$, $-S(O)_2R^{15}$, $-P(O)(OR^{15})(OR^{16})$, $=NOR^{15}$, $-N_3$, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below, provided that when one of $R^3$ or $R^4$ is selected from the group consisting of: $-OR^{15}$, $-CN$, $-SR^{15}$, $-NR^{15}R^{16}$, $-N(R^{15})C(O)R^{16}$, $-N(R^{15})S(O)R^{16}$, $-N(R^{15})S(O)_2R^{16}$, $-N(R^{15})S(O)_2N(R^{16})(R^{17})$, $-N(R^{15})S(O)N(R^{16})(R^{17})$, $-N(R^{15})C(O)N(R^{16})(R^{17})$, $-N(R^{15})C(O)OR^{16}$, $-S(O)N(R^{15})(R^{16})$, $-S(O)_2N(R^{15})(R^{16})$, $-S(O)R^{15}$, $-S(O)_2R^{15}$, $-P(O)(OR^{15})(OR^{16})$, $=NOR^{15}$, and $-N_3$, then the other is not selected from the group consisting of: $-OR^{15}$, $-CN$, $-SR^{15}$, and $-NR^{15}R^{16}$, $-N(R^{15})C(O)R^{16}$, $-N(R^{15})S(O)R^{16}$, $-N(R^{15})S(O)_2R^{16}$, $-N(R^{15})S(O)_2N(R^{16})(R^{17})$, $-N(R^{15})S(O)N(R^{16})(R^{17})$, $-N(R^{15})C(O)N(R^{16})(R^{17})$, $-N(R^{15})C(O)OR^{16}$, $-S(O)N(R^{15})(R^{16})$, $-S(O)_2N(R^{15})(R^{16})$, $-S(O)R^{15}$, $-S(O)_2R^{15}$, $-P(O)(OR^{15})(OR^{16})$, $=NOR^{15}$, and $-N_3$ (i.e., if one of $R^3$ or $R^4$ is $-OR^{15}$, $-CN$, $-SR^{15}$, $-NR^{15}R^{16}$, $-N(R^{15})C(O)R^{16}$, $-N(R^{15})S(O)R^{16}$, $-N(R^{15})S(O)_2R^{16}$, $-N(R^{15})S(O)_2N(R^{16})(R^{17})$, $-N(R^{15})S(O)N(R^{16})(R^{17})$, $-N(R^{15})C(O)N(R^{16})(R^{17})$, $-N(R^{15})C(O)OR^{16}$, $-S(O)N(R^{15})(R^{16})$, $-S(O)_2N(R^{15})(R^{16})$, $-S(O)R^{15}$, $-S(O)_2R^{15}$, $-P(O)(OR^{15})(OR^{16})$, $=NOR^{15}$, or $-N_3$, then the other one is not $-OR^{15}$, $-CN$, $-SR^{15}$, and $-NR^{15}R^{16}$, $-N(R^{15})C(O)R^{16}$, $-N(R^{15})S(O)R^{16}$, $-N(R^{15})S(O)_2R^{16}$, $-N(R^{15})S(O)_2N(R^{16})(R^{17})$, $-N(R^{15})S(O)N(R^{16})(R^{17})$, $-N(R^{15})C(O)N(R^{16})(R^{17})$, $-N(R^{15})C(O)OR^{16}$, $-S(O)N(R^{15})(R^{16})$, $-S(O)_2N(R^{15})(R^{16})$, $-S(O)R^{15}$, $-S(O)_2R^{15}$, $-P(O)(OR^{15})(OR^{16})$, $=NOR^{15}$, or $-N_3$);

provided that when one of $R^{11}$ or $R^{12}$ is selected from the group consisting of: $-OR^{15}$, $-CN$, $-SR^{15}$, $-NR^{15}R^{16}$, $-N(R^{15})C(O)R^{16}$, $-N(R^{15})S(O)R^{16}$, $-N(R^{15})S(O)_2R^{16}$, $-N(R^{15})S(O)_2N(R^{16})(R^{17})$, $-N(R^{15})S(O)N(R^{16})(R^{17})$, $-N(R^{15})C(O)N(R^{16})(R^{17})$, $-N(R^{15})C(O)OR^{16}$, $-S(O)N(R^{15})(R^{16})$, $-S(O)_2N(R^{15})(R^{16})$, $-S(O)R^{15}$, $-S(O)_2R^{15}$, $-P(O)(OR^{15})(OR^{16})$, $=NOR^{15}$, and $-N_3$, then the other is not selected from the group consisting of: $-OR^{15}$, $-CN$, $-SR^{15}$, $-NR^{15}R^{16}$, $-N(R^{15})C(O)R^{16}$, $-N(R^{15})S(O)R^{16}$, $-N(R^{15})S(O)_2R^{16}$, $-N(R^{15})S(O)_2N(R^{16})(R^{17})$, $-N(R^{15})S(O)N(R^{16})(R^{17})$, $-N(R^{15})C(O)N(R^{16})(R^{17})$, $-N(R^{15})C(O)OR^{16}$, $-S(O)N(R^{15})(R^{16})$, $-S(O)_2N(R^{15})(R^{16})$, $-S(O)R^{15}$, $-S(O)_2R^{15}$, $-P(O)(OR^{15})(OR^{16})$, $=NOR^{15}$, and $-N_3$ (i.e., if one of $R^{11}$ or $R^{12}$ is $-OR^{15}$, $-CN$, $-SR^{15}$, $-NR^{15}R^{16}$, $-N(R^{15})C(O)R^{16}$, $-N(R^{15})S(O)R^{16}$, $-N(R^{15})S(O)_2R^{16}$, $-N(R^{15})S(O)_2N(R^{16})(R^{17})$, $-N(R^{15})S(O)N(R^{16})(R^{17})$, $-N(R^{15})C(O)N(R^{16})(R^{17})$, $-N(R^{15})C(O)OR^{16}$, $-S(O)N(R^{15})(R^{16})$, $-S(O)_2N(R^{15})(R^{16})$, $-S(O)R^{15}$, $-S(O)_2R^{15}$, $-P(O)(OR^{15})(OR^{16})$, $=NOR^{15}$, or $-N_3$, then the other is not $-OR^{15}$, $-CN$, $-SR^{15}$, $-NR^{15}R^{16}$, $-N(R^{15})C(O)R^{16}$, $-N(R^{15})S(O)R^{16}$, $-N(R^{15})S(O)_2R^{16}$, $-N(R^{15})S(O)_2N(R^{16})(R^{17})$, $-N(R^{15})S(O)N(R^{16})(R^{17})$, $-N(R^{15})C(O)N(R^{16})(R^{17})$, $-N(R^{15})C(O)OR^{16}$, $-S(O)N(R^{15})(R^{16})$, $-S(O)_2N(R^{15})(R^{16})$, $-S(O)R^{15}$, $-S(O)_2R^{15}$, $-P(O)(OR^{15})(OR^{16})$, $=NOR^{15}$, or $-N_3$);

$R^{13}$ is independently selected from the group consisting of H, alkyl, arylalkyl-, heteroarylalkyl-, cycloalkylalkyl-, heterocycloalkylalkyl-, arylcycloalkylalkyl-, heteroarylcycloalkylalkyl-, arylheterocycloalkylalkyl-, heteroarylheterocycloalkylalkyl-, cycloalkyl, arylcycloalkyl-, heteroarylcycloalkyl-, heterocycloalkyl-, arylheterocycloalkyl-, heteroarylheterocycloalkyl-, alkenyl, arylalkenyl-, cycloalkenyl, arylcycloalkenyl-, heteroarylcycloalkenyl-, heterocycloalkenyl-, arylheterocycloalkenyl-, heteroarylheterocycloalkenyl-, alkynyl, arylalkynyl-, aryl, cycloalkylaryl-, heterocycloalkylaryl-, heterocycloalkenylaryl-, cycloalkyl heteroaryl-, heterocycloalkylheteroaryl-, cycloalkenylaryl-, heterocycloalkenylaryl-, $-OR^{15}$, $-CN$, $-C(O)R^8$, $-C(O)OR^9$, $-S(O)R^{10}$, $-S(O)_2R^{10}$, $-C(O)N(R^{11})(R^{12})$, $-S(O)N(R^{11})(R^{12})$, $-S(O)_2N(R^{11})(R^{12})$, $-NO_2$, $-N=C(R^8)_2$ and $-N(R^8)_2$; and wherein said $R^{13}$ alkyl, arylalkyl-, heteroarylalkyl-, cycloalkylalkyl-, heterocycloalkylalkyl-, arylcycloalkylalkyl-, heteroarylcycloalkylalkyl-, arylheterocycloalkylalkyl-, heteroarylheterocycloalkylalkyl-, cycloalkyl, arylcycloalkyl-, heteroarylcycloalkyl-, heterocycloalkyl, arylheterocycloalkyl-, heteroarylheterocycloalkyl-, alkenyl, arylalkenyl-, cycloalkenyl, arylcycloalkenyl-, heteroarylcycloalkenyl-, heterocycloalkenyl-, arylheterocycloalkenyl-, heteroarylheterocycloalkenyl-, alkynyl, arylalkynyl-, aryl, cycloalkylaryl-, heterocycloalkylaryl-, heterocycloalkenylaryl-, heteroaryl, cycloalkylheteroaryl-, heterocycloalkylheteroaryl-, cycloalkenylaryl-, and heterocycloalkenylaryl- groups are optionally substituted with 1 to 5 groups independently selected from the group consisting of: alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, halo, $-CN$, $-OR^{15}$, $-C(O)R^{15}$, $-C(O)OR^{15}$, $-C(O)N$ $(R^{15})(R^{16})$, —$SR^{15}$, —$S(O)N(R^{15})(R^{16})$, —$CH(R^{15})(R^{16})$, —$S(O)_2N(R^{15})(R^{16})$, —$C(=NOR^{15})R^{16}$, —$P(O)(OR^{15})(OR^{16})$, —$N(R^{15})(R^{16})$, -alkyl-$N(R^{15})(R^{16})$, —$N(R^{15})C(O)R^{16}$, —$CH_2$—$N(R^{15})C(O)R^{16}$, —$CH_2$—$N(R^{15})C(O)N(R^{16})(R^{17})$, —$CH_2$—$R^{15}$; —$CH_2N(R^{15})(R^{16})$, —$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$, —$CH_2$—$N(R^{15})C(O)OR^{16}$, —$S(O)R^{15}$, =$NOR^{15}$, —$N_3$, —$NO_2$ and —$S(O)_2R^{15}$;

$R^{14}$ is selected from the group consisting of H, alkyl, alkenyl, alkynyl, cycloalkyl, cycloalkylalkyl-, cycloalkenyl, heterocyclyl, heterocyclylalkyl, aryl, arylalkyl-, heteroaryl, heteroarylalkyl-, —CN, —$C(O)R^{15}$, —$C(O)OR^{15}$, —$C(O)N(R^{15})(R^{16})$, —$S(O)N(R^{15})(R^{16})$, —$S(O)_2N(R^{15})(R^{16})$, —$C(=NOR^{15})R^{16}$, and —$P(O)(OR^{15})(OR^{16})$;

$R^8$ is selected from the group consisting of H, alkyl, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, with each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- being unsubstituted or optionally independently substituted with 1-3 substituents which can be the same or different, each substituent being independently selected from the group consisting of the moieties shown below;

$R^{10}$ is selected from the group consisting of a bond, alkyl-, alkenyl- and alkynyl-, aryl-, arylalkyl-, alkylaryl-, cycloalkyl-, cycloalkylalkyl-, heteroaryl-, heteroarylalkyl-, heterocyclyl-, heterocyclylalkyl- and the moieties:

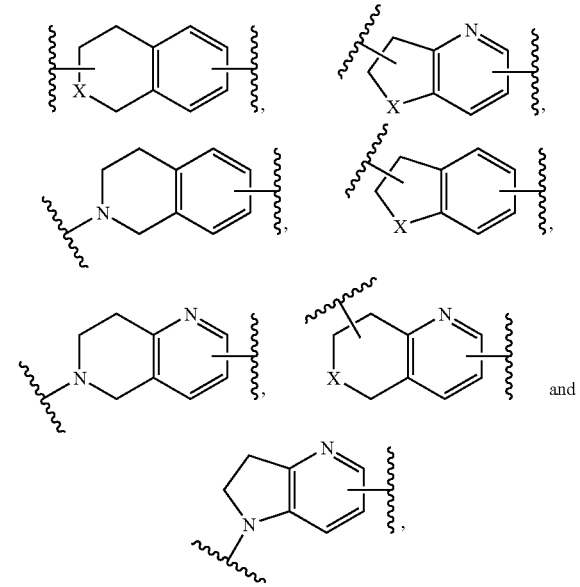

where X is O, $N(R^{14})$ or S;
wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl-heterocyclylalkyl- for $R^{10}$ as well as the above-noted moieties for $R^{10}$ can be unsubstituted or optionally independently substituted with 1-3 substituents which can be the same or different, each being independently selected from the group consisting of the moieties shown below; and $R^9$ is selected from the group consisting of alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-3 substituents which can be the same or different, each substituent being independently selected from the group consisting of the moieties shown below, $R^{15}$, $R^{16}$ and $R^{17}$ are independently selected from the group consisting of H, alkyl, alkenyl, alkynyl, cycloalkyl, cycloalkylalkyl-, heterocyclyl, heterocyclylalkyl-, aryl, arylalkyl-, heteroaryl, heteroarylalkyl-, arylcycloalkyl-, arylheterocyclyl-, $R^{18}$-alkyl, $R^{18}$-cycloalkyl, $R^{18}$-cycloalkylalkyl-, $R^{18}$-heterocyclyl, $R^{18}$-heterocyclylalkyl-, $R^{18}$-aryl, $R^{18}$-arylalkyl-, $R^{18}$-heteroaryl and $R^{18}$-heteroarylalkyl-;

$R^{18}$ is 1-5 substituents independently selected from the group consisting of alkyl, alkenyl, alkynyl, aryl, arylalkyl-, arylalkenyl-, arylalkynyl-, —$NO_2$, halo, heteroaryl, HO-alkyoxyalkyl-, —$CF_3$, —CN, alkyl-CN, —$C(O)R^{19}$, —$C(O)OH$, —$C(O)OR^{19}$, —$C(O)NHR^{20}$, —$C(O)NH_2$, —$C(O)NH_2$—$C(O)N(alkyl)_2$, —$C(O)N(alkyl)(aryl)$, —$C(O)N(alkyl)(heteroaryl)$, —$SR^{19}$, —$S(O)_2R^{20}$, —$S(O)NH_2$, —$S(O)NH(alkyl)$, —$S(O)N(alkyl)(alkyl)$, —$S(O)NH(aryl)$, —$S(O)_2NH_2$, —$S(O)_2NHR^{19}$, —$S(O)_2NH(heterocyclyl)$, —$S(O)_2N(alkyl)_2$, —$S(O)_2N(alkyl)(aryl)$, —$OCF_3$, —OH, —$OR^{20}$, —O-heterocyclyl, —O-cycloalkylalkyl, —O-heterocyclylalkyl, —$NH_2$, —$NHR^{20}$, —$N(alkyl)_2$, —$N(arylalkyl)_2$, —$N(arylalkyl)$-$(heteroarylalkyl)$, —$NHC(O)R^{20}$, —$NHC(O)NH_2$, —$NHC(O)NH(alkyl)$, —$NHC(O)N(alkyl)(alkyl)$, —$N(alkyl)C(O)NH(alkyl)$, —$N(alkyl)C(O)N(alkyl)(alkyl)$, —$NHS(O)_2R^{20}$, —$NHS(O)_2NH(alkyl)$, —$NHS(O)_2N(alkyl)(alkyl)$, —$N(alkyl)S(O)_2NH(alkyl)$ and —$N(alkyl)S(O)_2N(alkyl)(alkyl)$;

or, alternately, two $R^{18}$ moieties on adjacent carbons can be linked together to form:

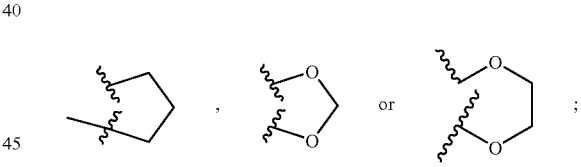

$R^{19}$ is alkyl, cycloalkyl, aryl, arylalkyl- or heteroarylalkyl-;
$R^{20}$ is alkyl, cycloalkyl, aryl, halo substituted aryl, arylalkyl-, heteroaryl or heteroarylalkyl-;

wherein each of the alkyl, cycloalkyl, cycloalkenyl, cycloalkylalkyl-, heterocyclyl, heterocyclylalkyl-, aryl, arylalkyl-, alkylaryl-, heteroaryl, heteroarylalkyl-, alkenyl and alkynyl groups in $R^1$, $R^2$, $R^1$-$R^2$, $R^2$-$R^6$, $R^3$, $R^4$, $R^5$, $R^6$, $R^7$, $R^8$, $R^9$, $R^{10}$, $R^{11}$, $R^{12}$ and $R^{14}$ is independently unsubstituted or optionally substituted by 1 to 5 $R^{21}$ groups independently selected from the group consisting of alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, halo, —CN, —$OR^{15}$, —$C(O)R^{15}$, —$C(O)OR^{15}$, —$C(O)N(R^{15})(R^{16})$, —$SR^{15}$, —$S(O)N(R^{15})(R^{16})$, —$CH(R^{15})(R^{16})$, —$S(O)_2N(R^{15})(R^{16})$, —$C(=NOR^{15})R^{16}$, —$P(O)(OR^{15})(OR^{16})$, —$N(R^{15})(R^{16})$, -alkyl-$N(R^{15})(R^{16})$, —$N(R^{15})C(O)R^{16}$, —$CH_2$—$N(R^{15})C(O)R^{16}$, —$CH_2$—$N(R^{15})C(O)N(R^{16})(R^{17})$, —$CH_2$—$R^{15}$; —$CH_2N(R^{15})(R^{16})$, —$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})(R^{17})$, —$N(R^{15})C$ (O)N($R^{16}$)($R^{17}$), —$CH_2$—N($R^{15}$)C(O)N($R^{16}$)($R^{17}$), —N($R^{15}$)C(O)O$R^{16}$, —$CH_2$—N($R^{15}$)C(O)O$R^{16}$, —S(O)$R^{15}$, =NO$R^{15}$, —$N_3$, —$NO_2$ and —S(O)$_2R^{15}$;

wherein each of the alkyl, cycloalkenyl, cycloalkyl, cycloalkylalkyl-, heterocyclyl, heterocyclylalkyl-, aryl, arylalkyl-, heteroaryl, heteroarylalkyl-, alkenyl and alkynyl groups in $R^{21}$ is independently unsubstituted or substituted by 1 to 5 $R^{22}$ groups independently selected from the group consisting of alkyl, cycloalkyl, cycloalkenyl, heterocyclyl, aryl, heteroaryl, halo, —$CF_3$, —CN, —O$R^{15}$, —C(O)$R^{15}$, —C(O)O$R^{15}$, -alkyl-C(O)O$R^{15}$, C(O)N($R^{15}$)($R^{16}$), —S$R^{15}$, —S(O)N($R^{15}$)($R^{16}$), —S(O)$_2$N($R^{15}$)($R^{16}$), —C(=NO$R^{15}$)$R^{16}$, —P(O)(O$R^{15}$)(O$R^{16}$), —N($R^{15}$)($R^{16}$), -alkyl-N($R^{15}$)($R^{16}$), —N($R^{15}$)C(O)$R^{16}$, —$CH_2$—N($R^{15}$)C(O)$R^{16}$, —N($R^{15}$)S(O)$R^{16}$, —N($R^{15}$)S(O)$_2R^{16}$, —$CH_2$—N($R^{15}$)S(O)$_2R^{16}$, —N($R^{15}$)S(O)$_2$N($R^{16}$)($R^{17}$), N($R^{15}$)S(O)N($R^{16}$)($R^{17}$), —N($R^{15}$)C(O)N($R^{16}$)($R^{17}$), —$CH_2$—N($R^{15}$)C(O)N($R^{16}$)$R^{17}$), —N($R^{15}$)C(O)O$R^{16}$, —$CH_2$—N($R^{15}$)C(O)O$R^{16}$, —$N_3$, =NO$R^{15}$, —$NO_2$, —S(O)$R^{15}$ and —S(O)$_2R^{15}$.

The statement above: "either (i) $R^1$ and $R^2$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; or (ii) $R^2$ and $R^6$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; or (iii) $R^1$ and $R^2$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; and $R^2$ and $R^6$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; or (iv) $R^6$ and either $R^3$ or $R^4$ of the —C($R^3$)($R^4$)— G moiety, are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; or (v) $R^6$ and $R^{13}$ of the —N($R^{13}$)— G moiety, are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below;" means that the occurrences of (i), (ii), (iii), (iv) and (v) are mutually exclusive and that only one of (i), (ii), (iii), (iv) and (v) can be present at any given time.

It should be understood that when $R^1$ and $R^2$ are joined together to form a C4-C8 cycloalkyl, C4-C8 cycloalkenyl, 5-8 membered heterocyclyl or 5-8 membered heterocyclenyl moiety, each of said cycloalkyl, cycloalkenyl, heterocyclyl or heterocyclenyl moiety independently may optionally additionally be fused with an aryl or heteroaryl ring, wherein the ring moiety resulting from the fusion may be unsubstituted or optionally independently substituted with 1-5 substituents which can be the same or different, each substituent being independently selected from the group consisting of the moieties shown above (i.e., each substitutent is independently selected from the group consisting of the $R^{21}$ substitutents).

It should also be understood that when $R^2$ and $R^6$ are joined together to form a C4-C8 cycloalkyl, C4-C8 cycloalkenyl, 5-8 membered heterocyclyl or 5-8 membered heterocyclenyl moiety, each of said cycloalkyl, cycloalkenyl, heterocyclyl or heterocyclenyl moiety independently may optionally additionally be fused with an aryl or heteroaryl ring, wherein the ring moiety resulting from the fusion may be unsubstituted or optionally independently substituted with 1-5 substituents which can be the same or different, each substituent being independently selected from the group consisting of the moieties shown above (i.e., each substitutent is independently selected from the group consisting of the $R^{21}$ substitutents).

It should be understood that when $R^6$ and either $R^3$ or $R^4$ of the —C($R^3$)($R^4$)— G moiety, are joined together to form a C4-C8 cycloalkyl, C4-C8 cycloalkenyl, 5-8 membered heterocyclyl or 5-8 membered heterocyclenyl moiety, each of said cycloalkyl, cycloalkenyl, heterocyclyl or heterocyclenyl moiety independently may optionally additionally be fused with an aryl or heteroaryl ring, wherein the ring moiety resulting from the fusion may be unsubstituted or optionally independently substituted with 1-5 substituents which can be the same or different, each substituent being independently selected from the group consisting of the moieties shown above (i.e., each substitutent is independently selected from the group consisting of the $R^{21}$ substitutents).

It should be understood that when $R^6$ and $R^{13}$ of the —N($R^{13}$)— G moiety, are joined together to form a C4-C8 cycloalkyl, C4-C8 cycloalkenyl, 5-8 membered heterocyclyl or 5-8 membered heterocyclenyl moiety, each of said cycloalkyl, cycloalkenyl, heterocyclyl or heterocyclenyl moiety independently may optionally additionally be fused with an aryl or heteroaryl ring, wherein the ring moiety resulting from the fusion may be unsubstituted or optionally independently substituted with 1-5 substituents which can be the same or different, each substituent being independently selected from the group consisting of the moieties shown above (i.e., each substitutent is independently selected from the group consisting of the $R^{21}$ substitutents).

In one embodiment, either:
(i) $R^1$ and $R^2$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown above (i.e., each substitutent is independently selected from the group consisting of the $R^{21}$ substitutents); or
(ii) $R^2$ and $R^6$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown above (i.e., each substituent is independently selected from the group consisting of the $R^{21}$ substitutents); or (iii) $R^1$ and $R^2$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; and $R^2$ and $R^6$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown above (i.e., each substitutent is independently selected from the group consisting of the $R^{21}$ substitutents).

In one embodiment, $R^1$ (when $R^1$ is not joined to $R^2$), $R^2$ (when $R^2$ is not joined to $R^1$ or $R^6$), $R^3$, $R^4$, $R^5$, $R^6$ (when $R^6$ is not joined to $R^2$), $R^7$, $R^{11}$ and $R^{12}$ can be the same or different, each being independently selected from the group consisting of H, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown above (i.e., each substitutent is independently selected from the group consisting of the $R^{21}$ substitutents).

In one embodiment, each of the alkyl, cycloalkyl, cycloalkylalkyl, heterocyclyl, heterocyclylalkyl, aryl, arylalkyl, heteroaryl, heteroarylalkyl, alkenyl and alkynyl groups in $R^1$, $R^2$, $R^1$-$R^2$, $R^2$-$R^6$, $R^3$, $R^4$, $R^5$, $R^6$, $R^7$, $R^8$, $R^9$, $R^{10}$, $R^{11}$, $R^{12}$ and $R^{14}$ is independently unsubstituted or optionally substituted by 1 to 5 $R^{21}$ groups independently selected from the group consisting of alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —CH(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —CH$_2$—N(R$^{15}$)C(O)N(R$^{16}$)(R$^{17}$), —CH$_2$—R$^{15}$; —CH$_2$N(R$^{15}$)(R$^{16}$), —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —S(O)R$^{15}$, =NOR$^{15}$, —N$_3$, —NO$_2$ and —S(O)$_2$R$^{15}$; and each of the alkyl, cycloalkenyl, cycloalkyl, cycloalkylalkyl, heterocyclyl, heterocyclylalkyl, aryl, arylalkyl, heteroaryl, heteroarylalkyl, alkenyl and alkynyl groups in $R^{21}$ is independently unsubstituted or substituted by 1 to 5 $R^{22}$ groups independently selected from the group consisting of alkyl, cycloalkyl, cycloalkenyl, heterocyclyl, aryl, heteroaryl, halo, —CF$_3$, —CN, —OR$^{15}$, —C(O)R$^{15}$, —C(O)OR$^{15}$, -alkyl-C(O)OR$^{15}$, C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$) (OR$^{16}$), —N(R$^{15}$)(R$^{16}$), -alkyl-N(R$^{15}$)(R$^{16}$), —N(R$^{15}$)C(O) R$^{16}$, —CH$_2$—N(R$^{15}$)C(O)R$^{16}$, —N(R$^{15}$)S(O)R$^{16}$, —N(R$^{15}$) S(O)$_2$R$^{16}$, —CH$_2$—N(R$^{15}$)S(O)$_2$R$^{16}$, —N(R$^{15}$)S(O)$_2$N(R$^{16}$) (R$^{17}$), —N(R$^{15}$)S(O)N(R$^{16}$)(R$^{17}$), —N(R$^{15}$)C(O)N(R$^{16}$) (R$^{17}$), —CH$_2$—N(R$^{15}$)C(O)N(R$^{16}$)(R$^{17}$), —N(R$^{15}$)C(O) OR$^{16}$, —CH$_2$—N(R$^{15}$)C(O)OR$^{16}$, —N$_3$, =NOR$^{15}$, —NO$_2$, —S(O)R$^{15}$ and —S(O)$_2$R$^{15}$.

In another embodiment, $R^1$ (when $R^1$ is not joined to $R^2$) and $R^8$ are taken together to form a bond (i.e., there is a triple bond between the carbon atom to which $R^1$ was bonded to and the carbon to which $R^8$ was bonded to, i.e., the compound of formula I is a compound of formula II:

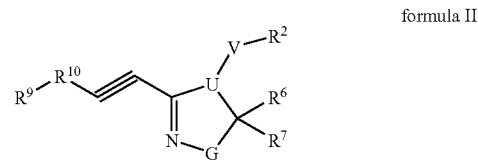

formula II and $R^2$, $R^3$, $R^4$, $R^5$, $R^6$, $R^7$, $R^{11}$ and $R^{12}$ are as defined above).

Thus, one embodiment is directed to a compound of formula I:

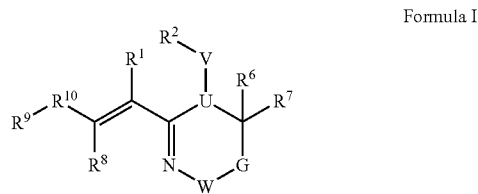

Formula I or a pharmaceutically acceptable salt, solvate, ester or prodrug thereof, wherein:

either (i) $R^1$ and $R^2$ are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, and (c) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or (ii) $R^2$ and $R^6$ are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, and (c) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or (iii)
(a) $R^1$ and $R^2$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, and (2) said heterocyclyl moiety is optionally substituted with 1-5 independently selected $R^{21}$ substituents, and (b) $R^2$ and $R^6$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, and (2) said heterocyclyl moiety is optionally substituted with 1-5 independently selected $R^{21}$ substituents; and (c) said $R^2$ and $R^6$ cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or (iv) $R^6$ and either $R^3$ or $R^4$ of the —C($R^3$)($R^4$)— G moiety, are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, and (c) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or (v) $R^6$ and $R^{13}$ of the —N($R^{13}$)— G moiety, are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, and (c) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents;

U is

or N;

W is selected from the group consisting of a bond; —O—, —C(O)—, —S—, —S(O)—, —S(O$_2$)—, and —C($R^{11}$)($R^{12}$)—;

G is selected from the group consisting of —C($R^3$)($R^4$)—, —C(O)— and —N($R^{13}$)—, with the proviso that when W is —O— or —S—, G is not —N($R^{13}$)— or —C(O)—;

V is selected from the group consisting of a bond, —O—, —C(O)— and —N($R^{14}$)—;

$R^1$ (when $R^1$ is not joined to $R^2$), $R^2$ (when $R^2$ is not joined to $R^1$ or $R^6$), $R^5$, $R^6$ (when $R^6$ is not joined to $R^2$), and W can be the same or different, each being independently selected from the group consisting of H, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below;

or, alternatively, $R^1$ (when $R^1$ is not joined to $R^2$) and $R^8$ are taken together to form a bond (i.e., there is a triple bond between the carbon atom to which $R^1$ was bonded to and the carbon to which $R^8$ was bonded to, i.e., the compound of formula I is a compound of formula II:

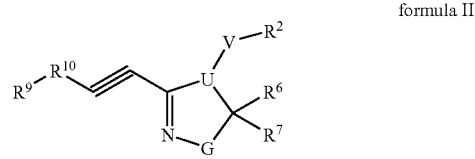

formula II and $R^2$, $R^5$, $R^6$, and $R^7$ are as defined above, and $R^3$, $R^4$, $R^{11}$ and $R^{12}$ are as defined below);

$R^3$ is selected from the group consisting of H, halo (and in one example, F), —O$R^{15}$ (and in one example $R^{15}$ is H), —CN, —S$R^{15}$, —N$R^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)O$R^{16}$, —C(O)$R^{15}$, —C(O)O$R^{15}$, —C(=NO$R^{15}$)$R^{16}$, —C(O)N($R^{15}$)($R^{16}$), —S(O)N($R^{15}$)($R^{16}$), S(O)$_2$N($R^{15}$)($R^{16}$), —S(O)$R^{15}$, —S(O)$_2R^{15}$, —P(O)(O$R^{15}$)(O$R^{16}$), =NO$R^{15}$, —N$_3$, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below; or $R^3$ and $R^6$ taken together form a bond (i.e., $R^3$ and $R^6$ form a bond between G and the carbon to which $R^6$ is bound), provided that when $R^3$ and $R^6$ form a bond: (1) W is not a bond, (2) $R^2$ and $R^6$ are not joined together to form a cycloalkyl, cycloalkenyl, heterocyclyl or heterocyclenyl moiety (as described in (ii) and (iii) above) (3) $R^6$ and either $R^3$ or $R^4$ of the —C($R^3$)($R^4$)— G moiety are not joined together to form a cycloalkyl, cycloalkenyl, heterocyclyl or heterocyclenyl moiety (as described in (iv) above), and (4) $R^6$ and $R^{13}$ of the —N($R^{13}$)— G moiety are not joined together to form a heterocyclyl or heterocyclenyl moiety (as described in (v) above);

$R^4$, $R^{11}$ and $R^{12}$ can be the same or different, each being independently selected from the group consisting of H, halo (and in one example, F), —O$R^{15}$ (and in one example $R^{15}$ is H), —CN, —S$R^{15}$, —N$R^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)O$R^{16}$, —C(O)$R^{15}$, —C(O)O$R^{15}$, —C(=NO$R^{15}$)$R^{16}$, —C(O)N($R^{15}$)($R^{16}$), —S(O)N($R^{15}$)($R^{16}$), —S(O)$_2$N($R^{15}$)($R^{16}$), —S(O)$R^{15}$, —S(O)$_2R^{15}$, —P(O)(O$R^{15}$)(O$R^{16}$), =NO$R^{15}$, —N$_3$, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below, and provided that when one of $R^3$ or $R^4$ is selected from the group consisting of: —$OR^{15}$, —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —$S(O)N(R^{15})(R^{16})$, —$S(O)_2N(R^{15})(R^{16})$, —$S(O)R^{15}$, —$S(O)_2R^{15}$, —$P(O)(OR^{15})(OR^{16})$, =$NOR^{15}$, and —$N_3$, then the other is not selected from the group consisting of: —$OR^{15}$, —CN, —$SR^{15}$, and —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —$S(O)N(R^{15})(R^{16})S(O)_2N(R^{15})(R^{16})$, —$S(O)R^{15}$, —$S(O)_2R^{15}$, —$P(O)(OR^{15})(OR^{16})$, =$NOR^{15}$, and —$N_3$ (i.e., if one of $R^3$ or $R^4$ is —$OR^{15}$, —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —$S(O)N(R^{15})(R^{16})$, —$S(O)_2N(R^{15})(R^{16})$, —$S(O)R^{15}$, —$S(O)_2R^{15}$, —$P(O)(OR^{15})(OR^{16})$, =$NOR^{15}$, or —$N_3$, then the other one is not —$OR^{15}$, —CN, —$SR^{15}$, and —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —$S(O)N(R^{15})(R^{16})$, —$S(O)_2N(R^{15})(R^{16})$, —$S(O)R^{15}$, —$S(O)_2R^{15}$, —$P(O)(OR^{15})(OR^{16})$, =$NOR^{15}$, or —$N_3$);

provided that when one of $R^{11}$ or $R^{12}$ is selected from the group consisting of: —$OR^{15}$, —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —$S(O)N(R^{15})(R^{16})$, —$S(O)_2N(R^{15})(R^{16})$, —$S(O)R^{15}$, —$S(O)_2R^{15}$, —$P(O)(OR^{15})(OR^{16})$, =$NOR^{15}$, and —$N_3$, then the other is not selected from the group consisting of: —$OR^{15}$, —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —$S(O)N(R^{15})(R^{16})$, —$S(O)_2N(R^{15})(R^{16})$, —$S(O)R^{15}$, —$S(O)_2R^{15}$, —$P(O)(OR^{15})(OR^{16})$, =$NOR^{15}$, and —$N_3$ (i.e., if one of $R^{11}$ or $R^{12}$ is —$OR^{15}$, —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —$S(O)N(R^{15})(R^{16})$, —$S(O)_2N(R^{15})(R^{16})$, —$S(O)R^{15}$, —$S(O)_2R^{15}$, —$P(O)(OR^{15})(OR^{16})$, =$NOR^{15}$, or —$N_3$, then the other is not —$OR^{15}$, —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —$S(O)N(R^{15})(R^{16})$, —$S(O)_2N(R^{15})(R^{16})$, —$S(O)R^{15}$, —$S(O)_2R^{15}$, —$P(O)(OR^{15})(OR^{16})$, =$NOR^{15}$, or —$N_3$);

$R^{13}$ is independently selected from the group consisting of H, alkyl, arylalkyl-, heteroarylalkyl-, cycloalkylalkyl-, heterocycloalkylalkyl-, arylcycloalkylalkyl-, heteroarylcycloalkylalkyl-, arylheterocycloalkylalkyl-, heteroarylheterocycloalkylalkyl-, cycloalkyl, arylcycloalkyl-, heteroarylcycloalkyl-, heterocycloalkyl, arylheterocycloalkyl-, heteroarylheterocycloalkyl-, alkenyl, arylalkenyl-, cycloalkenyl, arylcycloalkenyl-, heteroarylcycloalkenyl-, heterocycloalkenyl-, arylheterocycloalkenyl-, heteroarylheterocycloalkenyl-, alkynyl, arylalkynyl-, aryl, cycloalkylaryl-, heterocycloalkylaryl-, heterocycloalkenylaryl-, heteroaryl, cycloalkylheteroaryl-, heterocycloalkylheteroaryl-, cycloalkenylaryl-, heterocycloalkenylaryl-, —$OR^{15}$, —CN, —$C(O)R^8$, —$C(O)OR^9$, —$S(O)R^{10}$, —$S(O)_2R^{10}$, —$C(O)N(R^{11})(R^{12})$, —$S(O)N(R^{11})(R^{12})$, —$S(O)_2N(R^{11})(R^{12})$, —$NO_2$, —N=$C(R^8)_2$ and —$N(R^8)_2$; and wherein said $R^{13}$ alkyl, arylalkyl-, heteroarylalkyl-, cycloalkylalkyl-, heterocycloalkylalkyl-, arylcycloalkylalkyl-, heteroarylcycloalkylalkyl-, arylheterocycloalkylalkyl-, heteroarylheterocycloalkylalkyl-, cycloalkyl, arylcycloalkyl-, heteroarylcycloalkyl-, heterocycloalkyl, arylheterocycloalkyl-, heteroarylheterocycloalkyl-, alkenyl, arylalkenyl-, cycloalkenyl, arylcycloalkenyl-, heteroarylcycloalkenyl-, heterocycloalkenyl-, arylheterocycloalkenyl-, heteroarylheterocycloalkenyl-, alkynyl, arylalkynyl-, aryl, cycloalkylaryl-, heterocycloalkylaryl-, heterocycloalkenylaryl-, heteroaryl, cycloalkylheteroaryl-, heterocycloalkylheteroaryl-, cycloalkenylaryl-, and heterocycloalkenylaryl- groups are optionally substituted with 1 to 5 groups independently selected from the group consisting of: alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, halo, —CN, —$OR^{15}$, —$C(O)R^{15}$, —$C(O)OR^{15}$, —$C(O)N(R^{15})(R^{16})$, —$SR^{15}$, —$S(O)N(R^{15})(R^{16})$, —$CH(R^{15})(R^{16})$, —$S(O)_2N(R^{15})(R^{16})$, —$C(=NOR^{15})R^{16}$, —$P(O)(OR^{15})(OR^{16})$, —$N(R^{15})(R^{16})$, -alkyl-$N(R^{15})(R^{16})$, —$N(R^{15})C(O)R^{16}$, —$CH_2$—$N(R^{15})C(O)R^{16}$, —$CH_2$—$N(R^{15})C(O)N(R^{16})(R^{17})$, —$CH_2$—$R^{15}$; —$CH_2N(R^{15})(R^{16})$, —$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$, —$CH_2$—$N(R^{15})C(O)OR^{16}$, —$S(O)R^{15}$, =$NOR^{15}$, —$N_3$, —$NO_2$ and —$S(O)_2R^{15}$;

$R^8$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, with each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- being optionally substituted with 1-3 independently selected $R^{21}$ substituents;

$R^9$ is selected from the group consisting of alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each $R^9$ group is optionally substituted with 1-3 independently selected $R^{21}$ substituents;

$R^{10}$ is selected from the group consisting of a bond, alkyl-, alkenyl-, alkynyl-, aryl-, arylalkyl-, alkylaryl-, cycloalkyl-, cycloalkylalkyl-, heteroaryl-, heteroarylalkyl-, heterocyclyl-, heterocyclylalkyl- and the moieties:

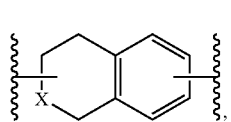 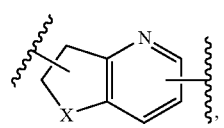

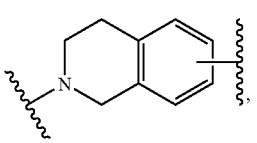 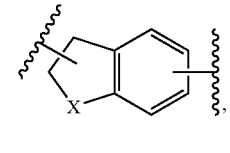

-continued

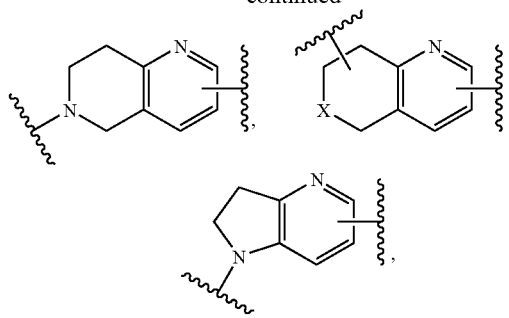

where X is O, N(R$^{14}$) or S;

wherein each R$^{10}$ group (except for the bond) is optionally substituted with 1-3 independently selected R$^{21}$ substituents;

R$^{14}$ is selected from the group consisting of H, alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, —CN, —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$), wherein each of said alkyl, alkenyl, alkynyl, cycloalkyl, cycloalkylalkyl-, cycloalkenyl, heterocyclyl, heterocyclylalkyl-, aryl, arylalkyl-, heteroaryl, and heteroarylalkyl- is optionally substituted with 1-5 independently selected R$^{21}$ substitutents;

R$^{15}$, R$^{16}$ and R$^{17}$ are independently selected from the group consisting of H, alkyl, alkenyl, alkynyl, cycloalkyl, cycloalkylalkyl-, heterocyclyl, heterocyclylalkyl-, aryl, arylalkyl-, heteroaryl, heteroarylalkyl-, arylcycloalkyl-, arylheterocyclyl-, (R$^{18}$)$_r$-alkyl, (R$^{18}$)$_r$-cycloalkyl, (R$^{18}$)$_r$-cycloalkylalkyl-, (R$^{18}$)$_r$-heterocyclyl, (R$^{18}$)$_r$-heterocyclylalkyl-, (R$^{18}$)$_r$-aryl, (R$^{18}$)$_r$-arylalkyl-, (R$^{18}$)$_r$-heteroaryl and (R$^{18}$)$_r$-heteroarylalkyl-; wherein r is 1-5;

Each R$^{18}$ is independently selected from the group consisting of alkyl, alkenyl, alkynyl, aryl, arylalkyl-, arylalkenyl-, arylalkynyl-, —NO$_2$, halo, heteroaryl, HO-alkyoxyalkyl-, —CF$_3$, —CN, alkyl-CN, —C(O)R$^{19}$, —C(O)OH, —C(O)OR$^{19}$, —C(O)NHR$^{20}$, —C(O)NH$_2$, —C(O)NH$_2$—C(O)N(alkyl)$_2$, —C(O)N(alkyl)(aryl), —C(O)N(alkyl)(heterocyclyl), —SR$^{19}$, —S(O)$_2$R$^{20}$, —S(O)NH$_2$, —S(O)NH(alkyl), —S(O)N(alkyl)(alkyl), —S(O)NH(aryl), —S(O)$_2$NH$_2$, —S(O)$_2$NHR$^{19}$, —S(O)$_2$NH(heterocyclyl), —S(O)$_2$N(alkyl)$_2$, —S(O)$_2$N(alkyl)(aryl), —OCF$_3$, —OH, —OR$^{20}$, —O-heterocyclyl, —O-cycloalkylalkyl, —O-heterocyclylalkyl, —NH$_2$, —NHR$^{20}$, —N(alkyl)$_2$, —N(arylalkyl)$_2$, —N(arylalkyl)-(heteroarylalkyl), —NHC(O)R$^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or, alternately, two R$^{18}$ moieties on adjacent carbons can be linked together to form:

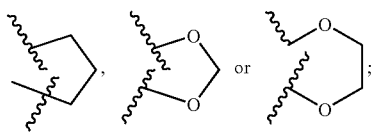

R$^{19}$ is selected from the group consisting of: alkyl, cycloalkyl, aryl, arylalkyl- and heteroarylalkyl-;

R$^{20}$ is selected from the group consisting of: alkyl, cycloalkyl, aryl, halo substituted aryl, arylalkyl-, heteroaryl and heteroarylalkyl-;

Each R$^{21}$ group is independently selected from the group consisting of alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —CH(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —CH$_2$—N(R$^{15}$)C(O)N(R$^{16}$)(R$^{17}$), —CH$_2$—R$^{15}$; —CH$_2$N(R$^{15}$)(R$^{16}$), —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —S(O)R$^{15}$, =NOR$^{15}$, —N$_3$, —NO$_2$ and —S(O)$_2$R$^{15}$; and wherein each of the R$^{21}$ alkyl, cycloalkenyl, cycloalkyl, cycloalkylalkyl-, heterocyclyl, heterocyclylalkyl-, aryl, arylalkyl-, heteroaryl, heteroarylalkyl-, alkenyl and alkynyl groups is optionally substituted with 1 to 5 independently selected R$^{22}$ groups; and Each R$^{22}$ is independently selected from the group consisting of: alkyl, cycloalkyl, cycloalkenyl, heterocyclyl, aryl, heteroaryl, halo, —CF$_3$, —CN, —OR$^{15}$, —C(O)R$^{15}$, —C(O)OR$^{15}$, -alkyl-C(O)OR$^{15}$, C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —N$_3$, =NOR$^{15}$, —NO$_2$, —S(O)R$^{15}$ and —S(O)$_2$R$^{15}$.

In another embodiment, the present application discloses a compound, or pharmaceutically acceptable salts, solvates, esters or prodrugs of said compound, said compound having the general structure shown in Formula I:

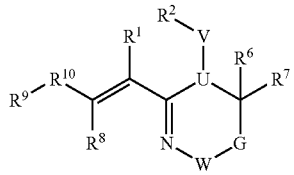

Formula I wherein:
R$^1$ and R$^2$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below;

U is

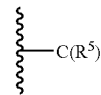

or N;

W is selected from the group consisting of a bond, —O—, —C(O)—, —S—, —S(O)—, —S(O$_2$)—, and —C(R$^{11}$)(R$^{12}$)—;

G is selected from the group consisting of —C($R^3$)($R^4$)—, —C(O)— and —N($R^{13}$)—; with the proviso that when W is —O— or —S—; G is not —N($R^{13}$)— or —C(O)—;

V is selected from the group consisting of a bond, —O—, —C(O)—, and —N($R^{14}$)—;

$R^5$, $R^6$, and $R^7$ can be the same or different, each being independently selected from the group consisting of H, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below;

$R^3$ is selected from the group consisting of H, halo (and in one example, F), —O$R^{15}$ (and in one example $R^{15}$ is H), —CN, —S$R^{15}$, —N$R^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)O$R^{16}$, —C(O)$R^{15}$, —C(O)O$R^{15}$, —C(=NO$R^{15}$)$R^{16}$, —C(O)N($R^{15}$)($R^{16}$), —S(O)N($R^{15}$)($R^{16}$), S(O)$_2$N($R^{15}$)($R^{16}$), —S(O)$R^{15}$, —S(O)$_2R^{15}$, —P(O)(O$R^{15}$)(O$R^{16}$), =NO$R^{15}$, —N$_3$, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below; or $R^3$ and $R^6$ taken together form a bond (i.e., $R^3$ and $R^6$ form a bond between G and the carbon to which $R^6$ is bound), provided that when $R^3$ and $R^6$ form a bond W is not a bond;

$R^4$, $R^{11}$ and $R^{12}$ can be the same or different, each being independently selected from the group consisting of H, halo (and in one example, F), —O$R^{15}$ (and in one example $R^{15}$ is H), —CN, —S$R^{15}$, —N$R^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)O$R^{16}$, —C(O)$R^{15}$, —C(O)O$R^{15}$, —C(=NO$R^{15}$)$R^{16}$, —C(O)N($R^{15}$)($R^{16}$), —S(O)N($R^{15}$)($R^{16}$), —S(O)$_2$N($R^{15}$)($R^{16}$), —S(O)$R^{15}$, —S(O)$_2R^{15}$, —P(O)(O$R^{15}$)(O$R^{16}$), =NO$R^{15}$, —N$_3$, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below, provided that when one of $R^3$ or $R^4$ is selected from the group consisting of: —O$R^{15}$, —CN, —S$R^{15}$, —N$R^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)O$R^{16}$, —S(O)N($R^{15}$)($R^{16}$), —S(O)$_2$N($R^{15}$)($R^{16}$), —S(O)$R^{15}$, —S(O)$_2R^{15}$, —P(O)(O$R^{15}$)(O$R^{16}$), =NO$R^{15}$, and —N$_3$, then the other is not selected from the group consisting of: —O$R^{15}$, —CN, —S$R^{15}$, and —N$R^{15}R^{16}$, —N($R^{15}$)C(O)$R^{16}$, —N($R^{15}$)S(O) $R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)O$R^{16}$, —S(O)N($R^{15}$)($R^{16}$), —S(O)$_2$N($R^{15}$)($R^{16}$), —S(O)N($R^{15}$)($R^{16}$), —S(O)$_2$N($R^{15}$)($R^{16}$), —S(O)$R^{15}$, —S(O)$_2R^{15}$, —P(O)(O$R^{15}$)(O$R^{16}$), =NO$R^{15}$, and —N$_3$ (i.e., if one of $R^3$ or $R^4$ is —O$R^{15}$, —CN, —S$R^{15}$, —N$R^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)O$R^{16}$, —S(O)N($R^{15}$)($R^{16}$), —S(O)$_2$N($R^{15}$)($R^{16}$), —S(O)$R^{15}$, —S(O)$_2R^{15}$, —P(O)(O$R^{15}$)(O$R^{16}$), =NO$R^{15}$, or —N$_3$, then the other one is not —O$R^{15}$, —CN, —S$R^{15}$, and —N$R^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)O$R^{16}$, —S(O)N($R^{15}$)($R^{16}$), —S(O)$_2$N($R^{15}$)($R^{16}$), —S(O)$R^{15}$, —S(O)$_2R^{15}$, —P(O)(O$R^{15}$)(O$R^{16}$), =NO$R^{15}$, or —N$_3$);

provided that when one of $R^{11}$ or $R^{12}$ is selected from the group consisting of: —O$R^{15}$, —CN, —S$R^{15}$, —N$R^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)O$R^{16}$, —S(O)N ($R^{15}$)($R^{16}$), —S(O)$_2$N($R^{15}$)($R^{16}$), —S(O)$R^{15}$, —S(O)$_2R^{15}$, —P(O)(O$R^{15}$)(O$R^{16}$), =NO$R^{15}$, and —N$_3$, then the other is not selected from the group consisting of: —O$R^{15}$, —CN, —S$R^{15}$, —N$R^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)O$R^{16}$, —S(O)N($R^{15}$)($R^{16}$), —S(O)$_2$N($R^{15}$)($R^{16}$), —S(O)$R^{15}$, —S(O)$_2R^{15}$, —P(O)(O$R^{15}$)(O$R^{16}$), =NO$R^{15}$, and —N$_3$ (i.e., if one of $R^{11}$ or $R^{12}$ is —O$R^{15}$, —CN, —S$R^{15}$, —N$R^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$) —N($R^{15}$)S(O)N($R^{16}$)($R^{17}$), —N($R^{15}$)C(O)N($R^{16}$)($R^{17}$), —N($R^{15}$)C(O)O$R^{16}$, —S(O)N($R^{15}$)($R^{16}$), —S(O)$_2$N($R^{15}$)($R^{16}$), —S(O)$R^{15}$, —S(O)$_2R^{15}$, —P(O)(O$R^{15}$)(O$R^{16}$), =NO$R^{15}$, or —N$_3$, then the other is not —O$R^{15}$, —CN, —S$R^{15}$, —N$R^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)O$R^{16}$, —S(O)N ($R^{15}$)($R^{16}$), —S(O)$_2$N($R^{15}$)($R^{16}$), —S(O)$R^{15}$, —S(O)$_2R^{15}$, —P(O)(O$R^{15}$)(O$R^{16}$), =NO$R^{15}$, or —N$_3$);

$R^{13}$ is independently selected from the group consisting of H, alkyl, arylalkyl-, heteroarylalkyl-, cycloalkylalkyl-, heterocycloalkylalkyl-, arylcycloalkylalkyl-, heteroarylcycloalkylalkyl-, arylheterocycloalkylalkyl-, heteroarylheterocycloalkylalkyl-, cycloalkyl, arylcycloalkyl-, heteroarylcycloalkyl-, heterocycloalkyl-, arylheterocycloalkyl-, heteroarylheterocycloalkyl-, alkenyl, arylalkenyl-, cycloalkenyl, arylcycloalkenyl-, heteroarylcycloalkenyl-, heterocycloalkenyl-, arylheterocycloalkenyl-, heteroarylheterocycloalkenyl-, alkynyl, arylalkynyl-, aryl, cycloalkylaryl-, heterocycloalkylaryl-, heterocycloalkenylaryl-, heteroaryl, cycloalkyl heteroaryl-, heterocycloalkylheteroaryl-, cycloalkenylaryl-, heterocycloalkenylaryl-, —O$R^{15}$, —CN, —C(O)$R^8$, —C(O)O$R^9$, —S(O)$R^{10}$, —S(O)$_2R^{10}$, —C(O)N($R^{11}$)($R^{12}$), —S(O)N($R^{11}$)($R^{12}$), —S(O)$_2$N($R^{11}$)($R^{12}$), —NO$_2$, —N=C($R^8$)$_2$ and —N($R^8$)$_2$; and wherein said $R^{13}$ alkyl, arylalkyl-, heteroarylalkyl-, cycloalkylalkyl-, heterocycloalkylalkyl-, arylcycloalkylalkyl-, heteroarylcycloalkylalkyl-, arylheterocycloalkylalkyl-, heteroarylheterocycloalkylalkyl-, cycloalkyl, arylcycloalkyl-, heteroarylcycloalkyl-, heterocycloalkyl-, arylheterocycloalkyl-, heterocycloarylheterocycloalkyl-, alkenyl, arylalkenyl-, cycloalkenyl, arylcycloalkenyl-, heteroarylcycloalkenyl-, heterocycloalkenyl-, arylheterocycloalkenyl-, heteroarylheterocycloalkenyl-, alkynyl, arylalkynyl-, aryl, cycloalkylaryl-, heterocycloalkylaryl-, heterocycloalkenylaryl-, heteroaryl, cycloalkylheteroaryl-, heterocycloalkylheteroaryl-, cycloalkenylaryl-, and heterocycloalkenylaryl- groups are optionally substituted with 1 to 5 groups independently selected from the group consisting of: alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —CH(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —CH$_2$—N(R$^{15}$)C(O)N(R$^{16}$)(R$^{17}$), —CH$_2$—R$^{15}$; —CH$_2$N(R$^{15}$)(R$^{16}$), —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —S(O)R$^{15}$, =NOR$^{15}$, —N$_3$, —NO$_2$ and —S(O)$_2$R$^{15}$;

R$^{14}$ is selected from the group consisting of H, alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, —CN, —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$);

R$^8$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, with each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- being unsubstituted or optionally independently substituted with 1-3 substituents which can be the same or different, each substituent being independently selected from the group consisting of the moieties shown below;

R$^{10}$ is selected from the group consisting of a bond, alkyl-, alkenyl- and alkynyl-, aryl-, arylalkyl-, alkylaryl-, cycloalkyl-, cycloalkylalkyl-, heteroaryl-, heteroarylalkyl-, heterocyclyl-, heterocyclylalkyl- and the moieties:

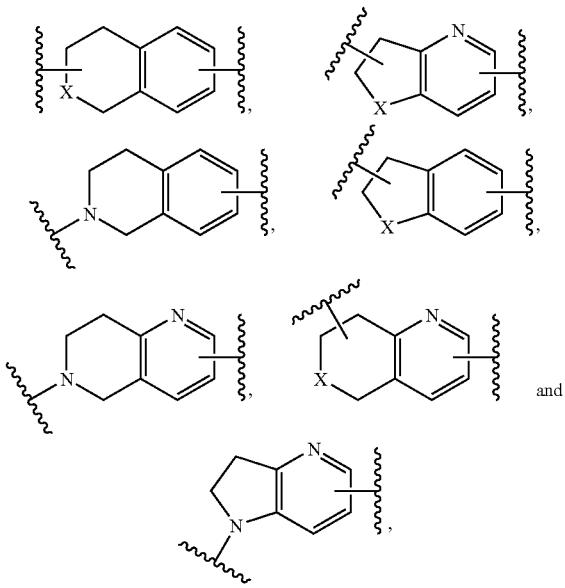

where X is O, N(R$^{14}$) or S;
wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl-heterocyclylalkyl- for R$^{10}$ as well as the above-noted moieties for R$^{10}$ can be unsubstituted or optionally independently substituted with 1-3 substituents which can be the same or different, each being independently selected from the group consisting of the moieties shown below; and R$^9$ is selected from the group consisting of alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-3 substituents which can be the same or different, each substituent being independently selected from the group consisting of the moieties shown below, R$^{15}$, R$^{16}$ and R$^{17}$ are independently selected from the group consisting of H, alkyl, alkenyl, alkynyl, cycloalkyl, cycloalkylalkyl-, heterocyclyl, heterocyclylalkyl-, aryl, arylalkyl-, heteroaryl, heteroarylalkyl-, arylcycloalkyl-, arylheterocyclyl, R$^{18}$-alkyl, R$^{18}$-cycloalkyl, R$^{18}$-cycloalkylalkyl-, R$^{18}$-heterocyclyl, R$^{18}$-heterocyclylalkyl-, R$^{18}$-aryl, R$^{18}$-arylalkyl-, R$^{18}$-heteroaryl and R$^{18}$-heteroarylalkyl-;

R$^{18}$ is 1-5 substituents independently selected from the group consisting of alkyl, alkenyl, alkynyl, aryl, arylalkyl-, arylalkenyl-, arylalkynyl-, —NO$_2$, halo, heteroaryl, HO-alkyoxyalkyl, —CF$_3$, —CN, alkyl-CN, —C(O)R$^{19}$, —C(O)OH, —C(O)OR$^{19}$, —C(O)NHR$^{20}$, —C(O)NH$_2$, —C(O)NH$_2$—C(O)N(alkyl)$_2$, —C(O)N(alkyl)(aryl), —C(O)N(alkyl)(heteroaryl), —SR$^{19}$, —S(O)$_2$R$^{20}$, —S(O)NH$_2$, —S(O)NH(alkyl), —S(O)N(alkyl)(alkyl), —S(O)NH(aryl), —S(O)$_2$NH$_2$, —S(O)$_2$NHR$^{19}$, —S(O)$_2$NH(heterocyclyl), —S(O)$_2$N(alkyl)$_2$, —S(O)$_2$N(alkyl)(aryl), —OCF$_3$, —OH, —OR$^{20}$, —O-heterocyclyl, —O-cycloalkylalkyl, —O-heterocyclylalkyl, —NH$_2$, —NHR$^{20}$, —N(alkyl)$_2$, —N(arylalkyl)$_2$, —N(arylalkyl)-(heteroarylalkyl), —NHC(O)R$^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or, alternately, two R$^{18}$ moieties on adjacent carbons can be linked together to form:

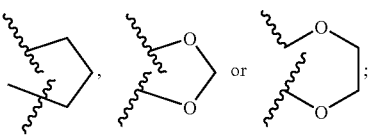

R$^{19}$ is alkyl, cycloalkyl, aryl, arylalkyl- or heteroarylalkyl-;
R$^{20}$ is alkyl, cycloalkyl, aryl, halo substituted aryl, arylalkyl-, heteroaryl or heteroarylalkyl-;

wherein each of the alkyl, cycloalkyl, cycloalkenyl, cycloalkylalkyl-, heterocyclyl, heterocyclylalkyl-, aryl, arylalkyl-, alkylaryl-, heteroaryl, heteroarylalkyl-, alkenyl and alkynyl groups in R$^1$-R$^2$, R$^3$, R$^4$, R$^5$, R$^6$, R$^7$, R$^8$, R$^9$, R$^{10}$, R$^{11}$, R$^{12}$ and R$^{14}$ is independently unsubstituted or optionally substituted by 1 to 5 R$^{21}$ groups independently selected from the group consisting of alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —CH(R$^{15}$)(R$^{16}$), —S(O)$_2$N $(R^{15})(R^{16})$, —$C(=NOR^{15})R^{16}$, —$P(O)(OR^{15})(OR^{16})$, —$N(R^{15})(R^{16})$, -alkyl-$N(R^{15})(R^{16})$, —$N(R^{15})C(O)R^{16}$, —$CH_2$—$N(R^{15})C(O)R^{16}$, —$CH_2$—$N(R^{15})C(O)N(R^{16})(R^{17})$, —$CH_2$—$R^{15}$; —$CH_2N(R^{15})(R^{16})$, —$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$, —$CH_2$—$N(R^{15})C(O)OR^{16}$, —$S(O)R^{15}$, =$NOR^{15}$, —$N_3$, —$NO_2$ and —$S(O)_2R^{15}$;

wherein each of the alkyl, cycloalkenyl, cycloalkyl, cycloalkylalkyl-, heterocyclyl, heterocyclylalkyl-, aryl, arylalkyl-, heteroaryl, heteroarylalkyl-, alkenyl and alkynyl groups in $R^{21}$ is independently unsubstituted or substituted by 1 to 5 $R^{22}$ groups independently selected from the group consisting of alkyl, cycloalkyl, cycloalkenyl, heterocyclyl, aryl, heteroaryl, halo, —$CF_3$, —CN, —$OR^{15}$, —$C(O)R^{15}$, —$C(O)OR^{15}$, -alkyl-$C(O)OR^{15}$, $C(O)N(R^{15})(R^{16})$, —$SR^{15}$, —$S(O)N(R^{15})(R^{16})$, —$S(O)_2N(R^{15})(R^{16})$, —$C(=NOR^{15})R^{16}$, —$P(O)(OR^{15})(OR^{16})$, —$N(R^{15})(R^{16})$, -alkyl-$N(R^{15})(R^{16})$, —$N(R^{15})C(O)R^{16}$, —$CH_2$—N—$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$, —$CH_2$—$N(R^{15})C(O)OR^{16}$, —$N_3$, =$NOR^{15}$, —$NO_2$, —$S(O)R^{15}$ and —$S(O)_2R^{15}$.

In another embodiment, the present application discloses a compound, or pharmaceutically acceptable salts, solvates, esters or prodrugs of said compound, said compound having the general structure shown in Formula I:

Formula I

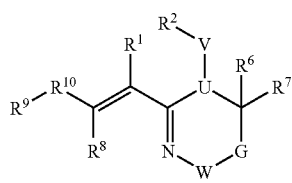

wherein:

$R^2$ and $R^6$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below;

U is

or N;

W is selected from the group consisting of a bond, —O—, —C(O)—, —S—, —S(O)—, —S(O$_2$)—, and —C($R^{11}$)($R^{12}$)—;

G is —C($R^3$)($R^4$)—, —C(O)— and —N($R^{13}$)—; with the proviso that when W is —O— or —S—, G is not —N($R^{13}$)— or —C(O)—;

V is selected from the group consisting of a bond, —O—, —C(O)—, and —N($R^{14}$)—;

$R^1$ (when $R^1$ is not joined to $R^2$), $R^5$, $R^6$ (when $R^6$ is not joined to $R^2$), and $R^7$ can be the same or different, each being independently selected from the group consisting of H, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below;

or, alternatively, $R^1$ (when $R^1$ is not joined to $R^2$) and $R^8$ are taken together to form a bond (i.e., there is a triple bond between the carbon atom to which $R^1$ was bonded to and the carbon to which $R^8$ was bonded to, i.e., the compound of formula I is a compound of formula II:

formula II

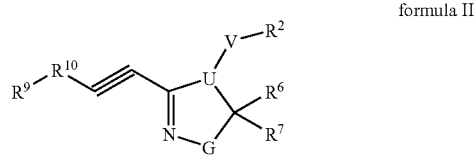

and $R^2$, $R^5$, $R^6$, and $R^7$ are as defined above, and $R^3$, $R^4$, $R^{11}$ and $R^{12}$ are as defined below);

$R^3$ is selected from the group consisting of H, halo (and in one example, F), —$OR^{15}$ (and in one example $R^{15}$ is H), —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —$C(O)R^{15}$, —$C(O)OR^{15}$, —$C(=NOR^{15})R^{16}$, —$C(O)N(R^{15})(R^{16})$, —$S(O)N(R^{15})(R^{16})$, $S(O)_2N(R^{15})(R^{16})$, —$S(O)R^{15}$, —$S(O)_2R^{15}$, —$P(O)(OR^{15})(OR^{16})$, =$NOR^{15}$, —$N_3$, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below; or $R^4$, $R^{11}$ and $R^{12}$ can be the same or different, each being independently selected from the group consisting of H, halo (and in one example, F), —$OR^{15}$ (and in one example $R^{15}$ is H), —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —$C(O)R^{15}$, —$C(O)OR^{15}$, —$C(=NOR^{15})R^{16}$, —$C(O)N(R^{15})(R^{16})$, —$S(O)N(R^{15})(R^{16})$, —$S(O)_2N(R^{15})(R^{16})$, —$S(O)R^{15}$, —$S(O)_2R^{15}$, —$P(O)(OR^{15})(OR^{16})$, =$NOR^{15}$, —$N_3$, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below, provided that when one of $R^3$ or $R^4$ is selected from the group consisting of: —$OR^{15}$, —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —$S(O)N(R^{15})(R^{16})$, —$S(O)_2N(R^{15})(R^{16})$, —$S(O)R^{15}$, —$S(O)_2R^{15}$, —$P(O)(OR^{15})(OR^{16})$, =$NOR^{15}$, and —$N_3$, then the other is not selected from the group consisting of: —$OR^{15}$, —CN, —$SR^{15}$, and —$NR^{15}R^{16}$, —$N(R^{15})C(O)R^{16}$, —$N(R^{15})S(O)R^{16}$, —$N(R^{15})S(O)_2R^{16}$—$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —$S(O)N(R^{15})(R^{16})$, —$S(O)_2N(R^{15})(R^{16})$, —$S(O)R^{15}$, —$S(O)_2R^{15}$, —$P(O)(OR^{15})(OR^{16})$, =$NOR^{15}$, and —$N_3$ (i.e., if one of $R^3$ or $R^4$ is —$OR^{15}$, —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —$S(O)N(R^{15})(R^{16})$, —$S(O)_2N(R^{15})(R^{16})$, —$S(O)R^{15}$, —$S(O)_2R^{15}$, —$P(O)(OR^{15})(OR^{16})$, =$NOR^{15}$, or —$N_3$, then the other one is not —$OR^{15}$, —CN, —$SR^{15}$, and —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —$S(O)N(R^{15})(R^{16})$, —$S(O)_2N(R^{15})(R^{16})$, —$S(O)R^{15}$, —$S(O)_2R^{15}$, —$P(O)(OR^{15})(OR^{16})$, =$NOR^{15}$, or —$N_3$);

provided that when one of $R^{11}$ or $R^{12}$ is selected from the group consisting of: —$OR^{15}$, —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —$S(O)N(R^{15})(R^{16})$, —$S(O)_2N(R^{15})(R^{16})$, —$S(O)R^{15}$, —$S(O)_2R^{15}$, —$P(O)(OR^{15})(OR^{16})$, =$NOR^{15}$, and —$N_3$, then the other is not selected from the group consisting of: —$OR^{15}$, —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —$S(O)N(R^{15})(R^{16})$, —$S(O)_2N(R^{15})(R^{16})$, —$S(O)R^{15}$, —$S(O)_2R^{15}$, —$P(O)(OR^{15})(OR^{16})$, =$NOR^{15}$, and —$N_3$ (i.e., if one of $R^{11}$ or $R^{12}$ is —$OR^{15}$, —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —$S(O)N(R^{15})(R^{16})$, —$S(O)_2N(R^{15})(R^{16})$, —$S(O)R^{15}$, —$S(O)_2R^{15}$, —$P(O)(OR^{15})(OR^{16})$, =$NOR^{15}$, or —$N_3$, then the other is not —$OR^{15}$, —CN, —$SR^{15}$, —$NR^{15}R^{16}$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$N(R^{15})C(O)OR^{16}$, —$S(O)N(R^{15})(R^{16})$, —$S(O)_2N(R^{15})(R^{16})$, —$S(O)R^{15}$, —$S(O)_2R^{15}$, —$P(O)(OR^{15})(OR^{16})$, =$NOR^{15}$, or —$N_3$);

$R^{13}$ is independently selected from the group consisting of H, alkyl, arylalkyl-, heteroarylalkyl-, cycloalkylalkyl-, heterocycloalkylalkyl-, arylcycloalkylalkyl-, heteroarylcycloalkylalkyl-, arylheterocycloalkylalkyl-, heteroarylheterocycloalkylalkyl-, cycloalkyl-, arylcycloalkyl-, heteroarylcycloalkyl-, heterocycloalkyl-, arylheterocycloalkyl-, heteroarylheterocycloalkyl-, alkenyl, arylalkenyl-, cycloalkenyl, arylcycloalkenyl-, heteroarylcycloalkenyl-, heterocycloalkenyl-, arylheterocycloalkenyl-, heteroarylheterocycloalkenyl-, alkynyl, arylalkynyl-, aryl, cycloalkylaryl-, heterocycloalkylaryl-, heterocycloalkenylaryl-, heteroaryl, cycloalkylheteroaryl-, heterocycloalkylheteroaryl-, cycloalkenylaryl-, heterocycloalkenylaryl-, —$OR^{15}$, —CN, —$C(O)R^8$, —$C(O)OR^9$, —$S(O)R^{19}$, —$S(O)_2R^{19}$, —$C(O)N(R^{11})(R^{12})$, —$S(O)N(R^{11})(R^{12})$, —$S(O)_2N(R^{11})(R^{12})$, —$NO_2$, —N=$C(R^8)_2$ and —$N(R^8)_2$; and wherein said $R^{13}$ alkyl, arylalkyl-, heteroarylalkyl-, cycloalkylalkyl-, heterocycloalkylalkyl-, arylcycloalkylalkyl-, heteroarylcycloalkylalkyl-, arylheterocycloalkylalkyl-, heteroarylheterocycloalkylalkyl-, cycloalkyl, arylcycloalkyl-, heteroarylcycloalkyl-, heterocycloalkyl, arylheterocycloalkyl-, heteroarylheterocycloalkyl-, alkenyl, arylalkenyl, cycloalkenyl, arylcycloalkenyl-, heteroarylcycloalkenyl-, heterocycloalkenyl, arylheterocycloalkenyl-, heteroarylheterocycloalkenyl-, alkynyl, arylalkynyl-, aryl, cycloalkylaryl, heterocycloalkylaryl-, heterocycloalkenylaryl-, heteroaryl, cycloalkylheteroaryl-, heterocycloalkylheteroaryl-, cycloalkenylaryl-, and heterocycloalkenylaryl- groups are optionally substituted with 1 to 5 groups independently selected from the group consisting of: alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, halo, —CN, —$OR^{15}$, —$C(O)R^{15}$, —$C(O)OR^{15}$, —$C(O)N(R^{15})(R^{16})$, —$SR^{15}$, —$S(O)N(R^{15})(R^{16})$, —$CH(R^{15})(R^{16})$, —$S(O)_2N(R^{15})(R^{16})$, —$C(=NOR^{15})R^{16}$, —$P(O)(OR^{15})(OR^{16})$, —$N(R^{15})(R^{16})$, -alkyl-$N(R^{15})(R^{16})$, —$N(R^{15})C(O)R^{16}$, —$CH_2$—$N(R^{15})C(O)R^{16}$, —$CH_2$—$N(R^{15})C(O)N(R^{16})(R^{17})$, —$CH_2$—$R^{15}$; —$CH_2N(R^{15})(R^{16})$, —$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$, —$CH_2$—$N(R^{15})C(O)OR^{16}$, —$S(O)R^{15}$, =$NOR^{15}$, —$N_3$, —$NO_2$ and —$S(O)_2R^{15}$;

$R^{14}$ is selected from the group consisting of H, alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, —CN, —$C(O)R^{15}$, —$C(O)OR^{15}$, —$C(O)N(R^{15})(R^{16})$, —$(O)N(R^{15})(R^{16})$, —$S(O)_2N(R^{15})(R^{16})$, —$C(=NOR^{15})R^{16}$, and —$P(O)(OR^{15})(OR^{16})$;

$R^8$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, with each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- being unsubstituted or optionally independently substituted with 1-3 substituents which can be the same or different, each substituent being independently selected from the group consisting of the moieties shown below;

$R^{10}$ is selected from the group consisting of a bond, alkyl-, alkenyl- and alkynyl-, aryl-, arylalkyl-, alkylaryl-, cycloalkyl-, cycloalkylalkyl-, heteroaryl-, heteroarylalkyl-, heterocyclyl-, heterocyclylalkyl- and the moieties:

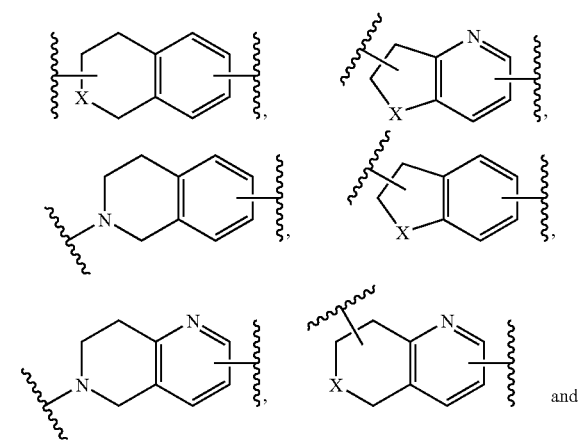

and

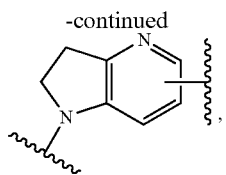

where X is O, N(R$^{14}$) or S;

wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl-heterocyclylalkyl- for R$^{10}$ as well as the above-noted moieties for R$^{10}$ can be unsubstituted or optionally independently substituted with 1-3 substituents which can be the same or different, each being independently selected from the group consisting of the moieties shown below;

R$^9$ is selected from the group consisting of alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-3 substituents which can be the same or different, each substituent being independently selected from the group consisting of the moieties shown below, R$^{15}$, R$^{16}$ and R$^{17}$ are independently selected from the group consisting of H, alkyl, alkenyl, alkynyl, cycloalkyl, cycloalkylalkyl-, heterocyclyl, heterocyclylalkyl-, aryl, arylalkyl-, heteroaryl, heteroarylalkyl-, arylcycloalkyl- arylheterocyclyl-, R$^{18}$-alkyl, R$^{18}$-cycloalkyl, R$^{18}$-cycloalkylalkyl-, R$^{18}$-heterocyclyl, R$^{18}$-heterocyclylalkyl-, R$^{18}$-aryl, R$^{18}$-arylalkyl-, R$^{18}$-heteroaryl and R$^{18}$-heteroarylalkyl-;

R$^{18}$ is 1-5 substituents independently selected from the group consisting of alkyl, alkenyl, alkynyl, aryl, arylalkyl-, arylalkenyl-, arylalkynyl-, —NO$_2$, halo, heteroaryl, HO-alkyoxyalkyl, —CF$_3$, —CN, alkyl-CN, —C(O)R$^{19}$, —C(O)OH, —C(O)OR$^{19}$, —C(O)NHR$^{20}$, —C(O)NH$_2$, —C(O)NH$_2$, —C(O)N(alkyl)$_2$, —C(O)N(alkyl)(aryl), —C(O)N(alkyl)(heteroaryl), —SR$^{19}$, —S(O)$_2$R$^{20}$, —S(O)NH$_2$, —S(O)NH(alkyl), —S(O)N(alkyl)(alkyl), —S(O)NH(aryl), —S(O)$_2$NH$_2$, —S(O)$_2$NHR$^{19}$, —S(O)$_2$NH(heterocyclyl), —S(O)$_2$N(alkyl)$_2$, —S(O)$_2$N(alkyl)(aryl), —OCF$_3$, —OH, —OR$^{20}$, —O-heterocyclyl, —O-cycloalkylalkyl, —O-heterocyclylalkyl, —NH$_2$, —NHR$^{20}$, —N(alkyl)$_2$, —N(arylalkyl)$_2$, —N(arylalkyl)-(heteroarylalkyl), —NHC(O)R$^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or, alternately, two R$^{18}$ moieties on adjacent carbons can be linked together to form:

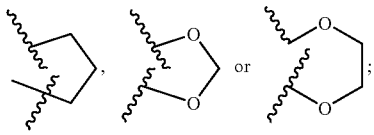

R$^{19}$ is alkyl, cycloalkyl, aryl, arylalkyl- or heteroarylalkyl-;
R$^{20}$ is alkyl, cycloalkyl, aryl, halo substituted aryl, arylalkyl-, heteroaryl or heteroarylalkyl-;

wherein each of the alkyl, cycloalkyl, cycloalkenyl, cycloalkylalkyl-, heterocyclyl, heterocyclylalkyl-, aryl, arylalkyl-, alkylaryl-, heteroaryl, heteroarylalkyl-, alkenyl and alkynyl groups in R$^1$, R$^2$-R$^6$, R$^3$, R$^4$, R$^5$, R$^7$, R$^8$, R$^9$, R$^{10}$, R$^{11}$, R$^{12}$ and R$^{14}$ is independently unsubstituted or optionally substituted by 1 to 5 R$^{21}$ groups independently selected from the group consisting of alkyl, alkenyl, alkynyl, cycloalkyl, cycloalkylalkyl-, cycloalkenyl, heterocyclyl, heterocyclylalkyl-, aryl, arylalkyl, heteroaryl, heteroarylalkyl-, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —CH(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —CH$_2$—N(R$^{15}$)C(O)N(R$^{16}$)(R$^{17}$), —CH$_2$—R$^{15}$, —CH$_2$N(R$^{15}$)(R$^{16}$), —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)C(O)N(R$^{16}$)(R$^{17}$), —N(R$^{15}$)C(O)OR$^{16}$, —CH$_2$—N(R$^{15}$)C(O)OR$^{16}$, —S(O)R$^{15}$, =NOR$^{15}$, —N$_3$, —NO$_2$ and —S(O)$_2$R$^{15}$;

wherein each of the alkyl, cycloalkenyl-, cycloalkyl, cycloalkylalkyl-, heterocyclyl, heterocyclylalkyl-, aryl, arylalkyl-, heteroaryl, heteroarylalkyl-, alkenyl and alkynyl groups in R$^{21}$ is independently unsubstituted or substituted by 1 to 5 R$^{22}$ groups independently selected from the group consisting of alkyl, cycloalkyl, cycloalkenyl-, heterocyclyl, aryl, heteroaryl, halo, —CF$_3$, —CN, —OR$^{15}$, —C(O)R$^{15}$, —C(O)OR$^{15}$, -alkyl-C(O)OR$^{15}$, C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —N$_3$, =NOR$^{15}$, —NO$_2$, —S(O)R$^{15}$ and —S(O)$_2$R$^{15}$ In another embodiment, the present application discloses a compound, or pharmaceutically acceptable salts, solvates, esters or prodrugs of said compound, said compound having the general structure shown in Formula I:

Formula I

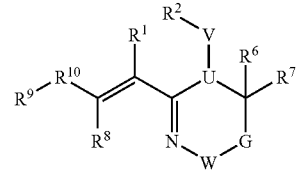

wherein:

R$^1$ and R$^2$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; and R$^2$ and R$^6$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below;

U is

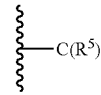

or N;

W is selected from the group consisting of a bond, —O—, —C(O)—, —S—, —S(O)—, —S(O$_2$)—, and —C(R$^{11}$)(R$^{12}$)—;

G is —C($R^3$)($R^4$)—, —C(O)— and —N($R^{13}$)—; with the proviso that when W is —O— or —S—, G is not —N($R^{13}$)— or —C(O)—;

V is selected from the group consisting of a bond, —O—, —C(O)— and —N($R^{14}$)—;

$R^5$, $R^6$, and $R^7$ can be the same or different, each being independently selected from the group consisting of H, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below;

$R^3$ is selected from the group consisting of H, halo (and in one example, F), —$OR^{15}$ (and in one example $R^{15}$ is H), —CN, —$SR^{15}$, —$NR^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)$OR^{16}$, —C(O)$R^{15}$, —C(O)$OR^{15}$, —C(=NO$R^{15}$)$R^{16}$, —C(O)N($R^{15}$)($R^{16}$), —S(O)N($R^{15}$)($R^{16}$), S(O)$_2$N($R^{15}$)($R^{16}$), —S(O)$R^{15}$, —S(O)$_2R^{15}$, —P(O)($OR^{15}$)($OR^{16}$), =NO$R^{15}$, —$N_3$, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below; or $R^4$, $R^{11}$ and $R^{12}$ can be the same or different, each being independently selected from the group consisting of H, halo (and in one example, F), —$OR^{15}$ (and in one example $R^{15}$ is H), —CN, —$SR^{15}$, —$NR^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)$OR^{16}$, —C(O)$R^{15}$, —C(O)$OR^{15}$, —C(=NO$R^{15}$)$R^{16}$, —C(O)N($R^{15}$)($R^{16}$), —S(O)N($R^{15}$)($R^{16}$), —S(O)$_2$N($R^{15}$)($R^{16}$), —S(O)$R^{15}$, —S(O)$_2R^{15}$, —P(O)($OR^{15}$)($OR^{16}$), =NO$R^{15}$, —$N_3$, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below, provided that when one of $R^3$ or $R^4$ is selected from the group consisting of: —$OR^{15}$, —CN, —$SR^{15}$, —$NR^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)$OR^{16}$, —S(O)N($R^{15}$)($R^{16}$), —S(O)$_2$N($R^{15}$)($R^{16}$), —S(O)$R^{15}$, —S(O)$_2R^{15}$, —P(O)($OR^{15}$)($OR^{16}$), =NO$R^{15}$, and —$N_3$, then the other is not selected from the group consisting of: —$OR^{15}$, —CN, —$SR^{15}$, and —$NR^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)$OR^{16}$, —S(O)N($R^{15}$)($R^{16}$), —S(O)$_2$N($R^{15}$)($R^{16}$), —S(O)$R^{15}$, —S(O)$_2R^{15}$, S(O)$_2R^{15}$, —P(O)($OR^{15}$)($OR^{16}$), =NO$R^{15}$, or —$N_3$);

provided that when one of $R^{11}$ or $R^{12}$ is selected from the group consisting of: —$OR^{15}$, —CN, —$SR^{15}$, —$NR^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)$OR^{16}$, —S(O)N($R^{15}$)($R^{16}$), —S(O)$_2$N($R^{15}$)($R^{16}$), —S(O)$R^{15}$, —S(O)$_2R^{15}$, —P(O)($OR^{15}$)($OR^{16}$), =NO$R^{15}$, and —$N_3$, then the other is not selected from the group consisting of: —$OR^{15}$, —CN, —$SR^{15}$, —$NR^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)$OR^{16}$, —S(O)N($R^{15}$)($R^{16}$), —S(O)$_2$N($R^{15}$)($R^{16}$), —S(O)$R^{15}$, —S(O)$_2R^{15}$, —P(O)($OR^{15}$)($OR^{16}$), =NO$R^{15}$, and —$N_3$ (i.e., if one of $R^{11}$ or $R^{12}$ is —$OR^{15}$, —CN, —$SR^{15}$, —$NR^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)$OR^{16}$, —S(O)N($R^{15}$)($R^{16}$), —S(O)$_2$N($R^{15}$)($R^{16}$), —S(O)$R^{15}$, —S(O)$_2R^{15}$, —P(O)($OR^{15}$)($OR^{16}$), =NO$R^{15}$, or —$N_3$, then the other is not —$OR^{15}$, —CN, —$SR^{15}$, —$NR^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$) —N($R^{15}$)S(O)N($R^{16}$)($R^{17}$), —N($R^{15}$)C(O)N($R^{16}$)($R^{17}$), —N($R^{15}$)C(O)$OR^{16}$, —S(O)N($R^{15}$)($R^{16}$), —S(O)$_2$N($R^{15}$)($R^{16}$), —S(O)$R^{15}$, —S(O)$_2R^{15}$, —P(O)($OR^{15}$)($OR^{16}$), =NO$R^{15}$, or —$N_3$);

$R^{13}$ is independently selected from the group consisting of H, alkyl, arylalkyl-, heteroarylalkyl-, cycloalkylalkyl-, heterocycloalkylalkyl-, arylcycloalkylalkyl-, heteroarylcycloalkylalkyl-, arylheterocycloalkylalkyl-, heteroarylheterocycloalkylalkyl-, cycloalkyl, arylcycloalkyl-, heteroarylcycloalkyl-, heterocycloalkyl-, arylheterocycloalkyl-, heteroarylheterocycloalkyl-, alkenyl, arylalkenyl-, cycloalkenyl, arylcycloalkenyl-, heteroarylcycloalkenyl-, heterocycloalkenyl, arylheterocycloalkenyl-, heteroarylheterocycloalkenyl-, alkynyl, arylalkynyl-, aryl, cycloalkylaryl-, heterocycloalkylaryl-, heterocycloalkenylaryl-, heteroaryl, cycloalkylheteroaryl-, heterocycloalkylheteroaryl-, cycloalkenylaryl-, heterocycloalkenylaryl-, —$OR^{15}$, —CN, —C(O)$R^8$, —C(O)$OR^9$, —S(O)$R^{19}$, —S(O)$_2R^{10}$, —C(O)N($R^{11}$)($R^{12}$), —S(O)N($R^{11}$)($R^{12}$), —S(O)$_2$N($R^{11}$)($R^{12}$), —$NO_2$, —N=C($R^8$)$_2$ and —N($R^8$)$_2$; and wherein said $R^{13}$ alkyl, arylalkyl-, heteroarylalkyl-, cycloalkylalkyl-, heterocycloalkylalkyl-, arylcycloalkylalkyl-, heteroarylcycloalkylalkyl-, arylheterocycloalkylalkyl-, heteroarylheterocycloalkylalkyl-, cycloalkyl, arylcycloalkyl-, heteroarylcycloalkyl-, heterocycloalkyl-, arylheterocycloalkyl-, heteroarylheterocycloalkyl-, alkenyl, arylalkenyl-, cycloalkenyl, arylcycloalkenyl, heteroarylcycloalkenyl-, heterocycloalkenyl-, arylheterocycloalkenyl-, heteroarylheterocycloalkenyl-, alkynyl, arylalkynyl, aryl, cycloalkylaryl-, heterocycloalkylaryl-, heterocycloalkenylaryl-, heteroaryl, cycloalkylheteroaryl-, heterocycloalkylheteroaryl-, cycloalkenylaryl-, and heterocycloalkenylaryl- groups are optionally substituted with 1 to 5 groups independently selected from the group consisting of: alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —CH(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —CH$_2$—N(R$^{15}$)C(O)N(R$^{16}$)(R$^{17}$), —CH$_2$—R$^{15}$; —CH$_2$N(R$^{15}$)(R$^{16}$), —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —S(O)R$^{15}$, =NOR$^{15}$, —N$_3$, —NO$_2$ and —S(O)$_2$R$^{15}$;

R$^{14}$ is selected from the group consisting of H, alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, —CN, —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$);

R$^8$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, with each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- being unsubstituted or optionally independently substituted with 1-3 substituents which can be the same or different, each substituent being independently selected from the group consisting of the moieties shown below;

R$^{10}$ is selected from the group consisting of a bond, alkyl-, alkenyl- and alkynyl-, aryl-, arylalkyl-, alkylaryl-, cycloalkyl-, cycloalkylalkyl-, heteroaryl-, heteroarylalkyl-, heterocyclyl-, heterocyclylalkyl- and the moieties:

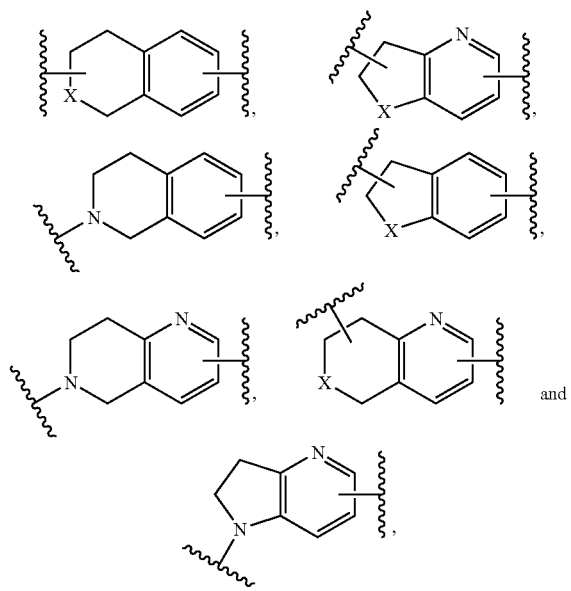

where X is O, N(R$^{14}$) or S;
wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl-heterocyclylalkyl- for R$^{10}$ as well as the above-noted moieties for R$^{10}$ can be unsubstituted or optionally independently substituted with 1-3 substituents which can be the same or different, each being independently selected from the group consisting of the moieties shown below; and R$^9$ is selected from the group consisting of alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-3 substituents which can be the same or different, each substituent being independently selected from the group consisting of the moieties shown below, R$^{15}$, R$^{16}$ and R$^{17}$ are independently selected from the group consisting of H, alkyl, alkenyl, alkynyl, cycloalkyl, cycloalkylalkyl-, heterocyclyl, heterocyclylalkyl-, aryl, arylalkyl-, heteroaryl, heteroarylalkyl-, arylcycloalkyl-, arylheterocyclyl-, R$^{18}$-alkyl, R$^{18}$-cycloalkyl, R$^{18}$-cycloalkylalkyl-, R$^{18}$-heterocyclyl, R$^{18}$-heterocyclylalkyl-, R$^{18}$-aryl, R$^{18}$-arylalkyl-, R$^{18}$-heteroaryl and R$^{18}$-heteroarylalkyl-;

R$^{18}$ is 1-5 substituents independently selected from the group consisting of alkyl, alkenyl, alkynyl, aryl, arylalkyl-, arylalkenyl-, arylalkynyl-, —NO$_2$, halo, heteroaryl, HO-alkyoxyalkyl, —CF$_3$, —CN, alkyl-CN, —C(O)R$^{19}$, —C(O)OH, —C(O)OR$^{19}$, —C(O)NHR$^{20}$, —C(O)NH$_2$, —C(O)NH$_2$—C(O)N(alkyl)$_2$, —C(O)N(alkyl)(aryl), —C(O)N(alkyl)(heteroaryl), —SR$^{19}$, —S(O)$_2$R$^{20}$, —S(O)NH$_2$, —S(O)NH(alkyl), —S(O)N(alkyl)(alkyl), —S(O)NH(aryl), —S(O)$_2$NH$_2$, —S(O)$_2$NHR$^{19}$, —S(O)$_2$NH(heterocyclyl), —S(O)$_2$N(alkyl)$_2$, —S(O)$_2$N(alkyl)(aryl), —OCF$_3$, —OH, —OR$^{20}$, —O-heterocyclyl, —O-cycloalkylalkyl, —O-heterocyclylalkyl, —NH$_2$, —NHR$^{20}$, —N(alkyl)$_2$, —N(arylalkyl)$_2$, —N(arylalkyl)-(heteroarylalkyl), —NHC(O)R$^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or, alternately, two R$^{18}$ moieties on adjacent carbons can be linked together to form:

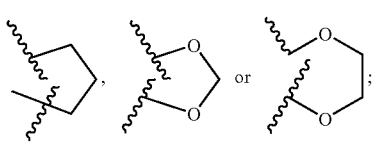

R$^{19}$ is alkyl, cycloalkyl, aryl, arylalkyl- or heteroarylalkyl-;
R$^{20}$ is alkyl, cycloalkyl, aryl, halo substituted aryl, arylalkyl-, heteroaryl or heteroarylalkyl-;
wherein each of the alkyl, cycloalkyl, cycloalkenyl, cycloalkylalkyl-, heterocyclyl, heterocyclylalkyl-, aryl, arylalkyl-, alkylaryl-, heteroaryl, heteroarylalkyl-, alkenyl and alkynyl groups in R$^1$-R$^2$, R$^2$-R$^6$, R$^3$, R$^4$, R$^5$, R$^7$, R$^8$, R$^9$, R$^{10}$, R$^{11}$, R$^{12}$ and R$^{14}$ is independently unsubstituted or optionally substituted by 1 to 5 R$^{21}$ groups independently selected from the group consisting of alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —CH(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)

$R^{16}$, —$CH_2$—$N(R^{15})C(O)R^{16}$, —$CH_2$—$N(R^{15})C(O)N(R^{16})(R^{17})$, —$CH_2$—$R^{15}$; —$CH_2N(R^{15})(R^{16})$, —$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$, —$CH_2$—$N(R^{15})C(O)OR^{16}$, —$S(O)R^{15}$, =$NOR^{15}$, —$N_3$, —$NO_2$ and —$S(O)_2R^{15}$;

wherein each of the alkyl, cycloalkenyl, cycloalkyl, cycloalkylalkyl, heterocyclyl, heterocyclylalkyl-, aryl, arylalkyl-, heteroaryl, heteroarylalkyl-, alkenyl and alkynyl groups in $R^{21}$ is independently unsubstituted or substituted by 1 to 5 $R^{22}$ groups independently selected from the group consisting of alkyl, cycloalkyl, cycloalkenyl, heterocyclyl, aryl, heteroaryl, halo, —$CF_3$, —CN, —$OR^{15}$, —$C(O)R^{15}$, —$C(O)OR^{15}$, -alkyl-$C(O)OR^{15}$, $C(O)N(R^{15})(R^{16})$, —$SR^{15}$, —$S(O)N(R^{15})(R^{16})$, —$S(O)_2N(R^{15})(R^{16})$, —$C(=NOR^{15})R^{16}$, —$P(O)(OR^{15})(OR^{16})$, —$N(R^{15})(R^{16})$, -alkyl-$N(R^{15})(R^{16})$, —$N(R^{15})C(O)R^{16}$, —$CH_2$—$N(R^{15})C(O)R^{16}$, —$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$, —$CH_2$—$N(R^{15})C(O)OR^{16}$, —$N_3$, =$NOR^{15}$, —$NO_2$, —$S(O)R^{15}$ and —$S(O)_2R^{15}$.

In another embodiment, U is $C(R^5)$.

In another embodiment, U is N.

In another embodiment, $R^2$ is H.

In another embodiment, $R^2$ is alkyl.

In another embodiment, $R^2$ is methyl.

In another embodiment, $R^2$ is alkoxyalkyl-.

In another embodiment, $R^2$ is 3-methoxypropyl-.

In another embodiment, U is N and $R^2$ is 3-methoxypropyl-.

In another embodiment, W is a bond.

In another embodiment, W is —O—.

In another embodiment, W is —C(O)—.

In another embodiment, W is —S—.

In another embodiment, W is —S(O)—.

In another embodiment, W is —$S(O_2)$—.

In another embodiment, W is —$C(R^{11})(R^{12})$—.

In another embodiment, =N—W-G- is =N—$C(R^{11}R^{12})$—C(O)—.

In another embodiment, G is —$C(R^3)(R^4)$—.

In another embodiment, G is —C(O)—.

In another embodiment, G is —$N(R^{13})$—.

In another embodiment, V is a bond.

In another embodiment, V is —O—.

In another embodiment, V is —C(O)—.

In another embodiment, V is —$N(R^{14})$—.

In another embodiment, $R^2$ is arylalkyl-.

In another embodiment, $R^2$ is phenylmethyl-.

In another embodiment, $R^2$ is (4-alkoxy)phenylmethyl-.

In another embodiment, $R^2$ is (4-methoxy)phenylmethyl-.

In another embodiment, $R^1$ is H.

In another embodiment, $R^1$ is alkyl.

In another embodiment, $R^1$ is methyl.

In another embodiment, $R^1$ and $R^2$ are joined together to form a cyclopentyl ring, which is unsubstituted.

In another embodiment, $R^1$ and $R^2$ are joined together to form a cyclopentyl ring, which is substituted with 1-3 substituents which can be the same or different, each being independently selected from the group consisting of halo, alkyl, —CN, —$NH_2$, —NH(alkyl), —$N(alkyl)_2$, hydroxy and alkoxy groups.

In another embodiment, $R^1$ and $R^2$ are joined together to form a cyclohexyl ring, which is unsubstituted.

In another embodiment, $R^1$ and $R^2$ are joined together to form a cyclohexyl ring, which is substituted with 1-3 substituents which can be the same or different, each being independently selected from the group consisting of halo, alkyl, —CN, —$NH_2$, —NH(alkyl), —$N(alkyl)_2$, hydroxy and alkoxy groups.

In another embodiment, U is N, and $R^1$ and $R^2$ are joined together to form a piperidinyl ring including the N of U as the nitrogen of said piperidinyl ring, which is unsubstituted.

In another embodiment, U is N, and $R^1$ and $R^2$ are joined together to form a piperidinyl ring including the N of U as the nitrogen of said piperidinyl ring, wherein said piperidinyl ring is substituted with 1-3 substituents which can be the same or different, each being independently selected from the group consisting of halo, alkyl, —CN, —$NH_2$, —NH(alkyl), —$N(alkyl)_2$, hydroxy and alkoxy groups.

In another embodiment, U is N, and $R^1$ and $R^2$ are joined together to form a pyrrolidinyl ring including the N of U as the nitrogen of said pyrrolidinyl ring, which is unsubstituted.

In another embodiment, U is N, and $R^1$ and $R^2$ are joined together to form a pyrrolidinyl ring including the N of U as the nitrogen of said pyrrolidinyl ring, wherein said pyrrolidinyl ring is substituted with 1-3 substituents which can be the same or different, each being independently selected from the group consisting of halo, alkyl, —CN, —$NH_2$, —NH(alkyl), —$N(alkyl)_2$, hydroxy and alkoxy groups.

In another embodiment, U is N, and $R^1$ and $R^2$ are joined together to form a piperazinyl ring including the N of U as a nitrogen of said piperazinyl ring, which is unsubstituted.

In another embodiment, U is N, and $R^1$ and $R^2$ are joined together to form a piperazinyl ring including the N of U as a nitrogen of said piperazinyl ring, wherein said piperazinyl ring is substituted with 1-3 substituents which can be the same or different, each being independently selected from the group consisting of halo, alkyl, —CN, —$NH_2$, —NH(alkyl), —$N(alkyl)_2$, hydroxy and alkoxy groups.

In another embodiment $R^1$ and $R^2$ are joined together to form a ring optionally substituted with 1 to 5 independently selected $R^{21}$ substitutents, and said ring is fused with an aryl or heteroaryl ring, and said resulting fused ring is optionally substituted with 1 to 5 independently selected $R^{21}$ substitutents.

In another embodiment $R^1$ and $R^2$ are joined together to form a ring substituted with 1 to 5 independently selected $R^{21}$ substitutents, and said ring is fused with an aryl or heteroaryl ring, and said resulting fused ring is optionally substituted with 1 to 5 independently selected $R^{21}$ substitutents.

In another embodiment $R^1$ and $R^2$ are joined together to form a ring optionally substituted with 1 to 5 independently selected $R^{21}$ substitutents.

In another embodiment $R^1$ and $R^2$ are joined together to form a ring.

In another embodiment $R^1$ and $R^2$ are joined together to form a heterocyclyl ring optionally substituted with 1 to 5 independently selected $R^{21}$ substitutents.

In another embodiment $R^1$ and $R^2$ are joined together to form a heterocyclyl ring substituted with 1 to 5 independently selected $R^{21}$ substitutents.

In another embodiment U is N, and $R^1$ and $R^2$ are joined together to form a heterocyclyl ring optionally substituted with 1 to 5 independently selected $R^{21}$ substitutents.

In another embodiment U is N, and $R^1$ and $R^2$ are joined together to form a heterocyclyl ring substituted with 1 to 5 independently selected $R^{21}$ substitutents.

In another embodiment $R^1$ and $R^2$ are joined together to form a ring, and said ring is fused with an aryl or heteroaryl ring, and said resulting fused ring is optionally substituted with 1 to 5 independently selected $R^{21}$ substitutents.

In another embodiment $R^1$ and $R^2$ are joined together to form a heterocyclyl ring.

In another embodiment U is N, and $R^1$ and $R^2$ are joined together to form a heterocyclyl ring.

In another embodiment $R^1$ and $R^2$ are joined together to form a piperidinyl ring optionally substituted with 1 to 5 independently selected $R^{21}$ substitutents.

In another embodiment $R^1$ and $R^2$ are joined together to form a piperidinyl ring substituted with 1 to 5 independently selected $R^{21}$ substitutents.

In another embodiment U is N, and $R^1$ and $R^2$ are joined together to form a piperidinyl ring optionally substituted with 1 to 5 independently selected $R^{21}$ substitutents.

In another embodiment U is N, and $R^1$ and $R^2$ are joined together to form a piperidinyl ring substituted with 1 to 5 independently selected $R^{21}$ substitutents.

In another embodiment $R^1$ and $R^2$ are joined together to form a piperidinyl ring optionally substituted with a =O moiety.

In another embodiment U is N, and $R^1$ and $R^2$ are joined together to form a piperidinyl ring optionally substituted with a =O moiety.

In another embodiment $R^1$ and $R^2$ are joined together to form a piperidinyl.

In another embodiment U is N, and $R^1$ and $R^2$ are joined together to form a piperidinyl ring.

In another embodiment $R^1$ and $R^2$ are joined together to form a piperidinyl ring substituted with a =O moiety.

In another embodiment U is N, and $R^1$ and $R^2$ are joined together to form a piperidinyl ring substituted with a =O moiety.

In another embodiment $R^2$ and $R^6$ are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, and (c) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents.

In another embodiment:
(a) $R^1$ and $R^2$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, and (2) said heterocyclyl moiety is optionally substituted with 1-5 independently selected $R^{21}$ substituents, and
(b) $R^2$ and $R^6$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, and (2) said heterocyclyl moiety is optionally substituted with 1-5 independently selected $R^{21}$ substituents; and
(c) said $R^2$ and $R^6$ cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents.

In another embodiment $R^6$ and either $R^3$ or $R^4$ of the —C($R^3$)($R^4$)— G moiety, are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, and (c) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5-8 membered heterocyclyl or 5-8 membered heterocyclenyl moiety, wherein: (a) said heterocyclyl moiety is optionally substituted with 1-5 independently selected $R^{21}$ substituents, and (b) said heterocyclyl or heterocyclenyl moiety is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5-8 membered heterocyclyl or 5-8 membered heterocyclenyl moiety, wherein said heterocyclyl moiety is optionally substituted with 1-5 independently selected $R^{21}$ substituents.

In another embodiment $R^6$ and $R^{13}$ of the —N($R^{13}$)— G moiety, are joined together to form a 5-8 membered heterocyclyl or 5-8 membered heterocyclenyl moiety, wherein said heterocyclyl moiety is substituted with 1-5 independently selected $R^{21}$ substituents.

In another embodiment $R^6$ and $R^{13}$ of the —N($R^{13}$)— G moiety, are joined together to form a 5-8 membered heterocyclyl or 5-8 membered heterocyclenyl moiety.

In another embodiment $R^6$ and $R^{13}$ of the —N($R^{13}$)— G moiety, are joined together to form a 5-8 membered heterocyclyl or 5-8 membered heterocyclenyl moiety, wherein: (a) said heterocyclyl moiety is optionally substituted with a =O and (b) said heterocyclyl or heterocyclenyl moiety is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5-8 membered heterocyclyl or 5-8 membered heterocyclenyl moiety, wherein said heterocyclyl moiety is optionally substituted with a =O.

In another embodiment $R^6$ and $R^{13}$ of the —N($R^{13}$)— G moiety, are joined together to form a 5-8 membered heterocyclyl or 5-8 membered heterocyclenyl moiety, wherein said heterocyclyl or heterocyclenyl moiety is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5-8 membered heterocyclyl or 5-8 membered heterocyclenyl moiety.

In another embodiment $R^6$ and $R^{13}$ of the —N($R^{13}$)— G moiety, are joined together to form a 5-8 membered heterocyclyl or 5-8 membered heterocyclenyl moiety, wherein: (a) said heterocyclyl moiety is substituted with a =O, and (b) said heterocyclyl or heterocyclenyl moiety is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5-8 membered heterocyclyl or 5-8 membered heterocyclenyl moiety, wherein said heterocyclyl moiety is substituted with a =O.

In another embodiment $R^6$ and $R^{13}$ of the —N($R^{13}$)— G moiety, are joined together to form a 5 membered heterocyclyl moiety, wherein: (a) said heterocyclyl moiety is optionally substituted with 1-5 independently selected $R^{21}$ substituents, and (b) said heterocyclyl moiety is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5 membered heterocyclyl moiety, wherein said heterocyclyl moiety is optionally substituted with 1-5 independently selected $R^{21}$ substituents.

In another embodiment $R^6$ and $R^{13}$ of the —N($R^{13}$)— G moiety, are joined together to form a 5 membered heterocyclyl moiety, wherein: (a) said heterocyclyl moiety is optionally substituted with a =O, and (b) said heterocyclyl moiety is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5 membered heterocyclyl moiety, wherein said heterocyclyl moiety is optionally substituted with a =O.

In another embodiment $R^6$ and $R^{13}$ of the —N($R^{13}$)— G moiety, are joined together to form a 5 membered heterocyclyl moiety, wherein said heterocyclyl moiety is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5 membered heterocyclyl moiety.

In another embodiment $R^6$ and $R^{13}$ of the —N($R^{13}$)— G moiety, are joined together to form a 5 membered heterocyclyl moiety, wherein: (a) said heterocyclyl moiety is substituted with a =O, and (b) said heterocyclyl moiety is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5 membered heterocyclyl moiety, wherein said heterocyclyl moiety is substituted with a =O.

In another embodiment $R^6$ and $R^{13}$ of the —N($R^{13}$)— G moiety, are joined together to form a pyrrolidinyl ring, wherein: (a) said pyrrolidinyl ring is optionally substituted with 1-5 independently selected $R^{21}$ substituents, and (b) said pyrrolidinyl ring is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5 pyrrolidinyl ring, wherein said pyrrolidinyl ring is optionally substituted with 1-5 independently selected $R^{21}$ substituents.

In another embodiment $R^6$ and $R^{13}$ of the —N($R^{13}$)— G moiety, are joined together to form a pyrrolidinyl ring, wherein: (a) said pyrrolidinyl ring is optionally substituted with a =O, and (b) said pyrrolidinyl ring is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a pyrrolidinyl ring, wherein said pyrrolidinyl ring is optionally substituted with a =O.

In another embodiment $R^6$ and $R^{13}$ of the —N($R^{13}$)— G moiety, are joined together to form a pyrrolidinyl ring, wherein said pyrrolidinyl ring is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a pyrrolidinyl ring.

In another embodiment $R^6$ and $R^{13}$ of the —N($R^{13}$)— G moiety, are joined together to form a pyrrolidinyl ring, wherein: (a) said pyrrolidinyl ring is substituted with a =O, and (b) said pyrrolidinyl ring is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a pyrrolidinyl ring, wherein said pyrrolidinyl ring is substituted with a =O.

In another embodiment $R^6$ and $R^{13}$ of the —N($R^{13}$)— G moiety, are joined together to form a 5 membered heterocyclyl moiety, wherein: (a) said heterocyclyl moiety is substituted with 1-5 independently selected $R^{21}$ substituents, and (b) said heterocyclyl moiety is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5 membered heterocyclyl moiety, wherein said heterocyclyl moiety is substituted with 1-5 independently selected $R^{21}$ substituents.

In another embodiment $R^6$ and $R^{13}$ of the —N($R^{13}$)— G moiety, are joined together to form a pyrrolidinyl ring, wherein: (a) said pyrrolidinyl ring is substituted with 1-5 independently selected $R^{21}$ substituents, and (b) said pyrrolidinyl ring is optionally fused with an aryl or heteroaryl ring, and the ring moiety resulting from the fusion is optionally substituted with 1-5 independently selected $R^{21}$ substituents.

In another embodiment $R^6$ and $R^{13}$ of the —N($R^{13}$)— G moiety, are joined together to form a 5 pyrrolidinyl ring, wherein said pyrrolidinyl ring is substituted with 1-5 independently selected $R^{21}$ substituents.

In another embodiment, $R^6$ is H.

In another embodiment, $R^6$ is alkyl.

In another embodiment, $R^6$ is methyl.

In another embodiment, $R^7$ is aryl.

In another embodiment, $R^7$ is an unsubstituted phenyl.

In another embodiment, $R^7$ is a phenyl which is substituted with 1-4 substituents which can be the same or different, each substituent being independently selected from the group consisting of halo, alkyl, —CN, —NH$_2$, —NH(alkyl), —N(alkyl)$_2$, hydroxy, alkoxy, aryl and heteroaryl groups.

In another embodiment, $R^7$ is unsubstituted naphthyl.

In another embodiment, $R^7$ is naphthyl which is substituted with 1-4 substituents which can be the same or different, each substituent being independently selected from the group consisting of halo, alkyl, —CN, —NH$_2$, —NH(alkyl), —N(alkyl)$_2$, hydroxy, alkoxy, aryl and heteroaryl groups.

In another embodiment, $R^7$ is unsubstituted biphenyl.

In another embodiment, $R^7$ is biphenyl which is substituted with 1-4 substituents which can be the same or different, each substituent being independently selected from the group consisting of halo, alkyl, —CN, —NH$_2$, —NH(alkyl), —N(alkyl)$_2$, hydroxy and alkoxy groups.

In another embodiment, $R^7$ is $R^7$ is 3-(1,1'-biphenyl)-yl.

In another embodiment, $R^7$ is $R^7$ is 4-(1,1'-biphenyl)-yl.

In another embodiment, $R^6$ is H and $R^7$ is a biphenyl which can be unsubstituted or optionally independently substituted with 1-4 substituents which can be the same or different, each substituent being independently selected from the group consisting of halo, alkyl, —CN, —NH$_2$, —NH(alkyl), —N(alkyl)$_2$, hydroxy and alkoxy groups.

In another embodiment, R$^6$ is methyl, and R$^7$ is a biphenyl which can be unsubstituted or optionally independently substituted with 1-4 substituents which can be the same or different, each substituent being independently selected from the group consisting of halo, alkyl, —CN, —NH$_2$, —NH(alkyl), —N(alkyl)$_2$, hydroxy and alkoxy groups.

In another embodiment, R$^6$ is H, and R$^7$ is a phenyl which can be unsubstituted or optionally independently substituted with 1-4 substituents which can be the same or different, each substituent being independently selected from the group consisting of halo, alkyl, —CN, —NH$_2$, —NH(alkyl), —N(alkyl)$_2$, hydroxy and alkoxy groups.

In another embodiment, R$^6$ is methyl, and R$^7$ is a biphenyl which can be unsubstituted or optionally independently substituted with 1-4 substituents which can be the same or different, each substituent being independently selected from the group consisting of halo, alkyl, —CN, —NH$_2$, —NH(alkyl), —N(alkyl)$_2$, hydroxy and alkoxy groups.

In another embodiment, R$^2$ and R$^6$ are joined together to form a cyclopentyl ring.

In another embodiment, R$^2$ and R$^6$ are joined together to form a cyclopentyl ring, which is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, R$^2$ and R$^6$ are joined together to form a cyclohexyl ring.

In another embodiment, R$^2$ and R$^6$ are joined together to form a cyclohexyl ring, which is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, U is N, and R$^2$ and R$^6$ are joined together to form a piperidinyl ring including the N of U as the nitrogen of said piperidinyl ring, which is unsubstituted.

In another embodiment, U is N, and R$^2$ and R$^6$ are joined together to form a piperidinyl ring including the N of U as the nitrogen of said piperidinyl ring, wherein said piperidinyl ring is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, U is N, and R$^2$ and R$^6$ are joined together to form a pyrrolidinyl ring including the N of U as the nitrogen of said pyrrolidinyl ring, which is unsubstituted.

In another embodiment, U is N, and R$^2$ and R$^6$ are joined together to form a pyrrolidinyl ring including the N of U as the nitrogen of said pyrrolidinyl ring, wherein said pyrrolidinyl ring is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, U is N, and R$^2$ and R$^6$ are joined together to form a piperazinyl ring including the N of U as a nitrogen of said piperazinyl ring, which is unsubstituted.

In another embodiment, U is N, and R$^2$ and R$^6$ are joined together to form a piperazinyl ring including the N of U as a nitrogen of said piperazinyl ring, wherein said piperazinyl ring is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, R$^2$ and R$^6$ are joined together to form a morpholinyl ring which is unsubstituted.

In another embodiment, R$^2$ and R$^6$ are joined together to form a morpholinyl ring, which is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, R$^2$ and R$^6$ are joined together to form a pyranyl ring which is unsubstituted.

In another embodiment, R$^2$ and R$^6$ are joined together to form a pyranyl ring, which is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, R$^2$ and R$^6$ are joined together to form a pyrrolidinyl ring which is unsubstituted.

In another embodiment, R$^2$ and R$^6$ are joined together to form a pyrrolidinyl ring, which is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, both (R$^1$ and R$^2$) and (R$^2$ and R$^6$) are joined together to form independent cycloalkyl rings.

In another embodiment, both (R$^1$ and R$^2$) and (R$^2$ and R$^6$) are joined together to form independent cycloalkyl rings, each of which is independently optionally substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, both (R$^1$ and R$^2$) and (R$^2$ and R$^6$) are joined together to form independent heterocyclyl rings.

In another embodiment, both (R$^1$ and R$^2$) and (R$^2$ and R$^6$) are joined together to form independent heterocyclyl rings, each of which is independently optionally substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, both (R$^1$ and R$^2$) and (R$^2$ and R$^6$) are joined together to form independent cycloalkyl rings.

In another embodiment, both R$^1$ and R$^2$ are joined together to form a cycloalkyl ring, and R$^2$ and R$^6$ are joined together to form a heterocyclyl ring, each of which is independently optionally substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, both R$^1$ and R$^2$ are joined together to form a heterocyclyl ring, and R$^2$ and R$^6$ are joined together to form a cycloalkyl ring, each of which is independently optionally substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, R$^7$ is aryl.

In another embodiment, R$^7$ is an unsubstituted phenyl.

In another embodiment, R$^7$ is a phenyl which is substituted with 1-4 substituents which can be the same or different, each substituent being independently selected from the group consisting of halo, alkyl, —CN, —NH$_2$, —NH(alkyl), —N(alkyl)$_2$, hydroxy, alkoxy, aryl and heteroaryl groups.

In another embodiment, R$^7$ is 4-fluorophenyl.

In another embodiment, R$^7$ is unsubstituted naphthyl.

In another embodiment, $R^7$ is naphthyl which is substituted with 1-4 substituents which can be the same or different, each substituent being independently selected from the group consisting of halo, alkyl, —CN, —NH$_2$, —NH(alkyl), —N(alkyl)$_2$, hydroxy, alkoxy, aryl and heteroaryl groups.

In another embodiment, $R^7$ is unsubstituted biphenyl.

In another embodiment, $R^7$ is biphenyl which is substituted with 1-4 substituents which can be the same or different, each substituent being independently selected from the group consisting of halo, alkyl, —CN, —NH$_2$, —NH(alkyl), —N(alkyl)$_2$, hydroxy and alkoxy groups.

In another embodiment, $R^7$ is $R^7$ is 3-(1,1'-biphenyl)-yl.
In another embodiment, $R^7$ is $R^7$ is 4-(1,1'-biphenyl)-yl.
In another embodiment, $R^8$ is H.
In another embodiment, $R^8$ is alkyl.
In another embodiment, $R^8$ is methyl.
In another embodiment, $R^{10}$ is aryl.
In another embodiment, $R^{10}$ is phenyl.
In another embodiment $R^{10}$ is aryl substituted with 1 halo.
In another embodiment $R^{10}$ is aryl substituted with 1 halo, and said halo is F.
In another embodiment $R^{10}$ is aryl substituted with 1 to 3 independently selected $R^{21}$ moieties.
In another embodiment $R^{10}$ is aryl substituted with 1 to 3 $R^{21}$ moieties, wherein each $R^{21}$ moiety is the same or different —OR$^{15}$ group.
In another embodiment $R^{10}$ is aryl substituted with 1 $R^{21}$ moiety.
In another embodiment $R^{10}$ is phenyl substituted with 1 halo.
In another embodiment $R^{10}$ is phenyl substituted with 1 halo, and said halo is F.
In another embodiment $R^{10}$ is 3-halo-phenyl:

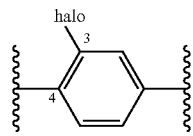

(wherein the bond from the carbon labeled as 4 is to the $R^9$ group).

In another embodiment $R^{10}$ is 3-F-phenyl:

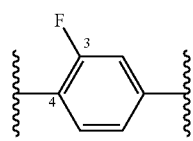

(wherein the bond from the carbon labeled as 4 is to the $R^9$ group).

In another embodiment $R^{10}$ is aryl substituted with one —OR$^{15}$ group.

In another embodiment $R^{10}$ is aryl substituted with one —OR$^{15}$ group, and said $R^{15}$ is alkyl (e.g., methyl).

In another embodiment $R^{10}$ is phenyl substituted with 1 to 3 independently selected $R^{21}$ moieties.

In another embodiment $R^{10}$ is phenyl substituted with 1 to 3 $R^{21}$ moieties, wherein each $R^{21}$ moiety is the same or different —OR$^{15}$ group.

In another embodiment $R^{10}$ is phenyl substituted with 1 $R^{21}$ moiety.

In another embodiment $R^{10}$ is phenyl substituted with one —OR$^{15}$ group.

In another embodiment $R^{10}$ is phenyl substituted with one —OR$^{15}$ group, and said $R^{15}$ is alkyl (e.g., methyl).

In another embodiment $R^{10}$ is 3-OR$^{15}$-phenyl:

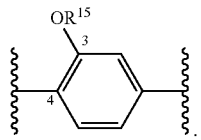

(wherein the bond from the carbon labeled as 4 is to the $R^9$ group).

In another embodiment $R^{10}$ is 3-OR$^{15}$-phenyl:

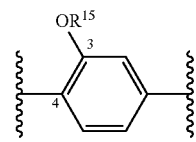

wherein $R^{15}$ is alkyl (wherein the bond from the carbon labeled as 4 is to the $R^9$ group).

In another embodiment $R^{10}$ is 3-OR$^{15}$-phenyl:

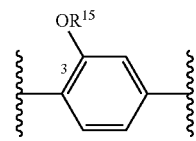

wherein $R^{15}$ is methyl (i.e., $R^{10}$ is 3-methoxy-phenyl).

In another embodiment, $R^{10}$ is heteroaryl.
In another embodiment, $R^{10}$ is unsubstituted heteroaryl.
In another embodiment $R^{10}$ is unsubstituted heteroaryl wherein said heteroaryl is pyridyl.

In another embodiment $R^{10}$ is:

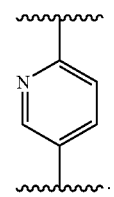 [SMILES: *c1ccc(*)nc1]

In another embodiment $R^{10}$ is:

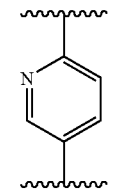 [SMILES: *c1ccc(*)nc1]

wherein the —$R^{10}$-$R^9$ moiety is:

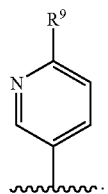

In another embodiment $R^{10}$ is aryl substituted with 1 to 3 $R^{21}$ moieties, wherein each $R^{21}$ moiety is the same or different halo.
In another embodiment $R^{10}$ is aryl substituted with 1 to 3 $R^{21}$ moieties, wherein each $R^{21}$ moiety is F.
In another embodiment $R^{10}$ is aryl substituted with one $R^{21}$ moiety, and said $R^{21}$ moiety is halo.
In another embodiment $R^{10}$ is aryl substituted with one $R^{21}$ moiety, said $R^{21}$ moiety is -halo, and said halo is F.
In another embodiment $R^{10}$ is phenyl substituted with 1 to 3 $R^{21}$ moieties, wherein each $R^{21}$ moiety is the same or different halo.
In another embodiment $R^{10}$ is phenyl substituted with 1 to 3 $R^{21}$ moieties, wherein each $R^{21}$ moiety is F.
In another embodiment $R^{10}$ is selected from the group consisting of:

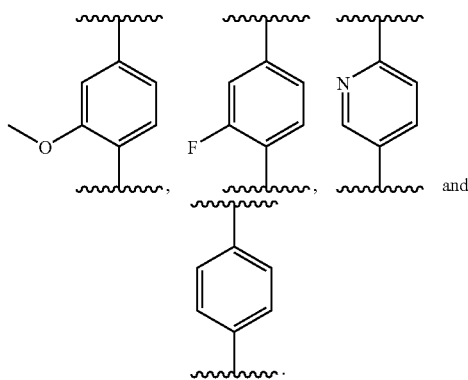

In another embodiment of this invention $R^9$ is selected from the group consisting of heteroaryl and heteroaryl substituted with 1-3 $R^{21}$ groups, and wherein each $R^{21}$ is independently selected.
In another embodiment, $R^9$ is unsubstituted heteroaryl.
In another embodiment, $R^9$ is heteroaryl which is substituted with 1-3 substituents which can be the same or different, each substituent being independently selected from the group consisting of halo, alkyl, CN, $NH_2$, NH(alkyl), N(alkyl)$_2$, hydroxy and alkoxy groups.
In another embodiment, $R^9$ is heteroaryl substituted with 1 to 3 independently selected alkyl groups.
In another embodiment, $R^9$ is heteroaryl substituted with one is alkyl group (e.g., methyl).
In another embodiment of this invention $R^9$ is selected from the group consisting of imidazolyl and imidazolyl substituted with 1-3 $R^{21}$ groups, and wherein each $R^{21}$ is independently selected.
In another embodiment of this invention $R^9$ is imidazolyl substituted with 1-3 $R^{21}$ groups, and wherein each $R^{21}$ is independently selected.
In another embodiment, $R^9$ is imidazolyl substituted with 1-3 substituents independently selected from the group consisting of halo, alkyl, CN, $NH_2$, NH(alkyl), N(alkyl)$_2$, hydroxy and alkoxy groups.

In another embodiment, $R^9$ is imidazol-1-yl.
In another embodiment, $R^9$ is 4-methyl-imidazol-1-yl:

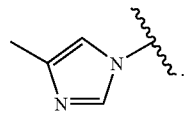

In another embodiment, $R^9$ is 5-chloro-4-methyl-imidazol-1-yl.
In another embodiment $R^{10}$ is selected from the group consisting of aryl and aryl substituted with one or more $R^{21}$ groups, and $R^9$ is selected from the group consisting of heteroaryl and heteroaryl substituted with one or more $R^{21}$ groups, and wherein each $R^{21}$ is independently selected.
In another embodiment $R^{10}$ is selected from the group consisting of phenyl and phenyl substituted with 1-3 independently selected $R^{21}$ groups, and $R^9$ is selected from the group consisting of imidazolyl and imidazolyl substituted with 1-3 independently selected $R^{21}$ groups.
In another embodiment $R^{10}$ is phenyl substituted with 1-3 independently selected $R^{21}$ groups, and $R^9$ is selected from the group consisting of imidazolyl and imidazolyl substituted with 1-3 independently selected $R^{21}$ groups.
In another embodiment $R^{10}$ is selected from the group consisting of heteroaryl and heteroaryl substituted with 1-3 $R^{21}$ groups, and the $R^9$ group is selected from the group consisting of heteroaryl and heteroaryl substituted with 1-3 $R^{21}$ groups, and wherein each $R^{21}$ is independently selected.
In another embodiment $R^{10}$ is selected from the group consisting of pyridyl and pyridyl substituted with 1-3 $R^{21}$ groups, and the $R^9$ group is selected from the group consisting of imidazolyl and imidazolyl substituted with 1-3 $R^{21}$ groups, and wherein each $R^{21}$ is independently selected.
In another embodiment $R^{10}$ is pyridyl, and the $R^9$ group is imidazolyl substituted with 1-3 $R^{21}$ groups, and wherein each $R^{21}$ is independently selected.
In another embodiment the $R^9$-$R^{10}$— moiety is:

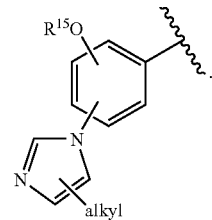

In another embodiment the $R^9$-$R^{10}$— moiety is:

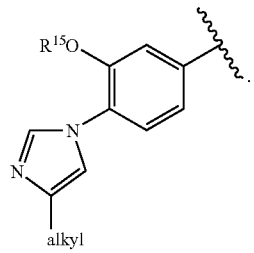

In another embodiment the R⁹-R¹⁰— moiety is:

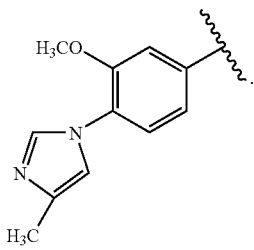 [SMILES: *c1ccc(-n2cnc(C)c2)c(OC)c1]

In another embodiment the R⁹— R¹⁰— moiety is:

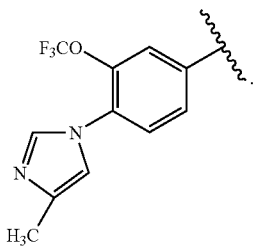 [SMILES: *c1ccc(-n2cnc(C)c2)c(OC(F)(F)F)c1]

In another embodiment the R⁹-R¹⁰— moiety is:

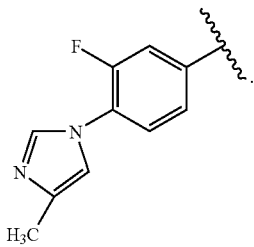 [SMILES: *c1ccc(-n2cnc(C)c2)c(F)c1]

In another embodiment R⁹-R¹⁰— moiety is:

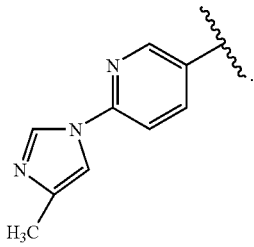 [SMILES: *c1ccc(-n2cnc(C)c2)nc1]

In another embodiment R⁹-R¹⁰— moiety is:

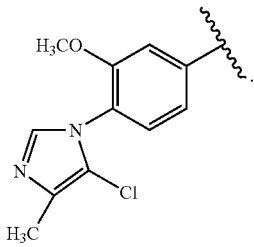 [SMILES: *c1ccc(-n2cnc(C)c2Cl)c(OC)c1]

In another embodiment, the present application discloses a compound of formula I, or pharmaceutically acceptable salts, solvates, esters or prodrugs of said compound, said compound having the general structure of Formula IB:

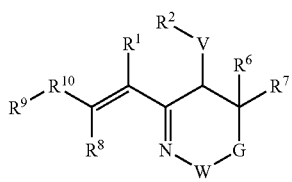

Formula IB wherein:
either (i) R¹ and R² are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; or (ii) R² and R⁶ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; or (iii) R¹ and R² are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; and R² and R⁶ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; and W is selected from the group consisting of a bond; —O—, —C(O)—, —S—, —S(O)—, —S(O₂)—, and —C(R¹¹)(R¹²)—;

G is selected from the group consisting of —C(R³)(R⁴)—, —C(O)—, —S—, —S(O)—, —S(O₂)—, —C(O)—O—, and —N(R¹³)—;

V is selected from the group consisting of a bond, —O—, and —N(R¹⁴)—;

R¹ (when R¹ is not joined to R²), R² (when R² is not joined to R¹ or R⁶), R³, R⁴, R⁵, R⁶ (when R⁶ is not joined to R²), R⁷, R¹¹ and R¹² can be the same or different, each being independently selected from the group consisting of H, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below;

R$^{13}$ is independently selected from the group consisting of H, alkyl, arylalkyl-, heteroarylalkyl-, cycloalkylalkyl-, heterocycloalkylalkyl-, arylcycloalkylalkyl-, heteroarylcycloalkylalkyl-, arylheterocycloalkylalkyl-, heteroarylheterocycloalkylalkyl-, cycloalkyl, arylcycloalkyl-, heteroarylcycloalkyl-, heterocycloalkyl-, arylheterocycloalkyl-, heteroarylheterocycloalkyl-, alkenyl, arylalkenyl-, cycloalkenyl, arylcycloalkenyl-, heteroarylcycloalkenyl-, heterocycloalkenyl-, arylheterocycloalkenyl-, heteroarylheterocycloalkenyl-, alkynyl, arylalkynyl-, aryl, cycloalkylaryl-, heterocycloalkylaryl-, heterocycloalkenylaryl-, heteroaryl, cycloalkyl heteroaryl-, heterocycloalkylheteroaryl-, cycloalkenylaryl-, heterocycloalkenylaryl-, —OR$^{15}$, —CN, —C(O)R$^{8}$, —C(O)OR$^{9}$, —S(O)R$^{19}$, —S(O)$_2$R$^{19}$, —C(O)N(R$^{11}$)(R$^{12}$), —S(O)N(R$^{11}$)(R$^{12}$), —S(O)$_2$N(R$^{11}$)(R$^{12}$), —NO$_2$, —N=C(R$^{8}$)$_2$ and —N(R$^{8}$)$_2$; and wherein said R$^{13}$ alkyl, arylalkyl-, heteroarylalkyl-, cycloalkylalkyl-, heterocycloalkylalkyl-, arylcycloalkylalkyl-, heteroarylcycloalkylalkyl-, arylheterocycloalkylalkyl-, heteroarylheterocycloalkylalkyl-, cycloalkyl, arylcycloalkyl-, heteroarylcycloalkyl-, heterocycloalkyl-, arylheterocycloalkyl-, heteroarylheterocycloalkyl-, alkenyl, arylalkenyl-, cycloalkenyl, arylcycloalkenyl-, heteroarylcycloalkenyl-, heterocycloalkenyl-, arylheterocycloalkenyl-, heteroarylheterocycloalkenyl-, alkynyl, arylalkynyl-, aryl, cycloalkylaryl-, heterocycloalkylaryl-, heterocycloalkenylaryl-, heteroaryl, cycloalkylheteroaryl-, heterocycloalkylheteroaryl-, cycloalkenylaryl-, and heterocycloalkenylaryl- groups are optionally substituted with 1 to 5 groups independently selected from the group consisting of: alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —CH(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —CH$_2$—N(R$^{15}$)C(O)N(R$^{16}$)(R$^{17}$), —CH$_2$—R$^{15}$; —CH$_2$N(R$^{15}$)(R$^{16}$), —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —S(O)R$^{15}$, =NOR$^{15}$, —N$_3$, —NO$_2$ and —S(O)$_2$R$^{15}$;

R$^{14}$ is selected from the group consisting of H, alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, —CN, —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$);

R$^{8}$ is selected from the group consisting of H, alkyl, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, with each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- being unsubstituted or optionally independently substituted with 1-3 substituents which can be the same or different, each substituent being independently selected from the group consisting of the moieties shown below;

R$^{10}$ is selected from the group consisting of a bond, alkyl-, alkenyl- and alkynyl-, aryl-, arylalkyl-, alkylaryl-, cycloalkyl-, cycloalkylalkyl-, heteroaryl-, heteroarylalkyl-, heterocyclyl-, heterocyclylalkyl- and the moieties:

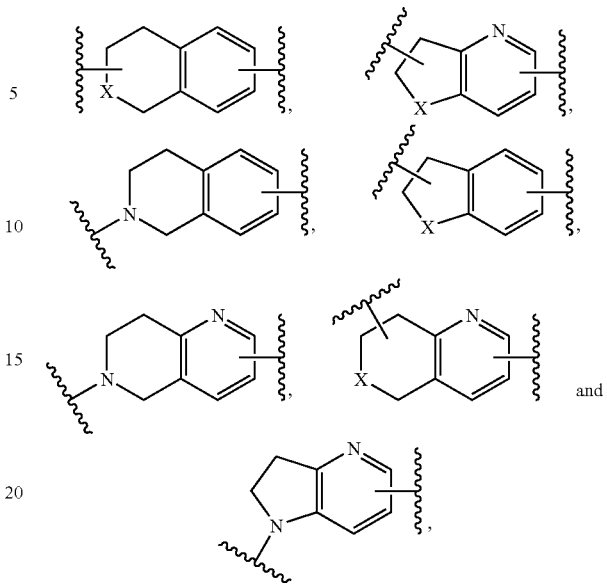

where X is O, N(R$^{14}$) or S;

wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl-heterocyclylalkyl- for R$^{10}$ as well as the above-noted moieties for R$^{10}$ can be unsubstituted or optionally independently substituted with 1-3 substituents which can be the same or different, each being independently selected from the group consisting of the moieties shown below; and R$^{9}$ is selected from the group consisting of alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-3 substituents which can be the same or different, each substituent being independently selected from the group consisting of the moieties shown below, R$^{15}$, R$^{16}$ and R$^{17}$ are independently selected from the group consisting of H, alkyl, alkenyl, alkynyl, cycloalkyl, cycloalkylalkyl-, heterocyclyl, heterocyclylalkyl-, aryl, arylalkyl, heteroaryl, heteroarylalkyl-, arylcycloalkyl-, arylheterocyclyl-, R$^{18}$-alkyl, R$^{18}$-cycloalkyl, R$^{18}$-cycloalkylalkyl-, R$^{18}$-heterocyclyl, R$^{18}$-heterocyclylalkyl-, R$^{18}$-aryl, R$^{18}$-arylalkyl, R$^{18}$-heteroaryl and R$^{18}$-heteroarylalkyl-;

R$^{18}$ is 1-5 substituents independently selected from the group consisting of alkyl, alkenyl, alkynyl, aryl, arylalkyl-, arylalkenyl-, arylalkynyl-, —NO$_2$, halo, heteroaryl, HO-alkyoxyalkyl, —CF$_3$, —CN, alkyl-CN, —C(O)R$^{19}$, —C(O)OH, —C(O)OR$^{19}$, —C(O)NHR$^{20}$, —C(O)NH$_2$, —C(O)NH$_2$—C(O)N(alkyl)$_2$, —C(O)N(alkyl)(aryl), —C(O)N(alkyl)(heteroaryl), —SR$^{19}$, —S(O)$_2$R$^{20}$, —S(O)NH$_2$, —S(O)NH(alkyl), —S(O)N(alkyl)(alkyl), —S(O)NH(aryl), —S(O)$_2$NH$_2$, —S(O)$_2$NHR$^{19}$, —S(O)$_2$NH(heterocyclyl), —S(O)$_2$N(alkyl)$_2$, —S(O)$_2$N(alkyl)(aryl), —OCF$_3$, —OH, —OR$^{26}$, —O-heterocyclyl, —O-cycloalkylalkyl, —O-heterocyclylalkyl, —NH$_2$, —NHR$^{20}$, —N(alkyl)$_2$, —N(arylalkyl)$_2$, —N(arylalkyl)-(heteroarylalkyl), —NHC(O)R$^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or, alternatively, two R$^{18}$ moieties on adjacent carbons can be linked together to form:

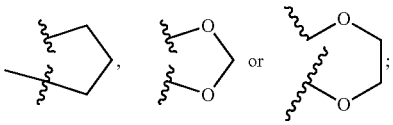

R$^{19}$ is alkyl, cycloalkyl, aryl, arylalkyl or heteroarylalkyl;
R$^{20}$ is alkyl, cycloalkyl, aryl, halo substituted aryl, arylalkyl, heteroaryl or heteroarylalkyl;
wherein each of the alkyl, cycloalkyl, cycloalkenyl, cycloalkylalkyl, heterocyclyl, heterocyclylalkyl, aryl, arylalkyl, alkylaryl, heteroaryl, heteroarylalkyl, alkenyl and alkynyl groups in R$^1$, R$^2$, R$^1$-R$^2$, R$^2$-R$^6$, R$^3$, R$^4$, R$^5$, R$^6$, R$^7$, R$^8$, R$^9$, R$^{10}$, R$^{11}$, R$^{12}$ and R$^{14}$ is independently unsubstituted or optionally substituted by 1 to 5 R$^{21}$ groups independently selected from the group consisting of alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —CH(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —CH$_2$—N(R$^{15}$)C(O)N(R$^{16}$)(R$^{17}$), —CH$_2$—R$^{15}$; —CH$_2$N(R$^{15}$)(R$^{16}$), —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —S(O)R$^{15}$, =NOR$^{15}$, —N$_3$, —NO$_2$ and —S(O)$_2$R$^{15}$;
wherein each of the alkyl, cycloalkenyl, cycloalkyl, cycloalkylalkyl-, heterocyclyl, heterocyclylalkyl-, aryl, arylalkyl-, heteroaryl, heteroarylalkyl-, alkenyl and alkynyl groups in R$^{21}$ is independently unsubstituted or substituted by 1 to 5 R$^{22}$ groups independently selected from the group consisting of alkyl, cycloalkyl, cycloalkenyl, heterocyclyl, aryl, heteroaryl, halo, —CF$_3$, —CN, —OR$^{15}$, —C(O)R$^{15}$, —C(O)OR$^{15}$, -alkyl-C(O)OR$^{15}$, C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —N$_3$, =NOR$^{15}$, —NO$_2$, —S(O)R$^{15}$ and —S(O)$_2$R$^{15}$.

In another embodiment, the present application discloses a compound of formula I, or pharmaceutically acceptable salts, solvates, esters or prodrugs of said compound, said compound having the general structure of Formula IB:

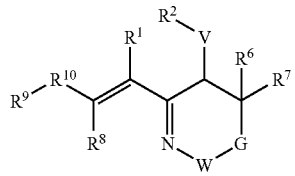

Formula IB wherein:
either
(i) R$^1$ and R$^2$ are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected R$^{21}$ substituents, (b) said heterocyclyl moiety is optionally substituted with 1-5 independently selected R$^{21}$ substituents, and (c) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected R$^{21}$ substituents; or (ii) R$^2$ and R$^6$ are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected R$^{21}$ substituents, (b) said heterocyclyl moiety is optionally substituted with 1-5 independently selected R$^{21}$ substituents, and (c) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected R$^{21}$ substituents; or (iii)
(a) R$^1$ and R$^2$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected R$^{21}$ substituents, and (2) said heterocyclyl moiety is optionally substituted with 1-5 independently selected R$^{21}$ substituents, and (b) R$^2$ and R$^6$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected R$^{21}$ substituents, and (2) said heterocyclyl moiety is optionally substituted with 1-5 independently selected R$^{21}$ substituents; and (c) said R$^2$ and R$^6$ cycloalkyl, cycloalkenyl, heterocyclyl or heterocyclenyl moiety is optionally fused with an aryl or heteroaryl ring, and the ring moiety resulting from the fusion is optionally substituted with 1-5 independently selected R$^{21}$ substituents; or (iv) R$^6$ and either R$^3$ or R$^4$ of the —C(R$^3$)(R$^4$)— G moiety, are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected R$^{21}$ substituents, (b) said heterocyclyl moiety is optionally substituted with 1-5 independently selected R$^{21}$ substituents, and (c) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected R$^{21}$ substituents; or (v) R$^6$ and R$^{13}$ of the —N(R$^{13}$)— G moiety, are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected R$^{21}$ substituents, (b) said heterocyclyl moiety is optionally substituted with 1-5 independently selected R$^{21}$ substituents, and (c) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; and W is selected from the group consisting of a bond, —O—, —C(O)—, —S—, —S(O)—, —S(O$_2$)—, and —C($R^{11}$)($R^{12}$)—;

G is selected from the group consisting of —C($R^3$)($R^4$)—, —C(O)—, —S—, —S(O)—, —S(O$_2$)—, —C(O)—O—, and —N($R^{13}$)—;

V is selected from the group consisting of a bond, —O—, —C(O)— and —N($R^{14}$)—;

$R^1$ (when $R^1$ is not joined to $R^2$), $R^2$ (when $R^2$ is not joined to $R^1$ or $R^6$), $R^5$, $R^6$ (when $R^6$ is not joined to $R^2$), and $R^7$ can be the same or different, each being independently selected from the group consisting of H, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below;

or, alternatively, $R^1$ (when $R^1$ is not joined to $R^2$) and $R^8$ are taken together to form a bond (i.e., there is a triple bond between the carbon atom to which $R^1$ was bonded to and the carbon to which $R^8$ was bonded to, i.e., the compound of formula I is a compound of formula IIA:

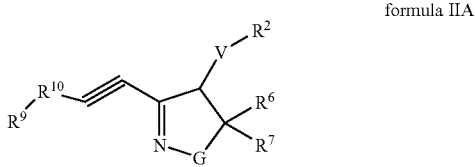

formula IIA and $R^2$, $R^5$, $R^6$, and $R^7$ are as defined above, and $R^3$, $R^4$, $R^{11}$ and $R^{12}$ are as defined below);

$R^3$ is selected from the group consisting of H, halo (and in one example, F), —O$R^{15}$ (and in one example $R^{15}$ is H), —CN, —S$R^{15}$, —N$R^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)C(O)N($R^{16}$)($R^{17}$), —N($R^{15}$)C(O)O$R^{16}$, —C(O)$R^{15}$, —C(O)O$R^{15}$, —C(=NO$R^{15}$)$R^{16}$, —C(O)N($R^{15}$)($R^{16}$), —S(O)N($R^{15}$)($R^{16}$), S(O)$_2$N($R^{15}$)($R^{16}$), —S(O)$R^{15}$, —S(O)$_2R^{15}$, —P(O)(O$R^{15}$)(O$R^{16}$), =NO$R^{15}$, —N$_3$, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below; or $R^3$ and $R^6$ taken together form a bond (i.e., $R^3$ and $R^6$ form a bond between G and the carbon to which $R^6$ is bound), provided that when $R^3$ and $R^6$ form a bond: (1) W is not a bond, (2) $R^2$ and $R^6$ are not joined together to form a cycloalkyl, cycloalkenyl, heterocyclyl or heterocyclenyl moiety (as described in (ii) and (iii) above) (3) $R^6$ and either $R^3$ or $R^4$ of the —C($R^3$)($R^4$)— G moiety are not joined together to form a cycloalkyl, cycloalkenyl, heterocyclyl or heterocyclenyl moiety (as described in (iv) above), and (4) $R^6$ and $R^{13}$ of the —N($R^{13}$)— G moiety are not joined together to form a heterocyclyl or heterocyclenyl moiety (as described in (v) above);

$R^4$, $R^{11}$ and $R^{12}$ can be the same or different, each being independently selected from the group consisting of H, halo (and in one example, F), —O$R^{15}$ (and in one example $R^{15}$ is H), —CN, —S$R^{15}$, —N$R^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)O$R^{16}$, —C(O)$R^{15}$, —C(O)O$R^{15}$, —C(=NO$R^{15}$)$R^{16}$, —C(O)N($R^{15}$)($R^{16}$), —S(O)N($R^{15}$)($R^{16}$), —S(O)$_2$N($R^{15}$)($R^{16}$), —S(O)$R^{15}$, —S(O)$_2R^{15}$, —P(O)(O$R^{15}$)(O$R^{16}$), =NO$R^{15}$, —N$_3$, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below, provided that when one of $R^3$ or $R^4$ is selected from the group consisting of: —O$R^{15}$, —CN, —S$R^{15}$, —N$R^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)O$R^{16}$, —S(O)N($R^{15}$)($R^{16}$), —S(O)$_2$N($R^{15}$)($R^{16}$), —S(O)$R^{15}$, —S(O)$_2R^{15}$, —P(O)(O$R^{15}$)(O$R^{16}$), =NO$R^{15}$, and —N$_3$, then the other is not selected from the group consisting of: —O$R^{15}$, —CN, —S$R^{15}$, and —N$R^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)O$R^{16}$, —S(O)N($R^{15}$)($R^{16}$), —S(O)$_2$N($R^{15}$)($R^{16}$), —S(O)$R^{15}$, —S(O)$_2R^{15}$, —P(O)(O$R^{15}$)(O$R^{16}$), =NO$R^{15}$, and —N$_3$ (i.e., if one of $R^3$ or $R^4$ is —O$R^{15}$, —CN, —S$R^{15}$, —N$R^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$) —N($R^{15}$)S(O)N($R^{16}$)($R^{17}$), —N($R^{15}$)C(O)N($R^{16}$)($R^{17}$), —N($R^{15}$)C(O)O$R^{16}$, —S(O)N($R^{15}$)($R^{16}$), —S(O)$_2$N($R^{15}$)($R^{16}$), —S(O)$R^{15}$, —S(O)$_2R^{15}$, —P(O)(O$R^{15}$)(O$R^{16}$), =NO$R^{15}$, or —N$_3$, then the other one is not —O$R^{15}$, —CN, —S$R^{15}$, and —N$R^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)O$R^{16}$, —S(O)N($R^{15}$)($R^{16}$), —S(O)$_2$N($R^{15}$)($R^{16}$), —S(O)$R^{15}$, —S(O)$_2R^{15}$, —P(O)(O$R^{15}$)(O$R^{16}$), =NO$R^{15}$, or —N$_3$);

provided that when one of $R^{11}$ or $R^{12}$ is selected from the group consisting of: —O$R^{15}$, —CN, —S$R^{15}$, —N$R^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)O$R^{16}$, —S(O)N($R^{15}$)($R^{16}$), —S(O)$_2$N($R^{15}$)($R^{16}$), —S(O)$R^{15}$, —S(O)$_2R^{15}$, —P(O)(O$R^{15}$)(O$R^{16}$), =NO$R^{15}$, and —N$_3$, then the other is not selected from the group consisting of: —O$R^{15}$, —CN, —S$R^{15}$, —N$R^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)O$R^{16}$, —S(O)N($R^{15}$)($R^{16}$), —S(O)$_2$N($R^{15}$)($R^{16}$), —S(O)$R^{15}$, —S(O)$_2R^{15}$, —P(O)(O$R^{15}$)(O$R^{16}$), =NO$R^{15}$, and —N$_3$ (i.e., if one of $R^{11}$ or $R^{12}$ is —O$R^{15}$, —CN, —S$R^{15}$, —N$R^{15}R^{16}$, —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)O$R^{16}$, —S(O)N($R^{15}$)($R^{16}$), —S(O)$_2$N($R^{15}$)($R^{16}$), —S(O)

$R^{15}$, —S(O)$_2R^{15}$, —P(O)(OR$^{15}$)(OR$^{16}$), =NOR$^{15}$, or —N$_3$, then the other is not —OR$^{15}$, —CN, —SR$^{15}$, —NR$^{15}R^{16}$, —N(R$^{15}$)C(O)R$^{16}$, —N(R$^{15}$)S(O)R$^{16}$, —N(R$^{15}$)S(O)$_2R^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —N(R$^{15}$)C(O)OR$^{16}$, —S(O)N(R$^{15}$)(R$^{16}$), —S(O)$_2$N(R$^{15}$)(R$^{16}$), —S(O)R$^{15}$, —S(O)$_2R^{15}$, —P(O)(OR$^{15}$)(OR$^{16}$), =NOR$^{15}$, or —N$_3$);

$R^8$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, with each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- being optionally substituted with 1-3 independently selected R$^{21}$ substituents;

$R^9$ is selected from the group consisting of alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, -, wherein each R$^9$ group is optionally substituted with 1-3 independently selected R$^{21}$ substituents;

$R^{10}$ is selected from the group consisting of a bond, alkyl-, alkenyl-, alkynyl-, aryl-, arylalkyl-, alkylaryl, cycloalkyl-, cycloalkylalkyl-, heteroaryl-, heteroarylalkyl-, heterocyclyl-, heterocyclylalkyl- and the moieties.

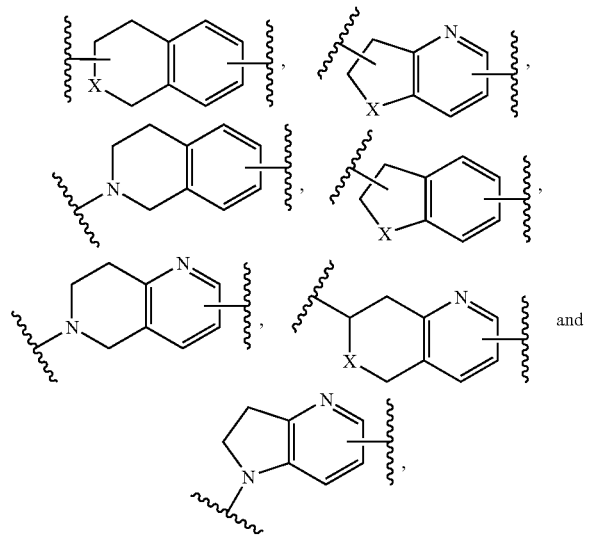

where X is O, N(R$^{14}$) or S;
wherein each R$^{10}$ group (except for the bond) is optionally substituted with 1-3 independently selected R$^{21}$ substituents;

$R^{13}$ is independently selected from the group consisting of H, alkyl, arylalkyl-, heteroarylalkyl-, cycloalkylalkyl-, heterocycloalkylalkyl-, arylcycloalkylalkyl-, heteroarylcycloalkylalkyl-, arylheterocycloalkylalkyl-, heteroarylheterocycloalkylalkyl-, cycloalkyl, arylcycloalkyl-, heteroarylcycloalkyl-, heterocycloalkyl-, arylheterocycloalkyl-, heteroarylheterocycloalkyl-, alkenyl, arylalkenyl-, cycloalkenyl, arylcycloalkenyl-, heteroarylcycloalkenyl-, heterocycloalkenyl-, arylheterocycloalkenyl-, heteroarylheterocycloalkenyl-, alkynyl, arylalkynyl-, aryl, cycloalkylaryl-, heterocycloalkylaryl-, heterocycloalkenylaryl-, heteroaryl, cycloalkylheteroaryl-, heterocycloalkylheteroaryl-, cycloalkenylaryl-, and heterocycloalkenylaryl-, —OR$^{15}$, —CN, —C(O)R$^8$, —C(O)OR$^9$, —S(O)R$^{10}$, —S(O)$_2R^{10}$, —C(O)N(R$^{11}$)(R$^{12}$), —S(O)N(R$^{11}$)(R$^{12}$), —S(O)$_2$N(R$^{11}$)(R$^{12}$), —NO$_2$, —N=C(R$^8$)$_2$ and —N(R$^8$)$_2$; and wherein said R$^{13}$ alkyl, arylalkyl-, heteroarylalkyl-, cycloalkylalkyl-, heterocycloalkylalkyl-, arylcycloalkylalkyl-, heteroarylcycloalkylalkyl-, arylheterocycloalkylalkyl-, heteroarylheterocycloalkylalkyl-, cycloalkyl, arylcycloalkyl-, heteroarylcycloalkyl-, heterocycloalkyl, arylheterocycloalkyl-, heteroarylheterocycloalkyl-, alkenyl, arylalkenyl-, cycloalkenyl, arylcycloalkenyl-, heteroarylcycloalkenyl-, heterocycloalkenyl-, arylheterocycloalkenyl-, heteroarylheterocycloalkenyl-, alkynyl, arylalkynyl-, aryl, cycloalkylaryl-, heterocycloalkylaryl-, heterocycloalkenylaryl-, heteroaryl, cycloalkylheteroaryl-, heterocycloalkylheteroaryl-, cycloalkenylaryl-, and heterocycloalkenylaryl- groups are optionally substituted with 1 to 5 groups independently selected from the group consisting of: alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —CH(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —CH$_2$—N(R$^{15}$)C(O)N(R$^{16}$)(R$^{17}$), —CH$_2$—R$^{15}$; —CH$_2$N(R$^{15}$)(R$^{16}$), —N(R$^{15}$)S(O)R$^{16}$, —N(R$^{15}$)S(O)$_2R^{16}$, —CH$_2$—N(R$^{15}$)S(O)$_2R^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —S(O)R$^{15}$, =NOR$^{15}$, —N$_3$, —NO$_2$ and —S(O)$_2R^{15}$;

$R^{14}$ is selected from the group consisting of H, alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, —CN, —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$), wherein each of said alkyl, alkenyl, alkynyl, cycloalkyl, cycloalkylalkyl-, cycloalkenyl, heterocyclyl, heterocyclylalkyl-, aryl, arylalkyl-, heteroaryl, and heteroarylalkyl- is optionally substituted with 1-5 independently selected R$^{21}$ substitutents;

$R^{15}$, $R^{16}$ and $R^{17}$ are independently selected from the group consisting of H, alkyl, alkenyl, alkynyl, cycloalkyl, cycloalkylalkyl-, heterocyclyl, heterocyclylalkyl-, aryl, arylalkyl, heteroaryl, heteroarylalkyl-, arylcycloalkyl-, arylheterocyclyl-, R$^{18}$)$_r$-alkyl, R$^{18}$)$_r$-cycloalkyl, R$^{18}$)$_r$-cycloalkylalkyl-, R$^{18}$)$_r$-heterocyclyl, R$^{18}$)$_r$-heterocyclylalkyl-, R$^{18}$)$_r$-aryl, R$^{18}$)$_r$-arylalkyl, R$^{18}$)$_r$-heteroaryl and R$^{18}$)$_r$-heteroarylalkyl-, wherein r is 1-5;

Each R$^{18}$ is independently selected from the group consisting of alkyl, alkenyl, alkynyl, aryl, arylalkyl-, arylalkenyl-, arylalkynyl-, —NO$_2$, halo, heteroaryl, HO-alkyoxyalkyl, —CF$_3$, —CN, alkyl-CN, —C(O)R$^{19}$, —C(O)OH, —C(O)OR$^{19}$, —C(O)NHR$^{20}$, —C(O)NH$_2$, —C(O)NH$_2$—C(O)N(alkyl)$_2$, —C(O)N(alkyl)(aryl), —C(O)N(alkyl)(heteroaryl), —SR$^{19}$, —S(O)$_2R^{20}$, —S(O)NH$_2$, —S(O)NH(alkyl), —S(O)N(alkyl)(alkyl), —S(O)NH(aryl), —S(O)$_2$NH$_2$, —S(O)$_2$NHR$^{19}$, —S(O)$_2$NH(heterocyclyl), —S(O)$_2$N(alkyl)$_2$, —S(O)$_2$N(alkyl)(aryl), —OCF$_3$, —OH, —OR$^{29}$, heterocyclyl, —O-cycloalkylalkyl, —O-heterocyclylalkyl, —NH$_2$, —NHR$^{20}$, —N(alkyl)$_2$, —N(arylalkyl)$_2$, —N(arylalkyl)-(heteroarylalkyl), —NHC(O)R$^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2R^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or, alternatively, two $R^{18}$ moieties on adjacent carbons can be linked together to form:

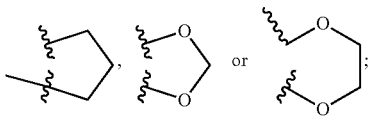

$R^{19}$ is selected from the group consisting of alkyl, cycloalkyl, aryl, arylalkyl- and heteroarylalkyl-;

$R^{29}$ is selected from the group consisting of alkyl, cycloalkyl, aryl, halo substituted aryl, arylalkyl-, heteroaryl or heteroarylalkyl-;

Each $R^{21}$ group is independently selected from the group consisting of alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, halo, —CN, —$OR^{15}$, —C(O)$R^{15}$, —C(O)O$R^{15}$, —C(O)N($R^{15}$)($R^{16}$), —S$R^{15}$, —S(O)N($R^{15}$)($R^{16}$), —CH($R^{15}$)($R^{16}$), —S(O)$_2$N($R^{15}$)($R^{16}$), —C(=NO$R^{15}$)$R^{16}$, —P(O)(O$R^{15}$)(O$R^{16}$), —N($R^{15}$)($R^{16}$), -alkyl-N($R^{15}$)($R^{16}$), —N($R^{15}$)C(O)$R^{16}$, —CH$_2$—N($R^{15}$)C(O)$R^{16}$, —CH$_2$—N($R^{15}$)C(O)N($R^{16}$)($R^{17}$), —CH$_2$—$R^{15}$; —CH$_2$N($R^{15}$)($R^{16}$), —N($R^{15}$)S(O)$R^{16}$, —N($R^{15}$)S(O)$_2R^{16}$, —CH$_2$—N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —CH$_2$—N($R^{15}$)C(O)N($R^{16}$)($R^{17}$), —N($R^{15}$)C(O)O$R^{16}$, —CH$_2$—N($R^{15}$)C(O)O$R^{16}$, —S(O)$R^{15}$, =NO$R^{15}$, —N$_3$, —NO$_2$ and —S(O)$_2R^{15}$; and wherein each of the $R^{21}$ alkyl, cycloalkenyl, cycloalkyl, cycloalkylalkyl-, heterocyclyl, heterocyclylalkyl-, aryl, arylalkyl-, heteroaryl, heteroarylalkyl-, alkenyl and alkynyl groups is optionally substituted with 1 to 5 independently selected $R^{22}$ groups; and Each $R^{22}$ is independently selected from the group consisting of alkyl, cycloalkyl, cycloalkenyl, heterocyclyl, aryl, heteroaryl, halo, —CF$_3$, —CN, —O$R^{15}$, —C(O)$R^{15}$, —C(O)O$R^{15}$, -alkyl-C(O)O$R^{15}$, C(O)N($R^{15}$)($R^{16}$), —S$R^{15}$, —S(O)N($R^{15}$)($R^{16}$), —S(O)$_2$N($R^{15}$)($R^{16}$), —C(=NO$R^{15}$)$R^{16}$, —P(O)(O$R^{15}$)(O$R^{16}$), —N($R^{15}$)($R^{16}$), alkyl-N($R^{15}$)($R^{16}$), —N($R^{15}$)C(O)$R^{16}$, —CH$_2$—N($R^{15}$)C(O)$R^{16}$, —N($R^{15}$)S(O)$R^{16}$, —N($R^{15}$)S(O)$_2R^{16}$, —CH$_2$—N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —CH$_2$—N($R^{15}$)C(O)N($R^{16}$), ($R^{17}$), —N($R^{15}$)C(O)O$R^{16}$, —CH$_2$—N($R^{15}$)C(O)O$R^{16}$, —N$_3$, =NO$R^{15}$, —NO$_2$, —S(O)$R^{15}$ and —S(O)$_2R^{15}$.

In another embodiment, this invention discloses a compound of formula I, or pharmaceutically acceptable salts, solvates, esters or prodrugs of said compound, said compound having the general structure of formula IC:

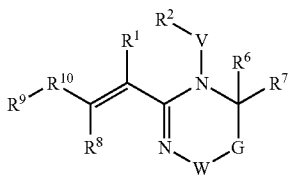

Formula IC wherein:

either (i) $R^1$ and $R^2$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; or (ii) $R^2$ and $R^6$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; or (iii) $R^1$ and $R^2$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; and $R^2$ and $R^6$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; and W is selected from the group consisting of a bond, —O—, —C(O)—, —S—, —S(O)—, —S(O$_2$)—, and —C($R^{11}$)($R^{12}$)—;

G is selected from the group consisting of —C($R^3$)($R^4$)—, —C(O)—, —S—, —S(O)—, —S(O$_2$)—, —C(O)—O—, and —N($R^{13}$)—;

V is selected from the group consisting of a bond, —O—, and —N($R^{14}$)—;

$R^1$ (when $R^1$ is not joined to $R^2$), $R^2$ (when $R^2$ is not joined to $R^1$ or $R^6$), $R^3$, $R^4$, $R^5$, $R^6$ (when $R^6$ is not joined to $R^2$), $R^7$, $R^{11}$ and $R^{12}$ can be the same or different, each being independently selected from the group consisting of H, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below;

$R^{14}$ is selected from the group consisting of H, alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, —C(O)$R^{15}$, —C(O)O$R^{15}$, —C(O)N($R^{15}$)($R^{16}$), —S(O)N($R^{15}$)($R^{16}$), —S(O)$_2$N($R^{15}$)($R^{16}$), —C(=NO$R^{15}$)$R^{16}$, and —P(O)(O$R^{15}$)(O$R^{16}$);

$R^8$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, with each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- being unsubstituted or optionally independently substituted with 1-3 substituents which can be the same or different, each substituent being independently selected from the group consisting of the moieties shown below;

$R^{10}$ is selected from the group consisting of a bond, alkyl-, alkenyl- and alkynyl-, aryl-, arylalkyl-, alkylaryl-, cycloalkyl-, cycloalkylalkyl-, heteroaryl-, heteroarylalkyl-, heterocyclyl-, heterocyclylalkyl- and the moieties:

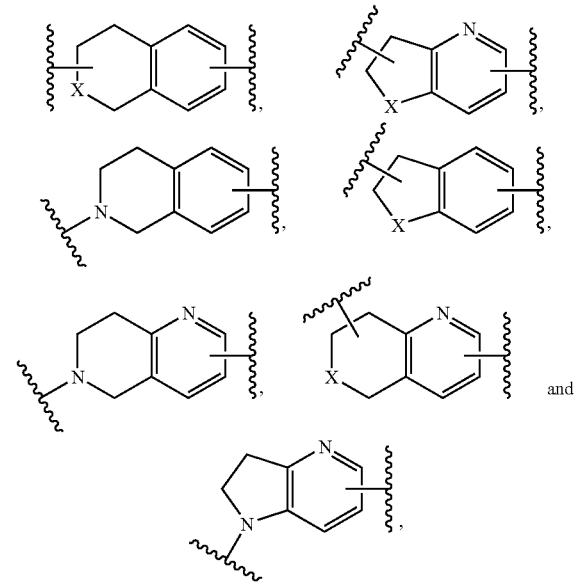

where X is O, $N(R^{14})$ or S;
wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl-heterocyclylalkyl- for $R^{10}$ as well as the above-noted moieties for $R^{10}$ can be unsubstituted or optionally independently substituted with 1-3 substituents which can be the same or different, each being independently selected from the group consisting of the moieties shown below; and $R^9$ is selected from the group consisting of alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-3 substituents which can be the same or different, each substituent being independently selected from the group consisting of the moieties shown below, $R^{15}$, $R^{16}$ and $R^{17}$ are independently selected from the group consisting of H, alkyl, alkenyl, alkynyl, cycloalkyl, cycloalkylalkyl-, heterocyclyl, heterocyclylalkyl-, aryl, arylalkyl-, heteroaryl, heteroarylalkyl-, arylcycloalkyl-, arylheterocyclyl-, $R^{18}$-alkyl, $R^{18}$-cycloalkyl, $R^{18}$-cycloalkylalkyl, $R^{18}$-heterocyclyl, $R^{18}$-heterocyclylalkyl, $R^{18}$-aryl, $R^{18}$-arylalkyl, $R^{18}$-heteroaryl and $R^{18}$-heteroarylalkyl;

$R^{18}$ is 1-5 substituents independently selected from the group consisting of alkyl, alkenyl, alkynyl, aryl, arylalkyl-, arylalkenyl-, arylalkynyl-, —NO₂, halo, heteroaryl, HO-alkyoxyalkyl, —CF₃, —CN, alkyl-CN, —C(O)R¹⁹, —C(O)OH, —C(O)OR¹⁹, —C(O)NHR²⁰, —C(O)NH₂, —C(O)NH₂—C(O)N(alkyl)₂, —C(O)N(alkyl)(aryl), —C(O)N(alkyl)(heteroaryl), —SR¹⁹, —S(O)₂R²⁰, —S(O)NH₂, —S(O)NH(alkyl), —S(O)N(alkyl)(alkyl), —S(O)NH(aryl), —S(O)₂NH₂, —S(O)₂NHR¹⁹, —S(O)₂NH(heterocyclyl), —S(O)₂N(alkyl)₂, —S(O)₂N(alkyl)(aryl), —OCF₃, —OH, —OR²⁶, —O-heterocyclyl, —O-cycloalkylalkyl, —O-heterocyclylalkyl, —NH₂, —NHR²⁰, —N(alkyl)₂, —N(arylalkyl)₂, —N(arylalkyl)-(heteroarylalkyl), —NHC(O)R²⁰, —NHC(O)NH₂, —NHC(O)NH(alkyl), —NHC(O)N(alkyl)(alkyl), —N(alkyl)C(O)NH(alkyl), —N(alkyl)C(O)N(alkyl)(alkyl), —NHS(O)₂R²⁰, —NHS(O)₂NH(alkyl), —NHS(O)₂N(alkyl)(alkyl), —N(alkyl)S(O)₂NH(alkyl) and —N(alkyl)S(O)₂N(alkyl)(alkyl);

or, alternately, two $R^{18}$ moieties on adjacent carbons can be linked together to form:

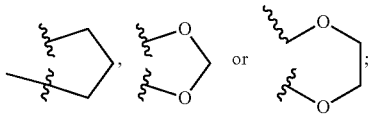

$R^{19}$ is alkyl, cycloalkyl, aryl, arylalkyl or heteroarylalkyl;
$R^{20}$ is alkyl, cycloalkyl, aryl, halo substituted aryl, arylalkyl, heteroaryl or heteroarylalkyl;
wherein each of the alkyl, cycloalkyl, cycloalkenyl, cycloalkylalkyl, heterocyclyl, heterocyclylalkyl, aryl, arylalkyl, alkylaryl-, heteroaryl, heteroarylalkyl, alkenyl and alkynyl groups in $R^1$, $R^2$, $R^1$-$R^2$, $R^2$-$R^6$, $R^3$, $R^4$, $R^5$, $R^6$, $R^7$, $R^8$, $R^9$, $R^{10}$, $R^{11}$, $R^{12}$ and $R^{14}$ is independently unsubstituted or optionally substituted by 1 to 5 $R^{21}$ groups independently selected from the group consisting of alkyl, alkenyl, alkynyl, cycloalkyl, cycloalkylalky-l, cycloalkenyl, heterocyclyl, heterocyclylalkyl-, aryl, arylalkyl-, heteroaryl, heteroarylalkyl-, halo, —CN, —OR¹⁵, —C(O)R¹⁵, —C(O)OR¹⁵, —C(O)N(R¹⁵)(R¹⁶), —SR¹⁵, —S(O)N(R¹⁵)(R¹⁶), —CH(R¹⁵)(R¹⁶), —S(O)₂N(R¹⁵)(R¹⁶), —C(=NOR¹⁵)R¹⁶, —P(O)(OR¹⁵)(OR¹⁶), —N(R¹⁵)(R¹⁶), -alkyl-N(R¹⁵)(R¹⁶), —N(R¹⁵)C(O)R¹⁶, —CH₂—N(R¹⁵)C(O)R¹⁶, —CH₂—N(R¹⁵)C(O)N(R¹⁶)(R¹⁷), —CH₂—R¹⁵, —CH₂N(R¹⁵)(R¹⁶), —N(R¹⁵)S(O)R¹⁶, —N(R¹⁵)S(O)₂R¹⁶, —CH₂—N(R¹⁵)S(O)₂R¹⁶, —N(R¹⁵)S(O)₂N(R¹⁶)(R¹⁷), —N(R¹⁵)S(O)N(R¹⁶)(R¹⁷), —N(R¹⁵)C(O)N(R¹⁶)(R¹⁷), —CH₂—N(R¹⁵)C(O)N(R¹⁶)(R¹⁷), —N(R¹⁵)C(O)OR¹⁶, —CH₂—N(R¹⁵)C(O)OR¹⁶, —S(O)R¹⁵, =NOR¹⁵, —N₃, —NO₂ and —S(O)₂R¹⁵;
wherein each of the alkyl, cycloalkenyl, cycloalkyl, cycloalkylalkyl-, heterocyclyl, heterocyclylalkyl-, aryl, arylalkyl-, heteroaryl, heteroarylalkyl-, alkenyl and alkynyl groups in $R^{21}$ is independently unsubstituted or substituted by 1 to 5 $R^{22}$ groups independently selected from the group consisting of alkyl, cycloalkyl, cycloalkenyl, heterocyclyl, aryl, heteroaryl, halo, —CF₃, —CN, —OR¹⁵, —C(O)R¹⁵, —C(O)OR¹⁵, -alkyl-C(O)OR¹⁵, C(O)N(R¹⁵)(R¹⁶), —SR¹⁵, —S(O)N(R¹⁵)(R¹⁶), —S(O)₂N(R¹⁵)(R¹⁶), —C(=NOR¹⁵)R¹⁶, —P(O)(OR¹⁵)(OR¹⁶), —N(R¹⁵)(R¹⁶), -alkyl-N(R¹⁵)(R¹⁶), —N(R¹⁵)C(O)R¹⁶, —CH₂—N(R¹⁵)C(O)R¹⁶, —N(R¹⁵)S(O)R¹⁶, —N(R¹⁵)S(O)₂R¹⁶, —CH₂—N(R¹⁵)S(O)₂R¹⁶, —N(R¹⁵)S(O)₂N(R¹⁶)(R¹⁷), —N(R¹⁵)S(O)N(R¹⁶)(R¹⁷), —N(R¹⁵)C(O)N(R¹⁶)(R¹⁷), —CH₂—N(R¹⁵)C(O)N(R¹⁶)(R¹⁷), —N(R¹⁵)C(O)OR¹⁶, —CH₂—N(R¹⁵)C(O)OR¹⁶, —N₃, =NOR¹⁵, —NO₂, —S(O)R¹⁵ and —S(O)₂R¹⁵.

In another embodiment, this invention discloses a compound of formula I, or pharmaceutically acceptable salts, solvates, esters or prodrugs of said compound, said compound having the general structure of formula IC:

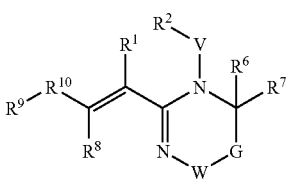

Formula IC wherein:
either
(i) $R^1$ and $R^2$ are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, and (c) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or (ii) $R^2$ and $R^6$ are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, and (c) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or (iii)
  (a) $R^1$ and $R^2$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, and (2) said heterocyclyl moiety is optionally substituted with 1-5 independently selected $R^{21}$ substituents, and
  (b) $R^2$ and $R^6$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, and (2) said heterocyclyl moiety is optionally substituted with 1-5 independently selected $R^{21}$ substituents; and
  (c) said $R^2$ and $R^6$ cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or (iv) $R^6$ and either $R^3$ or $R^4$ of the —C($R^3$)($R^4$)— G moiety, are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, and (c) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or (v) $R^6$ and $R^{13}$ of the —N($R^{13}$)— G moiety, are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, and (c) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; and W is selected from the group consisting of a bond, —O—, —C(O)—, —S—, —S(O)—, —S($O_2$)—, and —C($R^{11}$)($R^{12}$)—;

G is selected from the group consisting of —C($R^3$)($R^4$)—, —C(O)—, —S—, —S(O)—, —S($O_2$)—, —C(O)—O—, and —N($R^{13}$)—;

V is selected from the group consisting of a bond, —O—, —C(O)— and —N($R^{14}$)—;

$R^1$ (when $R^1$ is not joined to $R^2$), $R^2$ (when $R^2$ is not joined to $R^1$ or $R^6$), $R^5$, $R^6$ (when $R^6$ is not joined to $R^2$), and $R^7$ can be the same or different, each being independently selected from the group consisting of H, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below;

or, alternatively, $R^1$ (when $R^1$ is not joined to $R^2$) and $R^8$ are taken together to form a bond (i.e., there is a triple bond between the carbon atom to which $R^1$ was bonded to and the carbon to which $R^8$ was bonded to, i.e., the compound of formula I is a compound of formula II:

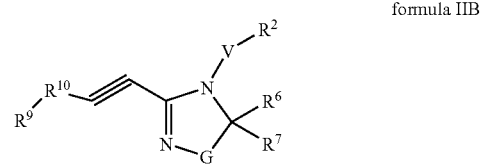

formula IIB and $R^2$, $R^5$, $R^6$, and $R^7$ are as defined above, and $R^3$, $R^4$, $R^{11}$ and $R^{12}$ are as defined below);

$R^3$ is selected from the group consisting of H, halo (and in one example, F), —O$R^{15}$ (and in one example $R^{15}$ is H), —CN, —S$R^{15}$, —N$R^{15}R^{16}$, —N($R^{15}$)C(O)$R^{16}$, —N($R^{15}$)S(O)$R^{16}$, —N($R^{15}$)S($O_2$)$R^{16}$, —N($R^{15}$)S($O_2$)N($R^{16}$)($R^{17}$), —N($R^{15}$)S(O)N($R^{16}$)($R^{17}$), —N($R^{15}$)C(O)N($R^{16}$)($R^{17}$), —N($R^{15}$)C(O)O$R^{16}$, —C(O)$R^{15}$, —C(O)O$R^{15}$, —C(=NO$R^{15}$)$R^{16}$, —C(O)N($R^{15}$)($R^{16}$), —S(O)N($R^{15}$)($R^{16}$), S($O_2$)N($R^{15}$)($R^{16}$), —S(O)$R^{15}$, —S($O_2$)$R^{15}$, —P(O)(O$R^{15}$)(O$R^{16}$), =NO$R^{15}$, —$N_3$, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below; or $R^3$ and $R^6$ taken together form a bond (i.e., $R^3$ and $R^6$ form a bond between G and the carbon to which $R^6$ is bound), provided that when $R^3$ and $R^6$ form a bond: (1) W is not a bond, (2) $R^2$ and $R^6$ are not joined together to form a cycloalkyl, cycloalkenyl, heterocyclyl or heterocyclenyl moiety (as described in (ii) and (iii) above) (3) $R^6$ and either $R^3$ or $R^4$ of the —C($R^3$)($R^4$)— G moiety are not joined together to form a cycloalkyl, cycloalkenyl, heterocyclyl or heterocyclenyl moiety (as described in (iv) above), and (4) $R^6$ and $R^{13}$ of the —N(R$^{13}$)— G moiety are not joined together to form a heterocyclyl or heterocyclenyl moiety (as described in (v) above);

R$^4$, R$^{11}$ and R$^{12}$ can be the same or different, each being independently selected from the group consisting of H, halo (and in one example, F), —OR$^{15}$ (and in one example R$^{15}$ is H), —CN, —SR$^{15}$, —NR$^{15}$R$^{16}$, —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$) —N(R$^{15}$)C(O)OR$^{16}$, —C(O)R$^{15}$, —C(O)OR$^{15}$, —C(=NOR$^{15}$)R$^{16}$, —C(O)N(R$^{15}$)(R$^{16}$), —S(O)N(R$^{15}$)(R$^{16}$), —S(O)$_2$N(R$^{15}$)(R$^{16}$), —S(O)R$^{15}$, —S(O)$_2$R$^{15}$, —P(O)(OR$^{15}$)(OR$^{16}$), =NOR$^{15}$, —N$_3$, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below, provided that when one of R$^3$ or R$^4$ is selected from the group consisting of: —OR$^{15}$, —CN, —SR$^{15}$, —NR$^{15}$R$^{16}$, —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —N(R$^{15}$)C(O)OR$^{16}$, —S(O)N(R$^{15}$)(R$^{16}$), —S(O)$_2$N(R$^{15}$)(R$^{16}$), —S(O)R$^{15}$, —S(O)$_2$R$^{15}$, —P(O)(OR$^{15}$)(OR$^{16}$), =NOR$^{15}$, and —N$_3$, then the other is not selected from the group consisting of: —OR$^{15}$, —CN, —SR$^{15}$, and —NR$^{15}$R$^{16}$, —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —N(R$^{15}$)C(O)OR$^{16}$, —S(O)N(R$^{15}$)(R$^{16}$), —S(O)$_2$N(R$^{15}$)(R$^{16}$), —S(O)R$^{15}$, —S(O)$_2$R$^{15}$, —P(O)(OR$^{15}$)(OR$^{16}$), =NOR$^{15}$, and —N$_3$ (i.e., if one of R$^3$ or R$^4$ is —OR$^{15}$, —CN, —SR$^{15}$, —NR$^{15}$R$^{16}$, —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —N(R$^{15}$)C(O)OR$^{16}$, —S(O)N(R$^{15}$)(R$^{16}$), —S(O)$_2$N(R$^{15}$)(R$^{16}$), —S(O)R$^{15}$, —S(O)$_2$R$^{15}$, —P(O)(OR$^{15}$)(OR$^{16}$), =NOR$^{15}$, or —N$_3$, then the other one is not —OR$^{15}$, —CN, —SR$^{15}$, and —NR$^{15}$R$^{16}$, —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —N(R$^{15}$)C(O)OR$^{16}$, —S(O)N(R$^{15}$)(R$^{16}$), —S(O)$_2$N(R$^{15}$)(R$^{16}$), —S(O)R$^{15}$, —S(O)$_2$R$^{15}$, —P(O)(OR$^{15}$)(OR$^{16}$), =NOR$^{15}$, or —N$_3$);

provided that when one of R$^{11}$ or R$^{12}$ is selected from the group consisting of: —OR$^{15}$, —CN, —SR$^{15}$, —NR$^{15}$R$^{16}$, —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —N(R$^{15}$)C(O)OR$^{16}$, —S(O)N(R$^{15}$)(R$^{16}$), —S(O)$_2$N(R$^{15}$)(R$^{16}$), —S(O)R$^{15}$, —S(O)$_2$R$^{15}$, —P(O)(OR$^{15}$)(OR$^{16}$), =NOR$^{15}$, and —N$_3$, then the other is not selected from the group consisting of: —OR$^{15}$, —CN, —SR$^{15}$, —NR$^{15}$R$^{16}$, —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —N(R$^{15}$)C(O)OR$^{16}$, —S(O)N(R$^{15}$)(R$^{16}$), —S(O)$_2$N(R$^{15}$)(R$^{16}$), —S(O)R$^{15}$, —S(O)$_2$R$^{15}$, —P(O)(OR$^{15}$)(OR$^{16}$), =NOR$^{15}$, and —N$_3$ (i.e., if one of R$^{11}$ or R$^{12}$ is —OR$^{15}$, —CN, —SR$^{15}$, —NR$^{15}$R$^{16}$, —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —S(O)N(R$^{15}$)(R$^{16}$), —S(O)$_2$N(R$^{15}$)(R$^{16}$), —S(O)R$^{15}$, —S(O)$_2$R$^{15}$, —P(O)(OR$^{15}$)(OR$^{16}$), =NOR$^{15}$, or —N$_3$, then the other is not —OR$^{15}$, —CN, —SR$^{15}$, —NR$^{15}$R$^{16}$, —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —N(R$^{15}$)C(O)OR$^{16}$, —S(O)N(R$^{15}$)(R$^{16}$), —S(O)$_2$N(R$^{15}$)(R$^{16}$), —S(O)R$^{15}$, —S(O)$_2$R$^{15}$, —P(O)(OR$^{15}$)(OR$^{16}$), =NOR$^{15}$, or —N$_3$);

R$^8$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, with each of said alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl- being optionally substituted with 1-3 independently selected R$^{21}$ substituents;

R$^9$ is selected from the group consisting of alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-3 independently selected R$^{21}$ substituents which can be the same or different, each substituent being independently selected from the group consisting of the moieties shown below, R$^{10}$ is selected from the group consisting of a bond, alkyl-, alkenyl-, alkynyl-, aryl-, arylalkyl-, alkylaryl-, cycloalkyl-, cycloalkylalkyl-, heteroaryl-, heteroarylalkyl-, heterocyclyl-, heterocyclylalkyl- and the moieties:

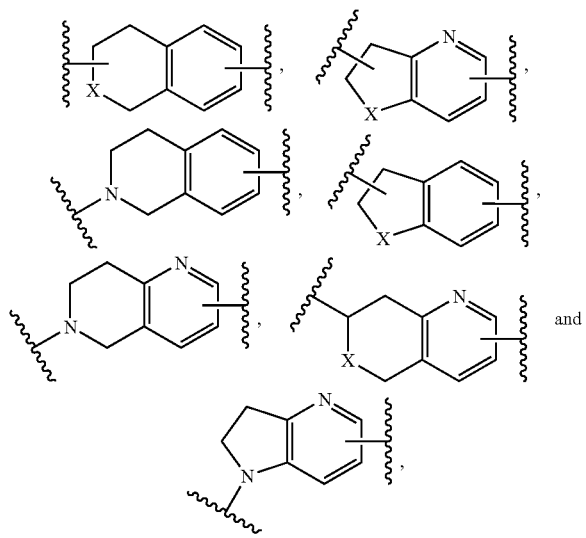

where X is O, N(R$^{14}$) or S;
wherein each of said R$^{10}$ moieties (except the bond) is optionally substituted with 1-3 independently selected R$^{21}$ substituents which can be the same or different, each being independently selected from the group consisting of the moieties shown below; and R$^{14}$ is selected from the group consisting of H, alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$), wherein each of said alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl is optionally substituted with 1-5 independently selected $R^{21}$ substitutents;

$R^{15}$, $R^{16}$ and $R^{17}$ are independently selected from the group consisting of H, alkyl, alkenyl, alkynyl, cycloalkyl, cycloalkylalkyl-, heterocyclyl, heterocyclylalkyl-, aryl, arylalkyl-, heteroaryl, heteroarylalkyl-, arylcycloalkyl-, arylheterocyclyl-, $(R^{18})_r$-alkyl, $(R^{18})_r$-cycloalkyl, $(R^{18})_r$-cycloalkylalkyl, $(R^{18})_r$-heterocyclyl, $(R^{18})_r$-heterocyclylalkyl, $(R^{18})_r$-aryl, $(R^{18})_r$-arylalkyl, $(R^{18})_r$-heteroaryl and $(R^{18})_r$-heteroarylalkyl, wherein r is 1-5;

Each $R^{18}$ is independently selected from the group consisting of alkyl, alkenyl, alkynyl, aryl, arylalkyl-, arylalkenyl-, arylalkynyl-, —$NO_2$, halo, heteroaryl, HO-alkyoxyalkyl, —$CF_3$, —CN, alkyl-CN, —C(O)$R^{19}$, —C(O)OH, —C(O)O$R^{19}$, —C(O)NH$R^{20}$, —C(O)$NH_2$, —C(O)$NH_2$—C(O)N(alkyl)$_2$, —C(O)N(alkyl)(aryl), —C(O)N(alkyl)(heteroaryl), —S$R^{19}$, —S(O)$_2R^{20}$, —S(O)$NH_2$, —S(O)NH(alkyl), —S(O)$_2$N(alkyl)(alkyl), —S(O)NH(aryl), —S(O)$_2NH_2$, —S(O)$_2NHR^{19}$, —S(O)$_2$NH(heterocyclyl), —S(O)$_2$N(alkyl)$_2$, —S(O)$_2$N(alkyl)(aryl), —$OCF_3$, —OH, —O$R^{20}$, heterocyclyl, —O-cycloalkylalkyl, —O-heterocyclylalkyl, —$NH_2$, —$NHR^{29}$, —N(alkyl)$_2$, —N(arylalkyl)$_2$, —N(arylalkyl)-(heteroarylalkyl), —NHC(O)$R^{20}$, —NHC(O)$NH_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2R^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or, alternately, two $R^{18}$ moieties on adjacent carbons can be linked together to form:

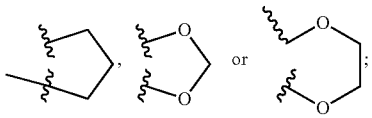

$R^{19}$ is selected from the group consisting of alkyl, cycloalkyl, aryl, arylalkyl- and heteroarylalkyl-;

$R^{20}$ is selected from the group consisting of alkyl, cycloalkyl, aryl, halo substituted aryl, arylalkyl-, heteroaryl and heteroarylalkyl-;

Each $R^{21}$ group independently selected from the group consisting of alkyl, alkenyl, alkynyl, cycloalkyl, cycloalkylalky-I, cycloalkenyl, heterocyclyl, heterocyclylalkyl-, aryl, arylalkyl-, heteroaryl, heteroarylalkyl-, halo, —CN, —O$R^{15}$, —C(O)$R^{15}$, —C(O)O$R^{15}$, —C(O)N($R^{15}$)($R^{16}$), —S$R^{15}$, —S(O)N($R^{15}$)($R^{16}$), —CH($R^{15}$)($R^{16}$), —S(O)$_2$N($R^{15}$)($R^{16}$), —C(=NO$R^{15}$)$R^{16}$, —P(O)(O$R^{15}$)(O$R^{16}$), —N($R^{15}$)($R^{16}$), -alkyl-N($R^{15}$)($R^{16}$), —N($R^{15}$)C(O)$R^{16}$, —$CH_2$—N($R^{15}$)C(O)$R^{16}$, —$CH_2$—N($R^{15}$)C(O)N($R^{16}$)($R^{17}$), —$CH_2$—$R^{15}$, —$CH_2$N($R^{15}$)($R^{16}$), —N($R^{15}$)S(O)$R^{16}$, —N($R^{15}$)S(O)$_2R^{16}$, —$CH_2$—N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —$CH_2$—N($R^{15}$)C(O)N($R^{16}$)($R^{17}$), —N($R^{15}$)C(O)O$R^{16}$, —$CH_2$—N($R^{15}$)C(O)O$R^{16}$, —S(O)$R^{15}$, =NO$R^{15}$, —$N_3$, —$NO_2$ and —S(O)$_2R^{15}$; and wherein each of the $R^{21}$ alkyl, cycloalkenyl, cycloalkyl, cycloalkylalkyl-, heterocyclyl, heterocyclylalkyl-, aryl, arylalkyl-, heteroaryl, heteroarylalkyl-, alkenyl and alkynyl groups is optionally substituted with 1 to 5 independently selected $R^{22}$ groups; and Each $R^{22}$ is independently selected from the group consisting of alkyl, cycloalkyl, cycloalkenyl, heterocyclyl, aryl, heteroaryl, halo, —$CF_3$, —CN, —O$R^{15}$, —C(O)$R^{15}$, —C(O)O$R^{15}$, -alkyl-C(O)O$R^{15}$, C(O)N($R^{15}$)($R^{16}$), —S$R^{15}$, —S(O)N($R^{15}$)($R^{16}$), —S(O)$_2$N($R^{15}$)($R^{16}$), —C(=NO$R^{15}$)$R^{16}$, —P(O)(O$R^{15}$)(O$R^{16}$), —N($R^{15}$)($R^{16}$), alkyl-N($R^{15}$)($R^{16}$), —N($R^{15}$)C(O)$R^{16}$, —$CH_2$—N($R^{15}$)C(O)$R^{16}$, —N($R^{15}$)S(O)$R^{16}$, —N($R^{15}$)S(O)$_2R^{16}$, —$CH_2$—N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —$CH_2$—N($R^{15}$)C(O)N($R^{16}$) ($R^{17}$), —N($R^{15}$)C(O)O$R^{16}$, —$CH_2$—N($R^{15}$)C(O)O$R^{16}$, —$N_3$, =NO$R^{15}$, —$NO_2$, —S(O)$R^{15}$ and —S(O)$_2R^{15}$.

In another embodiment, this invention discloses a compound, or pharmaceutically acceptable salts, solvates, esters or prodrugs of said compound, said compound having the general structure shown in the formula I:

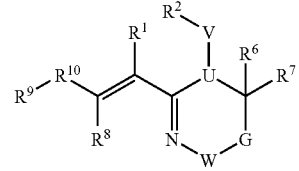

Formula I wherein U is C($R^5$);

$R^1$ is H;

$R^2$ and $R^6$ are connected to form a 4-7 membered cycloalkyl ring;

$R^7$ is 3-(1,1'-biphenyl)-yl;

$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is phenyl; and $R^9$ is imidazol-1-yl, and the other moieties are as defined earlier.

In another embodiment, this invention discloses a compound, or pharmaceutically acceptable salts, solvates, esters or prodrugs of said compound, said compound having the general structure shown in the formula I:

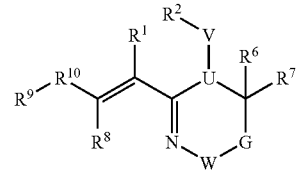

Formula I wherein U is C($R^5$);

$R^6$ is H;

$R^1$ and $R^2$ are connected to form a 4-7 membered cycloalkyl ring;

$R^7$ is 3-(1,1'-biphenyl)-yl;

$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyland alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is phenyl; and $R^9$ is imidazol-1-yl, and the other moieties are as defined earlier.

In another embodiment, this invention discloses a compound, or pharmaceutically acceptable salts, solvates, esters or prodrugs of said compound, said compound having the general structure shown in the formula I:

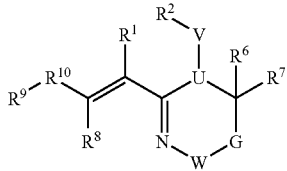

Formula I wherein U is $C(R^5)$ or N;

$R^1$ is H;

$R^2$ and $R^6$ are connected to form a 5-8 membered heterocyclyl ring;

$R^7$ is 3-(1,1'-biphenyl)-yl;

$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is phenyl; and $R^9$ is imidazol-1-yl, and the other moieties are as defined earlier.

In another embodiment, this invention discloses a compound, or pharmaceutically acceptable salts, solvates, esters or prodrugs of said compound, said compound having the general structure shown in the formula I:

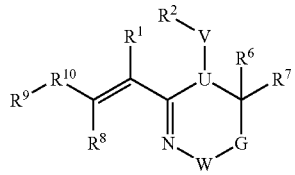

Formula I wherein U is $C(R^5)$;

$R^6$ is H;

$R^1$ and $R^2$ are connected to form a 5-8 membered heterocyclyl ring;

$R^7$ is 3-(1,1'-biphenyl)-yl;

$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is phenyl; and $R^9$ is imidazol-1-yl, and the other moieties are as defined earlier.

In another embodiment, this invention discloses a compound, or pharmaceutically acceptable salts, solvates, esters or prodrugs of said compound, said compound having the general structure shown in the formula I:

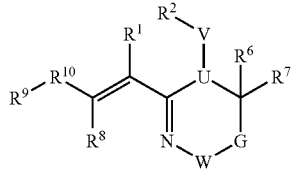

Formula I wherein U is $C(R^5)$ or N;

$R^1$ and $R^2$ are connected to form a 5-8 membered heterocyclyl ring;

$R^2$ and $R^6$ are connected to form a 5-8 membered heterocyclyl ring;

$R^7$ is 3-(1,1'-biphenyl)-yl;

$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is phenyl; and $R^9$ is imidazol-1-yl, and the other moieties are as defined earlier.

In another embodiment, this invention discloses a compound, or pharmaceutically acceptable salts, solvates, esters or prodrugs of said compound, said compound having the general structure shown in the formula I:

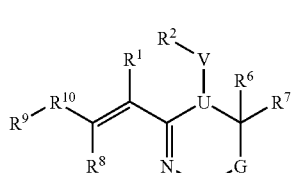

Formula I wherein U is $C(R^5)$;

$R^2$ and $R^6$ are connected to form a 4-7 membered cycloalkyl ring;

$R^1$ and $R^2$ are connected to form a 4-7 membered cycloalkyl ring;

$R^7$ is 3-(1,1'-biphenyl)-yl;

$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is phenyl; and $R^9$ is imidazol-1-yl, and the other moieties are as defined earlier.

In another embodiment, this invention discloses a compound, or pharmaceutically acceptable salts, solvates, esters or prodrugs of said compound, said compound having the general structure shown in the formula I:

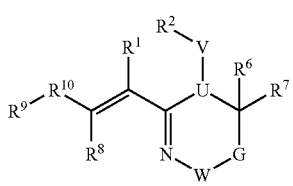

Formula I wherein U is C($R^6$) or N;

$R^1$ and $R^2$ are connected to form a piperidinyl ring;

$R^2$ and $R^6$ are connected to form a piperidinyl ring;

$R^7$ is 3-(1,1'-biphenyl)-yl;

$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is phenyl; and $R^9$ is imidazol-1-yl, and the other moieties are as defined earlier.

In another embodiment, this invention discloses a compound, or pharmaceutically acceptable salts, solvates, esters or prodrugs of said compound, said compound having the general structure shown in the formula I:

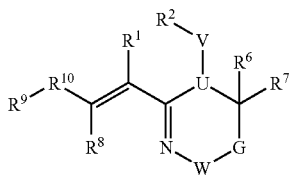

Formula I wherein U is N;

$R^1$ and $R^2$ are connected to form a piperazinyl ring;

$R^2$ and $R^6$ are connected to form a piperazinyl ring;

$R^7$ is 3-(1,1'-biphenyl)-yl;

$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is phenyl; and $R^9$ is imidazol-1-yl, and the other moieties are as defined earlier.

In another embodiment, this invention discloses a compound, or pharmaceutically acceptable salts, solvates, esters or prodrugs of said compound, said compound having the general structure shown in the formula I:

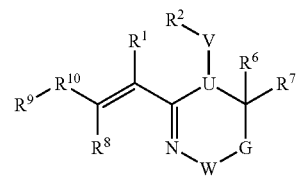

Formula I wherein U is C($R^5$) or N;

$R^1$ and $R^2$ are connected to form a piperidinyl ring;

$R^2$ and $R^6$ are connected to form a piperazinyl ring;

$R^7$ is 3-(1,1'-biphenyl)-yl;

$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is phenyl; and $R^9$ is imidazol-1-yl, and the other moieties are as defined earlier.

In another embodiment, this invention discloses a compound, or pharmaceutically acceptable salts, solvates, esters or prodrugs of said compound, said compound having the general structure shown in the formula I:

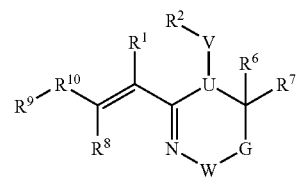

Formula I wherein U is C($R^5$) or N;

$R^1$ and $R^2$ are connected to form a piperazinyl ring;

$R^2$ and $R^6$ are connected to form a piperidnyl ring;

$R^7$ is 3-(1,1'-biphenyl)-yl;

$R^8$ is H;

R[5] is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

R[10] is phenyl; and

R[9] is imidazol-1-yl, and the other moieties are as defined earlier.

In another embodiment, this invention discloses a compound, or pharmaceutically acceptable salts, solvates, esters or prodrugs of said compound, said compound having the general structure shown in the formula I:

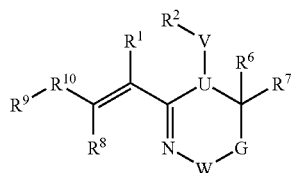

Formula I wherein U is C(R[5]);

R[1] and R[2] are connected to form a cyclohexyl ring;
R[2] and R[6] are connected to form a piperidinyl ring;
R[7] is 3-(1,1'-biphenyl)-yl;
R[8] is H;
R[5] is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

R[10] is phenyl; and

R[9] is imidazol-1-yl, and the other moieties are as defined earlier.

In another embodiment, this invention discloses a compound, or pharmaceutically acceptable salts, solvates, esters or prodrugs of said compound, said compound having the general structure shown in the formula I:

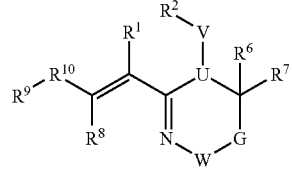

Formula I wherein U is C(R[5]);

R[1] and R[2] are connected to form a cyclohexyl ring;
R[2] and R[6] are connected to form a piperazinyl ring;
R[7] is 3-(1,1'-biphenyl)-yl;
R[8] is H;

R[5] is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

R[10] is phenyl; and

R[9] is imidazol-1-yl, and the other moieties are as defined earlier.

In another embodiment, this invention discloses a compound, or pharmaceutically acceptable salts, solvates, esters or prodrugs of said compound, said compound having the general structure shown in the formula I:

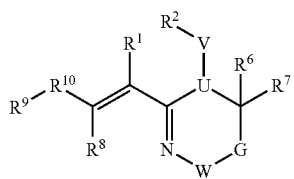

Formula I wherein U is C(R[5]);

R[1] and R[2] are connected to form a piperidinyl ring;
R[2] and R[6] are connected to form a cyclohexyl ring;
R[7] is 3-(1,1'-biphenyl)-yl;
R[8] is H;
R[5] is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

R[10] is 1 phenyl; and

R[9] is imidazol-1-yl, and the other moieties are as defined earlier.

In another embodiment, this invention discloses a compound, or pharmaceutically acceptable salts, solvates, esters or prodrugs of said compound, said compound having the general structure shown in the formula I:

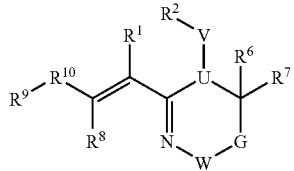

Formula I wherein U is C(R[5]);

R[1] and R[2] are connected to form a piperazinyl ring;
R[2] and R[6] are connected to form a cyclohexyl ring;
R[7] is 3-(1,1'-biphenyl)-yl;
R[8] is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is phenyl; and $R^9$ is imidazol-1-yl, and the other moieties are as defined earlier.

In another embodiment, this invention discloses a compound, or pharmaceutically acceptable salts, solvates, esters or prodrugs of said compound, said compound having the general structure shown in the formula I:

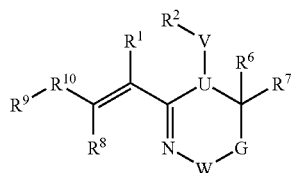

Formula I wherein U is $C(R^5)$ or N;
$R^6$ is H;
$R^1$ and $R^2$ are connected to form a piperidinyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is phenyl; and $R^9$ is imidazol-1-yl, and the other moieties are as defined earlier.

In another embodiment, this invention discloses a compound, or pharmaceutically acceptable salts, solvates, esters or prodrugs of said compound, said compound having the general structure shown in the formula I:

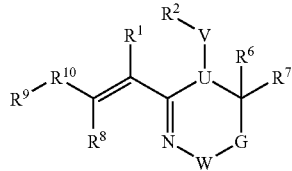

Formula I wherein U is $C(R^5)$ or N;
$R^6$ is H;
$R^1$ and $R^2$ are connected to form a piperazinyl ring;
$R^7$ is 3-(1,1'-biphenyl)-yl;
$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is phenyl; and $R^9$ is imidazol-1-yl, and the other moieties are as defined earlier.

In another embodiment, this invention discloses a compound, or pharmaceutically acceptable salts, solvates, esters or prodrugs of said compound, said compound having the general structure shown in the formula I:

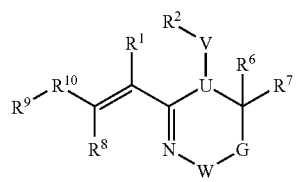

Formula I wherein U is $C(R^5)$ or N;
$R^1$ is H;
$R^6$ and $R^2$ are connected to form a piperidinyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is phenyl; and $R^9$ is imidazol-1-yl, and the other moieties are as defined earlier.

In another embodiment, this invention discloses a compound, or pharmaceutically acceptable salts, solvates, esters or prodrugs of said compound, said compound having the general structure shown in the formula I:

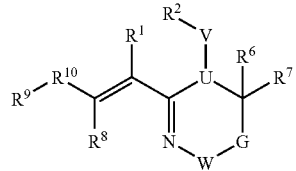

Formula I wherein U is $C(R^5)$ or N;
$R^1$ is H;
$R^6$ and $R^2$ are connected to form a piperazinyl ring;
$R^7$ is 3-(1,1'-biphenyl)-yl;
$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is phenyl; and $R^9$ is imidazol-1-yl, and the other moieties are as defined earlier.

In another embodiment, this invention discloses a compound, or pharmaceutically acceptable salts, solvates, esters or prodrugs of said compound, said compound having the general structure shown in the formula I:

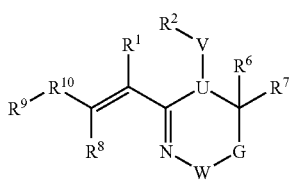

Formula I wherein U is $C(R^5)$;

$R^1$ is H;

$R^2$ and $R^6$ are connected to form a 4-7 membered cycloalkyl ring;

$R^7$ is 3-(1,1'-biphenyl)-yl;

$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is selected from the group consisting of: 3-methoxy-phenyl and 3-F-phenyl (and in one example $R^{10}$ is 3-methoxy-phenyl, and in another example $R^{10}$ is 3-F-phenyl);

$R^9$ is 4-methyl-imidazolyl-1-yl.

In another embodiment, this invention discloses a compound, or pharmaceutically acceptable salts, solvates, esters or prodrugs of said compound, said compound having the general structure shown in the formula I:

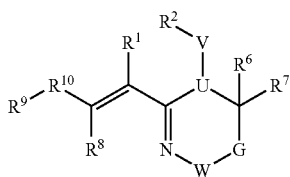

Formula I wherein U is $C(R^5)$;

$R^6$ is H;

$R^1$ and $R^2$ are connected to form a 4-7 membered cycloalkyl ring;

$R^7$ is 3-(1,1'-biphenyl)-yl;

$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is selected from the group consisting of: 3-methoxy-phenyl and 3-F-phenyl (and in one example $R^{10}$ is 3-methoxy-phenyl, and in another example $R^{10}$ is 3-F-phenyl);

$R^9$ is 4-methyl-imidazolyl-1-yl.

In another embodiment, this invention discloses a compound, or pharmaceutically acceptable salts, solvates, esters or prodrugs of said compound, said compound having the general structure shown in the formula I:

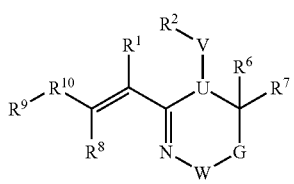

Formula I wherein U is $C(R^5)$ or N;

$R^1$ is H;

$R^2$ and $R^6$ are connected to form a 5-8 membered heterocyclyl ring;

$R^7$ is 3-(1,1'-biphenyl)-yl;

$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is selected from the group consisting of: 3-methoxy-phenyl and 3-F-phenyl (and in one example $R^{10}$ is 3-methoxy-phenyl, and in another example $R^{10}$ is 3-F-phenyl);

$R^9$ is 4-methyl-imidazolyl-1-yl.

In another embodiment, this invention discloses a compound, or pharmaceutically acceptable salts, solvates, esters or prodrugs of said compound, said compound having the general structure shown in the formula I:

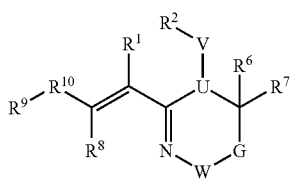

Formula I wherein U is $C(R^5)$;

$R^6$ is H;

$R^1$ and $R^2$ are connected to form a 5-8 membered heterocyclyl ring;

$R^7$ is 3-(1,1'-biphenyl)-yl;

$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is selected from the group consisting of: 3-methoxyphenyl and 3-F-phenyl (and in one example $R^{10}$ is 3-methoxy-phenyl, and in another example $R^{10}$ is 3-F-phenyl);

$R^9$ is 4-methyl-imidazolyl-1-yl.

In another embodiment, this invention discloses a compound, or pharmaceutically acceptable salts, solvates, esters or prodrugs of said compound, said compound having the general structure shown in the formula I:

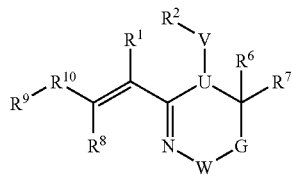

Formula I wherein U is C($R^5$) or N;

$R^1$ and $R^2$ are connected to form a 5-8 membered heterocyclyl ring;

$R^2$ and $R^6$ are connected to form a 5-8 membered heterocyclyl ring;

$R^7$ is 3-(1,1'-biphenyl)-yl;

$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is selected from the group consisting of: 3-methoxyphenyl and 3-F-phenyl (and in one example $R^{10}$ is 3-methoxy-phenyl, and in another example $R^{10}$ is 3-F-phenyl);

$R^9$ is 4-methyl-imidazolyl-1-yl.

In another embodiment, this invention discloses a compound, or pharmaceutically acceptable salts, solvates, esters or prodrugs of said compound, said compound having the general structure shown in the formula I:

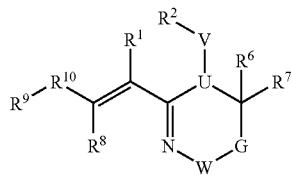

Formula I wherein U is C($R^5$);

$R^2$ and $R^6$ are connected to form a 4-7 membered cycloalkyl ring;

$R^1$ and $R^2$ are connected to form a 4-7 membered cycloalkyl ring;

$R^7$ is 3-(1,1'-biphenyl)-yl;

$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is selected from the group consisting of: 3-methoxyphenyl and 3-F-phenyl (and in one example $R^{10}$ is 3-methoxy-phenyl, and in another example $R^{10}$ is 3-F-phenyl);

$R^9$ is 4-methyl-imidazolyl-1-yl.

In another embodiment, this invention discloses a compound, or pharmaceutically acceptable salts, solvates, esters or prodrugs of said compound, said compound having the general structure shown in the formula I:

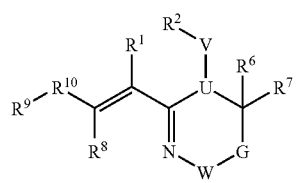

Formula I wherein U is C($R^5$) or N;

$R^1$ and $R^2$ are connected to form a piperidinyl ring;

$R^2$ and $R^6$ are connected to form a piperidinyl ring;

$R^7$ is 3-(1,1'-biphenyl)-yl;

$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is selected from the group consisting of: 3-methoxyphenyl and 3-F-phenyl (and in one example $R^{10}$ is 3-methoxy-phenyl, and in another example $R^{10}$ is 3-F-phenyl);

$R^9$ is 4-methyl-imidazolyl-1-yl.

In another embodiment, this invention discloses a compound, or pharmaceutically acceptable salts, solvates, esters or prodrugs of said compound, said compound having the general structure shown in the formula I:

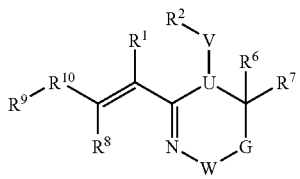

Formula I wherein U is N;

$R^1$ and $R^2$ are connected to form a piperazinyl ring;

$R^2$ and $R^6$ are connected to form a piperazinyl ring;

$R^7$ is 3-(1,1'-biphenyl)-yl;

$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is selected from the group consisting of: 3-methoxy-phenyl and 3-F-phenyl (and in one example $R^{10}$ is 3-methoxy-phenyl, and in another example $R^{10}$ is 3-F-phenyl);

$R^9$ is 4-methyl-imidazolyl-1-yl.

In another embodiment, this invention discloses a compound, or pharmaceutically acceptable salts, solvates, esters or prodrugs of said compound, said compound having the general structure shown in the formula I:

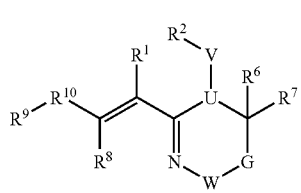

Formula I wherein U is $C(R^5)$ or N;
$R^1$ and $R^2$ are connected to form a piperidinyl ring;
$R^2$ and $R^6$ are connected to form a piperazinyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is selected from the group consisting of: 3-methoxy-phenyl and 3-F-phenyl (and in one example $R^{10}$ is 3-methoxy-phenyl, and in another example $R^{10}$ is 3-F-phenyl);

$R^9$ is 4-methyl-imidazolyl-1-yl.

In another embodiment, this invention discloses a compound, or pharmaceutically acceptable salts, solvates, esters or prodrugs of said compound, said compound having the general structure shown in the formula I:

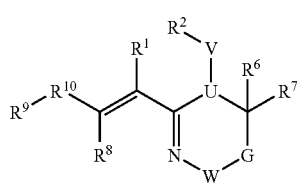

Formula I wherein U is $C(R^5)$ or N;
$R^1$ and $R^2$ are connected to form a piperazinyl ring;
$R^2$ and $R^6$ are connected to form a piperidnyl ring;
$R^7$ is 3-(1,1'-biphenyl)-yl;
$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is selected from the group consisting of: 3-methoxy-phenyl and 3-F-phenyl (and in one example $R^{10}$ is 3-methoxy-phenyl, and in another example $R^{10}$ is 3-F-phenyl);

$R^9$ is 4-methyl-imidazolyl-1-yl.

In another embodiment, this invention discloses a compound, or pharmaceutically acceptable salts, solvates, esters or prodrugs of said compound, said compound having the general structure shown in the formula I:

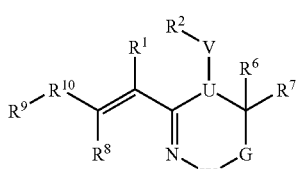

Formula I wherein U is $C(R^5)$;
$R^1$ and $R^2$ are connected to form a cyclohexyl ring;
$R^2$ and $R^6$ are connected to form a piperidinyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is selected from the group consisting of: 3-methoxy-phenyl and 3-F-phenyl (and in one example $R^{10}$ is 3-methoxy-phenyl, and in another example $R^{10}$ is 3-F-phenyl);

$R^9$ is 4-methyl-imidazolyl-1-yl.

In another embodiment, this invention discloses a compound, or pharmaceutically acceptable salts, solvates, esters or prodrugs of said compound, said compound having the general structure shown in the formula I:

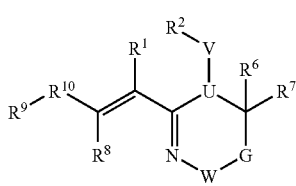

Formula I wherein U is $C(R^5)$;
$R^1$ and $R^2$ are connected to form a cyclohexyl ring;
$R^2$ and $R^6$ are connected to form a piperazinyl ring;
$R^7$ is 3-(1,1'-biphenyl)-yl;
$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is selected from the group consisting of: 3-methoxy-phenyl and 3-F-phenyl (and in one example $R^{10}$ is 3-methoxy-phenyl, and in another example $R^{10}$ is 3-F-phenyl);

$R^9$ is 4-methyl-imidazolyl-1-yl.

In another embodiment, this invention discloses a compound, or pharmaceutically acceptable salts, solvates, esters or prodrugs of said compound, said compound having the general structure shown in the formula I:

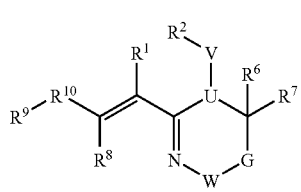

Formula I wherein U is $C(R^5)$;
$R^1$ and $R^2$ are connected to form a piperidinyl ring;
$R^2$ and $R^6$ are connected to form a cyclohexyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is selected from the group consisting of: 3-methoxy-phenyl and 3-F-phenyl (and in one example $R^{10}$ is 3-methoxy-phenyl, and in another example $R^{10}$ is 3-F-phenyl);

$R^9$ is 4-methyl-imidazolyl-1-yl.

In another embodiment, this invention discloses a compound, or pharmaceutically acceptable salts, solvates, esters or prodrugs of said compound, said compound having the general structure shown in the formula I:

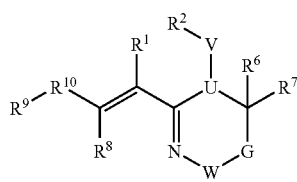

Formula I wherein U is $C(R^5)$;
$R^1$ and $R^2$ are connected to form a piperazinyl ring;
$R^2$ and $R^6$ are connected to form a cyclohexyl ring;
$R^7$ is 3-(1,1'-biphenyl)-yl;
$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is selected from the group consisting of: 3-methoxy-phenyl and 3-F-phenyl (and in one example $R^{10}$ is 3-methoxy-phenyl, and in another example $R^{10}$ is 3-F-phenyl);

$R^9$ is 4-methyl-imidazolyl-1-yl.

In another embodiment, this invention discloses a compound, or pharmaceutically acceptable salts, solvates, esters or prodrugs of said compound, said compound having the general structure shown in the formula I:

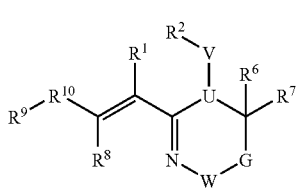

Formula I wherein U is $C(R^5)$ or N;
$R^6$ is H;
$R^1$ and $R^2$ are connected to form a piperidinyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is selected from the group consisting of: 3-methoxy-phenyl and 3-F-phenyl (and in one example $R^{10}$ is 3-methoxy-phenyl, and in another example $R^{10}$ is 3-F-phenyl);

$R^9$ is 4-methyl-imidazolyl-1-yl.

In another embodiment, this invention discloses a compound, or pharmaceutically acceptable salts, solvates, esters or prodrugs of said compound, said compound having the general structure shown in the formula I:

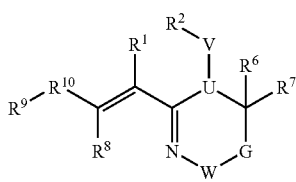

Formula I wherein U is $C(R^5)$ or N;
$R^6$ is H;
$R^1$ and $R^2$ are connected to form a piperazinyl ring;
$R^7$ is 3-(1,1'-biphenyl)-yl;
$R^8$ is H;

R⁵ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is selected from the group consisting of: 3-methoxyphenyl and 3-F-phenyl (and in one example $R^{10}$ is 3-methoxy-phenyl, and in another example $R^{10}$ is 3-F-phenyl);

$R^9$ is 4-methyl-imidazolyl-1-yl.

In another embodiment, this invention discloses a compound, or pharmaceutically acceptable salts, solvates, esters or prodrugs of said compound, said compound having the general structure shown in the formula I:

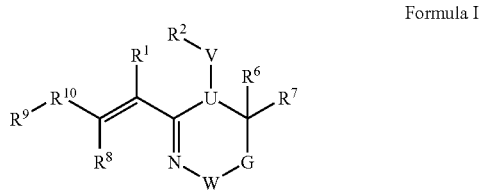

Formula I wherein U is $C(R^5)$ or N;
$R^1$ is H;
$R^6$ and $R^2$ are connected to form a piperidinyl ring;
$R^7$ is 3-(1,1'-biphenyl)-yl;
$R^8$ is H;
$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is selected from the group consisting of: 3-methoxyphenyl and 3-F-phenyl (and in one example $R^{10}$ is 3-methoxy-phenyl, and in another example $R^{10}$ is 3-F-phenyl);

$R^9$ is 4-methyl-imidazolyl-1-yl.

In another embodiment, this invention discloses a compound, or pharmaceutically acceptable salts, solvates, esters or prodrugs of said compound, said compound having the general structure shown in the formula I:

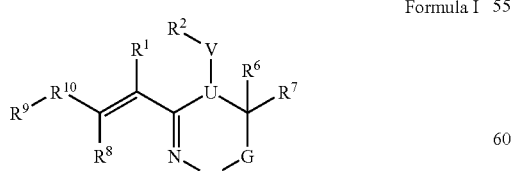

Formula I wherein U is $C(R^5)$ or N;
$R^1$ is H;
$R^6$ and $R^2$ are connected to form a piperazinyl ring;
$R^7$ is 3-(1,1'-biphenyl)-yl;
$R^8$ is H;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^{10}$ is selected from the group consisting of: 3-methoxyphenyl and 3-F-phenyl (and in one example $R^{10}$ is 3-methoxy-phenyl, and in another example $R^{10}$ is 3-F-phenyl);

$R^9$ is 4-methyl-imidazolyl-1-yl.

An illustrative group of compounds of the invention are shown in Table 1.

TABLE 1

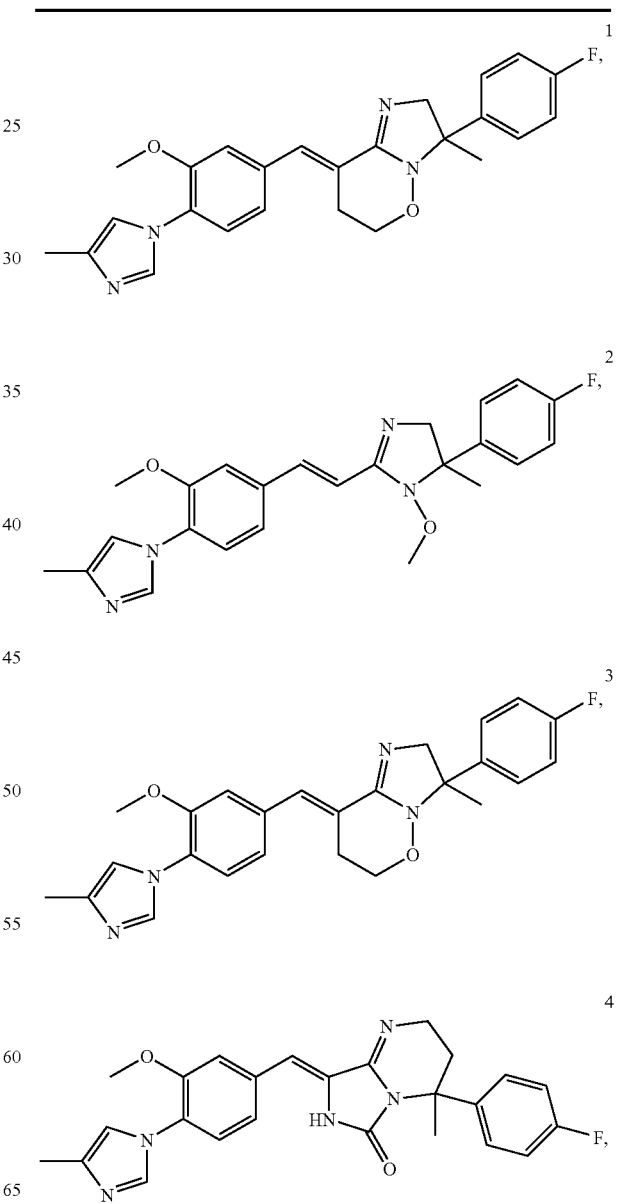

TABLE 1-continued
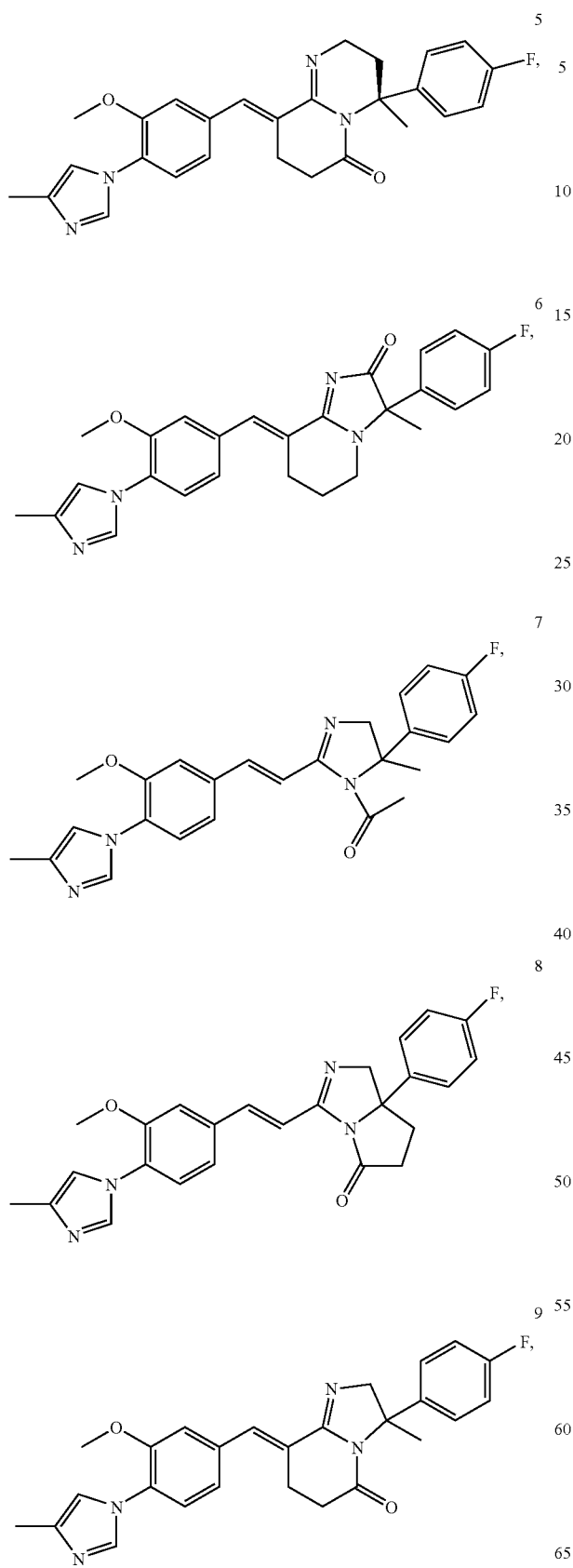
TABLE 1-continued
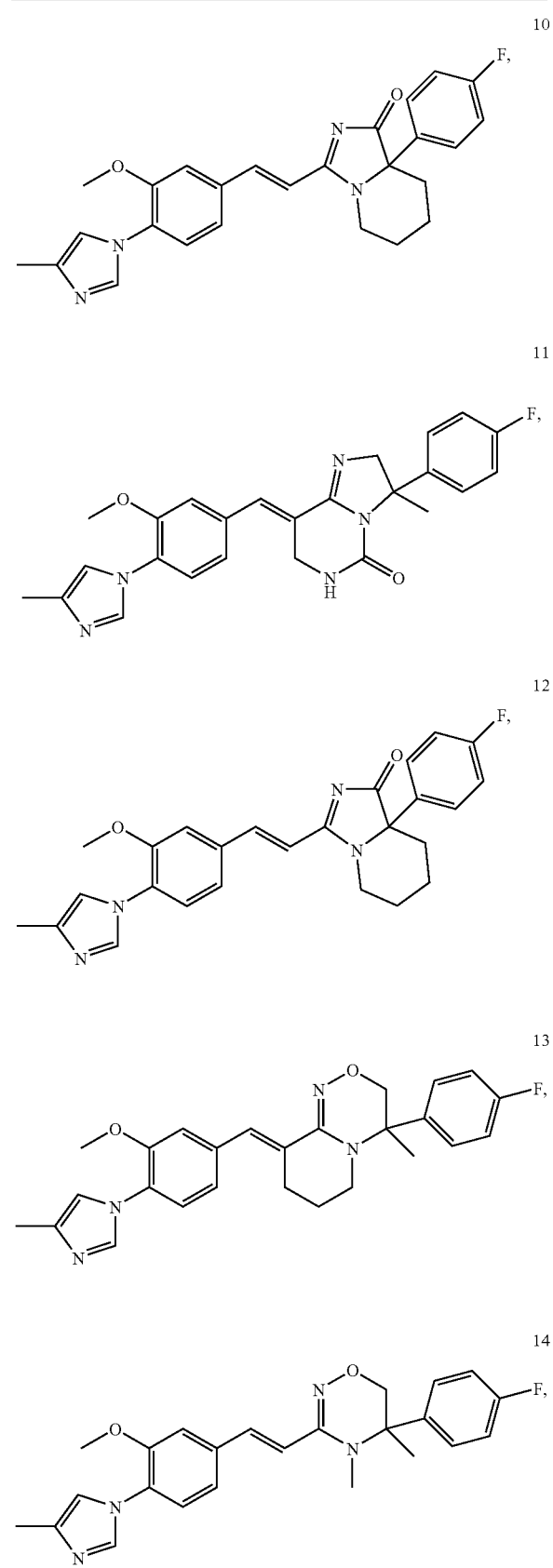

TABLE 1-continued
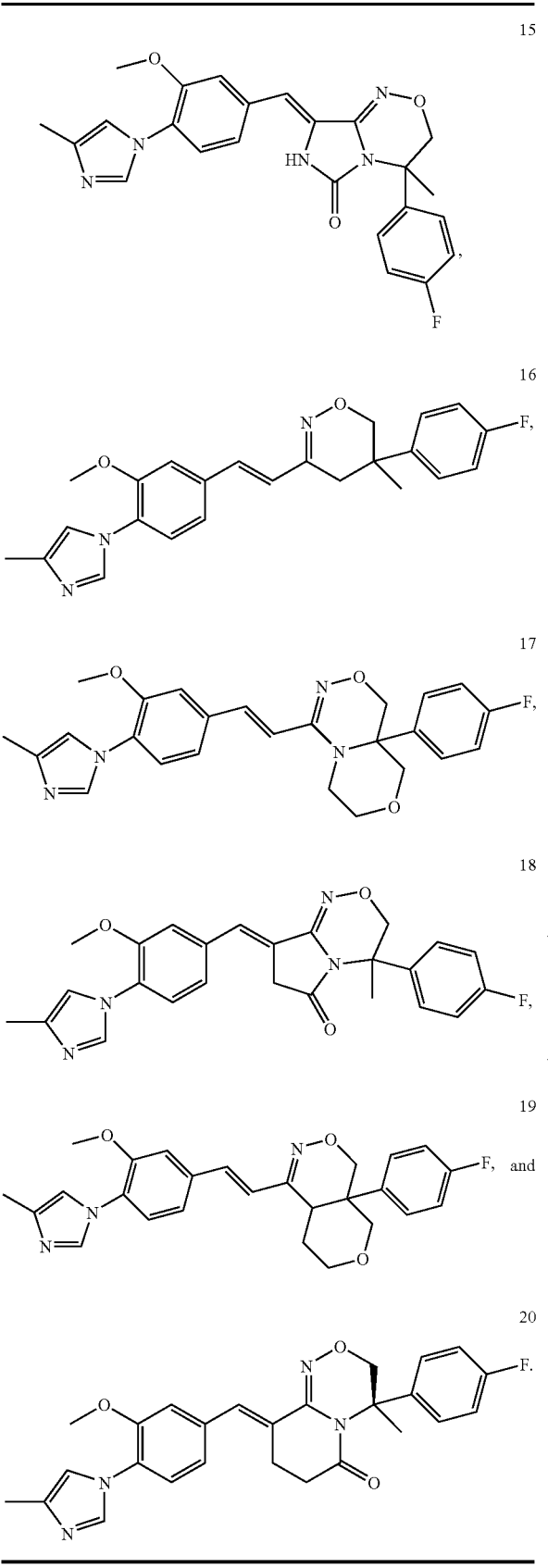
Representative compounds of this invention also include:
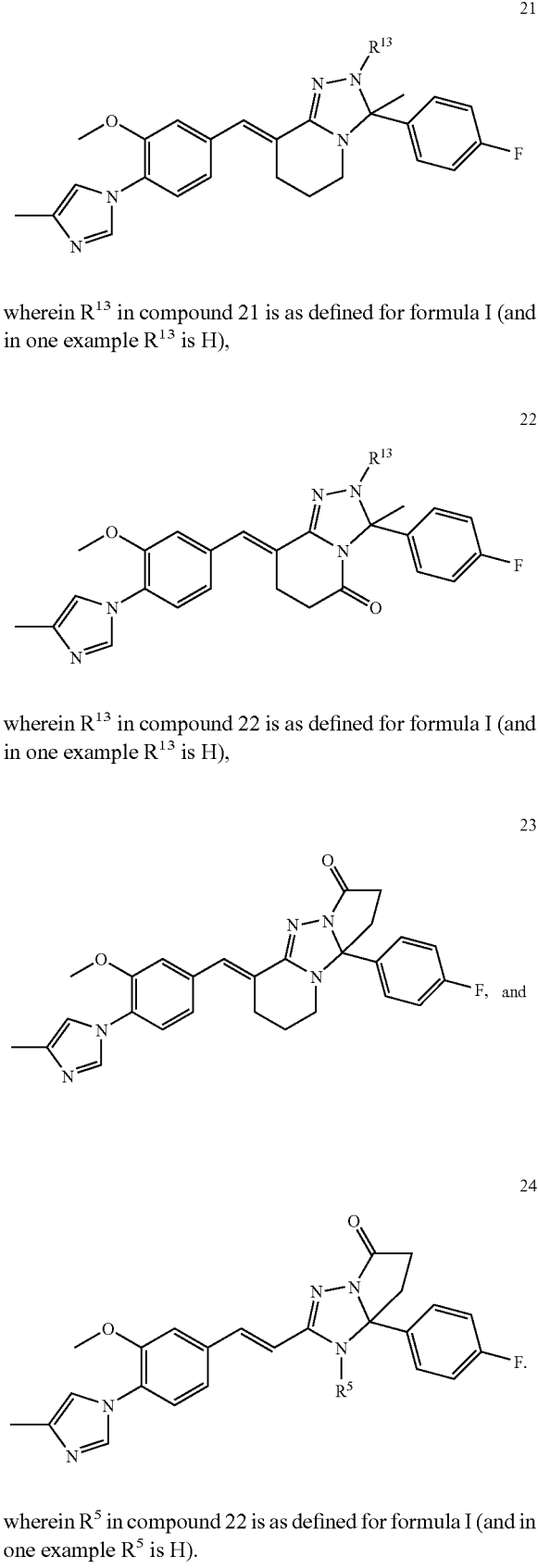
wherein $R^{13}$ in compound 21 is as defined for formula I (and in one example $R^{13}$ is H),
wherein $R^{13}$ in compound 22 is as defined for formula I (and in one example $R^{13}$ is H),
wherein $R^5$ in compound 22 is as defined for formula I (and in one example $R^5$ is H).

Representative compounds of this invention also include:
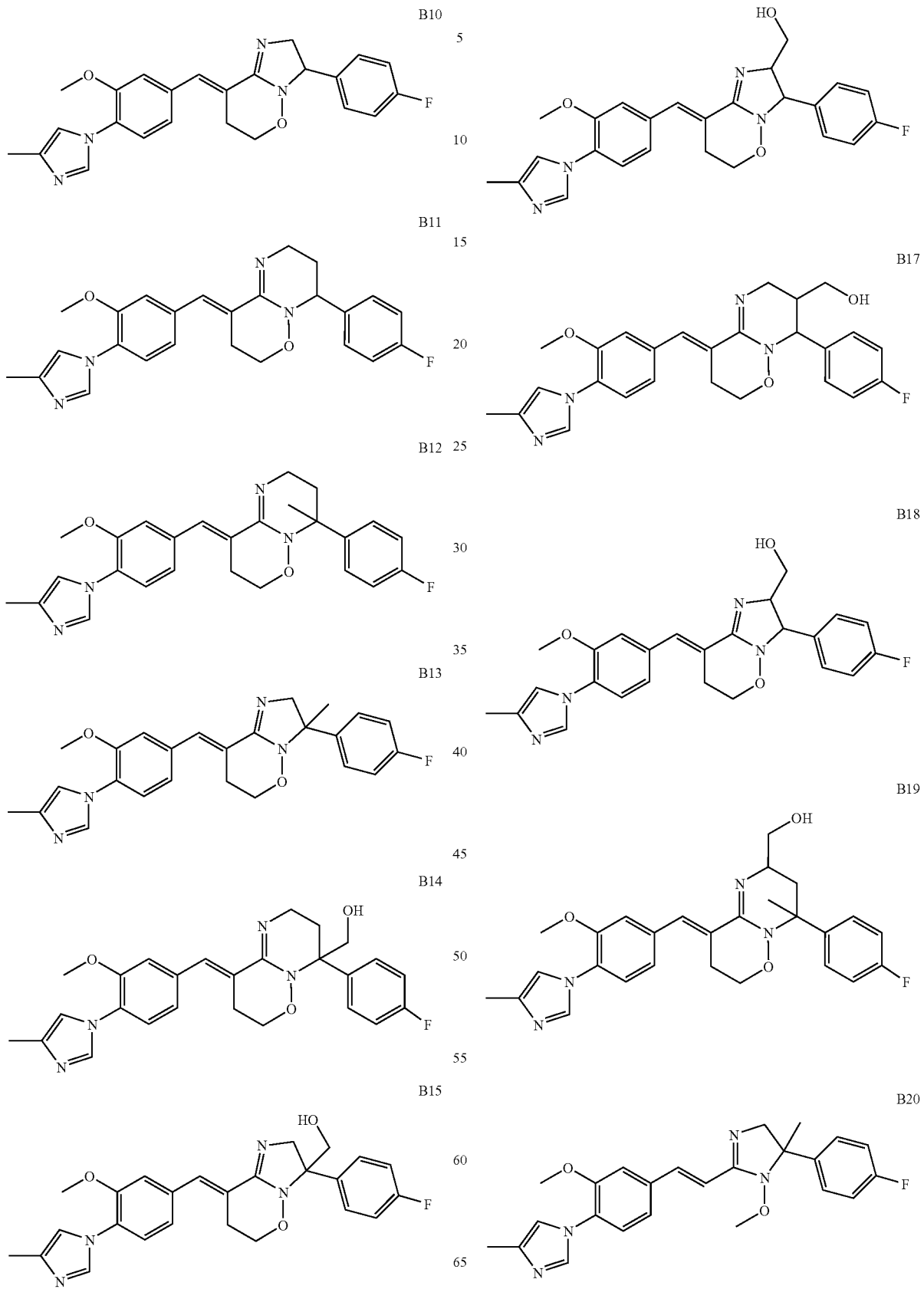

93
-continued
B21
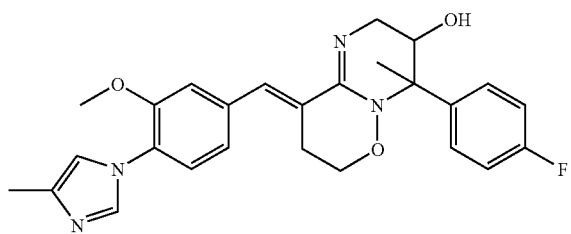
C5
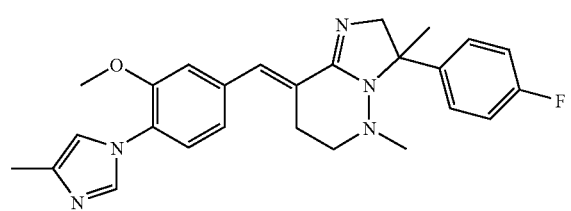
C6
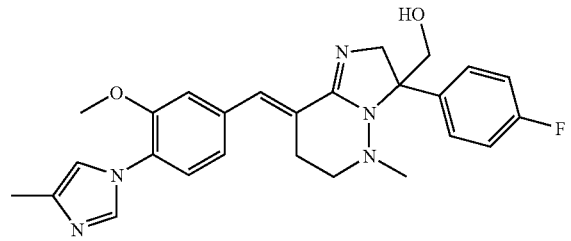
C7
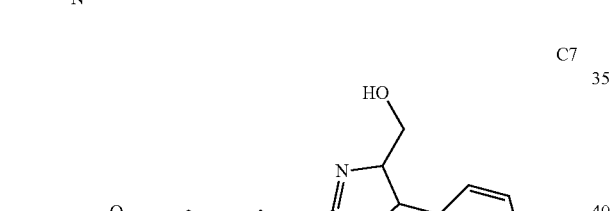
C8
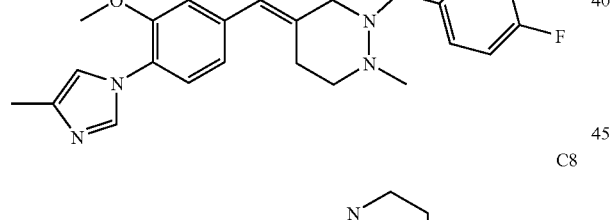
C9
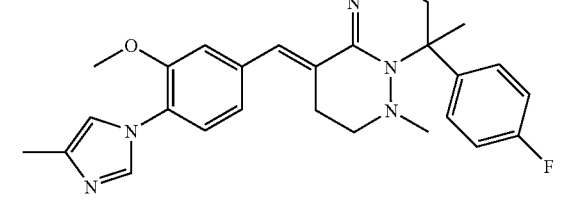
94
-continued
C10
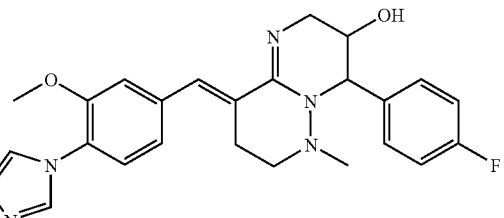
D9
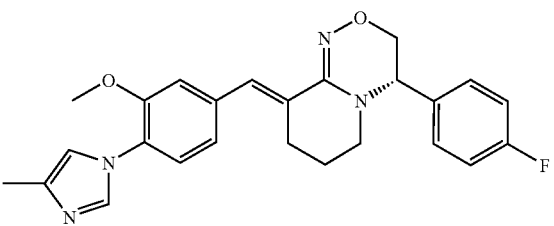
D10
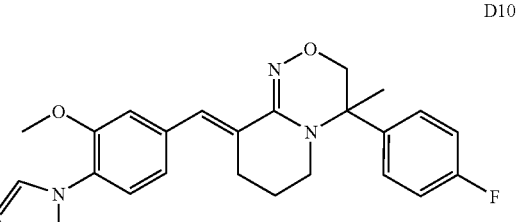
D11
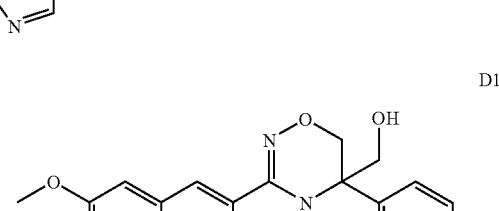
D12
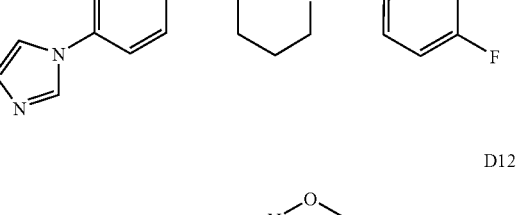
D13
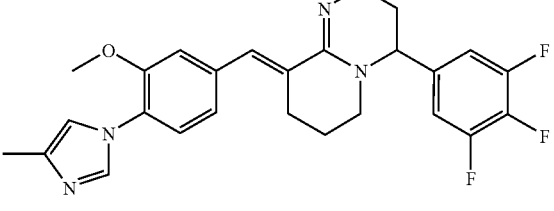

D14
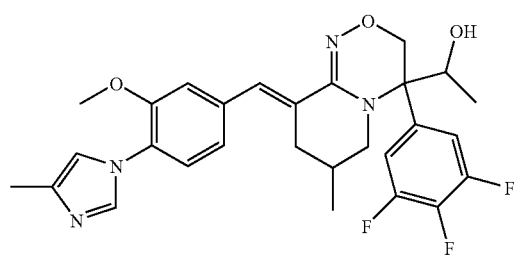
D15
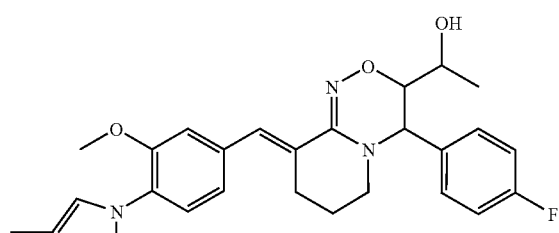
D16
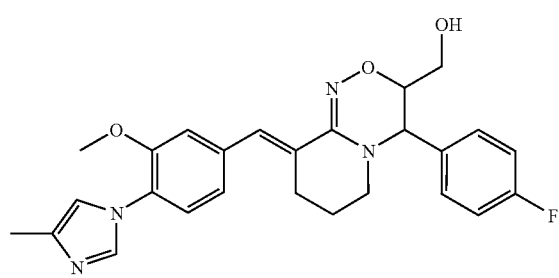
D17
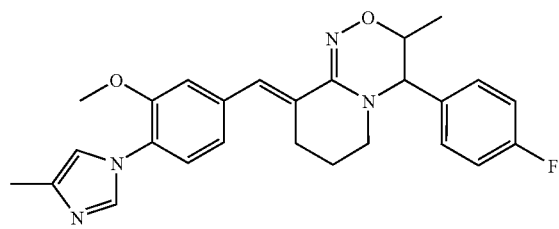
D18
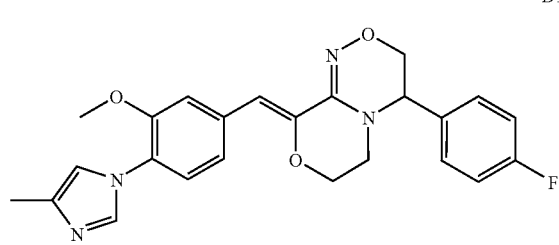
D19
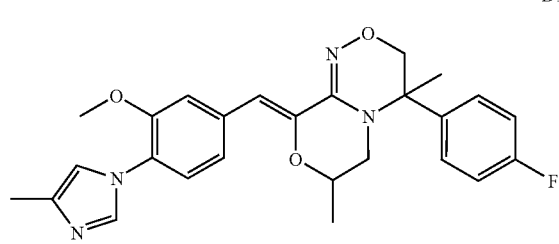
D20
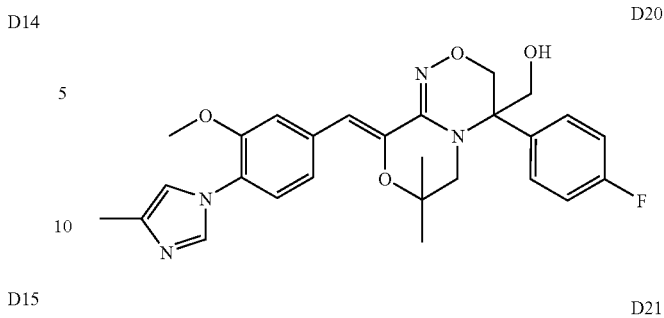
D21
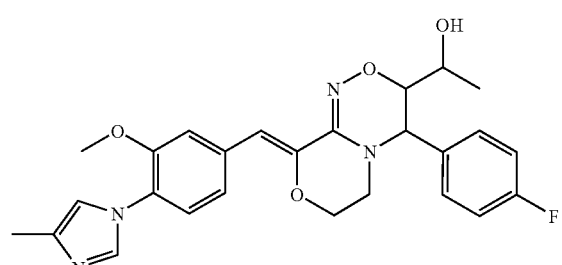
D22
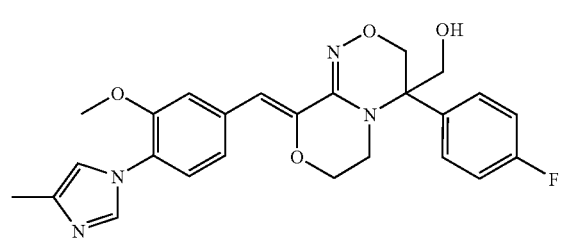
D23
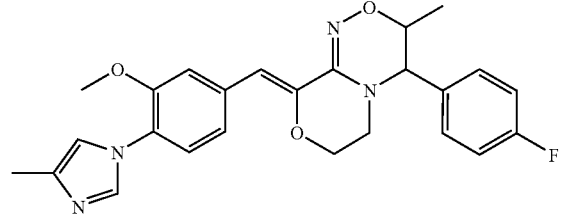
D24
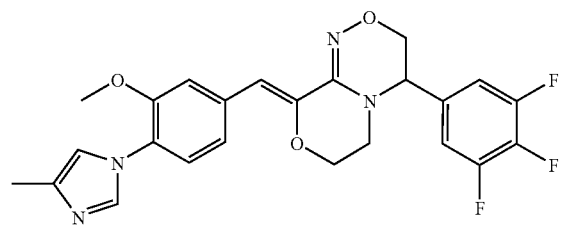
D25
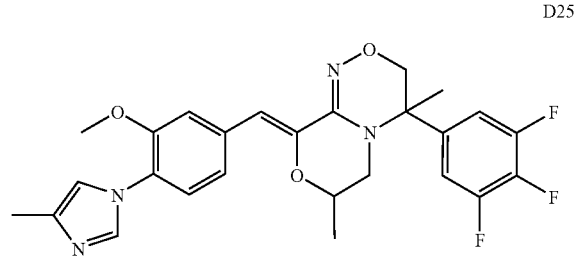

D26
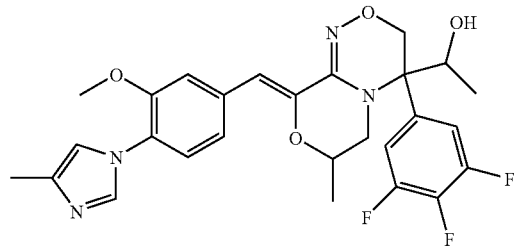
G4
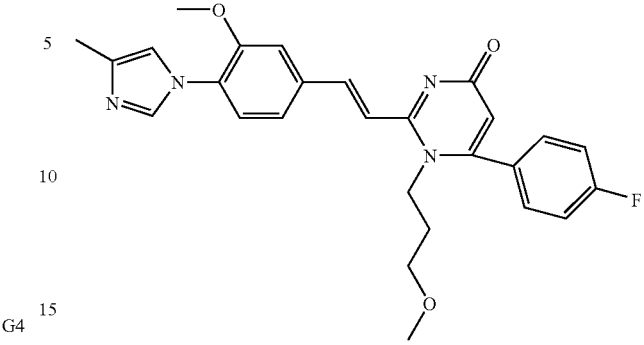
G5
G6
G7
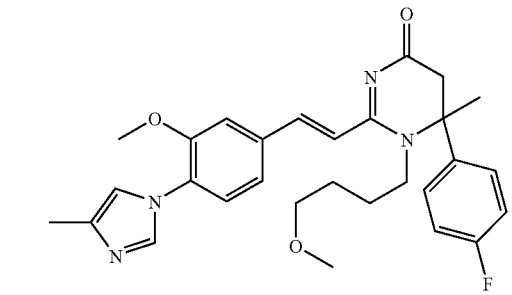
G8
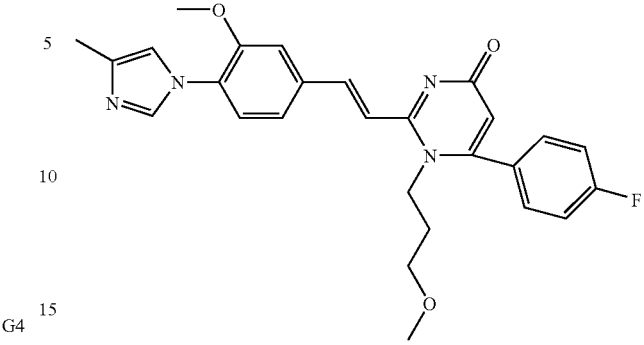
G9
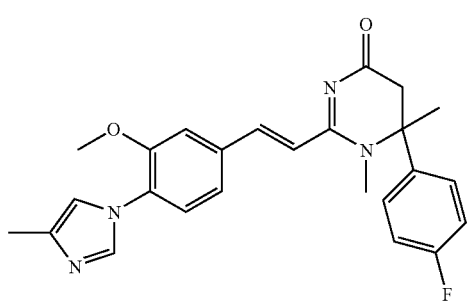
H3
H4
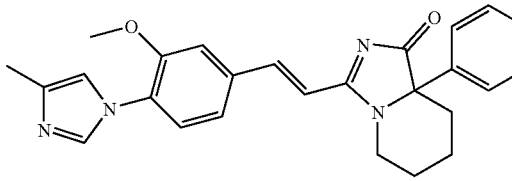
H5
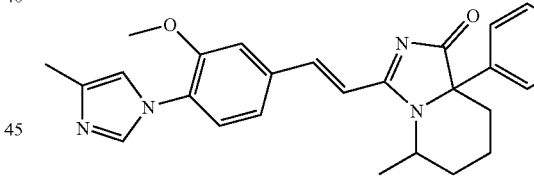
H6
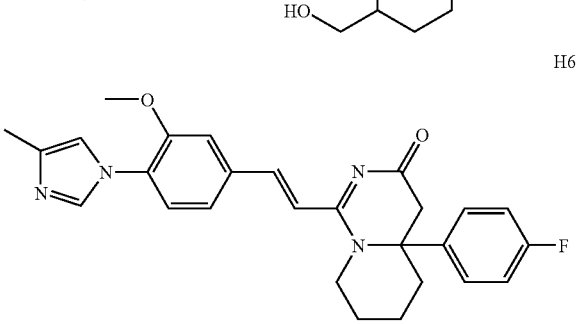

H7
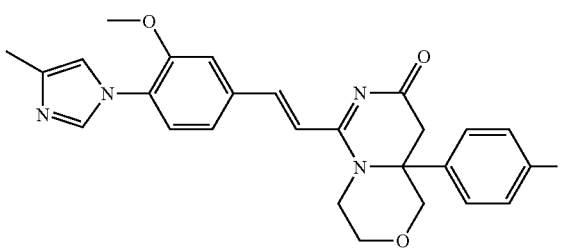
H8
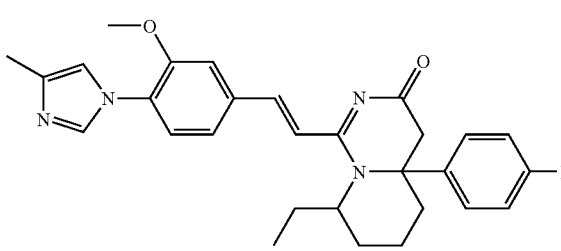
H9
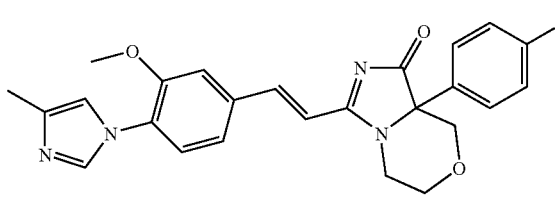
H10
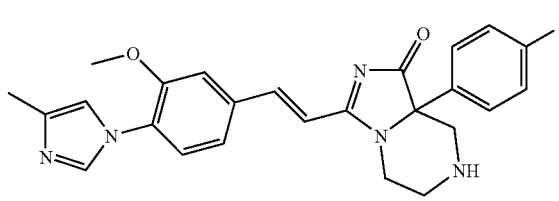
H11
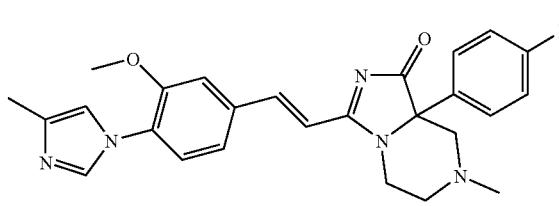
I5
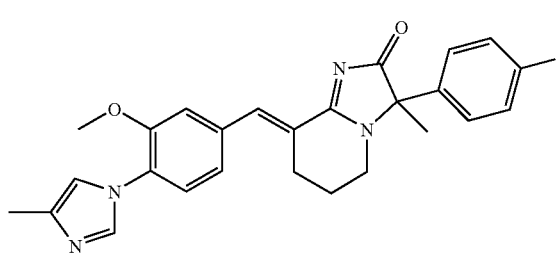
I6
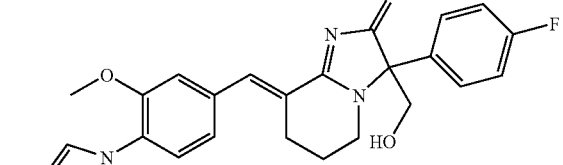
I6A
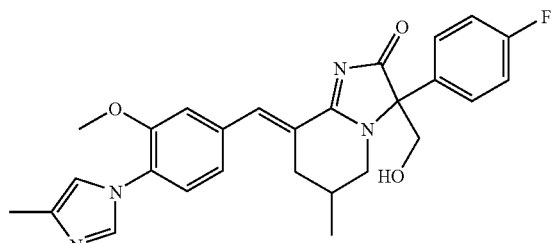
I7
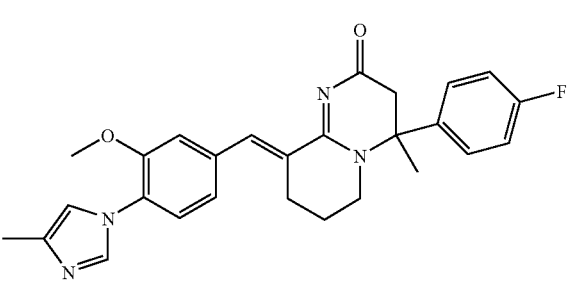
I8
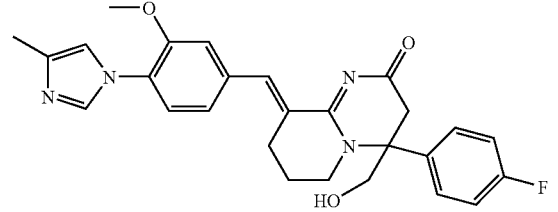
I8A
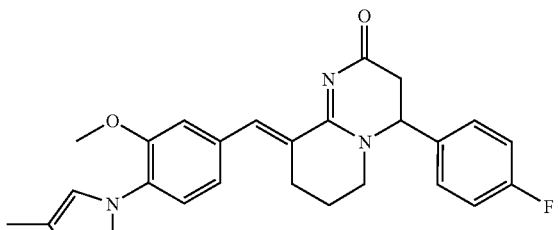
J4
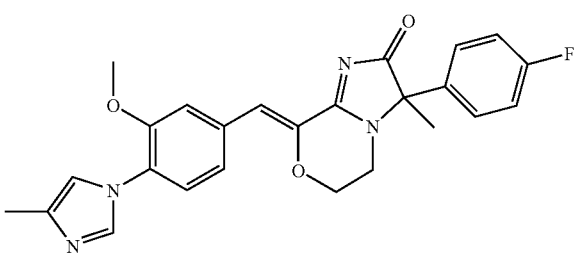

101
-continued
J5
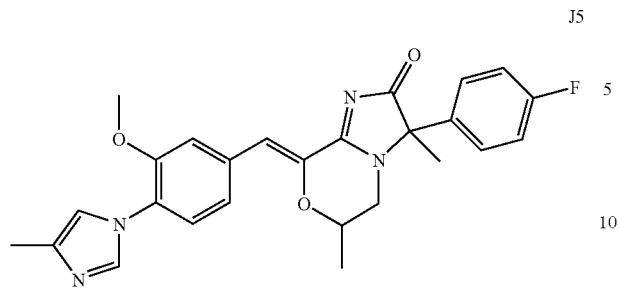
J6
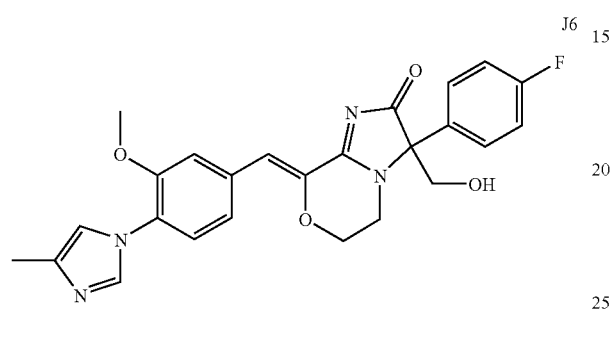
J7
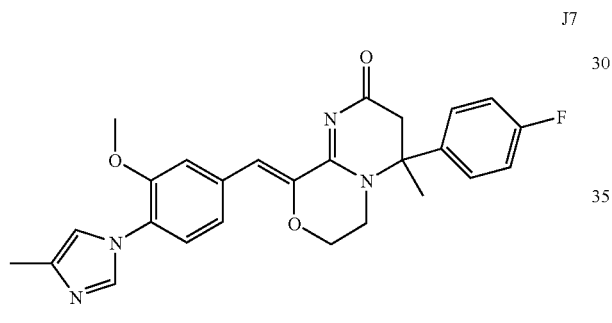
J8
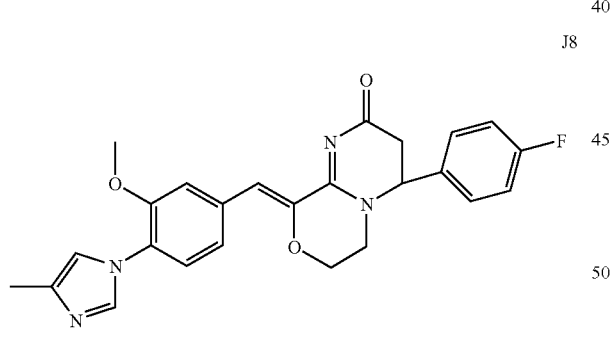
J9
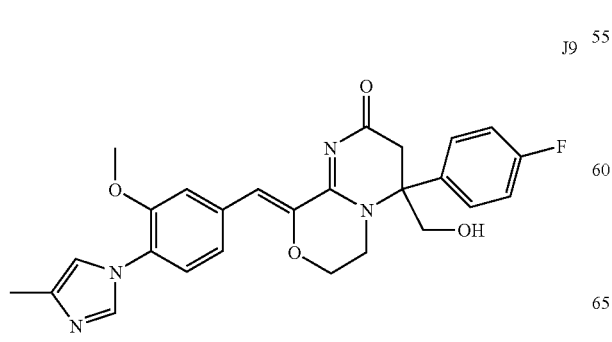
102
-continued
K1
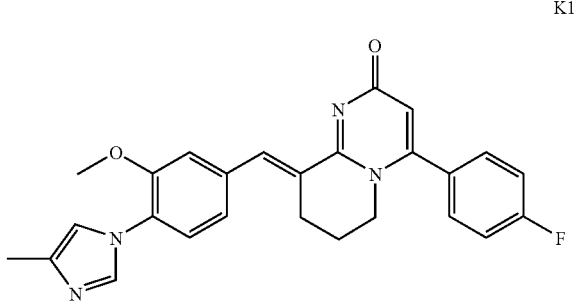
K2
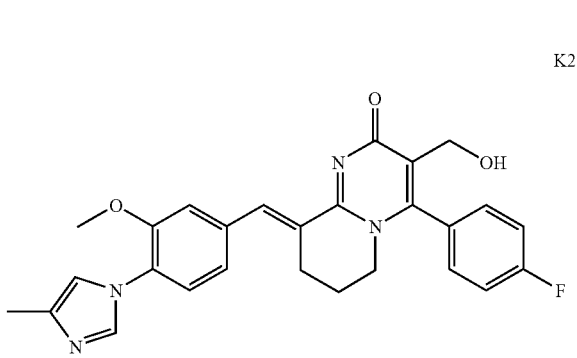
K3
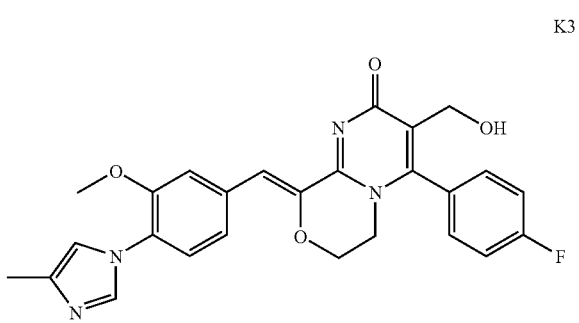
K4
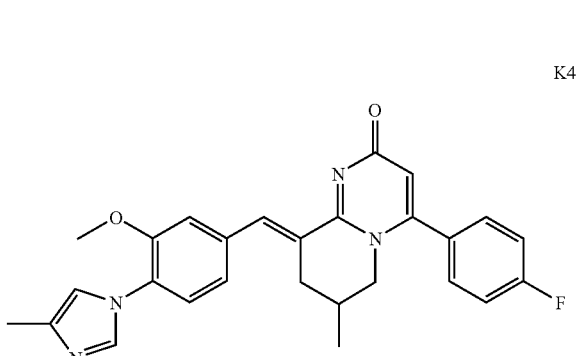
K5
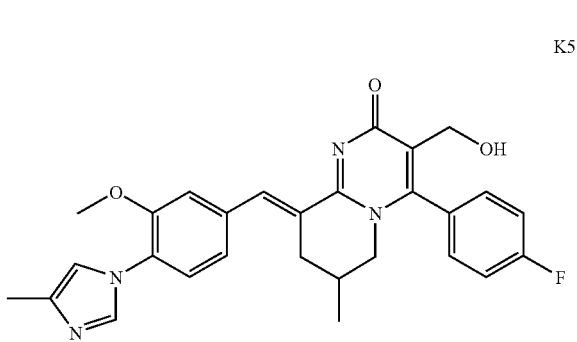

K6
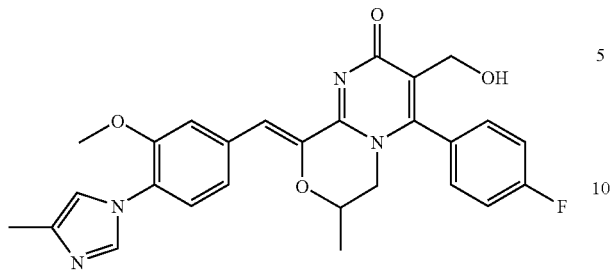
L4
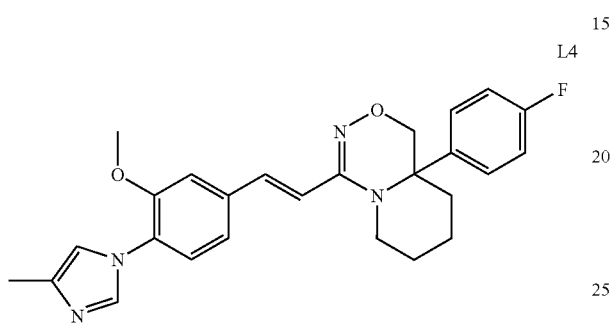
L5
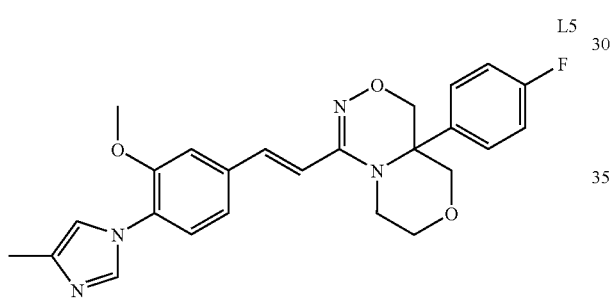
L6
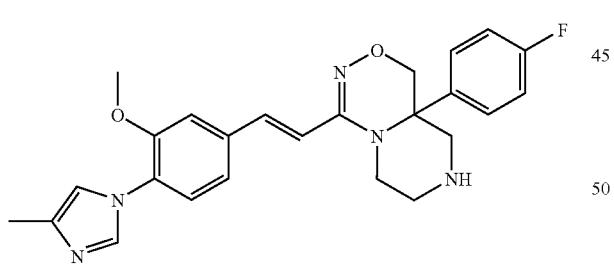
L7
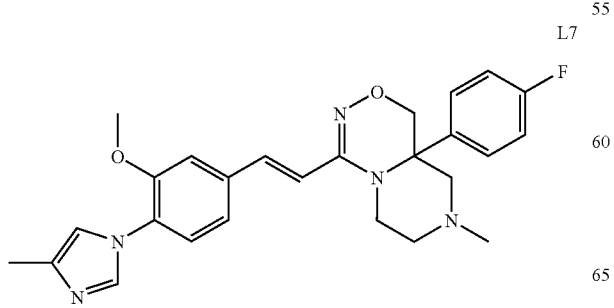
L8
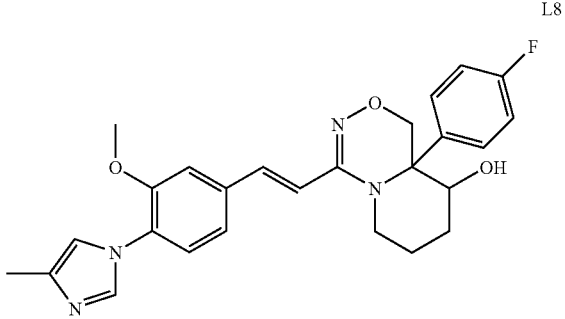
M5
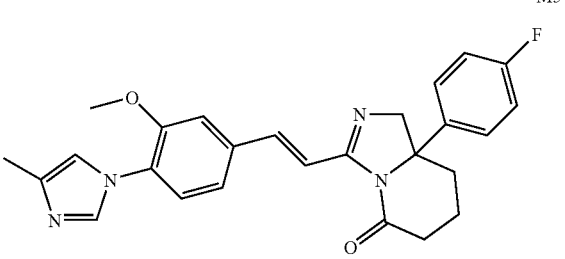
M6
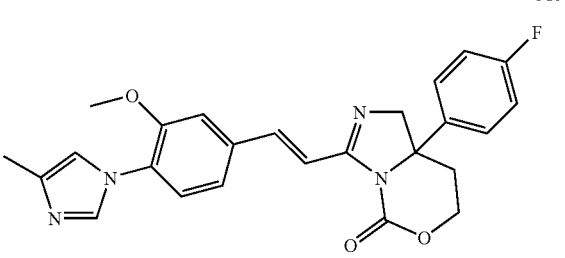
M7
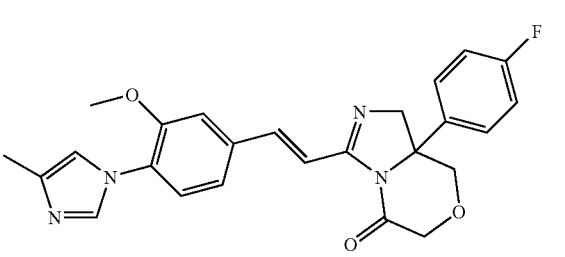
M8
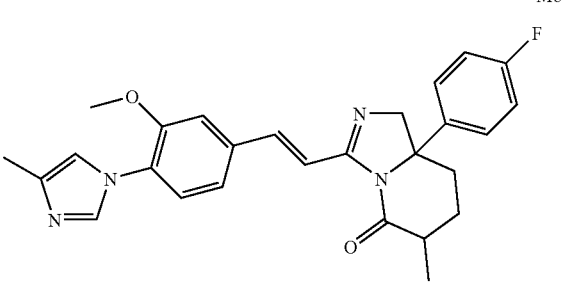
M9

M10 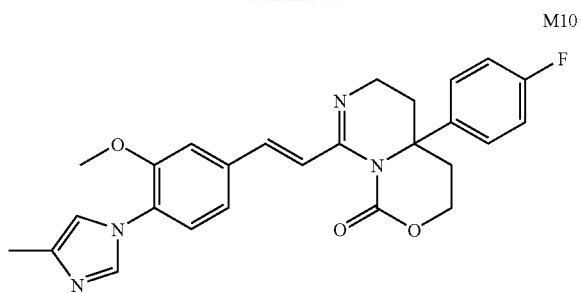
N6 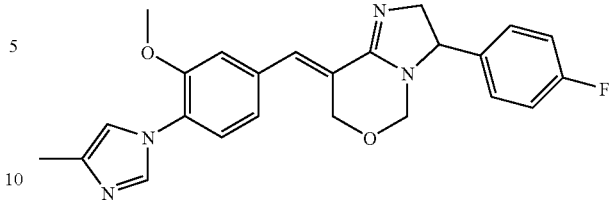
M11 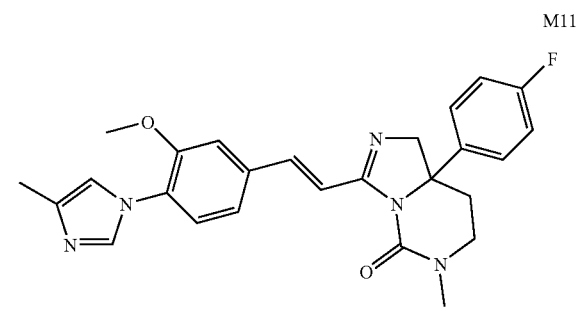
N7 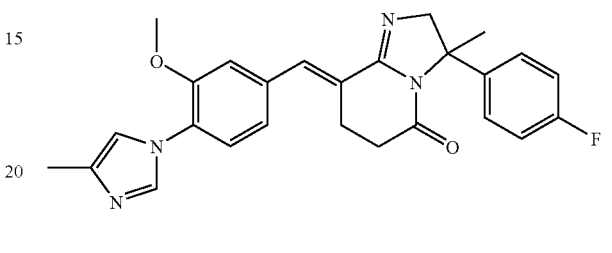
M12 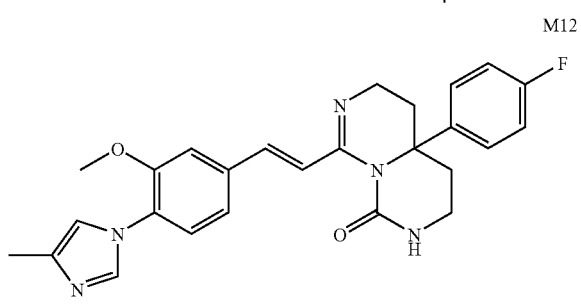
N8 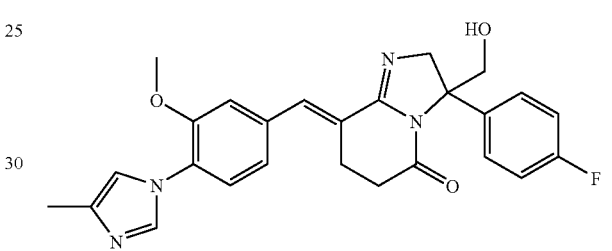
M13 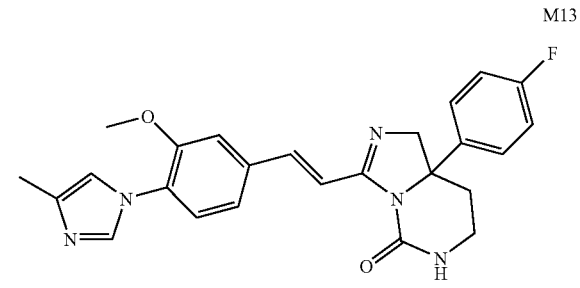
N9 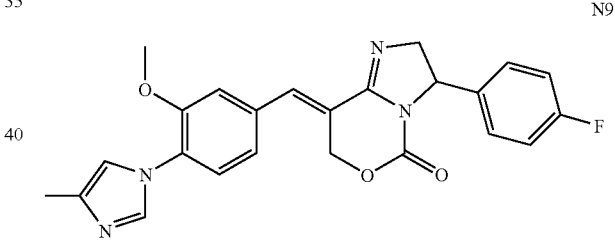
M14 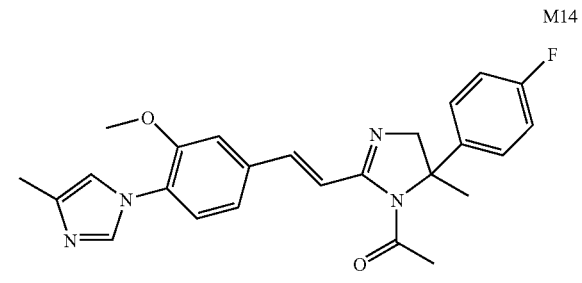
N10 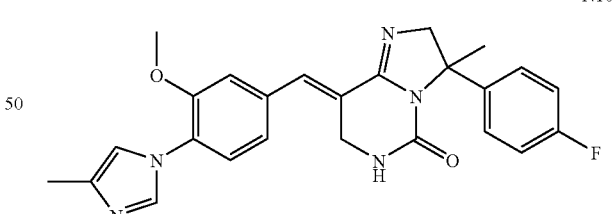
M15 
N11 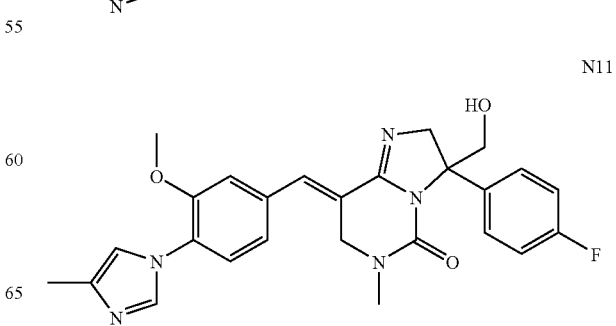

107
-continued
N12
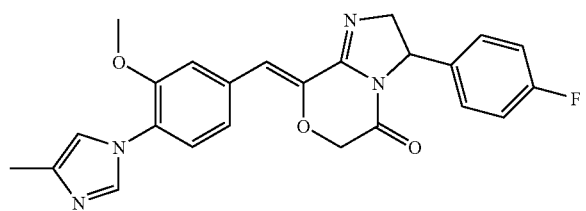
N13
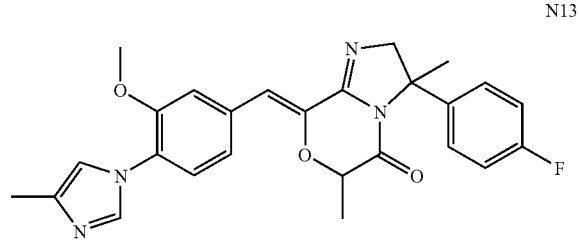
N14
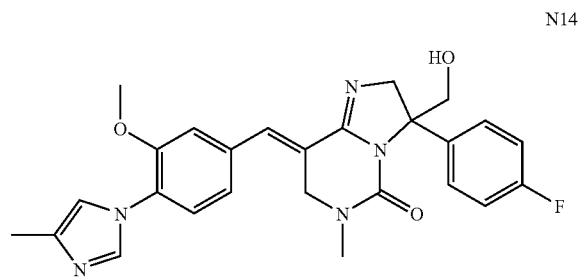
N15
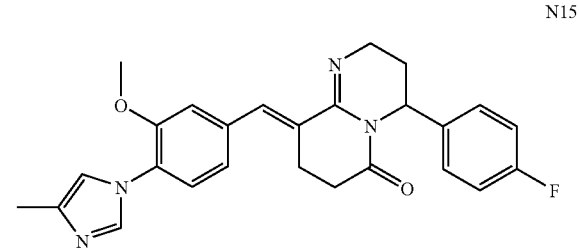
N16
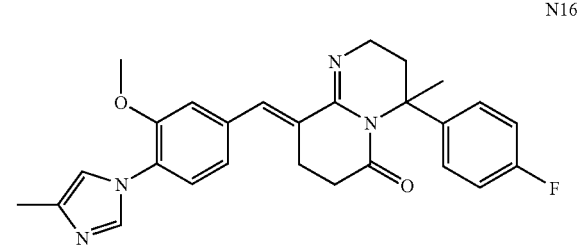
N17
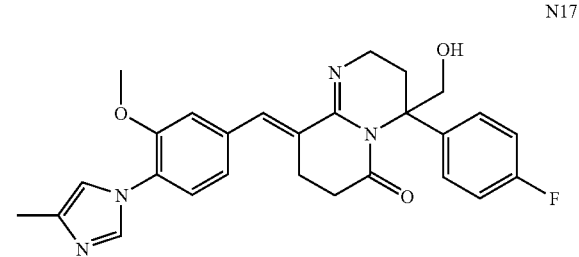
108
-continued
N18
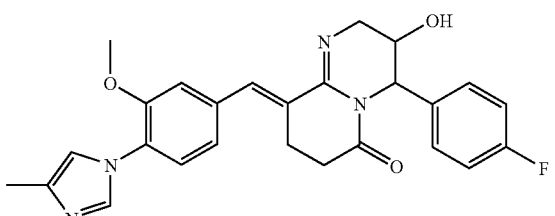
N19
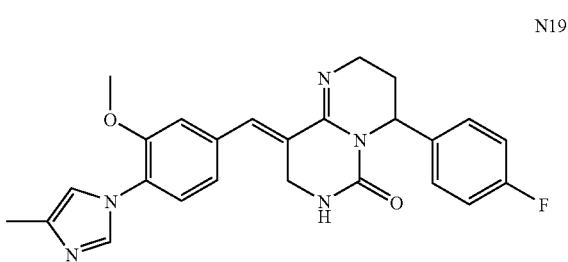
N20
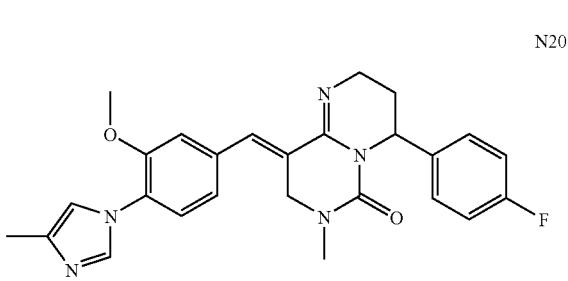
N21
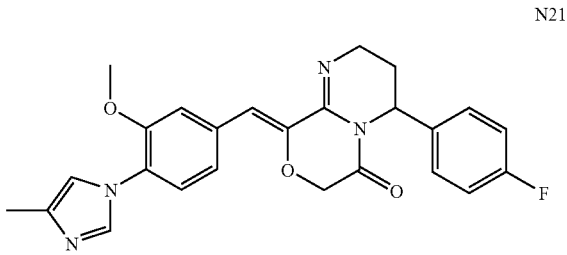
N22
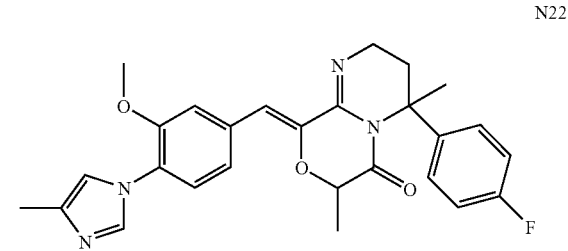
N23
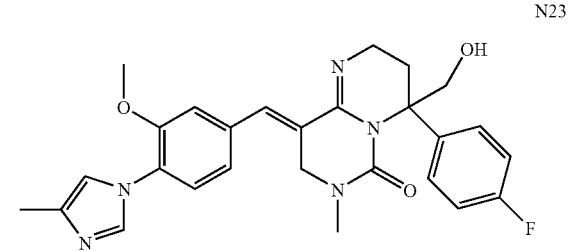

-continued

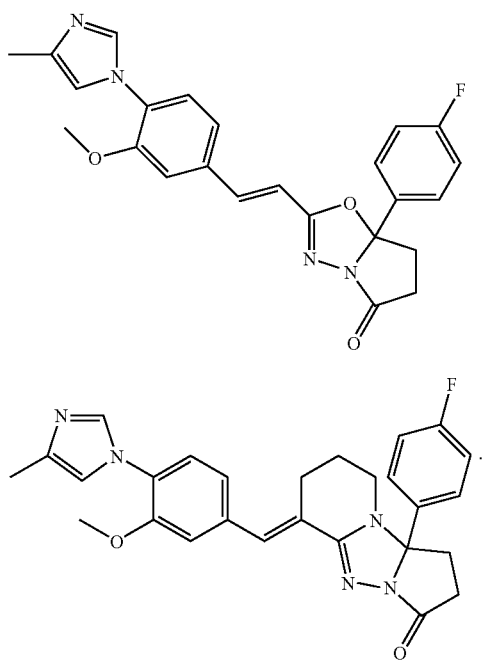

One embodiment of this invention is directed to compound 1.

Another embodiment of this invention is directed to compound 2.

Another embodiment of this invention is directed to compound 3.

Another embodiment of this invention is directed to compound 4.

Another embodiment of this invention is directed to compound 5.

Another embodiment of this invention is directed to compound 6.

Another embodiment of this invention is directed to compound 7.

Another embodiment of this invention is directed to compound 8.

Another embodiment of this invention is directed to compound 9.

Another embodiment of this invention is directed to compound 10.

Another embodiment of this invention is directed to compound 11.

Another embodiment of this invention is directed to compound 12.

Another embodiment of this invention is directed to compound 13.

Another embodiment of this invention is directed to compound 14.

Another embodiment of this invention is directed to compound 15.

Another embodiment of this invention is directed to compound 16.

Another embodiment of this invention is directed to compound 17.

Another embodiment of this invention is directed to compound 18.

Another embodiment of this invention is directed to compound 19.

Another embodiment of this invention is directed to compound 20.

Another embodiment of this invention is directed to compound 21.

Another embodiment of this invention is directed to compound 22.

Another embodiment of this invention is directed to compound 23.

Another embodiment of this invention is directed to compound 24.

Another embodiment of this invention is directed to compound B10.

Another embodiment of this invention is directed to compound B11.

Another embodiment of this invention is directed to compound B12.

Another embodiment of this invention is directed to compound B13.

Another embodiment of this invention is directed to compound B14.

Another embodiment of this invention is directed to compound B15.

Another embodiment of this invention is directed to compound B16.

Another embodiment of this invention is directed to compound B17.

Another embodiment of this invention is directed to compound B18.

Another embodiment of this invention is directed to compound B19.

Another embodiment of this invention is directed to compound B20.

Another embodiment of this invention is directed to compound B21.

Another embodiment of this invention is directed to compound C5.

Another embodiment of this invention is directed to compound C6.

Another embodiment of this invention is directed to compound C7.

Another embodiment of this invention is directed to compound C8.

Another embodiment of this invention is directed to compound C9.

Another embodiment of this invention is directed to compound C10.

Another embodiment of this invention is directed to compound D9.

Another embodiment of this invention is directed to compound D10.

Another embodiment of this invention is directed to compound D11.

Another embodiment of this invention is directed to compound D12.

Another embodiment of this invention is directed to compound D13.

Another embodiment of this invention is directed to compound D14.

Another embodiment of this invention is directed to compound D15.

Another embodiment of this invention is directed to compound D16.

Another embodiment of this invention is directed to compound D17.

Another embodiment of this invention is directed to compound D18.

Another embodiment of this invention is directed to compound D19.

Another embodiment of this invention is directed to compound D20.

Another embodiment of this invention is directed to compound D21.

Another embodiment of this invention is directed to compound D22.

Another embodiment of this invention is directed to compound D23.

Another embodiment of this invention is directed to compound D24.

Another embodiment of this invention is directed to compound D25.

Another embodiment of this invention is directed to compound D26.

Another embodiment of this invention is directed to compound G4.

Another embodiment of this invention is directed to compound G5.

Another embodiment of this invention is directed to compound G6.

Another embodiment of this invention is directed to compound G7.

Another embodiment of this invention is directed to compound G8.

Another embodiment of this invention is directed to compound G9.

Another embodiment of this invention is directed to compound H3.

Another embodiment of this invention is directed to compound H4.

Another embodiment of this invention is directed to compound H5.

Another embodiment of this invention is directed to compound H6.

Another embodiment of this invention is directed to compound H7.

Another embodiment of this invention is directed to compound H8.

Another embodiment of this invention is directed to compound H9.

Another embodiment of this invention is directed to compound H10.

Another embodiment of this invention is directed to compound H11.

Another embodiment of this invention is directed to compound I5.

Another embodiment of this invention is directed to compound I6.

Another embodiment of this invention is directed to compound I6A.

Another embodiment of this invention is directed to compound I7.

Another embodiment of this invention is directed to compound I8.

Another embodiment of this invention is directed to compound I8A.

Another embodiment of this invention is directed to compound J4.

Another embodiment of this invention is directed to compound J5.

Another embodiment of this invention is directed to compound J6.

Another embodiment of this invention is directed to compound J7.

Another embodiment of this invention is directed to compound J8.

Another embodiment of this invention is directed to compound J9.

Another embodiment of this invention is directed to compound K1.

Another embodiment of this invention is directed to compound K2.

Another embodiment of this invention is directed to compound K3.

Another embodiment of this invention is directed to compound K4.

Another embodiment of this invention is directed to compound K5.

Another embodiment of this invention is directed to compound K6.

Another embodiment of this invention is directed to compound L4.

Another embodiment of this invention is directed to compound L5.

Another embodiment of this invention is directed to compound L6.

Another embodiment of this invention is directed to compound L7.

Another embodiment of this invention is directed to compound L8.

Another embodiment of this invention is directed to compound M5.

Another embodiment of this invention is directed to compound M6.

Another embodiment of this invention is directed to compound M7.

Another embodiment of this invention is directed to compound M8.

Another embodiment of this invention is directed to compound M9.

Another embodiment of this invention is directed to compound M10.

Another embodiment of this invention is directed to compound M11.

Another embodiment of this invention is directed to compound M12.

Another embodiment of this invention is directed to compound M13.

Another embodiment of this invention is directed to compound M14.

Another embodiment of this invention is directed to compound M15.

Another embodiment of this invention is directed to compound N6.

Another embodiment of this invention is directed to compound N7.

Another embodiment of this invention is directed to compound N8.

Another embodiment of this invention is directed to compound N9.

Another embodiment of this invention is directed to compound N10.

Another embodiment of this invention is directed to compound N11.

Another embodiment of this invention is directed to compound N12.

Another embodiment of this invention is directed to compound N13.

Another embodiment of this invention is directed to compound N14.

Another embodiment of this invention is directed to compound N15.

Another embodiment of this invention is directed to compound N16.

Another embodiment of this invention is directed to compound N17.

Another embodiment of this invention is directed to compound N18.

Another embodiment of this invention is directed to compound N19.

Another embodiment of this invention is directed to compound N20.

Another embodiment of this invention is directed to compound N21.

Another embodiment of this invention is directed to compound N22.

Another embodiment of this invention is directed to compound N23.

Another embodiment of this invention is directed to compound O4_1.

Another embodiment of this invention is directed to compound P8_1.

As used above, and throughout this disclosure, the following terms, unless otherwise indicated, shall be understood to have the following meanings:

"ADDP" means 1,1'-(azodicarbonyl)dipiperidine.

"AIBN" means 2,2'-azobis(2-methylpropionitrile).

"CAN" means ammonium cerium (IV) nitrate.

"DCC" means N,N'-dicyclohexylcarbodiimide.

"DCM" means dichloromethane.

"DMF" means dimethylformamide.

"HOBT" means 1-hydroxylbenzotriazole.

"LDA" means lithium diisopropylamide.

"TBAF" means tetra-N-butylammonium fluoride.

"TBSO" means tert-butyldimethylsilyloxy.

"TfO" means trifluoromethylsulfonyloxy.

"At least one" means one or more than one, for example, 1, 2 or 3, or in another example, 1 or 2, or in another example 1.

"One or more" with reference to the use of the compounds of this invention means that one or more than one compound is used, for example, 1, 2 or 3, or in another example, 1 or 2, or in another example 1.

"Patient" includes both human and animals.

"Mammal" means humans and other mammalian animals.

It is noted that the carbons of formula I and other formulas herein may be replaced with 1 to 3 silicon atoms so long as all valency requirements are satisfied.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, oxime (e.g., =N—OH), —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or this before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl"

also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine. "Halo" refers to fluoro, chloro, bromo or iodo.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

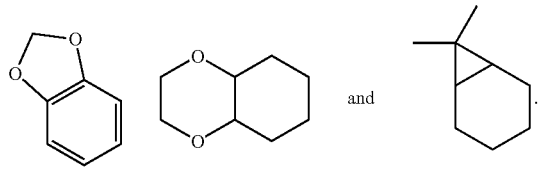

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a heterocyclyl ring wherein a single moiety (e.g. =O) simultaneously replaces two available hydrogens on the same carbon atom on a ring system. An example of such moiety is pyrrolidone:

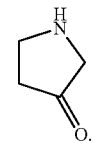

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

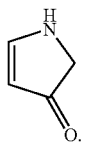

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

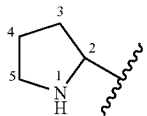 [SMILES: *C1CCCN1]

there is no —OH attached directly to carbons marked 2 and 5.

It should also be noted that tautomeric forms such as, for example, the moieties:

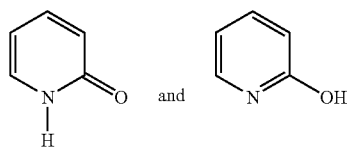 [SMILES: O=c1cccc[nH]1 ; Oc1ccccn1] and are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S- group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, (C1-$C_2$)alkylcarbamoyl-(C1-C2)alkyl and piperidino-, pyrrolidino- or morpholino$(C_2-C_3)$alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N-$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O$(C_1-C_6)$alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy (C1-C6)alkyl, amino (C1-C4)alkyl or mono-N- or di-N,N-$(C_1-C_6)$alkylaminoalkyl, —C(Y$^4$)Y$^5$ wherein Y$^4$ is H or methyl and Y$^5$ is mono-N- or di-N,N-$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, The Practice of Medicinal Chemistry (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion. of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula I, and salts, solvates, esters and prodrugs thereof, may exist in their tautomeric form (for example, as an amide, enol, keto or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I, and of the salts, solvates, esters and prodrugs of the compounds of Formula I, are intended to be included in the present invention.

The compounds according to the invention can have pharmacological properties; in particular, the compounds of Formula I can be modulators of gamma secretase (including inhibitors, antagonists and the like).

More specifically, the compounds of Formula I can be useful in the treatment of a variety of disorders of the central nervous system including, for example, including, but not limited to, Alzheimer's disease, AIDS-related dementia, Parkinson's disease, amyotrophic lateral sclerosis, retinitis pigmentosa, spinal muscular atrophy and cerebellar degeneration and the like.

Another aspect of this invention is a method of treating a mammal (e.g., human) having a disease or condition of the central nervous system by administering a therapeutically effective amount of at least one compound of Formula I, or a pharmaceutically acceptable salt, solvate, ester or prodrug of said compound to the mammal.

A preferred dosage is about 0.001 to 500 mg/kg of body weight/day of the compound of Formula I. An especially preferred dosage is about 0.01 to 25 mg/kg of body weight/day of a compound of Formula I, or a pharmaceutically acceptable salt or solvate of said compound.

The compounds of this invention may also be useful in combination (administered together or sequentially) with one or more additional agents listed above.

The compounds of this invention may also be useful in combination (administered together or sequentially) with one or more compounds selected from the group consisting of Aβ antibody inhibitors, gamma secretase inhibitors and beta secretase inhibitors.

If formulated as a fixed dose, such combination products employ the compounds of this invention within the dosage range described herein and the other pharmaceutically active agent or treatment within its dosage range.

Accordingly, in an aspect, this invention includes combinations comprising an amount of at least one compound of Formula I, or a pharmaceutically acceptable salt, solvate, ester or prodrug thereof, and an amount of one or more additional agents listed above wherein the amounts of the compounds/treatments result in desired therapeutic effect.

The pharmacological properties of the compounds of this invention may be confirmed by a number of pharmacological assays. Certain assays are exemplified later in this document.

This invention is also directed to pharmaceutical compositions which comprise at least one compound of Formula I, or a pharmaceutically acceptable salt, solvate, ester or prodrug of said compound and at least one pharmaceutically acceptable carrier.

Other embodiments of this invention are directed to pharmaceutically acceptable salts of any one of the embodiments above directed to any one of compounds 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

Other embodiments of this invention are directed to pharmaceutically acceptable esters of any one of the embodiments above directed to any one of compounds 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

Other embodiments of this invention are directed to solvates of any one of the embodiments above directed to any one of compounds 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

One embodiment of this invention is directed to a compound of formula I.

Another embodiment of this invention is directed to a pharmaceutically acceptable salt of a compound of formula I.

Another embodiment of this invention is directed to a pharmaceutically acceptable ester of a compound of formula I.

Another embodiment of this invention is directed to a solvate of a compound of formula I.

Another embodiment of this invention is directed to a compound of formula I in isolated form.

Another embodiment of this invention is directed to a compound of formula I in pure form.

Another embodiment of this invention is directed to a compound of formula I in pure and isolated form.

Another embodiment of this invention is directed to a pharmaceutical composition comprising an effective amount of one or more (e.g., one) compounds of formula I and a pharmaceutically acceptable carrier.

Another embodiment of this invention is directed to a pharmaceutical composition comprising an effective amount of a pharmaceutically acceptable salt of one or more (e.g., one) compounds of formula I and a pharmaceutically acceptable carrier.

Another embodiment of this invention is directed to a pharmaceutical composition comprising an effective amount of a pharmaceutically acceptable ester of one or more (e.g., one) compounds of formula I and a pharmaceutically acceptable carrier.

Another embodiment of this invention is directed to a pharmaceutical composition comprising an effective amount of a solvate of one or more (e.g., one) compounds of formula I and a pharmaceutically acceptable carrier.

Another embodiment of this invention is directed to a pharmaceutical composition comprising an effective amount of one or more (e.g., one) compounds of formula I, and an effective amount of one or more (e.g., one) other pharmaceutically active ingredients (e.g.,) drugs, and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase.

Another embodiment of this invention is directed to a pharmaceutical composition comprising an effective amount of one or more (e.g., one) compounds of formula I, and effective amount of one or more BACE inhibitors, and a pharmaceutically acceptable carrier.

Another embodiment of this invention is directed to a pharmaceutical composition comprising an effective amount of one or more (e.g., one) compounds of formula I, and effective amount of one or more cholinesterase inhibitors (e.g., acetyl- and/or butyrylchlolinesterase inhibitors), and a pharmaceutically acceptable carrier.

The compounds of formula I can be useful as gamma secretase modulators and can be useful in the treatment and prevention of diseases such as, for example, central nervous system disorders such as Alzheimers disease and Downs Syndrome.

Thus, another embodiment of this invention is directed to a method for modulating (including inhibiting, antagonizing and the like) gamma-secretase comprising administering an effective amount of one or more (e.g., one) compounds of formula I to a patient in need of such treatment.

Another embodiment of this invention is directed to a method for modulating (including inhibiting, antagonizing and the like) gamma-secretase, comprising administering an effective amount of a compound of formula I to a patient in need of treatment.

Another embodiment of this invention is directed to a method of treating one or more neurodegenerative diseases, comprising administering an effective amount of one or more (e.g., one) compounds of formula I to a patient in need of treatment.

Another embodiment of this invention is directed to a method of treating one or more neurodegenerative diseases, comprising administering an effective amount of a compound of formula I to a patient in need of treatment.

Another embodiment of this invention is directed to a method of inhibiting the deposition of amyloid protein (e.g., amyloid beta protein) in, on or around neurological tissue (e.g., the brain), comprising administering an effective amount of one or more (e.g., one) compounds of formula I to a patient in need of treatment.

Another embodiment of this invention is directed to a method of inhibiting the deposition of amyloid protein (e.g., amyloid beta protein) in, on or around neurological tissue (e.g., the brain), comprising administering an effective amount of a compound of formula I to a patient in need of treatment.

Another embodiment of this invention is directed to a method of treating Alzheimer's disease, comprising administering an effective amount of one or more (e.g., one) compounds of formula I to a patient in need of treatment.

Another embodiment of this invention is directed to a method of treating Alzheimer's disease, comprising administering an effective amount of a compound of formula I to a patient in need of treatment.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of an effective amount of one or more (e.g. one) compounds of formula I and the administration of an effective amount of one or more (e.g., one) other pharmaceutical active ingredients (e.g., drugs). The compounds of formula I and the other drugs can be administered separately (i.e., each is in its own separate dosage form), or the compounds of formula I can be combined with the other drugs in the same dosage form.

Thus, other embodiments of this invention are directed to any one of the methods of treatment, or methods of inhibiting, described herein, wherein an effective amount of the compound of formula I is used in combination with an effective amount of one or more other pharmaceutically active ingredients selected from the group consisting of: BACE inhibitors (beta secretase inhibitors), muscarinic antagonists (e.g., $m_1$ agonists or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors (e.g., ezetimibe).

Another embodiment of this invention is directed to a method of treating Alzheimer's disease, comprising administering an effective amount of one or more (e.g., one) compounds of formula I, in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective amount of a compound of formula I, in combination with an effective amount of one or more (e.g., one) cholinesterase inhibitors (such as, for example, (±)-2,3-dihydro-5,6-dimethoxy-2-[[1-(phenylmethyl)-4-piperidinyl]methyl]-H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective amount of one or more (e.g., one) compounds of formula I, in combination with an effective amount of one or more compounds selected from the group consisting of Aβ antibody inhibitors, gamma secretase inhibitors and beta secretase inhibitors.

Another embodiment of this invention is directed to a method of treating Alzheimer's disease, comprising administering an effective amount of one or more (e.g., one) compounds of formula I, in combination with an effective amount of one or more BACE inhibitors.

Another embodiment of this invention is directed to a method of treating Alzheimer's disease, comprising administering an effective amount of one or more compounds of formula I, in combination with an effective amount of Exelon (rivastigmine).

Another embodiment of this invention is directed to a method of treating Alzheimer's disease, comprising administering an effective amount of one or more compounds of formula I, in combination with an effective amount of Cognex (tacrine).

Another embodiment of this invention is directed to a method of treating Alzheimer's disease, comprising administering an effective amount of one or more compounds of formula I, in combination with an effective amount of a Tau kinase inhibitor.

Another embodiment of this invention is directed to a method of treating Alzheimer's disease, comprising administering an effective amount of one or more compounds of formula I, in combination with an effective amount of one or more Tau kinase inhibitor (e.g., GSK3beta inhibitor, cdk5 inhibitor, ERK inhibitor).

This invention also provides a method of treating Alzheimer's disease, comprising administering an effective amount of one or more compounds of formula I, in combination with an effective amount of one anti-Abeta vaccination (active immunization).

Another embodiment of this invention is directed to a method of treating Alzheimer's disease, comprising administering an effective amount of one or more compounds of formula I, in combination with an effective amount of one or more APP ligands.

Another embodiment of this invention is directed to a method of treating Alzheimer's disease, comprising administering an effective amount of one or more compounds of formula I, in combination with an effective amount of one or more agents that upregulate insulin degrading enzyme and/or neprilysin.

Another embodiment of this invention is directed to a method of treating Alzheimer's disease, comprising administering an effective amount of one or more compounds of formula I, in combination with an effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe).

This invention also provides a method of treating Alzheimer's disease, comprising administering an effective amount of one or more compounds of formula I, in combination with an effective amount of one or more fibrates (for example, clofibrate, Clofibride, Etofibrate, Aluminium Clofibrate).

Another embodiment of this invention is directed to a method of treating Alzheimer's disease, comprising administering an effective amount of one or more compounds of formula. I, in combination with an effective amount of one or more LXR agonists.

Another embodiment of this invention is directed to a method of treating Alzheimer's disease, comprising administering an effective amount of one or more compounds of formula I, in combination with an effective amount of one or more LRP mimics.

Another embodiment of this invention is directed to a method of treating Alzheimer's disease, comprising administering an effective amount of one or more compounds of formula I, in combination with an effective amount of one or more 5-HT6 receptor antagonists.

Another embodiment of this invention is directed to a method of treating Alzheimer's disease, comprising administering an effective amount of one or more compounds of formula I, in combination with an effective amount of one or more nicotinic receptor agonists.

Another embodiment of this invention is directed to a method of treating Alzheimer's disease, comprising administering an effective amount of one or more compounds of formula I, in combination with an effective amount of one or more H3 receptor antagonists.

This invention also provides a method of treating Alzheimer's disease, comprising administering an effective amount of one or more compounds of formula I, in combination with an effective amount of one or more histone deacetylase inhibitors.

Another embodiment of this invention is directed to a method of treating Alzheimer's disease, comprising administering an effective amount of one or more compounds of formula I, in combination with an effective amount of one or more hsp90 inhibitors.

Another embodiment of this invention is directed to a method of treating Alzheimer's disease, comprising administering an effective amount of one or more compounds of formula I, in combination with an effective amount of one or more m1 muscarinic receptor agonists.

Another embodiment of this invention is directed to a method of treating Alzheimer's disease, comprising administering an effective amount of one or more compounds of formula I, in combination with an effective amount of one or more 5-HT6 receptor antagonists mGluR1 or mGluR5 positive allosteric modulators or agonists Another embodiment of this invention is directed to a method of treating Alzheimer's disease, comprising administering an effective amount of one or more compounds of formula I, in combination with an effective amount of one or more mGluR2/3 antagonists.

Another embodiment of this invention is directed to a method of treating Alzheimer's disease, comprising administering an effective amount of one or more compounds of formula I, in combination with an effective amount of one or more anti-inflammatory agents that can reduce neuroinflammation.

Another embodiment of this invention is directed to a method of treating Alzheimer's disease, comprising administering an effective amount of one or more compounds of formula I, in combination with an effective amount of one or more Prostaglandin EP2 receptor antagonists.

This invention also provides a method of treating Alzheimer's disease, comprising administering an effective amount of one or more compounds of formula I, in combination with an effective amount of one or more PAI-1 inhibitors.

This invention also provides a method of treating Alzheimer's disease, comprising administering an effective amount of one or more compounds of formula I, in combination with an effective amount of one or more agents that can induce Abeta efflux such as gelsolin.

This invention also provides a method of treating Downs syndrome, comprising administering an effective amount of one or more (e.g., one) compounds of formula I to a patient in need of treatment.

This invention also provides a method of treating Downs syndrome, comprising administering an effective amount of a compound of formula I to a patient in need of treatment.

This invention also provides a method of treating Downs syndrome, comprising administering an effective amount of one or more (e.g., one) compounds of formula I, in combination with an effective amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides a method of treating Downs syndrome, comprising administering an effective amount of a compound of formula I, in combination with an effective amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides a method of treating mild cognitive impairment, comprising administering an effective amount of one or more (e.g., one) compounds of formula I to a patient in need of treatment.

This invention also provides a method of treating glaucoma, comprising administering an effective amount of one or more (e.g., one) compounds of formula I to a patient in need of treatment.

This invention also provides a method of treating cerebral amyloid angiopathy, comprising administering an effective amount of one or more (e.g., one) compounds of formula I to a patient in need of treatment.

This invention also provides a method of treating stroke, comprising administering an effective amount of one or more (e.g., one) compounds of formula I to a patient in need of treatment.

This invention also provides a method of treating dementia, comprising administering an effective amount of one or more (e.g., one) compounds of formula I to a patient in need of treatment.

This invention also provides a method of treating microgliosis, comprising administering an effective amount of one or more (e.g., one) compounds of formula I to a patient in need of treatment.

This invention also provides a method of treating brain inflammation, comprising administering an effective amount of one or more (e.g., one) compounds of formula I to a patient in need of treatment.

This invention also provides a method of treating olfactory function loss, comprising administering an effective amount of one or more (e.g., one) compounds of formula I to a patient in need of treatment.

This invention also provides combinations (i.e., pharmaceutical compositions) comprising an effective amount of one or more (e.g., one) compounds of formula I, in combination with an effective amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), Aβ antibody inhibitors, gamma secretase inhibitors and beta secretase inhibitors. The pharmaceutical compositions also comprise a pharmaceutically acceptable carrier.

This invention also provides a kit comprising, in separate containers, in a single package, pharmaceutical compositions for use in combination, wherein one container comprises an effective amount of a compound of formula I in a pharmaceutically acceptable carrier, and another container (i.e., a second container) comprises an effective amount of another pharmaceutically active ingredient (as described above), the combined quantities of the compound of formula I and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Another embodiment of this invention is directed to a pharmaceutically acceptable salt of a compound of formula (I), said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4__1, and P8__1.

Another embodiment of this invention is directed to a pharmaceutically acceptable ester of a compound of formula (I), said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4__1, and P8__1.

Another embodiment of this invention is directed to a solvate of a compound of formula (I), said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4__1, and P8__1.

Another embodiment of this invention is directed to a compound of formula (I) in isolated form, said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4__1, and P8__1.

Another embodiment of this invention is directed to a compound of formula (I) in pure form, said compound of formula (I) being selected from the group consisting of: said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4__1, and P8__1.

Another embodiment of this invention is directed to a compound of formula (I) in pure and isolated form, said compound of formula (I) being selected from the group consisting of: said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4__1, and P8__1.

Another embodiment is directed to a pharmaceutical composition comprising an effective amount of one or more (e.g., one) compounds of formula (I) and a pharmaceutically acceptable carrier, said compound of formula (I) being selected from the group consisting of: said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4__1, and P8__1.

Another embodiment is directed to a pharmaceutical composition comprising an effective amount of a pharmaceutically acceptable salt of one or more (e.g., one) compounds of formula (I) and a pharmaceutically acceptable carrier, said compound of formula (I) being selected from the group consisting of: said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4__1, and P8__1.

Another embodiment is directed to a pharmaceutical composition comprising an effective amount of a pharmaceutically acceptable ester of one or more (e.g., one) compounds of formula (I) and a pharmaceutically acceptable carrier, said compound of formula (I) being selected from the group consisting of: said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4__1, and P8__1.

Another embodiment is directed to a pharmaceutical composition comprising an effective amount of a solvate of one or more (e.g., one) compounds of formula (I) and a pharmaceutically acceptable carrier, said compound of formula (I) being selected from the group consisting of: said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

Another embodiment of this invention is directed to a pharmaceutical composition comprising an effective amount of one or more (e.g., one) compounds of formula (I), and an effective amount of one or more (e.g., one) other pharmaceutically active ingredients (e.g., drugs), and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase, said compound of formula (I) being selected from the group consisting of: said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

Another embodiment of this invention is directed to a pharmaceutical composition comprising an effective amount of one or more (e.g., one) compounds of formula (I), and effective amount of one or more BACE inhibitors, and a pharmaceutically acceptable carrier, said compound of formula (I) being selected from the group consisting of: said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and an effective amount of one or more cholinesterase inhibitors (e.g., acetyl- and/or butyrylchlolinesterase inhibitors), and a pharmaceutically acceptable carrier.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one or more muscarinic antagonists (e.g., $m_1$ agonists or $m_2$ antagonists), and a pharmaceutically acceptable carrier.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of Exelon (rivastigmine), and a pharmaceutically acceptable carrier.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of Cognex (tacrine), and a pharmaceutically acceptable carrier.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of a Tau kinase inhibitor, and a pharmaceutically acceptable carrier.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one or more Tau kinase inhibitor (e.g., GSK3beta inhibitor, cdk5 inhibitor, ERK inhibitor), and a pharmaceutically acceptable carrier.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one anti-Abeta vaccine (active immunization), and a pharmaceutically acceptable carrier.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one or more APP ligands, and a pharmaceutically acceptable carrier.

Another embodiment of this invention is directed to a pharmaceutical composition comprising an effective amount of one or more (e.g., one) compounds selected from the group consisting of: consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one or more agents that upregulate insulin degrading enzyme and/or neprilysin, and a pharmaceutically acceptable carrier.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe), and a pharmaceutically acceptable carrier.

Another embodiment of this invention is directed to a pharmaceutical composition comprising an effective amount of one or more (e.g., one) compounds selected from the group consisting of: consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one or more fibrates (for example, clofibrate, Clofibride, Etofibrate, Aluminium Clofibrate), and a pharmaceutically acceptable carrier.

Another embodiment of this invention is directed to a pharmaceutical composition comprising an effective amount of one or more (e.g., one) compounds selected from the group consisting of: consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one or more LXR agonists, and a pharmaceutically acceptable carrier.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one or more LRP mimics, and a pharmaceutically acceptable carrier.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one or more 5-HT6 receptor antagonists, and a pharmaceutically acceptable carrier.

Another embodiment of this invention is directed to a pharmaceutical composition comprising an effective amount of one or more (e.g., one) compounds selected from the group consisting of: consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one or more nicotinic receptor agonists, and a pharmaceutically acceptable carrier.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one or more H3 receptor antagonists, and a pharmaceutically acceptable carrier.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one or more histone deacetylase inhibitors, and a pharmaceutically acceptable carrier.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one or more hsp90 inhibitors, and a pharmaceutically acceptable carrier.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one or more m1 muscarinic receptor agonists, and a pharmaceutically acceptable carrier.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one or more 5-HT6 receptor antagonists mGluR1 or mGluR5 positive allosteric modulators or agonists, and a pharmaceutically acceptable carrier.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one or more one mGluR2/3 antagonists, and a pharmaceutically acceptable carrier.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one or more anti-inflammatory agents that can reduce neuroinflammation, and a pharmaceutically acceptable carrier.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one or more Prostaglandin EP2 receptor antagonists, and a pharmaceutically acceptable carrier.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one or more PAI-1 inhibitors, and a pharmaceutically acceptable carrier.

Another embodiment of this invention is directed to a pharmaceutical composition comprising an effective amount of one or more (e.g., one) compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and effective amount of one or more agents that can induce Abeta efflux such as gelsolin, and a pharmaceutically acceptable carrier.

The compounds of formula I selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1 can be useful as gamma secretase modulators and can be useful in the treatment and prevention of diseases such as, for example, central nervous system disorders (such as Alzheimers disease and Downs Syndrome), and treating mild cognitive impairment, glaucoma, cerebral amyloid angiopathy, stroke, dementia, microgliosis, brain inflammation, and olfactory function loss.

Thus, another embodiment of this invention is directed to a method for modulating (including inhibiting, antagonizing and the like) gamma-secretase comprising administering an effective (i.e., therapeutically effective) amount of one or more (e.g., one) compounds of formula (I) to a patient in need of such treatment, said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

Another embodiment of this invention is directed to a method for modulating (including inhibiting, antagonizing and the like) gamma-secretase, comprising administering an effective (i.e., therapeutically effective) amount of a compound of formula (I) to a patient in need of treatment, said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

Another embodiment of this invention is directed to a method of treating one or more neurodegenerative diseases, comprising administering an effective (i.e., therapeutically effective) amount of one or more (e.g., one) compounds of formula (I) to a patient in need of treatment, said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

Another embodiment of this invention is directed to a method of treating one or more neurodegenerative diseases, comprising administering an effective (i.e., therapeutically effective) amount of a compound of formula (I) to a patient in need of treatment, said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

Another embodiment of this invention is directed to a method of inhibiting the deposition of amyloid protein (e.g., amyloid beta protein) in, on or around neurological tissue (e.g., the brain), comprising administering an effective (i.e., therapeutically effective) amount of one or more (e.g., one) compounds of formula (I) to a patient in need of treatment, said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

Another embodiment of this invention is directed to a method of inhibiting the deposition of amyloid protein (e.g., amyloid beta protein) in, on or around neurological tissue (e.g., the brain), comprising administering an effective (i.e., therapeutically effective) amount of a compound of formula (I) to a patient in need of treatment, said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

Another embodiment of this invention is directed to a method of treating Alzheimer's disease, comprising administering an effective (i.e., therapeutically effective) amount of one or more (e.g., one) compounds of formula (I) to a patient in need of treatment, said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

Another embodiment of this invention is directed to a method of treating Alzheimer's disease, comprising administering an effective (i.e., therapeutically effective) amount of a compound of formula (I) to a patient in need of treatment, said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

Another embodiment of this invention is directed to a method of treating mild cognitive impairment, glaucoma, cerebral amyloid angiopathy, stroke, dementia, microgliosis, brain inflammation, or olfactory function loss, comprising administering an effective (i.e., therapeutically effective) amount of one or more (e.g., one) compounds of formula (I) to a patient in need of treatment, said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

Another embodiment of this invention is directed to a method of treating mild cognitive impairment, glaucoma, cerebral amyloid angiopathy, stroke, dementia, microgliosis, brain inflammation, or olfactory function loss, comprising administering an effective (i.e., therapeutically effective) amount of a compound of formula (I) to a patient in need of treatment, said compound of formula (I) being selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of one or more (e.g. one) compounds of formula (I), and the administration of one or more (e.g., one) other pharmaceutical active ingredients (e.g., drugs). The compounds of formula (I), and the other drugs can be administered separately (i.e., each is in its own separate dosage form), or the compounds of formula (I) can be combined with the other drugs in the same dosage form.

Thus, other embodiments of this invention are directed to any one of the methods of treatment, or methods of inhibiting, described herein, wherein the compounds of formula (I) are used in combination with an effective amount of one or more other pharmaceutically active ingredients selected from the group consisting of: BACE inhibitors (beta secretase inhibitors); muscarinic antagonists (e.g., $m_1$ agonists or $m_2$ antagonists); cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Exelon (rivastigmine); Cognex (tacrine); Tau kinase inhibitors (e.g., GSK3beta inhibitors, cdk5 inhibitors, or ERK inhibitors); anti-Abeta vaccine; APP ligands; agents that upregulate insulin cholesterol lowering agents (for example, statins such as Atorvastatin, Fluvastatin, Lovastatin, Mevastatin, Pitavastatin, Pravastatin, Rosuvastatin, Simvastatin); cholesterol absorption inhibitors (such as Ezetimibe); fibrates (such as, for example, for example, clofibrate, Clofibride, Etofibrate, and Aluminium Clofibrate); LXR agonists; LRP mimics; nicotinic receptor agonists; H3 receptor antagonists; histone deacetylase inhibitors; hsp90 inhibitors; ml muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux such as gelsolin.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of one or more (e.g. one) compounds of formula (I) selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and the administration of one or more (e.g., one) other pharmaceutical active ingredients (e.g., drugs). The compounds of formula I to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, and the other drugs can be administered separately (i.e., each is in its own separate dosage form), or the compounds of formula I to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1 can be combined with the other drugs in the same dosage form.

Thus, other embodiments of this invention are directed to any one of the methods of treatment, or methods of inhibiting, described herein, wherein the compounds of formula (I), selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1 are used in combination with an effective amount of one or more other pharmaceutically active ingredients selected from the group consisting of: BACE inhibitors (beta secretase inhibitors), muscarinic antagonists (e.g., $m_1$ agonists or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Exelon (rivastigmine); Cognex (tacrine); Tau kinase inhibitors (e.g., GSK3beta inhibitors, cdk5 inhibitors, or ERK inhibitors); anti-Abeta vaccine; APP ligands; agents that upregulate insulin cholesterol lowering agents (for example, statins such as Atorvastatin, Fluvastatin, Lovastatin, Mevastatin, Pitavastatin, Pravastatin, Rosuvastatin, Simvastatin); cholesterol absorption inhibitors (such as Ezetimibe); fibrates (such as, for example, for example, clofibrate, Clofibride, Etofibrate, and Aluminium Clofibrate); LXR agonists; LRP mimics; nicotinic receptor agonists; H3 receptor antagonists; histone deacetylase inhibitors; hsp90 inhibitors; ml muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux such as gelsolin.

Other embodiments of this invention are directed to any one of the methods of treatment, or methods of inhibiting, described herein, wherein the compounds of formula (I), selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1 are used in combination with an effective amount of one or more other pharmaceutically active ingredients selected from the group consisting of: BACE inhibitors (beta secretase inhibitors), muscarinic antagonists (e.g., $m_1$ agonists or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; and cholesterol absorption inhibitors (e.g., ezetimibe).

Other embodiments of this invention are directed to any one of the methods of treatment, or methods of inhibiting, described herein, wherein the compounds of formula (I), selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1 are used in combination with an effective amount of one or more other pharmaceutically active ingredients selected from the group consisting of: Exelon (rivastigmine); Cognex (tacrine); Tau kinase inhibitors (e.g., GSK3beta inhibitors, cdk5 inhibitors, or ERK inhibitors); anti-Abeta vaccine; APP ligands; agents that upregulate insulin cholesterol lowering agents (for example, statins such as Atorvastatin, Fluvastatin, Lovastatin, Mevastatin, Pitavastatin, Pravastatin, Rosuvastatin, Simvastatin); cholesterol absorption inhibitors (such as Ezetimibe); fibrates (such as, for example, for example, clofibrate, Clofibride, Etofibrate, and Aluminium Clofibrate); LXR agonists; LRP mimics; nicotinic receptor agonists; H3 receptor antagonists; histone deacetylase inhibitors; hsp90 inhibitors; ml muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux such as gelsolin.

Another embodiment of this invention is directed to a method of treating Alzheimer's disease, comprising administering an effective (i.e., therapeutically effective) amount of one or more (e.g., one) compounds of formula (I) selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, in combination with an effective (i.e., therapeutically effective) amount of one or more cholinesterase inhibitors (such as, for example, (±)-2,3-dihydro-5,6-dimethoxy-2[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective (i.e., therapeutically effective) amount of a compound of formula (I) selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective (i.e., therapeutically effective) amount of one or more (e.g., one) compounds of formula (I) selected from the group consisting of: in combination with an effective (i.e., therapeutically effective) amount of one or more compounds selected from the group consisting of Aβ antibody inhibitors, gamma secretase inhibitors and beta secretase inhibitors.

Another embodiment of this invention is directed to a method of treating Alzheimer's disease, comprising administering an effective (i.e., therapeutically effective) amount of one or more (e.g., one) compounds of formula (I) selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, in combination with an effective (i.e., therapeutically effective) amount of one or more BACE inhibitors.

Another embodiment of this invention is directed to a method of treating Alzheimer's disease, comprising administering an effective (i.e., therapeutically effective) amount of a compound of formula (I) selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, in combination with an effective (i.e., therapeutically effective) amount of one or more BACE inhibitors.

Another embodiment of this invention is directed to a method of treating Downs syndrome, comprising administering an effective (i.e., therapeutically effective) amount of one or more (e.g., one) compounds of formula (I) selected format the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1 to a patient in need of treatment.

Another embodiment of this invention is directed to a method of treating Downs syndrome, comprising administering an effective (i.e., therapeutically effective) amount of a compound of formula (I) selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, to a patient in need of treatment.

Another embodiment of this invention is directed to a method of treating Downs syndrome, comprising administering an effective (i.e., therapeutically effective) amount of one or more (e.g., one) compounds of formula (I) selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Downs syndrome, comprising administering an effective (i.e., therapeutically effective) amount of a compound of formula (I) selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1, in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to combinations (i.e., pharmaceutical compositions) comprising an effective (i.e., therapeutically effective) amount of one or more (e.g., one) compounds of formula (I) selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1 in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), Aβ antibody inhibitors, gamma secretase inhibitors and beta secretase inhibitors. The pharmaceutical compositions also comprise a pharmaceutically acceptable carrier.

This invention also provides a kit comprising, in separate containers, in a single package, pharmaceutical compositions for use in combination, wherein one container comprises an effective amount of one or more (e.g., one) compounds of formula (I) (e.g., compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1 in a pharmaceutically acceptable carrier, and another container (i.e., a second container) comprises an effective amount of another pharmaceutically active ingredient (as described above), the combined quantities of the compounds of formula (I) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

This invention also provides a kit comprising, in separate containers, in a single package, pharmaceutical compositions for use in combination, wherein one container comprises an effective amount of a compound selected from the group consisting of the compounds of formulas (I) (e.g. the compounds selected from the group consisting of: 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1) in a pharmaceutically acceptable carrier, and another container (i.e., a second container) comprises an effective amount of another pharmaceutically active ingredient (as described above), the combined quantities of the compound of formulas (I) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Other embodiments of this invention are directed to any one of the above methods of treatment, pharmaceutical compositions, or kits wherein the compound of formula I is any one of the compounds 1 to 24, B10-B21, C5-C10, D9-D26, G4-G9, H3-H11, I5, I6, I6A, I7, I8, I8A, J4-J9, K1-K6, L4-L8, M5-M15, N6-N23, O4_1, and P8_1.

Examples of cholinesterase inhibitors are tacrine, donepezil, rivastigmine, galantamine, pyridostigmine and neostigmine, with tacrine, donepezil, rivastigmine and galantamine being preferred.

Examples of $m_1$ agonists are known in the art. Examples of $m_2$ antagonists are also known in the art; in particular, $m_2$ antagonists are disclosed in U.S. Pat. Nos. 5,883,096; 6,037,352; 5,889,006; 6,043,255; 5,952,349; 5,935,958; 6,066,636; 5,977,138; 6,294,554; 6,043,255; and 6,458,812; and in WO 03/031412, all of which are incorporated herein by reference.

Examples of BACE inhibitors include those described in: US2005/0119227 published Jun. 2, 2005 (see also WO2005/016876 published Feb. 24, 2005), US2005/0043290 published Feb. 24, 2005 (see also WO2005/014540 published Feb. 17, 2005), WO2005/058311 published Jun. 30, 2005 (see also US2007/0072852 published Mar. 29, 2007), US2006/0111370 published May 25, 2006 (see also WO2006/065277 published Jun. 22, 2006), U.S. application Ser. No. 11/710,582 filed Feb. 23, 2007, US2006/0040994 published Feb. 23, 2006 (see also WO2006/014762 published Feb. 9, 2006), WO2006/014944 published Feb. 9, 2006 (see also US2006/0040948 published Feb. 23, 2006), WO2006/138266 published Dec. 28, 2006 (see also US2007/0010667 published Jan. 11, 2007), WO2006/138265 published Dec. 28, 2006, WO2006/138230 published Dec. 28, 2006, WO2006/138195 published Dec. 28, 2006 (see also US2006/0281729 published Dec. 14, 2006), WO2006/138264 published Dec. 28, 2006 (see also US2007/0060575 published Mar. 15, 2007), WO2006/138192 published Dec. 28, 2006 (see also US2006/0281730 published Dec. 14, 2006), WO2006/138217 published Dec. 28, 2006 (see also US2006/0287294 published Dec. 21, 2006), US2007/0099898 published May 3, 200 (see also WO2007/050721 published May 3, 2007), WO2007/053506 published May 10, 2007 (see also US2007/099875 published May 3, 2007), U.S. application Ser. No. 11/759,336 filed Jun. 7, 2007, U.S. Application Ser. No. 60/874,362 filed Dec. 12, 2006, and U.S. Application Ser. No. 60/874,419 filed Dec. 12, 2006, the disclosures of each being incorporated herein by reference thereto.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams; lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula I, or a pharmaceutically acceptable salt, solvate, ester or prodrug of said compound and a pharmaceutically acceptable carrier, vehicle or diluent.

Yet another aspect of this invention is a kit comprising an amount of at least one compound of Formula I, or a pharmaceutically acceptable salt, solvate, ester or prodrug of said compound and an amount of at least one additional agent listed above, wherein the amounts of the two or more ingredients result in desired therapeutic effect.

The invention disclosed herein is exemplified by the following illustrative example which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The observed parent ion is given.

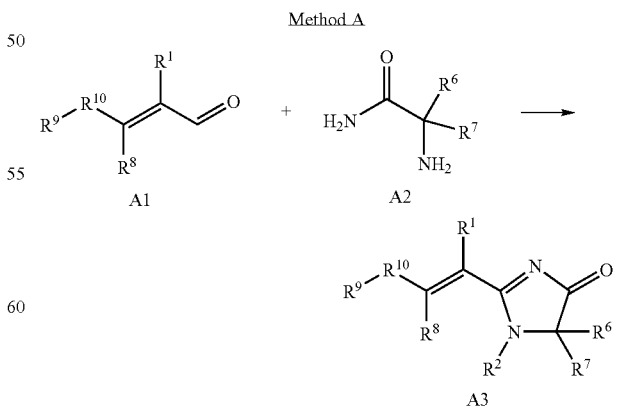

To a dichloromethane solution of A1 (R$^1$=H, R$^8$=H, R$^{10}$=3-(methoxy)phenyl, R$^9$=4-(4-Me-imidazol-yl) and A2 (R$^6$=

Me, $R^7$=4-fluorophenyl) is added N-chlorosuccinimide and the reaction mixture is stirred overnight and then is worked up to give compound A3 ($R^2$=H, $R^8$=H, $R^{10}$=3-(methoxy)phenyl, $R^9$=4-(4-Me-imidazol-yl), $R^6$=Me, $R^7$=4-fluorophenyl).

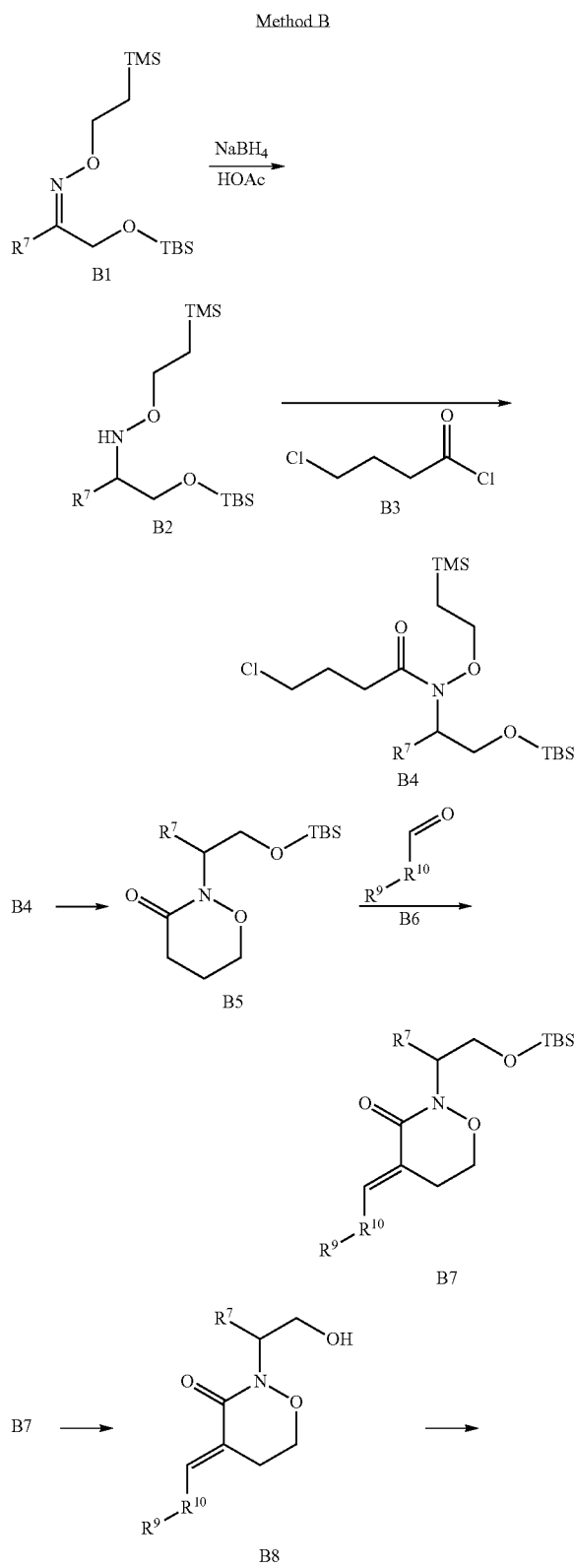

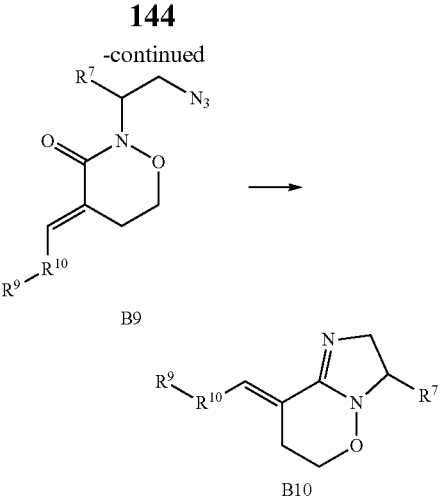

Method B, Step 1;

Compound B1 ($R^7$=p-F-Ph), which is obtained from the corresponding ketone and oxime, is reduced to hydroxylamine using $NaBH_4$ and HOAc as the solvent to give compound B2 ($R^7$=p-F-Ph).

Method B, Step 2;

Compound B2 ($R^7$=p-F-Ph) is converted to B4 ($R^7$=p-F-Ph) using standard amide formation conditions.

Method B, Step 3;

Compound B4 ($R^7$=p-F-Ph) is treated with 1.5 eq. of TBAF to generate compound B5 ($R^7$=p-F-Ph) through selective deprotection of trimethylsilylethyl group which is followed by cyclization.

Method B, Step 4

Compound B5 ($R^7$=p-F-Ph) is treated with LDA followed by compound B6 ($R^9$=4-(4'-methylimidazol-1-yl) and $R^{10}$=3-MeOPhenyl) to give compound B7 ($R^7$=p-F-Ph, $R^9$=4-(4-methylimidazol-1-yl) and $R^{10}$=3-MeOPhenyl).

Method B, Step 5

Compound B7 ($R^7$=p-F-Ph, $R^9$=4-(4-methylimidazol-1-yl) and $R^{10}$=3-MeOPhenyl) is treated with TFA to give compound B8 ($R^7$=p-F-Ph, $R^9$=4-(4-methylimidazol-1-yl) and $R^{10}$=3-MeOPhenyl).

Method B, Step 6

Compound B8 ($R^7$=p-F-Ph, 4-(4-methylimidazol-1-yl) and $R^{19}$=3-MeOPhenyl) is treated with DPPA to give compound B9 ($R^7$=p-F-Ph, $R^9$=4-(4'-methylimidazol-1-yl) and $R^{19}$=3-MeOPhenyl)

Method B, Step 7

Compound B9 ($R^7$=p-F-Ph, $R^9$=4-(4'-methylimidazol-1-yl) and $R^{19}$=3-MeOPhenyl) is treated with tributylphosphine in reflux toluene to give compound B10A ($R^7$=p-F-Ph, $R^9$=4-(4'-methylimidazol-1-yl) and $R^{19}$=3-MeOPhenyl).

Alternatively, Analogs of B2 can be generated using a method similar to the following: *Diastereoselective additions of organolithium reagents to the C=N bond of protected erythrulose oxime ethers. Synthesis of enantiopure α,α-disubstituted .α-amino acids* Marco, J. Alberto; Carda, Miguel; Murga, Juan; Gonzalez, Florenci; Falomir, Eva. *Tetrahedron Letters* (1997), 38(10), 1841-1844.

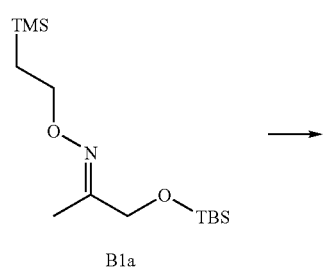
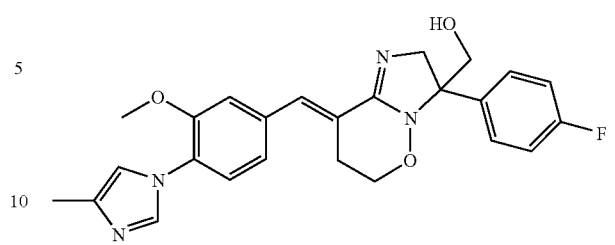
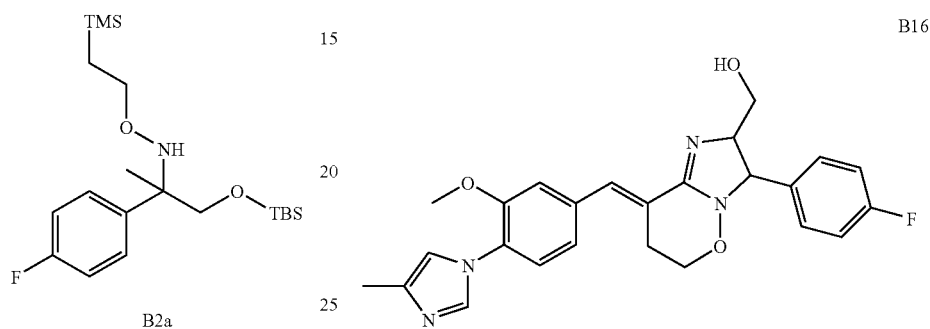
To an ether solution of B1a is added phenyl lithium to give compound B2a which is applied to the rest of the synthetic route in Method B.
The following compounds are synthesized using method similar to Method B.
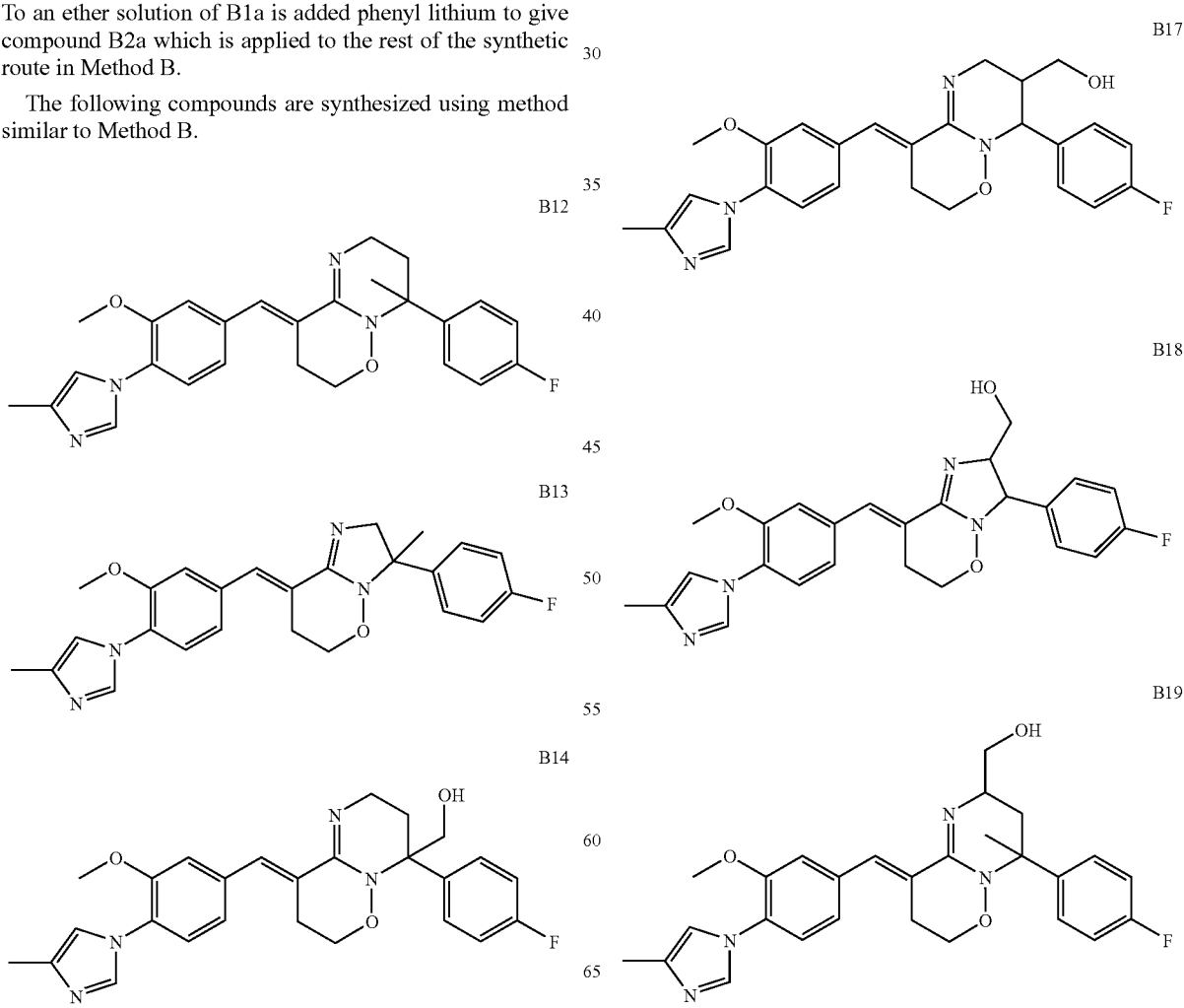

-continued

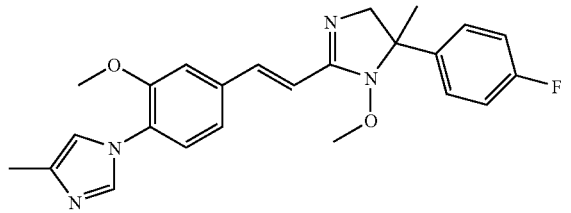
B20

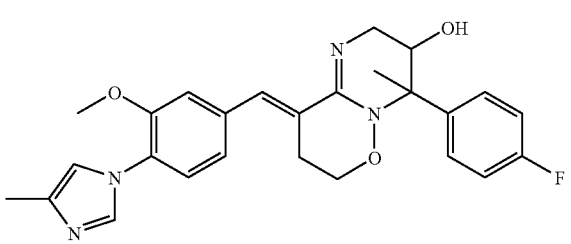
B21

($R^6$=Me, $R^7$=p-F-phenyl) using conditions similar to the following literature: *Enantioselective syntheses of carbocyclic ribavirin and its analogs: linear versus convergent approaches*. Kuang, R.; Ganguly, A. K.; Chan, T.-M.; Pramanik, B. N.; Blythin, D. J.; McPhail, A. T.; Saksena, A. K. *Tetrahedron Letters* (2000), 41(49), 9575-9579.

Method C, Step 2

C2 ($R^6$=Me, $R^7$=p-F-phenyl) is treated with Zn/HOAc/$H_2O$ to give compound C3 ($R^6$=Me, $R^7$=p-F-phenyl).

Method C, Step 3

Compound C3 ($R^6$=Me, $R^7$=p-F-phenyl) is treated with NaH which is followed by MeI to give compound C4 ($R^6$=Me, $R^7$=p-F-phenyl).

Method C, Step 4

Compound C4 ($R^6$=Me, $R^7$=p-F-phenyl) is converted to compound C5 ($R^6$=Me, $R^7$=p-F-phenyl, $R^9$=4-(4-methylimidazol-1-yl), $R^{19}$=3-MeOphenyl) using a procedure similar to Method B Steps 4, 5, 6 and 7.

The following compounds are obtained using methods similar to Method C:

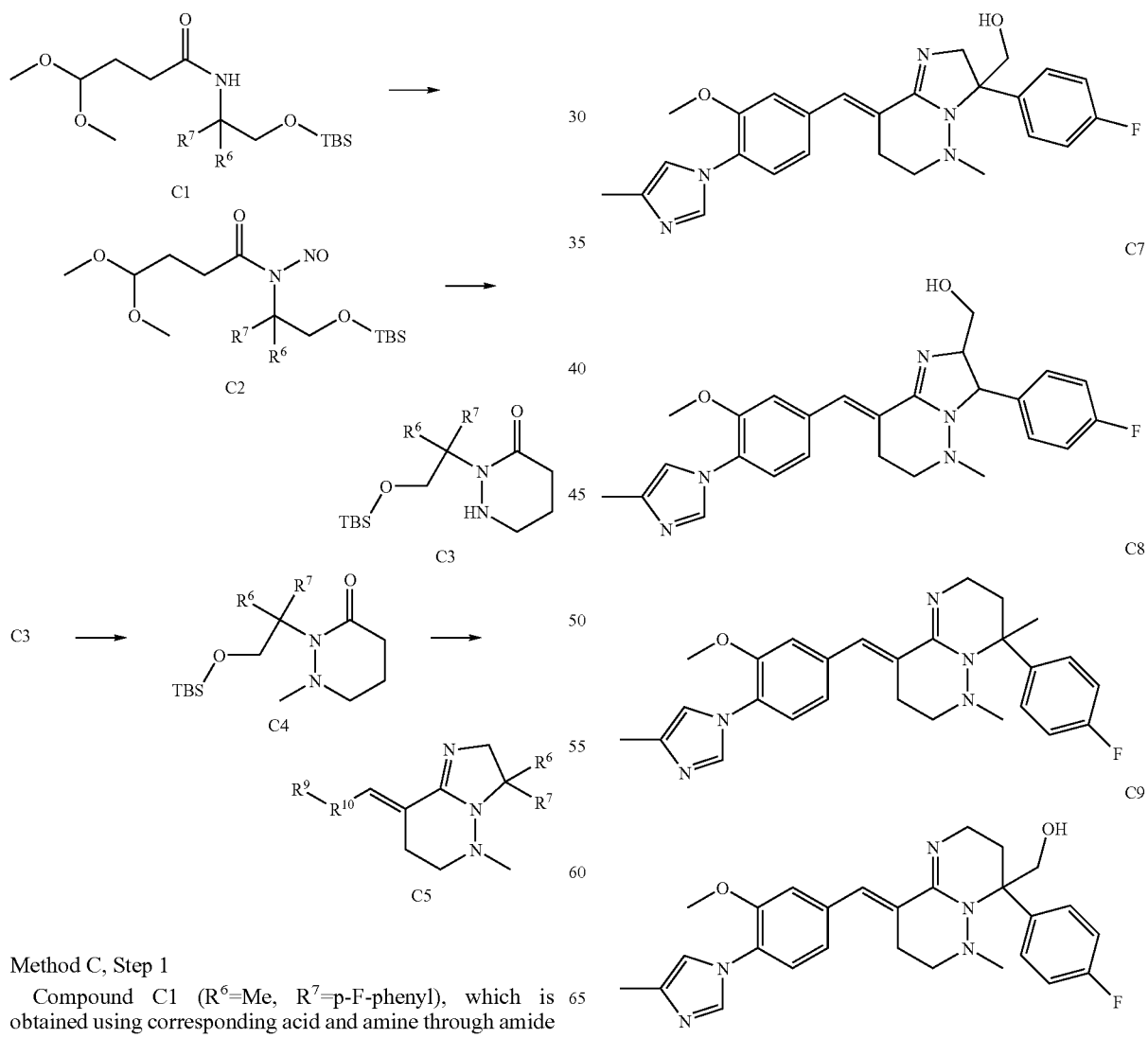

Method C, Step 1

Compound C1 ($R^6$=Me, $R^7$=p-F-phenyl), which is obtained using corresponding acid and amine through amide coupling chemistry, is converted to N-nitroso product C2

-continued

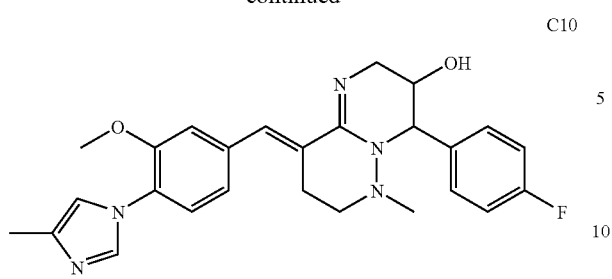

C10

-continued

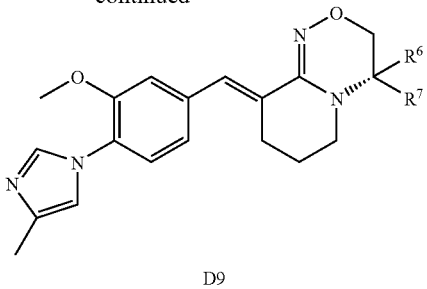

D9

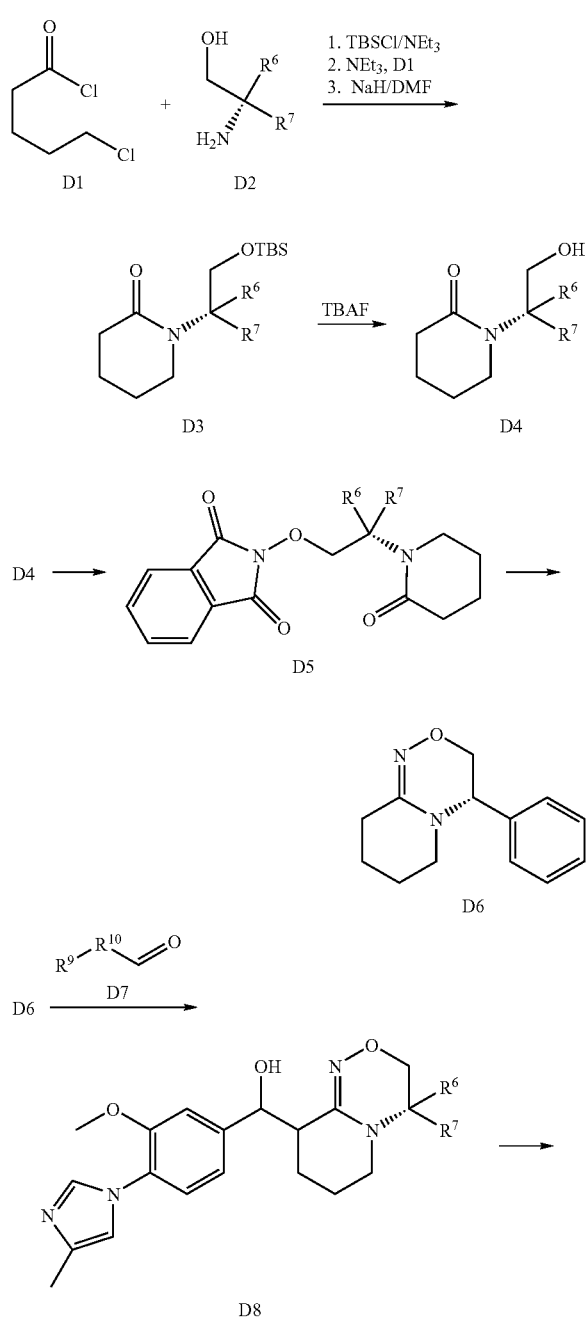

Method D, Step 1:

TBSCl (5.6 g, 37.2 mmol) in $CH_2Cl_2$ (10 mL) was added dropwise to a solution of D2 ((S), $R^6$=H, $R^7$=Ph) (5.1 g, 37.2 mmol), $NEt_3$ (10.4 mL, 74.4 mmol) and DMAP (20 mg) in $CH_2Cl_2$ (20) at room temperature. The mixture was then stirred over night. The mixture was diluted with $CH_2Cl_2$ (200 mL) and $NH_4Cl$ solution (30 mL). The organic layer was washed with water, brine, dried over $MgSO_4$, and concentrated to give the crude product (6.0 g) which was taken up in $CH_2Cl_2$ (50 mL) and treated with $NEt_3$ (3.8 mL, 27.45 mmol). Compound D1 was added dropwise to the mixture at 0° C. The resulting reaction mixture was stirred at room temperature over night. The mixture was diluted with EtOAc (200 mL) and $NaHCO_3$ solution (40 mL). The organic layer was washed with water, brine, dried over $MgSO_4$, and concentrated to give the crude product. The crude residue was dissolved in DMF (50 mL) and treated with NaH (1.25 g, 28.6 mmol, 60% in paraffin) at room temperature. The resulting mixture was then heated at 60° C. over night. The mixture was diluted with EtOAc (200 mL) and aq. $NH_4Cl$ solution (40 mL). The organic layer was washed with water (3×), brine, dried over $MgSO_4$, and concentrated to give the crude product which was purified by column chromatography eluting with EtOAc/hexanes to yield compound D3 ((S), $R^6$=H, $R^7$=Ph; 5.0 g).

Method D, Step 2:

TBAF (3.15 mL, 3.15 mmol, 1.0 M in THF) was added dropwise to a solution of compound D3 ((S), $R^6$=H, $R^7$=Ph; 0.7 g, 2.1 mmol) in THF (10 mL). The mixture was stirred for 2 hours before it was diluted with EtOAc (100 mL) and HCl solution (20 mL, 0.5 M). The organic layer was washed with water, brine, dried over $MgSO_4$, and concentrated to give the crude product which was purified by column chromatography eluting with EtOAc/hexanes to yield hydroxyl compound D4 ((S), $R^6$=H, $R^7$=Ph; 0.44 g).

Method D, Step 3:

$PBu_3$ (0.2 mL, 0.82 mmol) was added to a solution of compound D4 ((S), $R^6$=H, $R^7$=Ph; 0.1 g, 0.457 mmol), ADDP (0.2 g, 0.82 mmol) and phthalimide (0.12 g, 0.685 mmol) in THF (5 mL) at room temperature. The resulting mixture was then heated at 80° C. for 2 hours. The mixture was diluted with EtOAc (100 mL) and $NaHCO_3$ solution (20 mL). The organic layer was washed with $NaHCO_3$ solution, brine, dried over $MgSO_4$, and concentrated to give the crude product which was purified by column chromatography eluting with EtOAc/hexanes to yield compound D5 ((S), $R^6$=H, $R^7$=Ph; 0.1 g, 0.457 mmol, 0.14 g).

Method D, Step 4, $NH_2NH_2 \cdot xH_2O$ (54.4 uL, 1.12 mmol) was added to a solution of compound D5 ((S), $R^6$=H, $R^7$=Ph; 0.14 g, 0.373 mmol) in MeOH (2.0 mL) and $CH_2Cl_2$ (2.0 mL) at room temperature. The resulting mixture was stirred for 2 hours before it was diluted with EtOAc (50 mL) and $NaHCO_3$ solution (10 mL). The organic layer was washed with water, brine, dried over MgSO₄, and concentrated to give the crude product which was dissolved in EtOH (3.0 mL) and treated with P₂O₅ (0.53 g, 3.72 mmol). The resulting mixture was heated at 80° C. over night. The mixture was cooled and diluted with EtOAc (50 mL) and NaHCO₃ solution (20 mL). The organic layer was washed with NaHCO₃ solution, brine, dried over MgSO₄, and concentrated to give the crude product which was purified by column chromatography eluting with EtOAc/hexanes to yield compound D6 ((S), R⁶=H, R⁷=Ph; 46 mg).

¹H NMR (CDCl₃) δ: 7.43-7.32 (m, 5 H); 4.30 (dd, J=5.0, 4.0 Hz, 1 H); 4.16 (AB quart, J=11.5, 4.0 Hz, 1 H); 3.96 (AB quart, J=11.5, 5.0 Hz, 1 H); 3.07 (m, 1H); 2.89 (m, 1 H); 2.50 (m, 2 H); 1.84 (m, 2 H); 1.76 (m, 2 H). Electrospray LCMS: Obs. Mass: 217.2.

Method D, Step 5, t-BuLi (0.188 mL, 0.32 mmol, 1.7 M) was added dropwise to a solution of compound D6 ((S), R⁶=H, R⁷=Ph; 46 mg, 0.21 mmol) in THF (1.5 mL) at −78° C. The mixture was stirred for 45 minutes before compound D7 (R¹⁰=3-MeO -Phenyl, R⁹=4-(4-methylimidazol-1-yl)) was added in THF (1.0 mL) in fast drops. The resulting mixture was stirred for 2 hours before it was diluted with EtOAc (50 mL) and NH₄Cl solution (10 mL). The organic layer was washed with brine, dried over MgSO₄, and concentrated to give the crude product which was purified by column chromatography eluting with EtOAc/hexanes to yield compound D8 ((S), R⁶=H, R⁷=Ph; R¹⁰=3-MeO-Phenyl, R⁹=4-(4-methylimidazol-1-yl)).

Method D, Step 7,

Compound D8 ((S), R⁶=H, R⁷=Ph; R¹⁰=3-MeO-Phenyl, R⁹=4-(4-methylimidazol-1-yl)) will be dissolved in toluene and treated with p-TSA (10 mol %). The mixture will be heated at reflux condition with a Dean-Stark apparatus over night. The solvent will be removed and crude residue will be purified with column chromatography to give compound D9 ((S), R⁶=H, R⁷=Ph; R¹⁰=3-MeO-Phenyl, R⁹=4-(4-methylimidazol-1-yl)).

The following compounds are synthesized using methods similar to method D:

D10

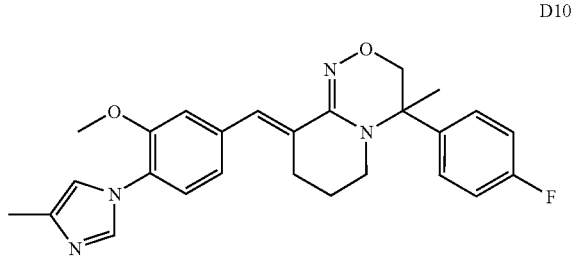

D11

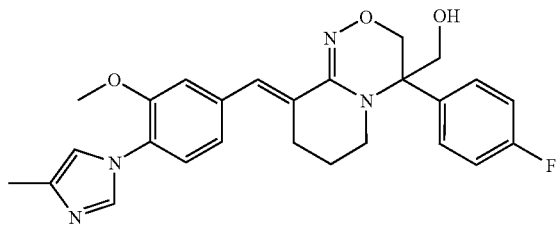

D12

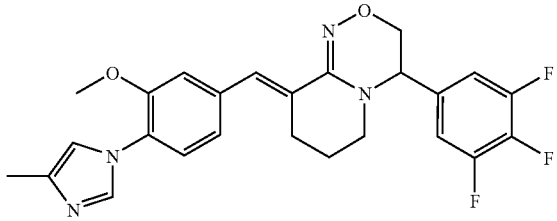

D13

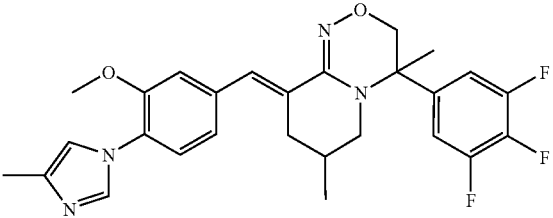

D14

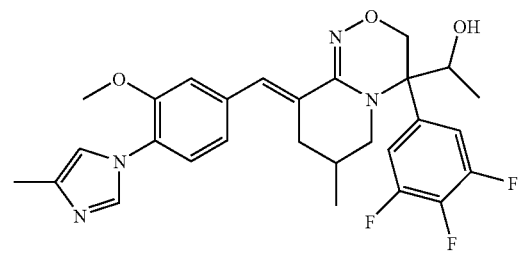

D15

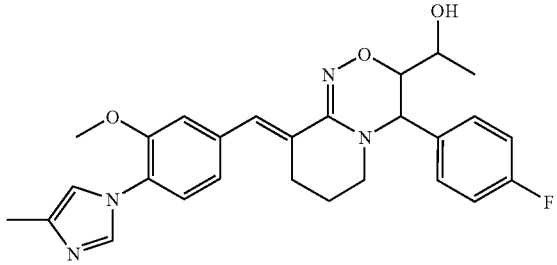

D16

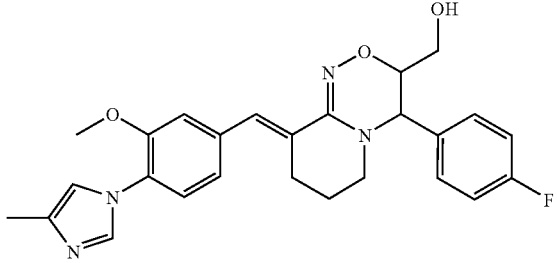

D17

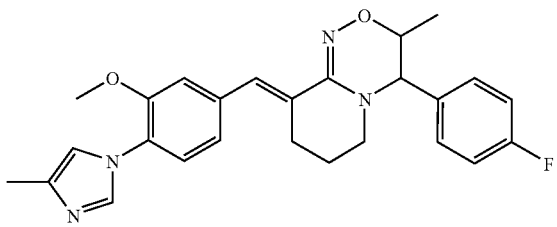

-continued
D18
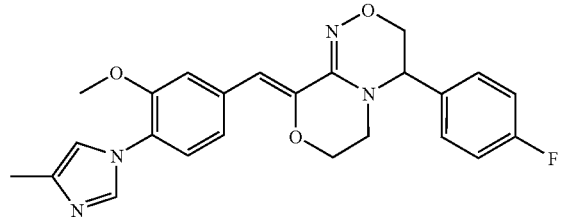
D19
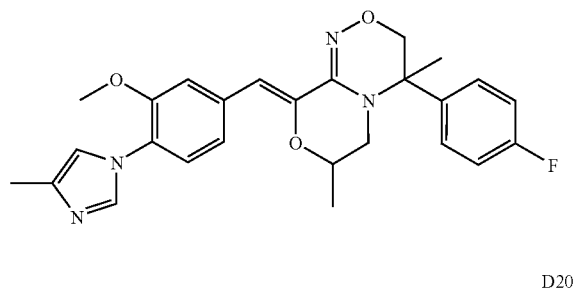
D20
D21
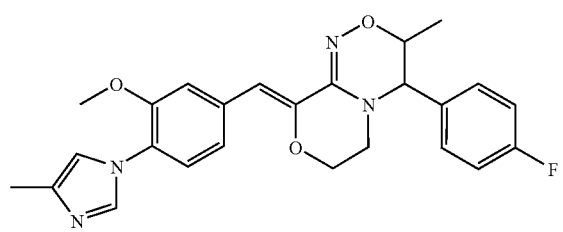
D22
D23
-continued
D24
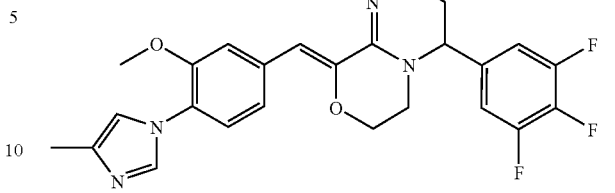
D25
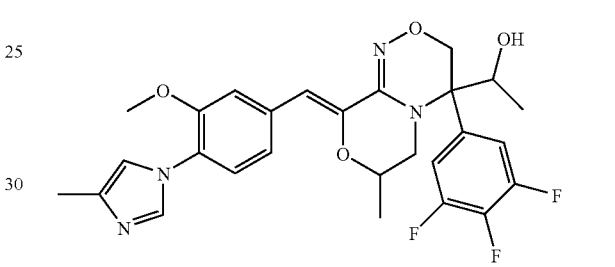
D26
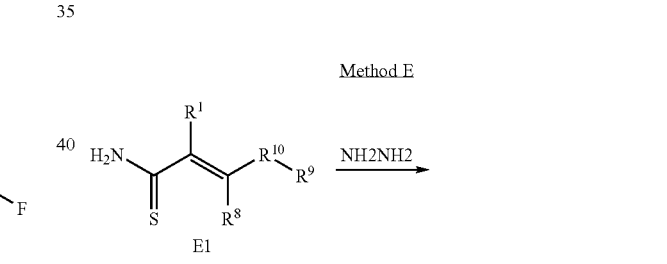
Method E
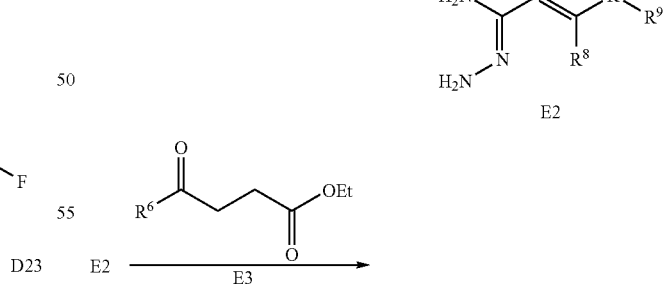

Method E, Step 1.

Compounds of E1 (R$^1$=R$^8$=H, R$^{10}$=3-MeOPhenyl, R$^9$=4-(4-Me-imidazol-1-yl)) are prepared from the corresponding thioamides or nitriles by treatment with hydrazine with a catalytic amount of acid in a solvent such as ethanol with heating.

Method E, Step 2.

E1 (R$^1$=R$^5$=H, R$^{10}$=3-MeOPhenyl, R$^9$=4-(4-Me-imidazol-1-yl)) is reacted with keto esters of E3 (R$^6$=p-F-phenyl) under dehydrating conditions such as treatment with a catalytic amount of acid (e.g. TsOH, or AcOH) in solvents such as Toluene or DCM. In some cases heating in toluene to remove water through azeotropic distillation will facilitate the reaction. to produce compounds E4 (R$^1$=R8=H, R$^{10}$=3-MeOPhenyl, R$^9$=4-(4-Me-imidazol-1-yl), R$^6$=p-F-phenyl).

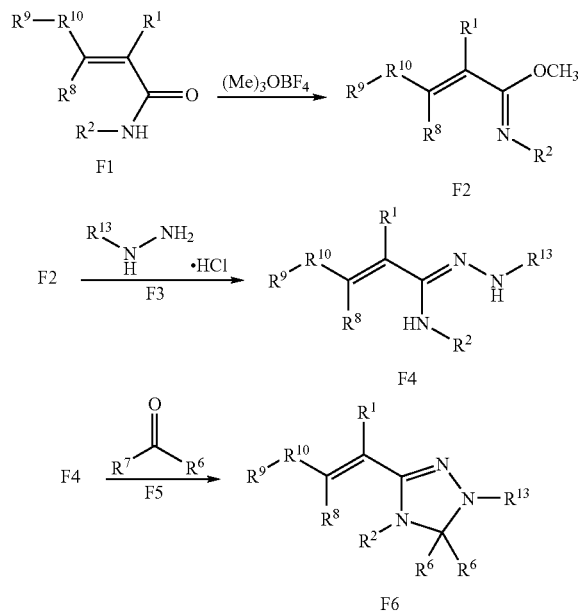

Method F

Method F, Step 1,

To a dichloromethane solution of F1 (R$^1$=H, R$^2$=H, R$^8$=H, R$^{19}$=3-(methoxy)phenyl, R$^9$=4-(4-Me-imidazol-1-yl) is added trimethyloxonium tetrafluoroborate, and the reaction mixture is stirred at room temperature overnight. The solvent is evaporated to yield the crude iminoether B2 as its tetrafluoroborate salt. Optionally, the crude tetrafluoroborate salt is triturated with ether and the resulting precipitated tetrafluoroborate salt of F2 (R$^1$=H, R$^2$=H, R$^8$=H, R$^{10}$=3-(methoxy)phenyl, R$^9$=4-(4-Me-imidazol-1-yl) is filtered and is dried. This is converted to the free base by partionining between dichloromethane and excess 1M NaOH. The methylene chloride layer is dried over K$_2$CO$_3$ and is evaporated to give the free base of F2 (R$^1$=H, R$^2$=H, R$^8$=H, R$^{10}$=3-(methoxy)phenyl, R$^9$=4-(4-Me-imidazol-1-yl)), which is used immediately.

Method F, Step 2:

F2 (R$^1$=H, R$^2$=H, R$^8$=H, R$^{10}$=3-(methoxy)phenyl, R$^9$=4-(4-Me-imidazol-1-yl)) is treated with hydrazine F3 (R$^{13}$=H) optionally as the hydrochloride or hydrate in refluxing methanol overnight. The reaction mixture is neutralized with sodium bicarbonate, filtered and evaporated to give the crude amidohyrazide F4 (R$^1$=H, R$^2$=H, R$^{13}$=H, R$^8$=H, R$^{19}$=3-(methoxy)phenyl, R$^9$=4-(4-Me-imidazol-1-A)).

Method F, Step 3:

F4 (R$^1$=H, R$^2$=H, R$^{13}$=H, R$^8$=H, R$^{19}$=3-(methoxy)phenyl, R$^9$=4-(4-Me-imidazol-1-yl)) is treated with ketone F5 (R$^6$=Me, R$^7$=4-fluorophenyl) and p-toluenesulfonic acid in refluxing ethanol overnight to give, after neutralization and evaporation, compound F6 (R$^1$=H, R$^2$=H, R$^8$=H, R$^{10}$=R$^{10}$=3-(methoxy)phenyl, R$^9$=4-(4-Me-imidazol-1-yl), R$^6$=Me, R$^7$=4-fluorophenyl).

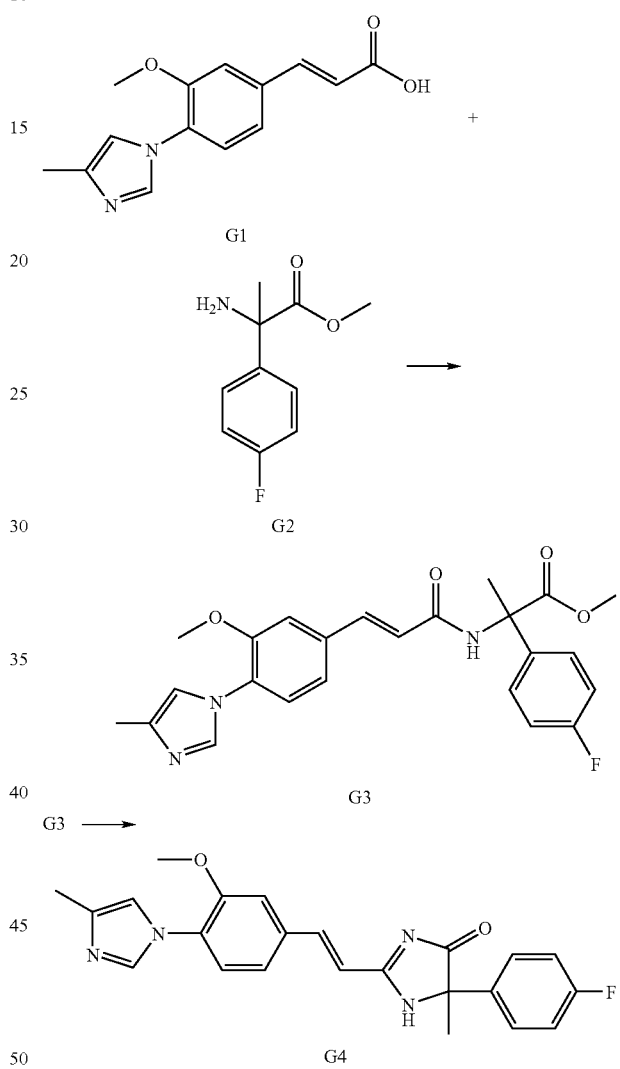

Method G

Method G, Step 1

Compound G1 (200 mg), generated from the corresponding aldehyde and carbomethoxymethyl diethylphosphonate, followed by LiOH hydrolysis, was reacted with compound G2 (230 mg) with HOBT (135 mg) and EDCI (197 mg) in 10 mL DMF to give compound G3 after routine work-up and purification in 66% yield.

$^1$H NMR of G3 (CDCl$_3$, ppm); δ 7.35 s, 1H, 7.55 d, 1H, 7.45 m, 2H, 7.25, d, 1H, 7.15, m, 3H, 7.10, m, 1H, 6.95, s, 1H, 6.5, s, 1H, 3.9 s, 3H, 3.75 s, 3H, 2.3 s, 3H, 2.15 s, 3H.

Method G, Step 2

A solution of ammonia in THF was treated with Me$_3$Al in hexane before compound G3 was added slowly. The final mixture was refluxed overnight before it was quenched with sat. aqueous ammonium chloride and extracted with EtOAc. The organic layer was washed with brine, dried over and solvent evaporated. The residue was chromatographed to give the corresponding amide. The product amide was dissolved in 1 mL EtOH and 2 mL of 1N NaOH. After the starting material disappeared, the reaction mixture was partitioned in DCM/sat. aq ammonium chloride. The organic layer was dried and solvent evaporated. The residue was chromatographed to give compound G4.

$^1$H NMR of G4 (CDCl$_3$, ppm); δ 10.5 br. 1H, 7.9, s, 1H, 7.6 m, 2H, 7.4, m, 1H, 7.3, m 2H, 7.2, m, 1H, 7.05, m, 2H, 7.0 s, 1H, 6.9 m 1H, 3.9 s, 3H, 2.3 s, 3H.

The following compounds are obtained using methods similar to method G:

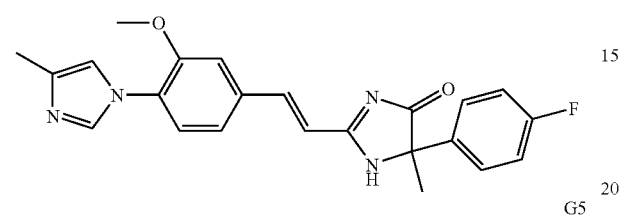

G4

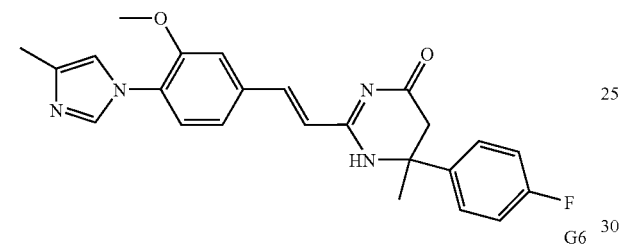

G5

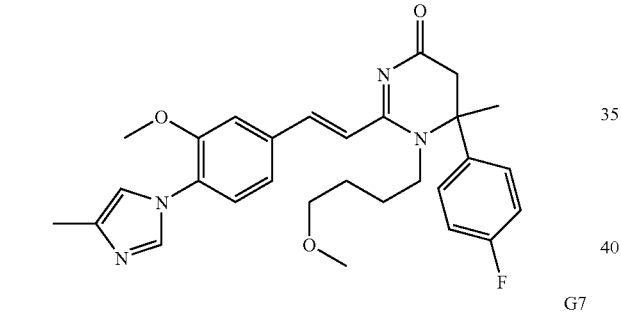

G6

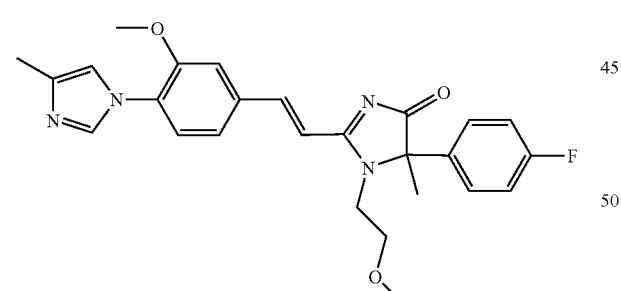

G7

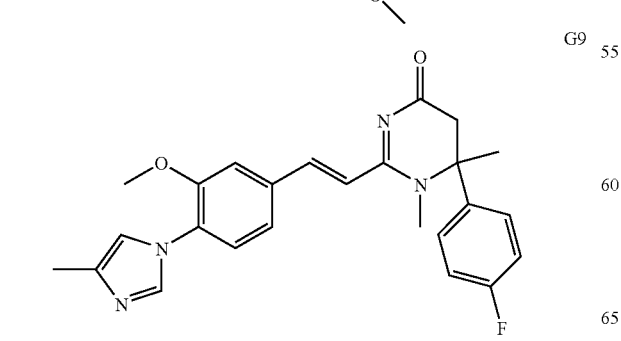

G9

Method H

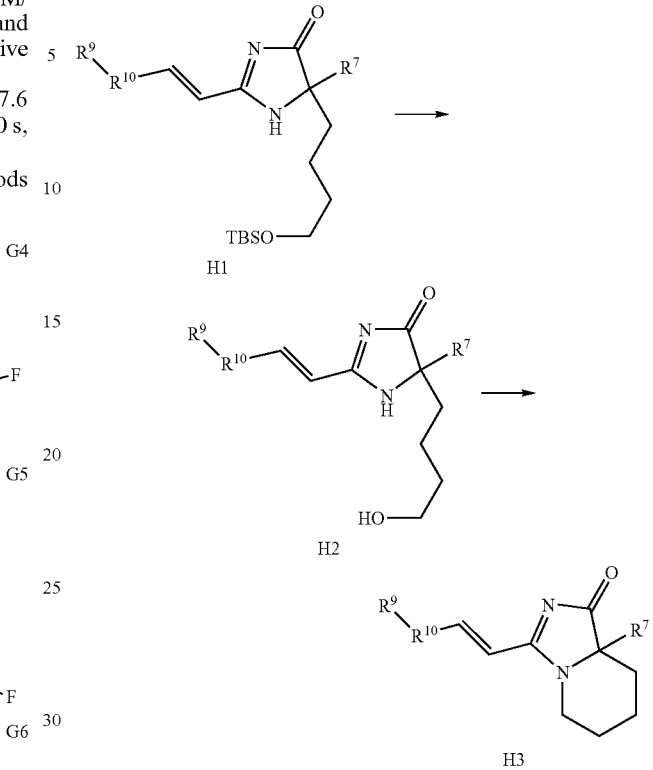

Method H, Step 1

Compound H1 (R$^7$=p-F-phenyl, R$^{10}$=3-MeO-Phenyl, R$^9$=4-(4-methyl-imidazol-1-yl), is prepared using methods similar to method G, is treated with TBAF to give compound H2 (R$^7$=p-F-phenyl, R$^{10}$=3-MeO-Phenyl, R$^9$=4-(4-methyl-imidazol-1-yl) after purification.

Method H, Step 2

Compound H2 (R$^7$=p-F-phenyl, R$^{10}$=3-MeO-Phenyl, R$^9$=4-(4-methyl-imidazol-1-yl) is converted to the triflate. The product triflate is treated with NaH in DMF to give compound H3 (R$^7$=p-F-phenyl, R$^{10}$=3-MeO-Phenyl, R$^9$=4-(4-methyl-imidazol-1-yl) after routing work up and purification.

The following compounds are obtained using methods similar to method H:

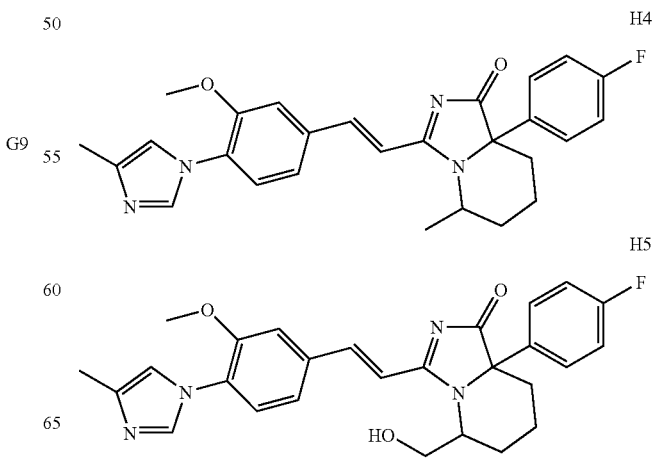

H4

H5

H6

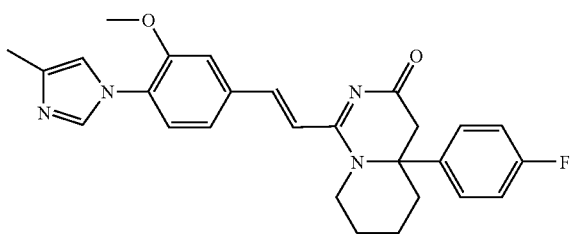

H7

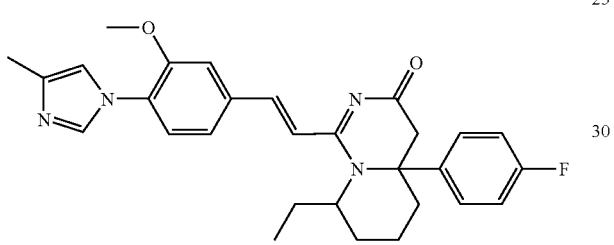

H8

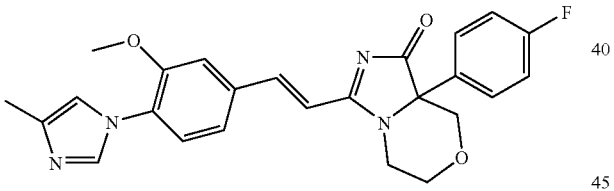

H9

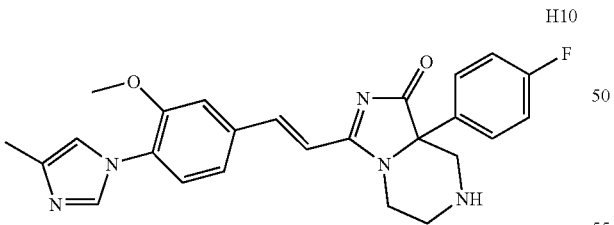

H10

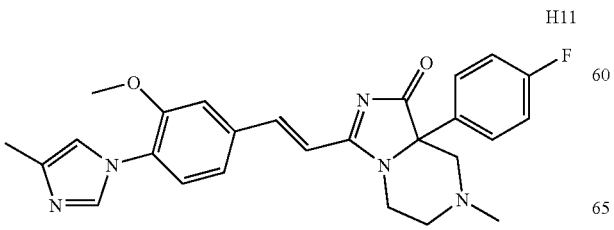

H11

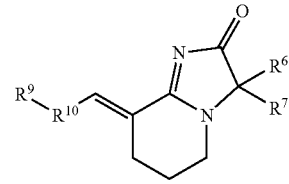

Method I

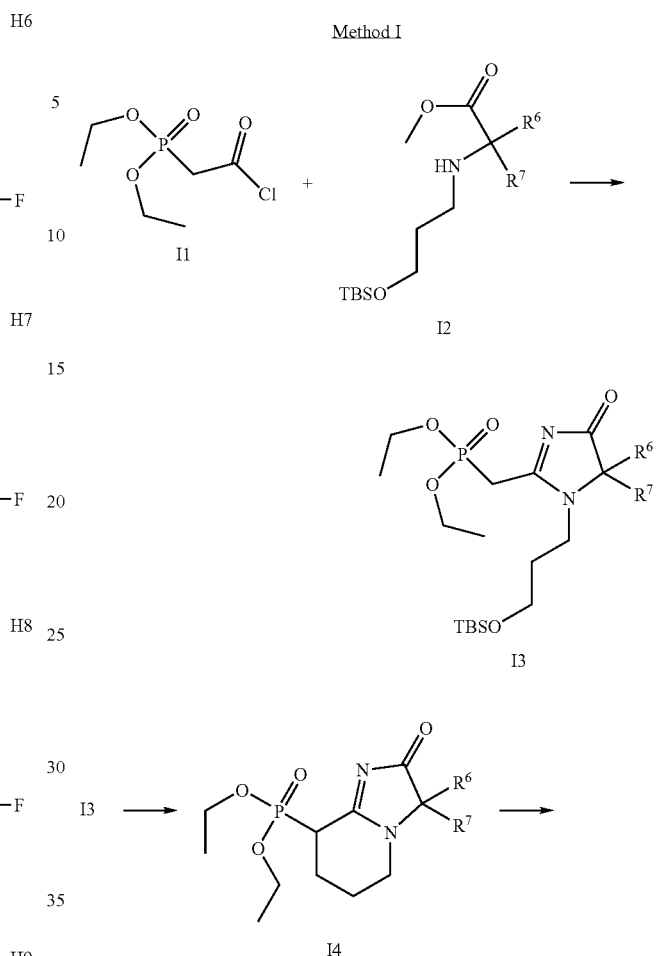

Method I, Step 1

Compound I3 ($R^6$=p-F-Phenyl, $R^7$=Me) is obtained using methods similar to method G using starting material 11 and 12 ($R^6$=p-F-Phenyl, $R^7$=Me).

Method I, Step 2

Compound I3 ($R^6$=p-F-Phenyl, $R^7$=Me) is treated with TBAF which is followed by purification to give the corresponding alcohol which is transformed into triflate. The triflate is treated with NaH in DMF to give compound I4 ($R^6$=p-F-Phenyl, $R^7$=Me).

Method I, Step 3

Compound I5 ($R^6$=p-F-Phenyl, $R^7$=Me, $R^{19}$=3-MeOphenyl, $R^9$=4-(4-methylimidazol-1-yl)) is obtained using compound I4 ($R^6$=p-F-Phenyl, $R^7$=Me) reacting with D7 ($R^{19}$=3-MeOphenyl, $R^9$=4-(4-methylimidazol-1-yl)) and a base after purification.

The following compounds are obtained using method similar to method I.

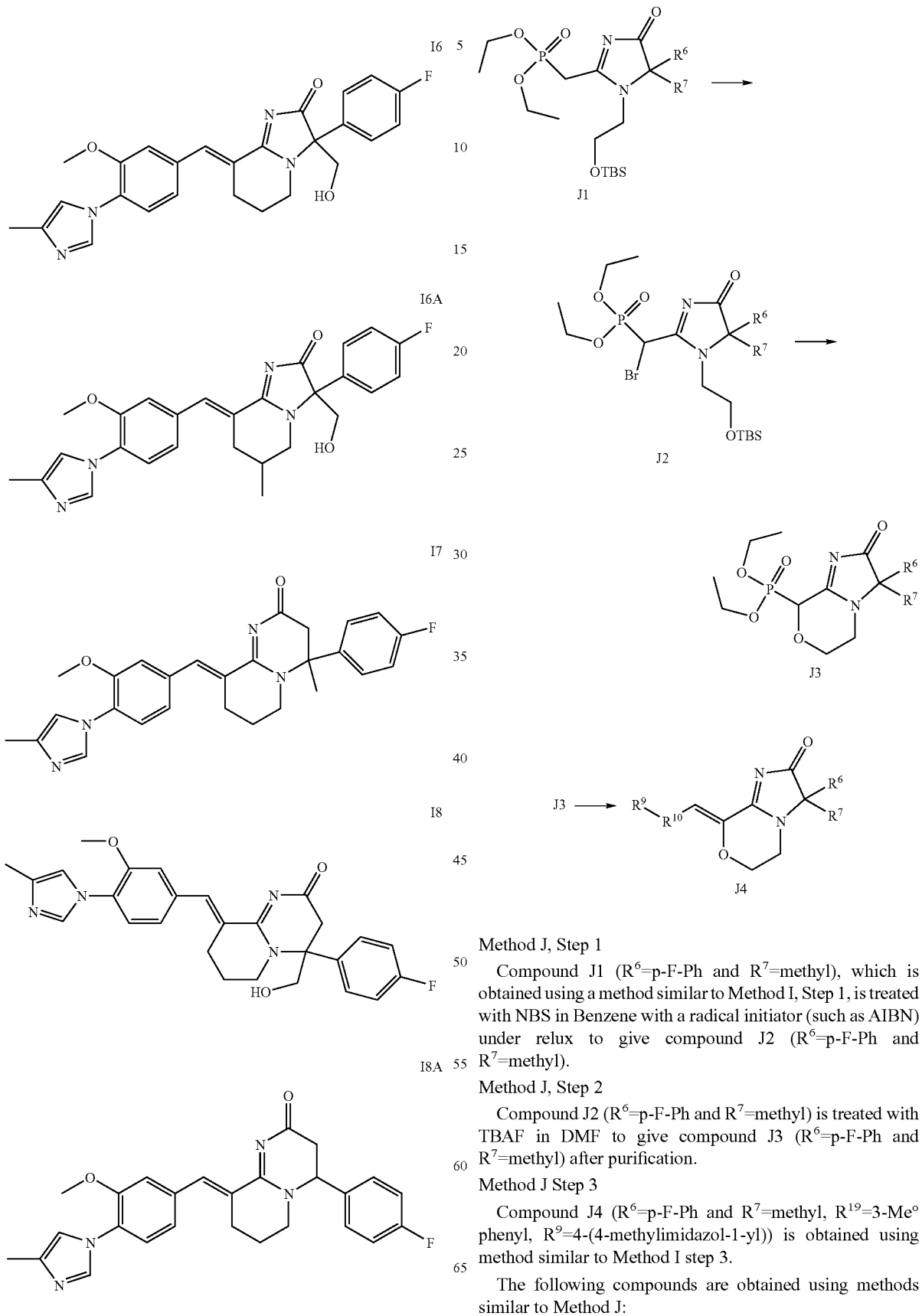

Method J, Step 1

Compound J1 ($R^6$=p-F-Ph and $R^7$=methyl), which is obtained using a method similar to Method I, Step 1, is treated with NBS in Benzene with a radical initiator (such as AIBN) under reflux to give compound J2 ($R^6$=p-F-Ph and $R^7$=methyl).

Method J, Step 2

Compound J2 ($R^6$=p-F-Ph and $R^7$=methyl) is treated with TBAF in DMF to give compound J3 ($R^6$=p-F-Ph and $R^7$=methyl) after purification.

Method J Step 3

Compound J4 ($R^6$=p-F-Ph and $R^7$=methyl, $R^{19}$=3-Me° phenyl, $R^9$=4-(4-methylimidazol-1-yl)) is obtained using method similar to Method I step 3.

The following compounds are obtained using methods similar to Method J:

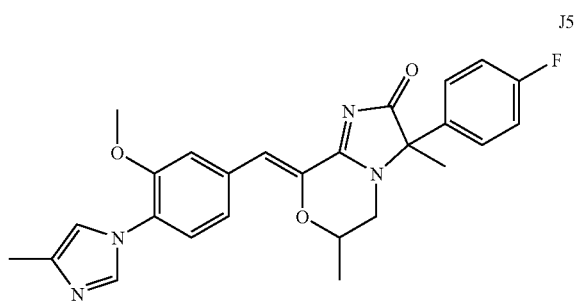
J5
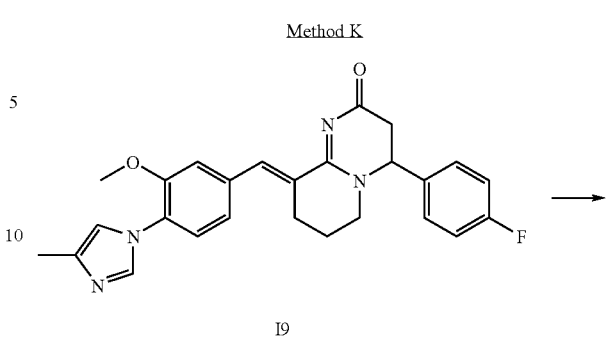
Method K
I9
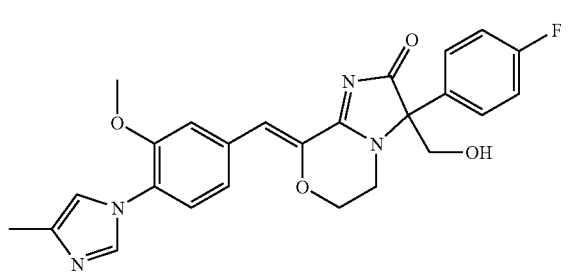
J6
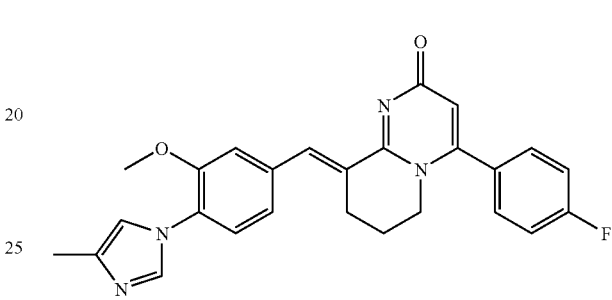
K1
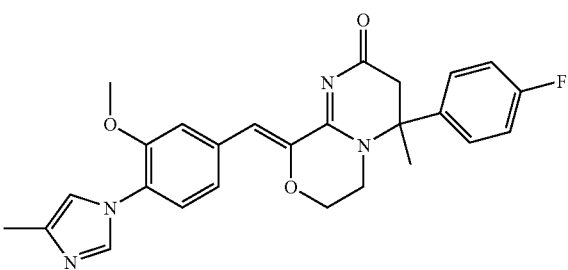
J7
Compound I9 is treated with 1.2 eq of LDA at −78 C before it is reacted with phenylselenium bromide. After the reaction is warmed to r.t. it is treated with $H_2O_2$ and is worked up, and is purified to give compound K1.
The following compounds are obtained using methods similar to Method K:
J8
K2
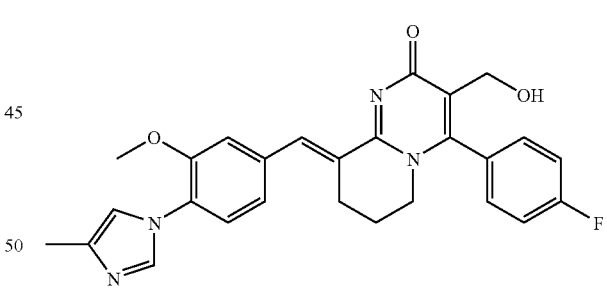
J9
K3
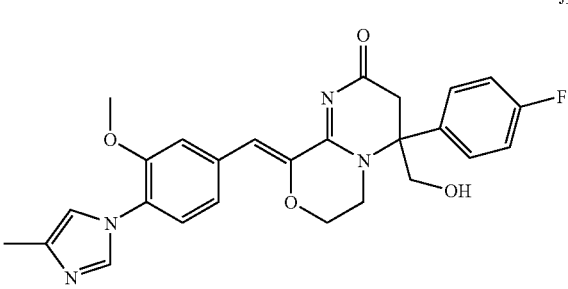
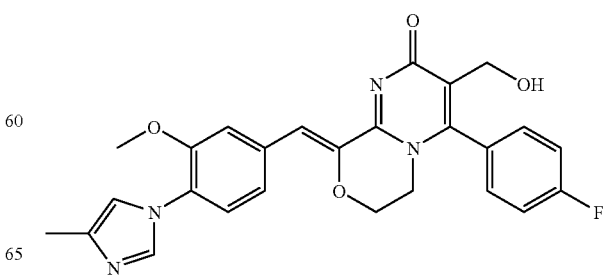

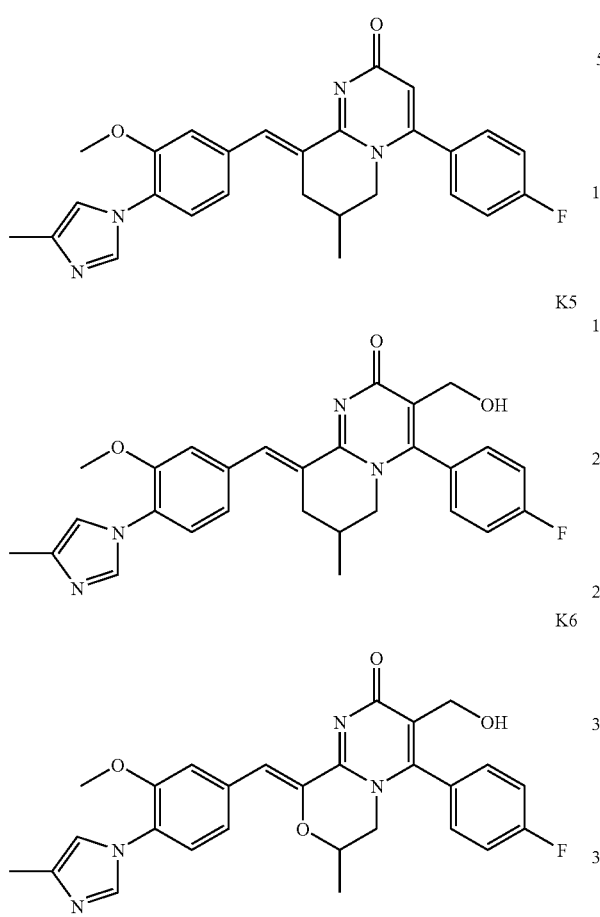
K4
K5
K6
G8
Method L
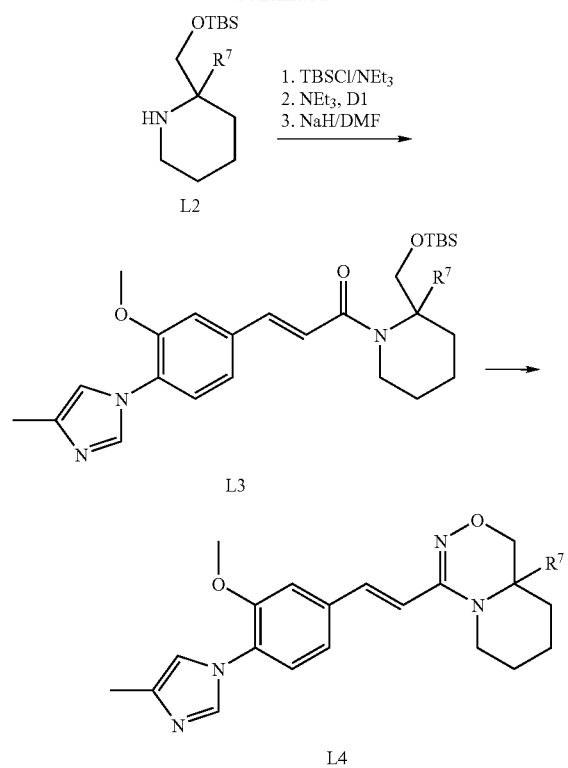
L2
L3
L4
Method L, Step 1
Compound L3 (R⁷=p-F-Phenyl) is obtained using amide coupling chemistry from L1 and L2
Method L, Step 2
Compound L4 (R⁷=p-F-Phenyl) is obtained using methods similar to method D, Steps 2 to 5.
The following compounds are obtained using methods similar to method L:
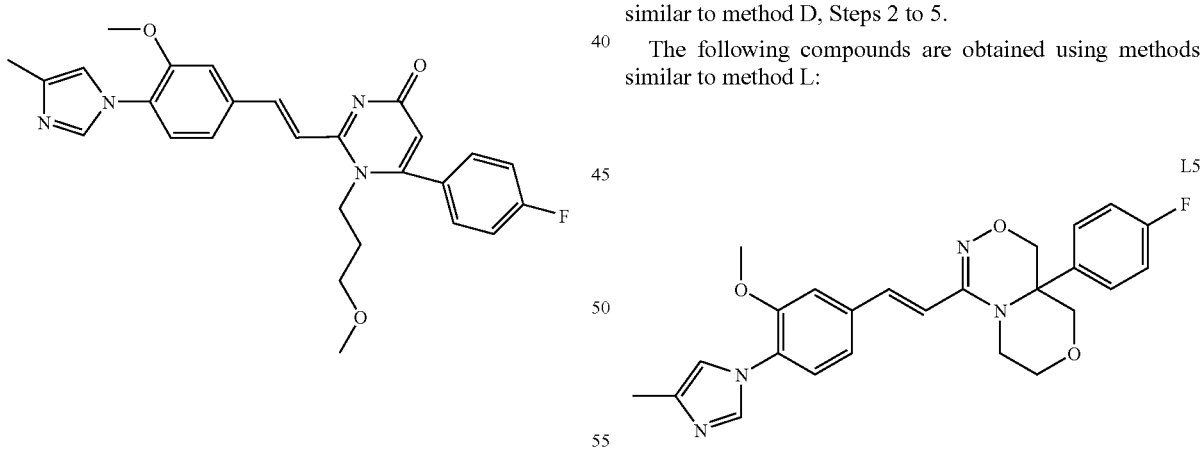
L5
L6

167
-continued

L7

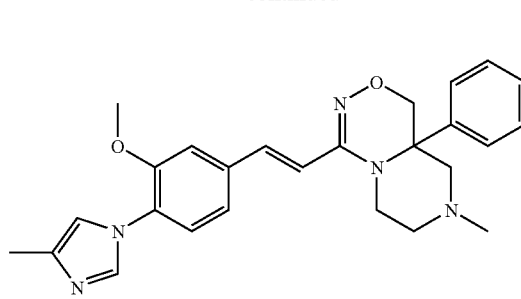

L8

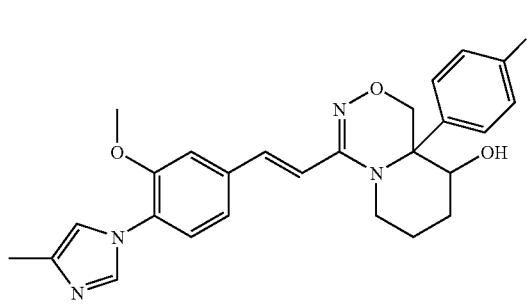

Method M

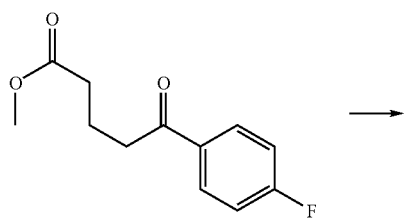
M1

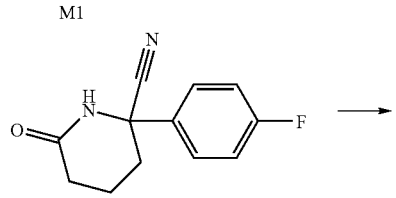
M2

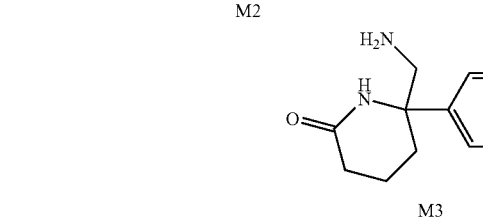
M3

M3 ⟶

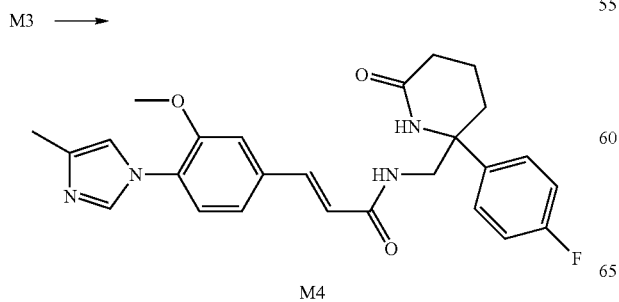
M4

168
-continued

M4 ⟶

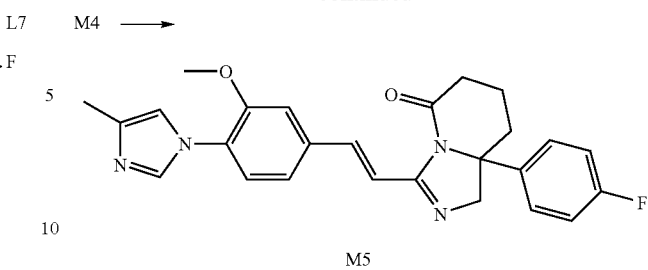
M5

Method M, Step 1

Compound M1 is converted to M2 through Strecker amine synthesis by reacting M1 with Ammonium Cyanide in alcohol.

Method M, Step 2

Compound M3 is obtained using a Ni mediated hydrogenation of M2.

Method M, Step 3

Compound M4 is obtained using a normal amide coupling conditions.

Method M, Step 4

Compound M5 is obtained through treatment of M4 with POCl₃ in reflux toluene.

The following compounds will be obtained using method similar to method M.

M6

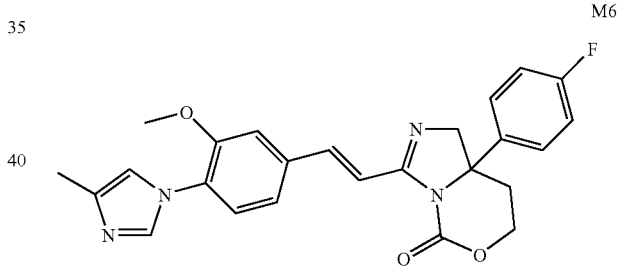

M7

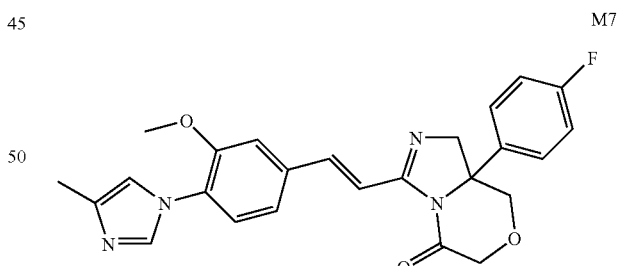

M8

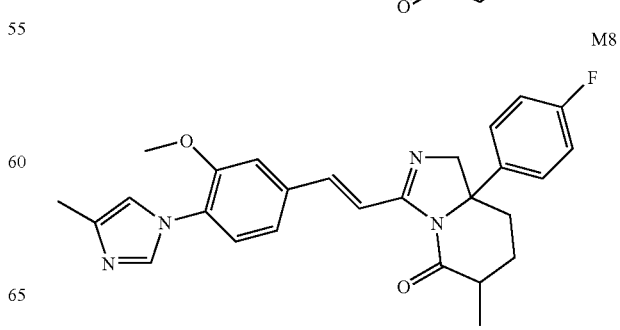

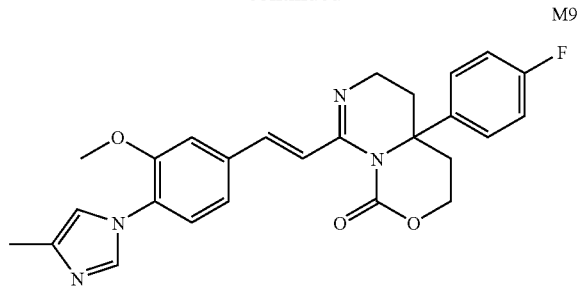
M9
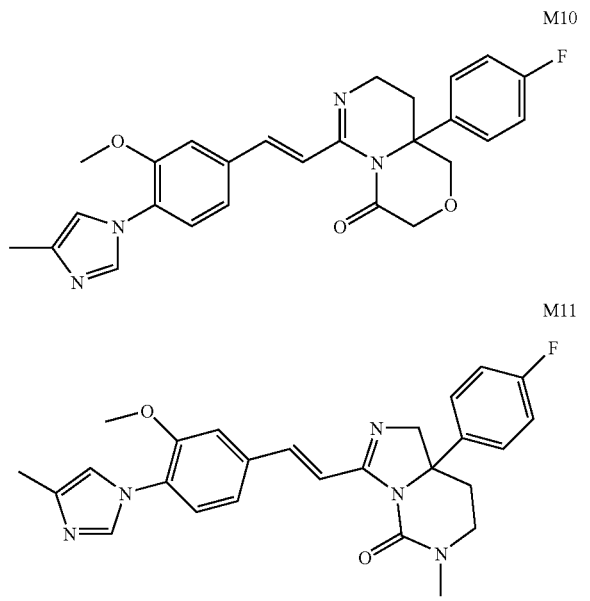
M10
M11
M12
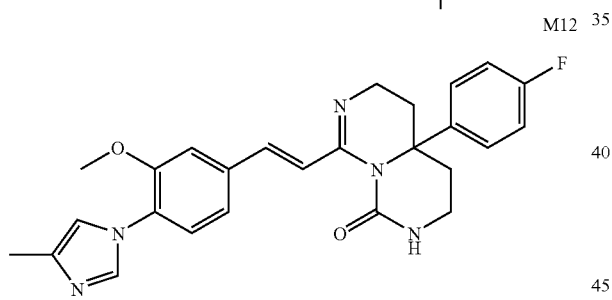
M13
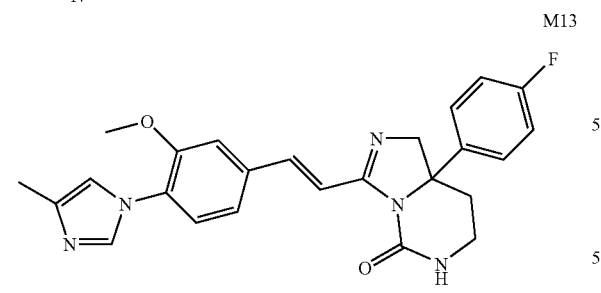
M14
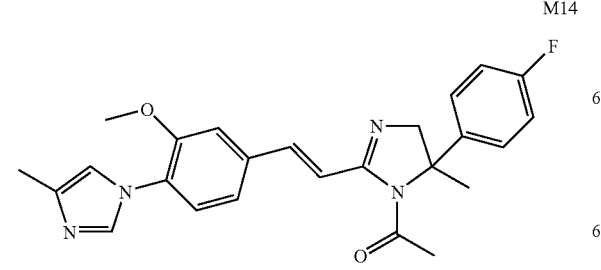
M15
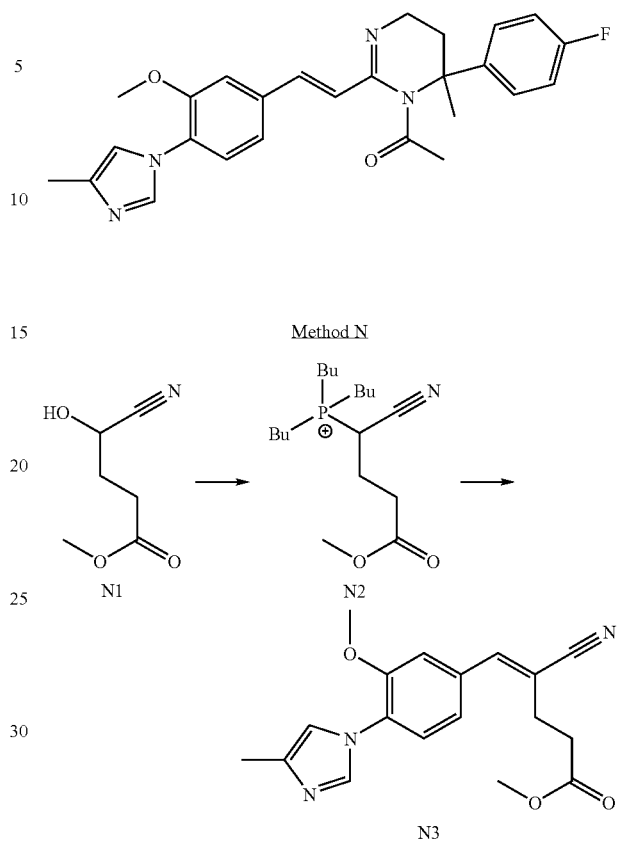
Method N
N1 N2
N3
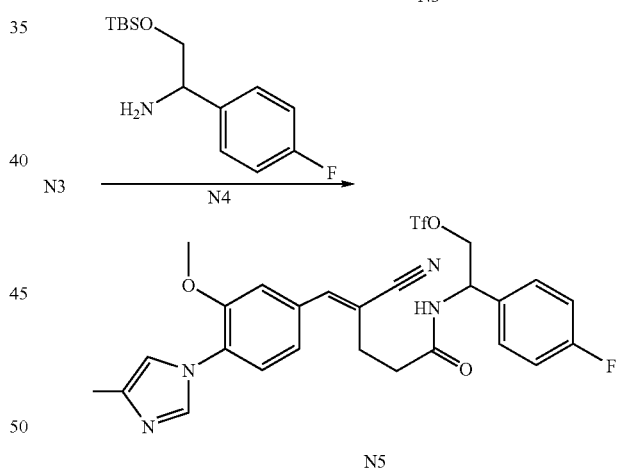
N5
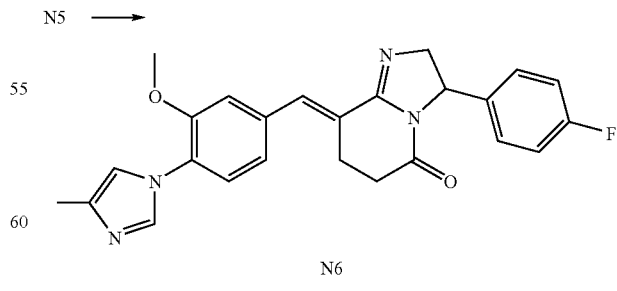
N6
Method N, Step 1
N2 is obtained from N1 after the triflate ester generation which is followed by tributylphosphine treatment.

Method N, Step 2

Compound N3 is obtained through Wittig reaction with appropriate aldehyde with N2

Method N, Step 3

Compound N5 is obtained through hydrolysis of N3 to its corresponding acid which is followed by standard amide coupling with compound N4 which is followed by TBS deprotection and triflate generation.

Method N, Step 4

Compound N6 is obtained using compound N5 following treatment of NaH in DMF.

The following compounds are obtained using methods similar to method N:

N7

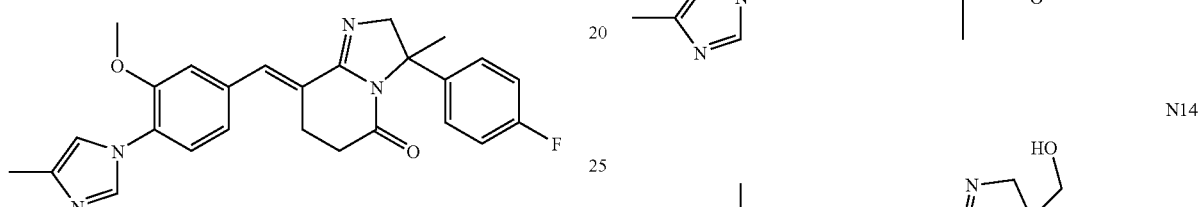

N8

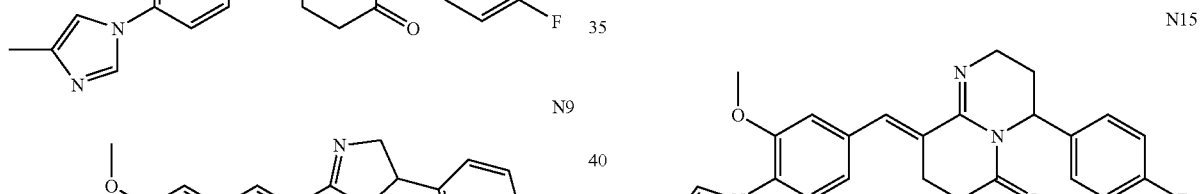

N9

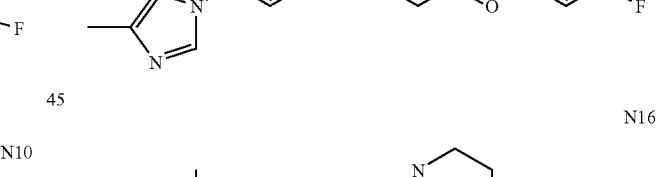

N10

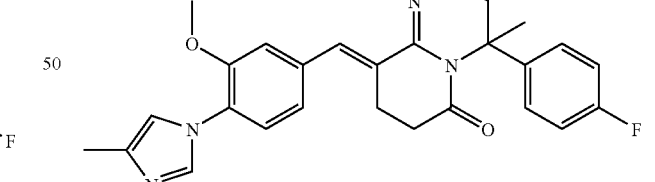

N11

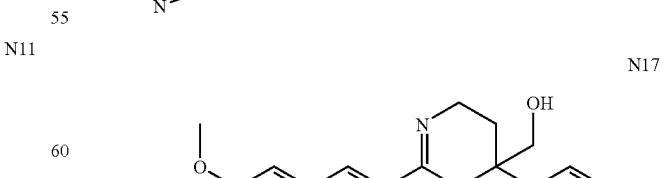

N12

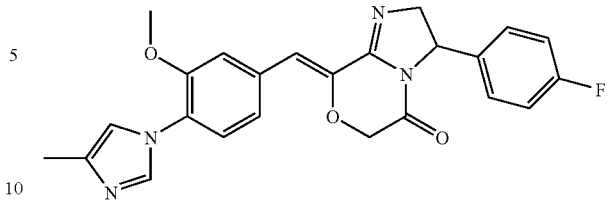

N13

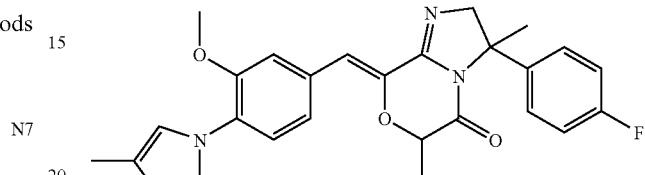

N14

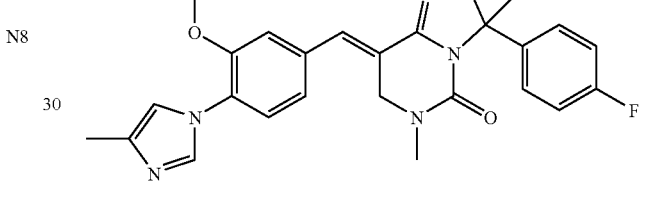

N15

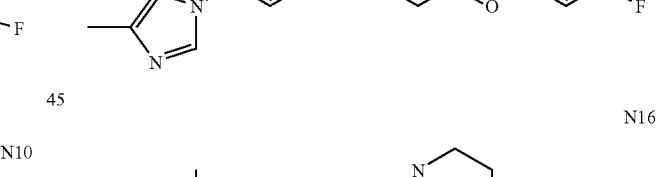

N16

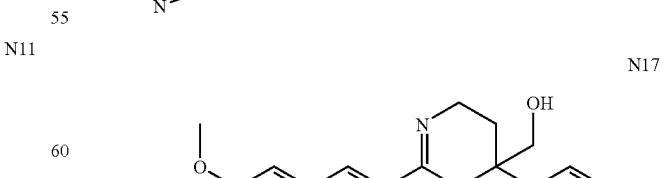

N17

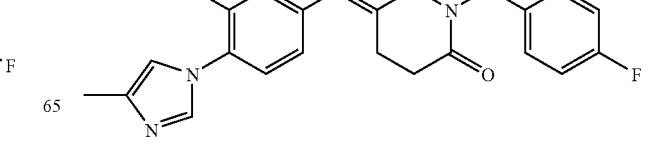

N18
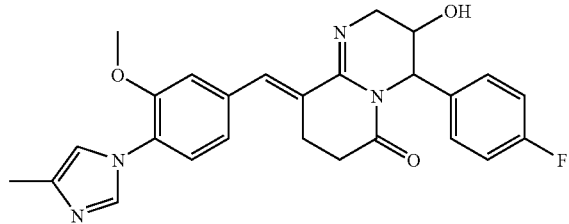

N19
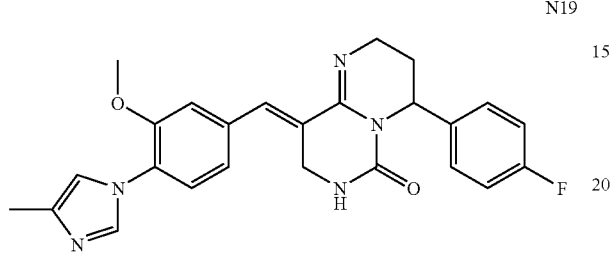

N20
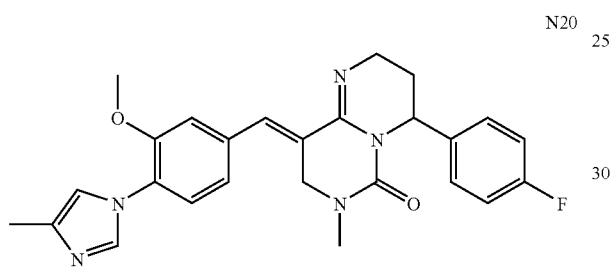

N21
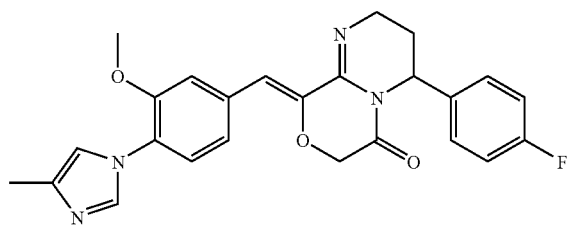

N22
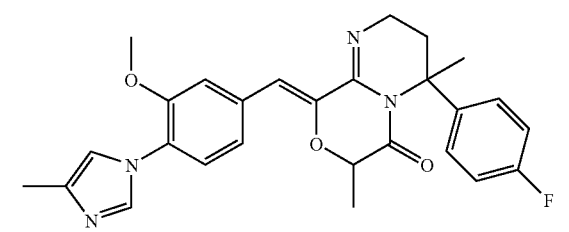

N23
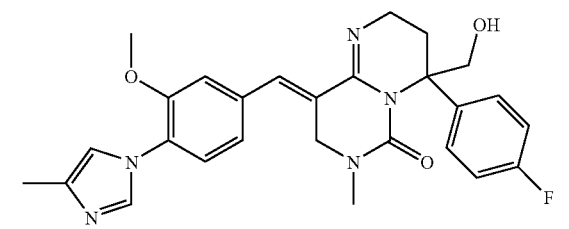

Method O

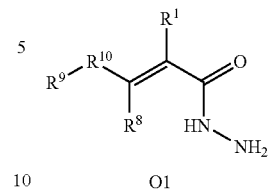
O1

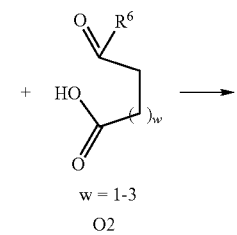
w = 1-3
O2

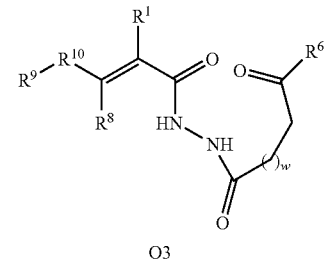
O3

O3 →
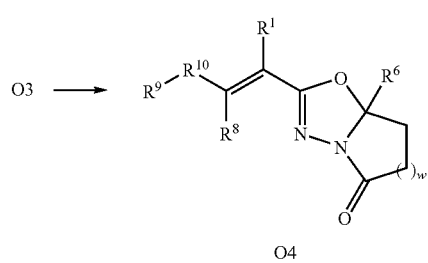
O4

The reaction of acylhydrazines O1 (which are prepared by coupling the corresponding acid with hydrazine under peptide coupling conditions, or by reaction of hydrazine with the appropriate methyl ester) with keto acids (O2) is performed using standard carbodiimide conditions or other coupling procedures widely used to make an amide bond in peptide chemistry. The subsequent dehydration of compound O3 is accomplished by treatment with a catalytic amount of acid such as TsOH, or AcOH in solvents such as Toluene or DCM. In some cases heating in toluene to azeotrope off the $H_2O$ will facilitate the reaction. to produce compounds of Formula O4.

Alternatively, a modified scheme can be used wherein the ketone O2 is first condensed with the amine O1 to give the imine O5. Subsequent treatment of O5 with a dehydrating agent such as $SOCl_2$, $Ac_2O$, or a carbodiimide will provide compounds of formula O4

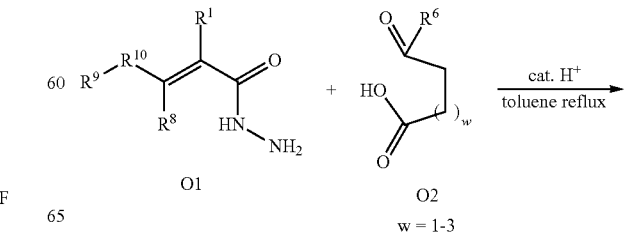
O1        O2
          w = 1-3

175

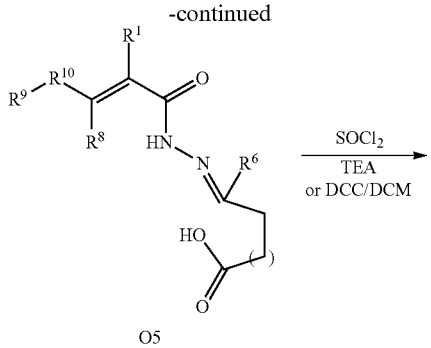

O5

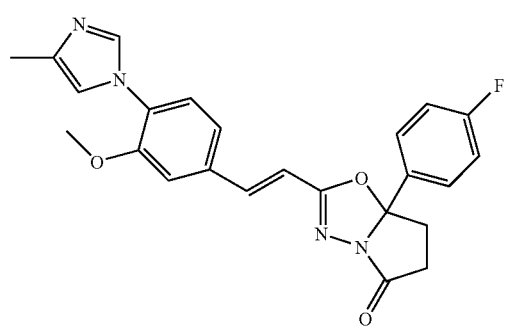

O4

EXAMPLE METHOD O (E)-7a-(4-fluorophenyl)-2-(3-methoxy-4-(4-methyl-1H-imidazol-1-yl)styryl)-7,7a-dihydropyrrolo[2,1-b][1,3,4]oxadiazol-5(6H)-one

O4_1

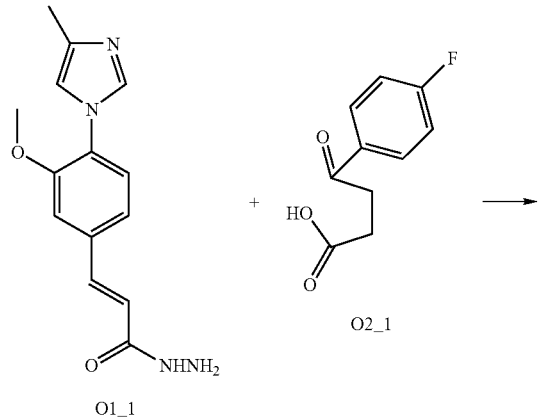

Step 1: Reaction Scheme

176

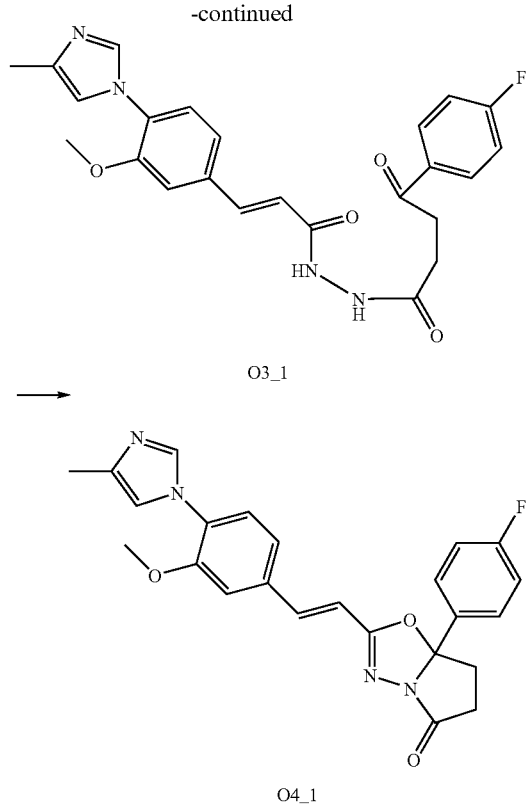

O3_1

O4_1

Step 1

Compound O3_1 is prepared by treating a solution of 1 gram of compound O1_1 in DCM (100 ml), and 1 equivalent of DCC with 1 equivalent of known compound O2_1. After stirring for 12 hrs, add brine (100 ml) and separate the organic layer. Evaporate this to dryness and purify the residue by flash chromatography to obtain O3_1. Treat compound O3_1 in toluene with TsOH (0.1 equivalents) and heat to reflux under a Dean Stark trap overnight. After cooling to room temperature add dilute $NaHCO_3$ solution and brine and separate the organic layer. Evaporate this to dryness and purify the residue by flash chromatography to obtain the compound O4_1.

METHOD P

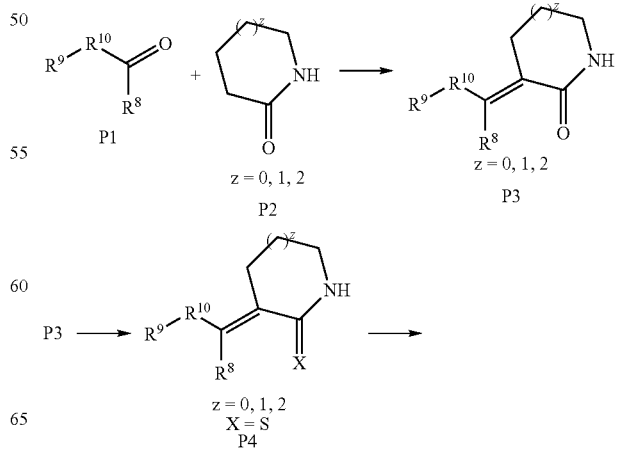

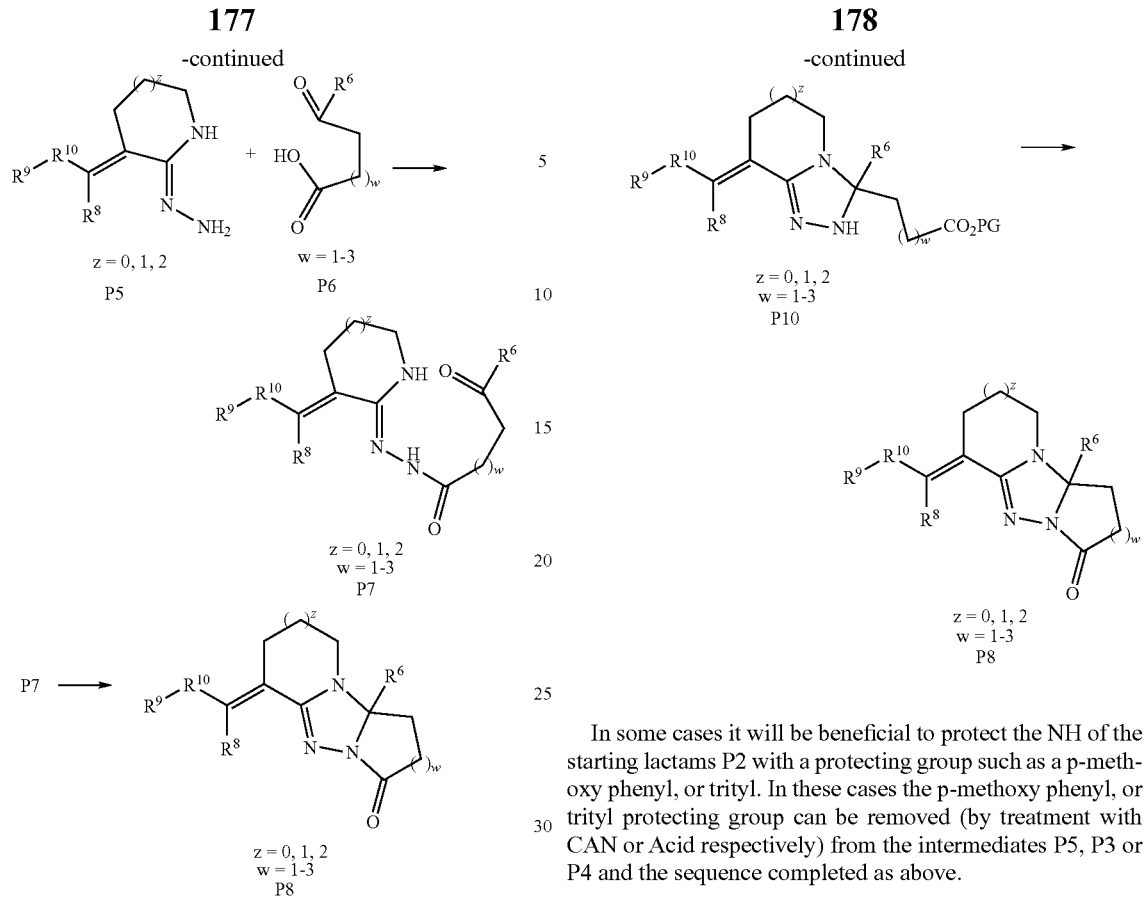

The condensation of a carbonyl containing compound such as P1 with the lactams P2 under basic conditions (using for example NaH and LDA to form the dianion of P2, and then treatment with P1) will provide compounds P3. Reaction of P3 with Lawesson's reagent provides the thioamides P4. These can be converted into the compounds of type P5, by direct treatment with hydrazine in a solvent such as isopropanol or toluene. Alternatively, in some cases the reaction may be facilitated by first reacting P4 with MeI to prepare the thiomethyl ether as an intermediate which is then treated with hydrazine to provide compounds of type P5. Reaction of P5 with a keto acid P6 and a dehydrating agent such as DCC in DCM will provide an intermediate P7 which can be converted into compounds of formula P8 upon further heating or use of an acid catalyst such as TsOH in refluxing toluene.

Alternatively, a modified reaction scheme will provide compounds of formula P8. For example, the amine P5 can be reacted with the ketone P9 (where PG is a protecting group such as a tBu, Et, TMSCH$_2$CH$_2$) under dehydrating conditions to provide the triazine P10. After removing the PG, the acid is converted in compounds of formula P8 by treatment with DCC in DCM or other dehydrating reaction conditions.

In some cases it will be beneficial to protect the NH of the starting lactams P2 with a protecting group such as a p-methoxy phenyl, or trityl. In these cases the p-methoxy phenyl, or trityl protecting group can be removed (by treatment with CAN or Acid respectively) from the intermediates P5, P3 or P4 and the sequence completed as above.

METHOD P EXAMPLES

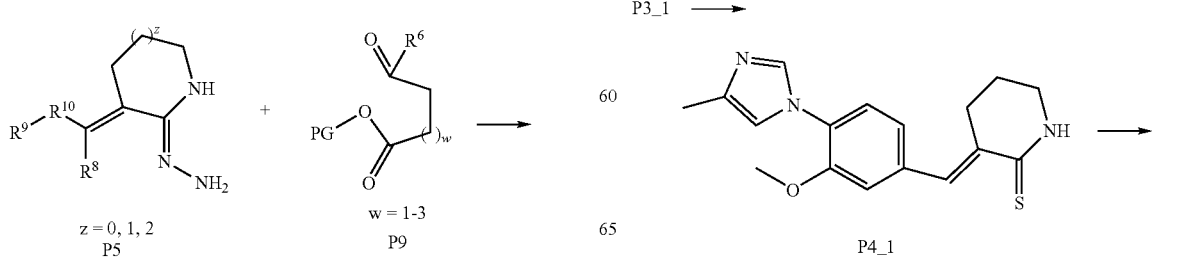

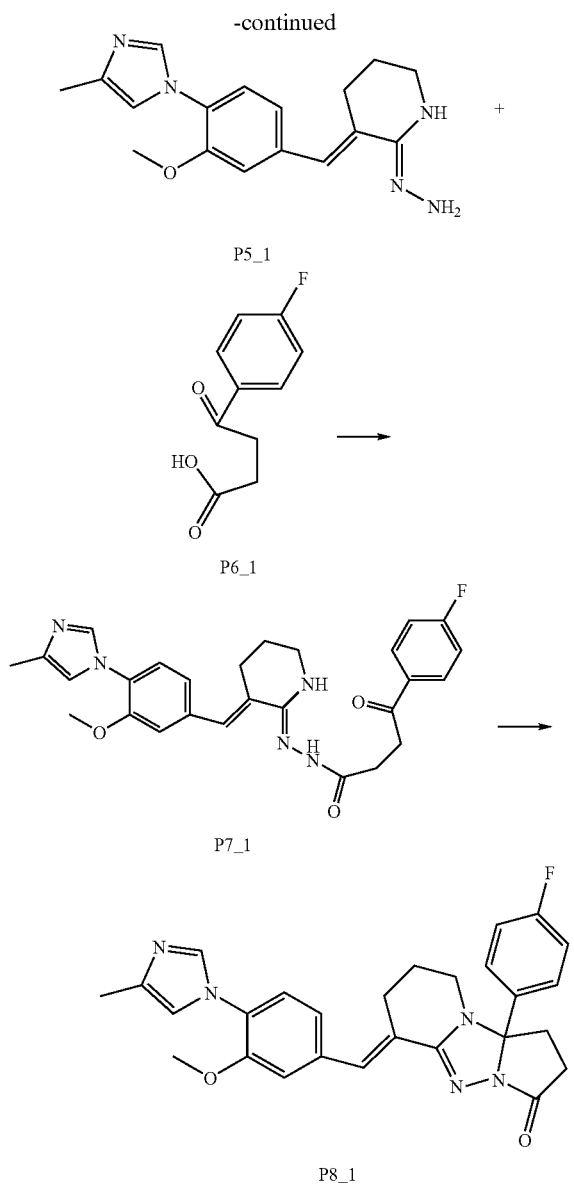

hrs at RT, concentrate to dryness, and redissolve the residue in dioxane and add an excess of hydrazine. After heating for 6 hrs at 50 C cool to room temperature, evaporate to dryness and partition the residue between DCM and brine. Separate the organic layer, evaporate this to dryness and purify the residue by flash chromatography to obtain the intermediate P5__1.

Step 4

Compound P8__1 can be prepared by treating a solution of 1 gram of compound P5__1 in DCM (100 ml), and 1 equivalent of DCC with 1 equivalent of known acid P6__1. After stirring for 12 hrs, add brine (100 ml) and separate the organic layer. Evaporate this to dryness and purify the residue by flash chromatography to obtain the intermediate P7__1. Treat compound P7__1 in toluene (100 mls) with TsOH (0.1 equivalents) and heat to reflux under a Dean Stark trap overnight. After cooling to room temperature, add dilute NaHCO$_3$ solution and brine and separate the organic layer. Evaporate this to dryness and purify the residue by flash chromatography to obtain the desired compound P8__1.

Assay:

Secretase Reaction and Aβ Analysis in Whole Cells: HEK293 cells overexpressing APP with Swedish and London mutations were treated with the specified compounds for 5 hour at 37° C. in 100 ml of DMEM medium containing 10% fetal bovine serum. At the end of the incubation, total Aβ, Aβ40 and Aβ42 were measured using electrochemiluminescence (ECL) based sandwich immunoassays. Total Aβ was determined using a pair of antibodies TAG-WO2 and biotin-4G8, Aβ40 was identified with antibody pairs TAG-G2-10 and biotin-4G8, while Aβ42 was identified with TAG-G2-11 and biotin-4G8. The ECL signal was measured using Sector Imager 2400 (Meso Scale Discovery).

MS Analysis of Aβ Profile: Aβ profile in conditioned media was determined using surface enhanced laser desorption/ionization (SELDI) mass spectrometry. Conditioned media was incubated with antibody WO2 coated PS20 ProteinChip array. Mass spectra of Aβ captured on the array were read on SELDI ProteinChip Reader (Bio-Rad) according to manufacture's instructions.

CSF Aβ Analysis: Aβ in rat CSF was determined using MSD technology as described above. Aβ40 was measured using antibody pair Tag-G2-10 and biotin-4G8, while Aβ42 was measured using Tag-anti Aβ42 (Meso Scale Discovery) and biotin-4G8. The ECL signal was measured using Sector Imager 2400 (Meso Scale Discovery).

Matrix-assisted laser desorption/ionization mass spectrometric (MALDI MS) analysis of Aβ is performed on a Voyager-DE STR mass spectrometer (ABI, Framingham, Mass.). The instrument is equipped with a pulsed nitrogen laser (337 nm). Mass spectra are acquired in the linear mode with an acceleration voltage of 20 kV. Each spectrum presented in this work represents an average of 256 laser shots. To prepare the sample-matrix solution, 1 μL of immunoprecipitated Aβ sample is mixed with 3 μL of saturated α-cyano-4-hydroxycinnamic acid solution in 0.1% TFA/acetonitrile. The sample-matrix solution is then applied to the sample plate and dried at ambient temperature prior to mass spectrometric analysis. All the spectra are externally calibrated with a mixture of bovine insulin and ACTH (18-39 clip).

Compound G4 had an Ab42 IC50 of 1114 nM with an Abtotal/Ab42 selectivity of 11 fold.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

Step 1

Add a solution of the lactam P2__1 (1 gram) in THF (100 mls) to a suspension of NaH (1.5 equivalents) in THF at RT under an inert atmosphere. After stirring for 15 minutes, cool the reaction mixture to −78 C and then add to this 1 equivalent of LDA in THF via syringe. Allow this to warm to 0 C for 1 hr then recool this to −78 C and add a THF solution of .the aldehyde P1__1 via syringe. Allow the reaction mixture to warm to room temperature followed by addition of a saturated solution of NH$_4$Cl. Partition the mixture with EtOAc, separate the organic layer, evaporate to dryness and purify by flash chromatography to provide compound P3__1.

Step 2

Treat 1 gram of compound P3__1 with 1 equivalent of Lawesson's reagent in toluene (100 ml) at between 50 and 100 C overnight. After cooling to room temperature partition with brine and separate the organic layer. Evaporate this to dryness and purify the residue by flash chromatography to obtain the intermediate P4__1.

Step 3:

Treat 1 gram of compound P4__1 in DCM (100 ml) with 1 equivalent of MeI and 1 equivalent of triethylamine. After 3

What is claimed is:

1. A compound of the general formula:

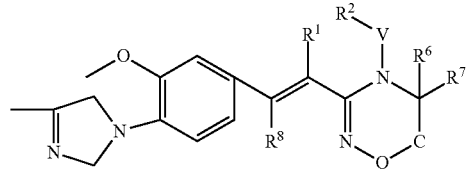

or a pharmaceutically acceptable salt thereof,
wherein
- $R^1$ and $R^2$ are joined together to form a piperidinyl ring or a morpholinyl ring, wherein the piperidinyl ring or morpholinyl ring is optionally substituted by alkyl;
- $R^6$ and $R^7$ are each independently selected from the group consisting of hydrogen, alkyl, alkenyl, alkynyl, or phenyl, wherein each alkyl, alkenyl, alkynyl or phenyl is optionally substituted with 1-3 substituents selected from —OH or halo;
- R8 is selected from the group consisting of hydrogen, alkyl, alkenyl or alkynyl; and
- V is a bond.

2. The compound according to claim 1 or a pharmaceutically acceptable salt thereof, wherein $R^6$ or $R^7$ is phenyl optionally substituted by 1-3 fluoro.

3. The compound according to claim 1 or a pharmaceutically acceptable salt thereof, wherein $R^8$ is hydrogen.

4. The compound according to claim 1 or a pharmaceutically acceptable salt thereof, wherein $R^1$ and $R^2$ join together to form a piperidinyl ring optionally substituted with a methyl.

5. The compound according to claim 4 or a pharmaceutically acceptable salt thereof, wherein $R^6$ or $R^7$ are alkyl optionally substituted with —OH, or phenyl optionally substituted with 1-3 fluoro.

6. The compound according to claim 1 or a pharmaceutically acceptable salt thereof, wherein the compound is selected from the group consisting of D9
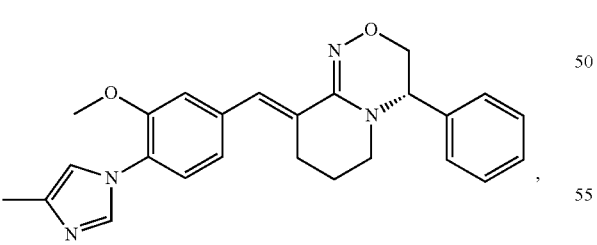

D10
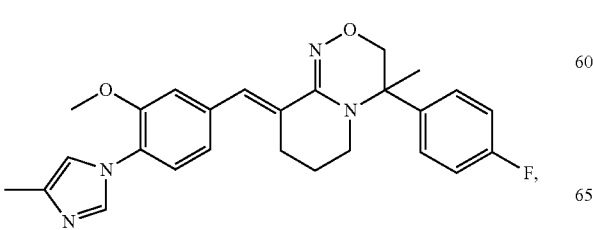

D11
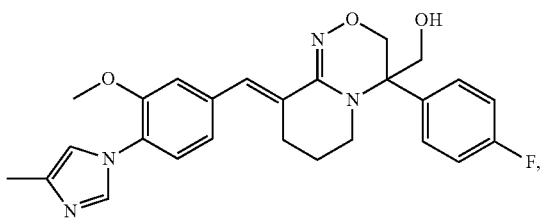

D12
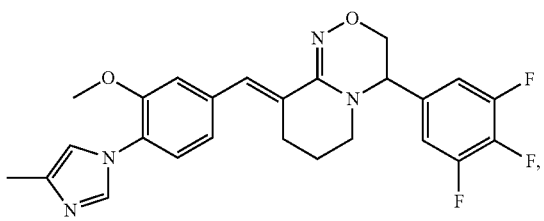

D13
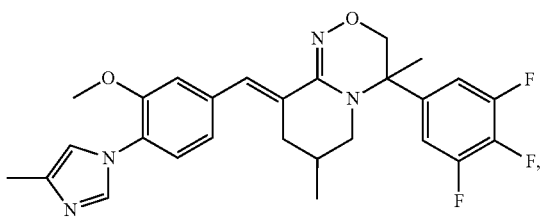

D14
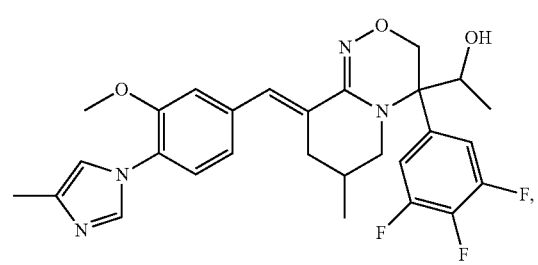

D15
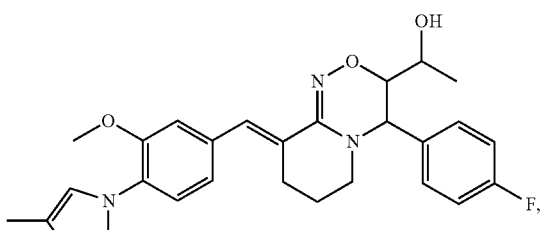

D16
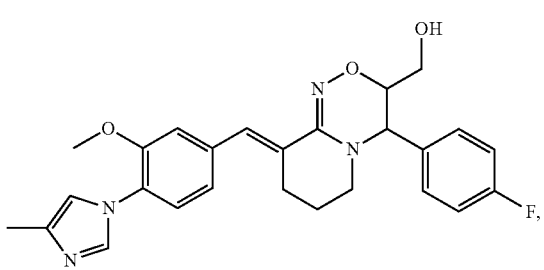

-continued

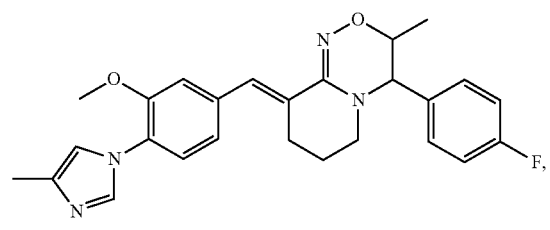
D17

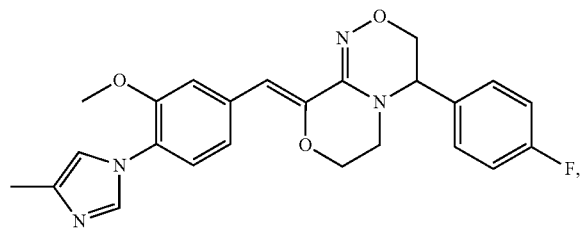
D18

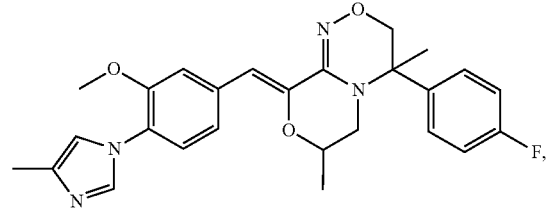
D19

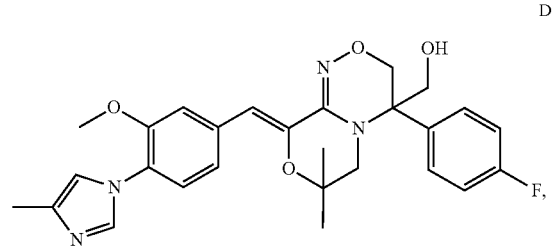
D20

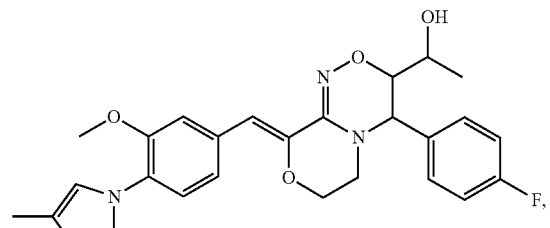
D21

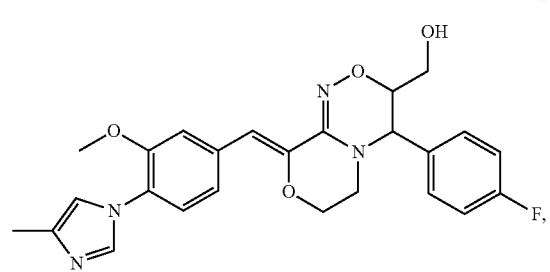
D22

-continued

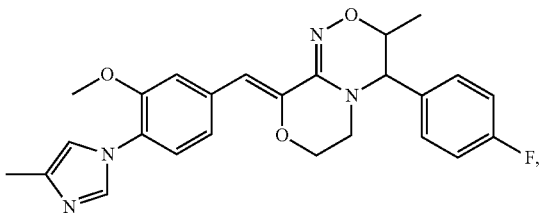
D23

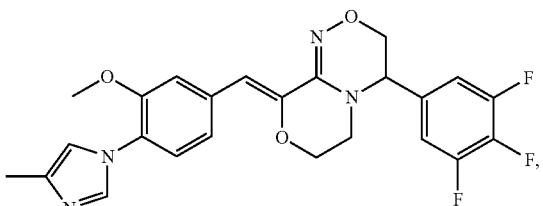
D24

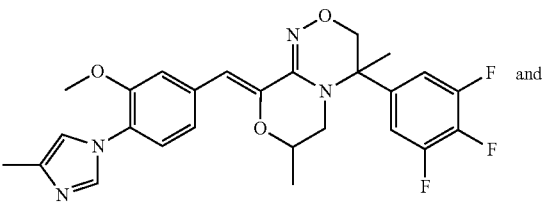
D25

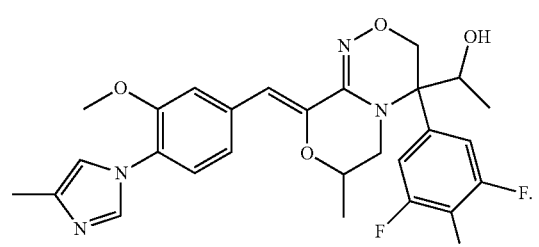
D26

7. The compound according to claim 6 or a pharmaceutically acceptable salt thereof, wherein the compound is

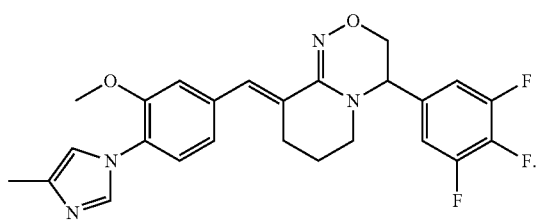
D12

8. A pharmaceutical composition comprising a compound according to claim 1 or a pharmaceutically acceptable salt thereof and a pharmaceutically acceptable carrier.

9. A pharmaceutical composition comprising a compound according to claim 6 or a pharmaceutically acceptable salt thereof and a pharmaceutically acceptable carrier.

* * * * *

UNITED STATES PATENT AND TRADEMARK OFFICE
CERTIFICATE OF CORRECTION

PATENT NO. : 8,426,403 B2
APPLICATION NO. : 12/601322
DATED : April 23, 2013
INVENTOR(S) : Zhaoning Zhu Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 675 days.

Signed and Sealed this
Twenty-second Day of October, 2013

Teresa Stanek Rea
*Deputy Director of the United States Patent and Trademark Office*